United States Patent
Qian et al.

(10) Patent No.: US 11,753,473 B2
(45) Date of Patent: Sep. 12, 2023

(54) ANTI-PD-L1 ANTIBODIES

(71) Applicant: SUZHOU TRANSCENTA THERAPEUTICS CO., LTD., Suzhou (CN)

(72) Inventors: Xueming Qian, Thousand Oaks, CA (US); Teng Fei, Suzhou (CN); Zhen Li, Suzhou (CN)

(73) Assignee: SUZHOU TRANSCENTA THERAPEUTICS CO., LTD., Suzhou (CN)

( * ) Notice: Subject to any disclaimer, the term of this patent is extended or adjusted under 35 U.S.C. 154(b) by 410 days.

(21) Appl. No.: 17/033,970

(22) Filed: Sep. 28, 2020

(65) Prior Publication Data

US 2021/0009693 A1    Jan. 14, 2021

Related U.S. Application Data

(63) Continuation of application No. 16/086,013, filed as application No. PCT/CN2017/073242 on Feb. 10, 2017, now Pat. No. 10,822,416.

(30) Foreign Application Priority Data

Mar. 23, 2016 (WO) ................ PCT/CN2016/077082

(51) Int. Cl.
| | | |
|---|---|---|
| C07K 16/28 | (2006.01) | |
| A61K 39/395 | (2006.01) | |
| A61P 35/00 | (2006.01) | |
| A61K 39/00 | (2006.01) | |

(52) U.S. Cl.
CPC .... C07K 16/2827 (2013.01); A61K 39/39558 (2013.01); A61P 35/00 (2018.01); C07K 16/2863 (2013.01); A61K 2039/507 (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,560,655 A | 12/1985 | Baker |
| 4,657,760 A | 4/1987 | Kung et al. |
| 4,657,866 A | 4/1987 | Kumar |
| 4,767,704 A | 8/1988 | Cleveland et al. |
| 4,816,397 A | 3/1989 | Boss et al. |
| 4,816,567 A | 3/1989 | Cabilly et al. |
| 4,927,762 A | 5/1990 | Darfler |
| 5,122,469 A | 6/1992 | Mather et al. |
| 5,206,344 A | 4/1993 | Katre et al. |
| 5,225,212 A | 7/1993 | Martin et al. |
| 5,225,539 A | 7/1993 | Winter |
| 5,530,101 A | 6/1996 | Queen et al. |
| 5,807,715 A | 9/1998 | Morrison et al. |
| 5,859,205 A | 1/1999 | Adair et al. |
| 6,005,079 A | 12/1999 | Casterman et al. |
| 6,407,213 B1 | 6/2002 | Carter et al. |
| 6,881,557 B2 | 4/2005 | Foote |
| 7,943,743 B2 | 5/2011 | Korman et al. |
| 8,217,149 B2 | 7/2012 | Irving et al. |
| 8,217,849 B2 | 7/2012 | Sardariani et al. |
| 8,741,295 B2 | 6/2014 | Olive |
| 8,779,108 B2 | 7/2014 | Queva et al. |
| 9,102,725 B2 | 8/2015 | Korman et al. |
| 9,175,082 B2 | 11/2015 | Zhou et al. |
| 9,212,224 B2 | 12/2015 | Cogswell et al. |
| 9,637,546 B2 | 5/2017 | Olive et al. |
| 9,709,568 B2 | 7/2017 | Pierce et al. |
| 2014/0341917 A1 | 11/2014 | Nastri et al. |

FOREIGN PATENT DOCUMENTS

| | | |
|---|---|---|
| CN | 103987405 A | 8/2014 |
| CN | 104736168 A | 6/2015 |
| CN | 104994873 A | 10/2015 |
| EP | 0402226 A1 | 12/1990 |
| EP | 0183070 B1 | 10/1991 |
| EP | 0239400 B1 | 8/1994 |
| EP | 0404097 B1 | 9/1996 |
| EP | 0244234 B2 | 11/2001 |
| EP | 0125023 B2 | 3/2002 |
| JP | 2008-544755 A | 12/2008 |
| JP | 2012-511329 A | 5/2012 |
| JP | 2013-511959 A | 4/2013 |
| JP | 2015-500207 A | 1/2015 |
| JP | 2015-519375 A | 7/2015 |

(Continued)

OTHER PUBLICATIONS

Al-Lazikani et al., "Standard conformations for the canonical structures of immunoglobulins" J. Mol. Biol (1997) 273 (4), 927-948.
Altschul et al., "Basic local alignment search tool" J. Mol. Biol. (1990) 215(3):403-410.
Altschul et al., "Gapped BLAST and PSI-BLAST: a new generation of protein database search programs" Nucleic Acids Res. (1997) 25(17):13389-3402.
Barnes et al., "Methods for growth of cultured cells in serum-free medium" Anal. Biochem. (1980) 102(2):255-270.
Carter et al., "High level *Escherichia coli* expression and production of a bivalent humanized antibody fragment" Biol Technology (1992) 10(2):163-167.

(Continued)

*Primary Examiner* — Laura B Goddard
(74) *Attorney, Agent, or Firm* — Jun He Law Offices P.C.; James J. Zhu

(57) ABSTRACT

The present disclosure relates to an isolated PD-L1 antibody whose binding to PD-L1 at acidic pH is substantially lower than its binding to PD-L1 at neutral pH at the same assay setting and an isolated PD-L1 antibody that is not pH dependent in binding to PD-L1. Also provided is the pharmaceutical composition of the antibody, encoding polynucleotide and expression vector, isolated host cell thereof as well as a kit comprising the PD-L1 antibody. Also provided herein are methods of treating a PD-L1 associated condition using the PD-L1 antibody.

28 Claims, 55 Drawing Sheets

Specification includes a Sequence Listing.

(56) References Cited

FOREIGN PATENT DOCUMENTS

| | | | |
|---|---|---|---|
| JP | 2015-535691 A | 12/2015 |
| RU | 2416645 C2 | 4/2011 |
| WO | 8700195 A1 | 1/1987 |
| WO | 9003430 A1 | 4/1990 |
| WO | 9007861 A1 | 7/1990 |
| WO | 9311161 A1 | 6/1993 |
| WO | 9404678 A1 | 3/1994 |
| WO | 9425591 A1 | 11/1994 |
| WO | 9602576 A1 | 2/1996 |
| WO | 2007/005874 A2 | 1/2007 |
| WO | 2010/077634 A1 | 7/2010 |
| WO | 2011/066389 A1 | 6/2011 |
| WO | 2013055404 A1 | 4/2013 |
| WO | 2013079174 A1 | 6/2013 |
| WO | 2013173223 A1 | 11/2013 |
| WO | 2014055897 A2 | 4/2014 |
| WO | 2014151006 A2 | 9/2014 |
| WO | 2014165082 A3 | 10/2014 |

OTHER PUBLICATIONS

Cheng et al., "Structure and interactions of the human programmed cell death 1 receptor" J. Biol. Chem. (2013) 288 (17):111771-11785.
Chothia et al., "Domain association in immunoglobulin molecules. The packing of variable domains" J. Mol. Biol. (1985) 186(3):651-663.
Chothia et al., "Canonical structures for the hypervariable regions of immunoglobulins" J Mol. Biol. (1987) 196 (4):901-917.
Chothia et al., "Conformations of immunoglobulin hypervariable regions" Nature. (1989) 342(6252):877-883.
Freeman et al., "Engagement of the PD-1 immunoinhibitory receptor by a novel B7 family member leads to negative regulation of lymphocyte activation" J. Exp. Med. (2000)192(7):1027-1034.
Graham et al., "Characteristics of a human cell line transformed by DNA from human adenovirus type 5" J. Gen. Virol. (1977) 36(1):59-74.
Guss et al., "Structure of the IgG-binding regions of streptococcal protein G" EMBO J. (1986) 5(7):1567-1575.
Ham et al., "Media and growth requirements" Meth. Enz. (1979) 58:44-93.
Hamers-Casterman et al., "Naturally occurring antibodies devoid of light chains" Nature. (1993) 363 (6428):446-448.
He et al., "Screening of monoclonal antibody formulations based on high-throughput thermostability and viscosity measurements: design of experiment and statistical analysis" J Pharm. Sci (2011) 100(4):1330-1340.
Higgins et al., "Using CLUSTAL for multiple sequence alignments" Methods Enzymol. (1996) 266:383-402.
Holliger et al., ""Diabodies": small bivalent and bispecific antibody fragments" Proc. Natl. Acad. Sci. U S A (1993) 90(14):6444-6448.
Huston et al., "Protein engineering of antibody binding sites: recovery of specific activity in an anti-digoxin single-chain Fv analogue produced in *Escherichia coli*" Proc. Natl. Acad. Sci. USA (1988) 85(16):5879-5883.
Koch-Nolte et al., "Single domain antibodies from llama effectively and specifically block T cell ecto-ADP-ribosyltransferase ART2.2 in vivo" FASEB J. (2007) 21(13):3490-3498.
Langer, "Polymer-controlled drug delivery systems" Acc. Chem. Res. (1993) 26(10):537-542.
Larkin et al., "Clustal W and Clustal X version 2.0" Bioinformatics (2007) 23(21): 2947-2948.
Latchman et al., "PD-L2 is a second ligand for PD-1 and inhibits T cell activation" Nat. Immunol. (2001) 2 (3):261-268.
Lin et al., "The PD-1/PD-L1 complex resembles the antigen-binding Fv domains of antibodies and T cell receptors" Proc. Natl. Acad. Sci. U S A. (2008), 105(8):3011-3016.
Lindmark et al., "Binding of immunoglobulins to protein A and immunoglobulin levels in mammalian sera" J. Immunol. Meth. (1983) 62(1):1-13.

Mather, "Establishment and characterization of two distinct mouse testicular epithelial cell lines" Biol. Reprod. (1980) 23 (1):243-252.
Mather et al., "Culture of testicular cells in hormone-supplemented serum-free medium" Ann. N.Y. Acad. Sci. (1982) 383:44-68.
Muyldermans, "Single domain camel antibodies: current status" J. Biotechnol. (2001) 74(4):277-302.
Nguyen et al., "Heavy-chain antibodies in Camelidae; a case of evolutionary innovation" Immunogenetics (2002) 54 (1):39-47.
Nguyen et al., "Heavy-chain only antibodies derived from dromedary are secreted and displayed by mouse B cells". Immunology (2003) 109(1):93-101.
Riechmann et al., "Single domain antibodies: comparison of camel VH and camelised human VH domains" J. Immunol. Methods (1999) 231(1-2):25-38.
Salmeron et al., "A conformational epitope expressed upon association of CD3-epsilon with either CD3-delta or CD3-gamma is the main target for recognition by anti-CD3 monoclonal antibodies." J. Immunol. (1991) 147 (9):3047-3052.
Shields et al., "High resolution mapping of the binding site on human IgG1 for Fc gamma RI, Fc gamma RII, Fc gamma RII, and FcRn and design of IgG1 variants with improved binding to the Fc gamma R" J. Biol. Chem. (2001) 276 (9): 6591-6604.
Urlaub et al., "Isolation of Chinese hamster cell mutants deficient in dihydrofolate reductase activity" Proc. Natl. Acad Sci. USA (1980) 77(7):4216-4220.
International Search Report of PCT/CN0217/073242, dated May 4, 2017.
Teng MW et al., "GenBank database, NCBI Reference sequence: NP_054862.1", programmed cell death 1 ligand 1 isoform a precursor[*Homo sapiens*], Sep. 25, 2015 (Sep. 25, 2015), see the sequence information.
Xueming Qian et al.: "Characterization of a humanized PD-L1 blocking antibody with pH-dependent antigen binding in a humanized syngenic tumor model. | Journal of Clinical Oncology", Journal of Clinical Oncology, vol. 35, No. 7, suppl 1, Mar. 1, 2017 (Mar. 1, 2017), p. 81, XP055693308. The whole document.
The extended European search report of European application No. 17769253.0, dated May 19, 2020.
Ohaegbulam, K. C. et al., "Human cancer immunotherapy with antibodies to the PD-1 and PD-L1 pathway", Trends in Molecular Medicine (Jan. 2015), vol. 21(1), pp. 24-33.
Philips, G. K. et al., "Therapeutic uses of anti-PD-1 and anti-PD-L1 antibodies", International Immunology (2014), vol. 27(1), pp. 39-46.
The second office action of Chinese application No. 202010174431.5, dated Jul. 13, 2021.
The Decision on Grant of Russian application No. 2018124602, dated Jan. 15, 2021.
Benjamin Boyerinas et al., "Antibody-dependent cellular cytotoxicity (ADCC) activity of a ovel anti-PD-L1 antibody avelumab (MSB0010718C) on human tumor cells", Cancer Immunol Res., Oct. 31, 2015, 3(10): 1148-1157.
Rong Deng et al., "Preclinical pharmacokinetics, pharmacodynamics, tissue distribution, and tumor penetration of anti-PD-L1 monoclonal antibody, an immune checkpoint inhibitor", MABS, 2016, vol. 8, No. 3, 593-603.
The first office action of Chinese application No. 202010174431.5, dated Mar. 9, 2021.
The search report of Chinese application No. 202010174431.5, dated Mar. 9, 2021.
The office action of Japanese application No. 2019-500712, dated Mar. 2, 2021.
Pakula, A. A. et al., "Genetic Analysis of Protein Stability and Function", Annu. Rev. Genet. (1989), vol. 23, pp. 289-310.
Rudikoff, S. et al., "Single amino acid substitution altering antigen-binding specificity", Proc. Natl. Acad. Sci.USA (Mar. 1982), vol. 79, pp. 1979-1983 (see Implications for Generation of Diversity).
Chen C. et al., "Enhancement and destruction of antibody function by somatic mutation: unequal occurrence is controlled by V gene combinatorial associations", The EMBO Journal(1995), vol. 14, No. 12, pp. 2784-2794, (see abstract).
M. Singer et al.,"Genes & genomes", Moscow, "Mir", 1998, vol. 1, pp. 63-64.
Roitt I et al.,"Immunologia", Moscow, "Mir", 2000, pp. 110-111.

(56) References Cited

OTHER PUBLICATIONS

Jakubke H.-D. et al.,Aminokisloty, peptidy, belky, Translated from German Mir,1985.—456 p., Figures; pp. 356-363.

Lu, D. et al.,"Acquired antagonistic activity of a bispecific diabody directed against two different epitopes on vascular endothelial growth factor receptor 2", Journal of Immunological Methods (1999), vol. 230, pp. 159-171. (Discussion).

Official Action for Russian Patent Application No. 2018124602/10(039044), dated Jun. 30, 2020.

Note: the inoculation day was designed as Day1

Day 29 Post Inoculation
Note: the inoculation day was designed as Day1

Note: the inoculation day was designed as Day 1; the dose administration was conducted on the day marked with red arrow.
* p value <0.05 vs. vehicle
** p value <0.005 vs. vehicle Note: the inoculation day was designed as Day 1; the dose administration was conducted on the day marked with red arrow.

* p value <0.05

Note:
Net: TV between 100~150 mm^3 at initiation of dosing;
Grey: TV between 150~200 mm^3 at initiation of dosing;
Strip: TV between 200~300 mm^3 at initiation of dosing.

| Names | Sequences | SEQ ID NOs: |
|---|---|---|
| 22C9 H-CDR1 | SYWMH | 7 |
| 22C9 H-CDR2 | MIHPNSDITNCNENFKH | 8 |
| 22C9 H-CDR3 | SDGSSYWYFDV | 9 |
| 22C9 L-CDR1 | KAGQSVNNDVA | 10 |
| 22C9 L-CDR2 | YASNRYT | 11 |
| 22C9 L-CDR3 | QQDFSSPLT | 12 |
| 22C9 HC in mouse/chimeric antibody | QVQLQQSGAELVKPGASVKLSCKASGYTFTSYWMHWVWQRPGQGLEWIGMIHPNSDITNCNENFKHTVTLTVDKSSSTAYMQLSSLTSEDSAVFYCARSDGSSYWYFDVWGTGTTVTVSS | 21 |
| 22C9 LC in mouse/chimeric antibody | SIVMTQTPKFLSVSAGDRVTITCKAGQSVNNDVAWYQQKPGQSPKLLIYYASNRYTGVPDRFTGSGYGTDFTFTISTVQAEDLAVYFCQQDFSSPLTFGAGTKLELK | 22 |
| 18G4 H-CDR1 | SSYYIH | 29 |
| 18G4 H-CDR2 | NINPFNGGSIYNEKFKN | 30 |
| 18G4 H-CDR3 | WHFDY | 31 |
| 18G4 L-CDR1 | KSSQSLLWSGNQNNYLS | 32 |
| 18G4 L-CDR2 | GASIRES | 33 |
| 18G4 L-CDR3 | QHNHGSFLPYT | 34 |
| 21F11 H-CDR1 | SNWMH | 35 |
| 21F11 H-CDR2 | MMHPNSGSINYNEKFKN | 36 |
| 21F11 H-CDR3 | SYYGSSPYYFDY | 37 |
| 21F11 L-CDR1 | RASQDISNYLN | 38 |
| 21F11 L-CDR2 | YTSRLHS | 39 |
| 21F11 L-CDR3 | QQGDTLPWT | 40 |
| 26F5 H-CDR1 | SYWMH | 41 |
| 26F5 H-CDR2 | MIQPSTSGTIYNERFKN | 42 |
| 26F5 H-CDR3 | GTGTVDYFDY | 43 |
| 26F5 L-CDR1 | RASESVDSYGNSFIH | 44 |
| 26F5 L-CDR2 | RASNLES | 45 |
| 26F5 L-CDR3 | QQSKEDPYTF | 46 |
| 18G4 HC in mouse/chimeric antibody | QVQLQQPGTALVKPGASVKLSCKASGYTFSSYYIHWVKQRPGQGLEWIGNINPFNGGSIYNEKFKNKASLTVDTSSNTAYMQLSSLTSEDSAVYYCARWHFDYWGQGTSLTVSS | 55 |
| 18G4 LC in mouse/chimeric antibody | DIVMTQSPSSLAVTAGEKVTLKCKSSQSLLWSGNQNNYLSWYQQKQGQPPKLLIYGASIRESWVPDRFTGSGSGTDFTLTIGNVSAEDLAVYYCQHNHGSFLPYTFGGGTRLEIK | 56 |
| 21F11 HC in mouse/chimeric antibody | QVQLQQPGAELVKPGASVKLSCKASGYTFTSNWMHWVKQRPGQGLEWIGMMHPNSGSINYNEKFKNKATLTADKSSSTAYMQLSSLTSEDSAVYYCARSYYGSSPYYFDYWGQGTTLTVSS | 57 |
| 21F11 LC in mouse/chimeric antibody | DIQMTQTTSSLSASLGDRVTISCRASQDISNYLNWYQQKPDGTVKLLIYYTSRLHSGVPSRFSGSGSGTDFSLTISNLEEEDIATYFCQQGDTLPWTFGGGTKLEIK | 58 |
| 26F5 HC in mouse/chimeric antibody | QVQLQQPGAELVKPGASVKLSCKASGYTFPSYWMHWMKQRPGQGLEWIGMIQPSTSGTIYNERFKNQVTLTVDKSSSTAYMQLSSQTSEDSAVYYCARGTGTVDYFDYWGQGTTLTVSS | 59 |
| 26F5 LC in mouse/chimeric antibody | DIVLTQSPASLAVSLGQRATISCRASESVDSYGNSFIHWYQQKPGQPPKLLIHRASNLESGIPATFSGSGSRTDFTLTINPVEADDVATYYCQQSKEDPYTFGGGTKLEIK | 60 |
| 23A11 H3 in CHO cells | QVQLVQSGAEVKKPGASVKLSCKASGYIFTTYWIHWVKQRPGQGLEWIGMIQPNSGGTKYNDQFKNRATLTVDKSISTAYMELSRLTSDDTAVYYCARGAGTVDYFDYWGQGTTLSISS | 61 |
| 23A11 L5 in CHO cells | DIVLTQSPASLAVSVGQRATITCRASESVDIYGNSFMHWYQQKPGQAPKLLIYRASNLESGIPARFSGSGSRTDFTLTINPVEAQ | 62 |

Figure 34

| | | |
|---|---|---|
| | DTATYYCQQSNDDPYTFGGGTKLETK | |
| 23F11 H4 in CHO cells | QVQLVQSGAEVKKPGASVKLSCKASGYIFTTYWMHWVKQ RPGQGLEWIGMIQPNSGGTKYNEKFKKKATLTVDKSISTAY MELSRLTSDDTAVYYCARGAGTVDYFDYWGQGSTLTVSS | 63 |
| 23F11 L4 in CHO cells | DIVLTQSPASLAVSVGQRATITCRASESVDIYGNSFMHWYQQ KPGQPPKLLIYRASNLESGIPARFSGSGSRTDFTLTINPVEAQ DTATYYCQQSTEDPYTFGGGTKLEIK | 64 |
| 4B6 H3 in CHO cells | QVQLVQSGAEVVKPGASVKISCKASGYVFTDYYMNWVKQ APGQGLEWIGDINPNNGGTSYNQKFQGRATVTVDKSTRTAY MELSRLRSDDTAVYYCVKWGDGPFAYWGQGTLVTVSS | 65 |
| 4B6 L3 in CHO cells | DIQMTQSQSSLSASVGDRVTITCQASQNVGAAVAWYQQKPG KAPKLLIYSASNRYTGVPSRFSGSGSGTDFTLTISSMQPEDIA TYFCQQYSNYPTFGSGTKLGIK | 66 |
| 4B6 H4 in CHO cells | QVQLVQSGAEVKKPGASVKVSCKASGYVFTDYYMNWVRQ APGQGLEWIGDINPNNGGTSYNQKFQGRVTVTVDTSIRTAY MELSRLRSDDTAVYYCVKWGDGPFAYWGQGTLVTVSS | 67 |
| 4B6 L4 in CHO cells | DIQMTQSPSSLSASVGDRVTITCQASQNVGAAVAWYQQKPG KAPKLLIYSASNLYTGVPSRFSGSGSGTDFTLTISSLQPEDIAT YFCQQYSNYPTFGSGTKLGIK | 68 |
| 23A11 H5 in HEK293 cells | LVQLVQSGAEVKKPGASVKVSCKASGYIFTTYWIHWVRQA PGQGLEWIGMIQPNSGGTKYNDQFKNRVTLTVDTSISTAYM ELSRLRSDDTAVYYCARGAGTVDYFDYWGQGTTLSISS | 69 |
| 23A11 L5 in HEK293 cells | DIVLTQSPASLAVSVGQRATITCRASESVDIYGNSFMHWYQQ KPGQAPKLLIYRASNLESGIPARFSGSGSRTDFTLTINPVEAN DTATYYCQQSNDDPYTFGGGTKLETK | 70 |
| 23A11 H3 in HEK293 cells | LVQLVQSGAEVKKPGASVKLSCKASGYIFTTYWIHWVKQRP GQGLEWIGMIQPNSGGTKYNDQFKNRATLTVDKSISTAYME LSRLTSDDTAVYYCARGAGTVDYFDYWGQGTTLSISS | 71 |
| 23A11 L3 in HEK293 cells | DIVLTQSPASLAVSVGQRATITCRASESVDIYGNSFMHWYQQ KPGQSPKLLIYRASNLESGIPARFSGSGSRTDFTLTINPVEAN DTATYYCHQSNDDPYTFGGGTKLETK | 72 |
| 23A11 HC in mouse/chimeric antibody | LVQLQQPGAELVKPGASVKLSCKASGYIFTTYWIHWVKQRP GQGLEWIGMIQPNSGGTKYNDQFKNRATLTVDKSSTTASM QLSGLTSEDSAVYYCARGAGTVDYFDYWGQGTTLSISS | 73 |
| 23A11 LC in mouse/chimeric antibody | DIVLTQSPASLTVSLGQRATISCRASESVDIYGNSFMHWYQQ KPGQSPKLLIYRASNLESGIPARFSGSGSRTDFTLTINPVEAD DVATYYCHQSNDDPYTFGGGTKLETK | 74 |
| 23F11 H4 in HEK293 cells | QVQLVQSGAEVKKPGASVKLSCKASGYIFTTYWMHWVKQ RPGQGLEWIGMIQPNSGGTKYNEKFKKKATLTVDKSISTAY MELSRLTSDDTAVYYCARGAGTVDYFDYWGQGSTLTVSS | 75 |
| 23F11 L4 in HEK293 cells | DIVLTQSPASLAVSVGQRATITCRASESVDIYGNSFMHWYQQ KPGQPPKLLIYRASNLESGIPARFSGSGSRTDFTLTINPVEAN DTATYYCQQSTEDPYTFGGGTKLEIK | 76 |
| 23F11 H6 in HEK293 cells | QVQLVQSGAEVKKPGASVKVSCKASGYIFTTYWMHWVRQ APGQGLEWIGMIQPNSGGTKYNEKFKKKATLTVDTSISTAY MELSRLSDDTAVYYCARGAGTVDYFDYWGQGSTLTVSS | 77 |
| 23F11 L6 in HEK293 cells | DIVLTQSPASLAVSVGQRATITCRASESVDIYGNSFMHWYQQ KPGQPPKLLIYRASNLESGIPARFSGSGSRTDFTLTINPVEAN DTATYYCHQSTEDPYTFGGGTKLEIK | 78 |
| 23F11 HC in mouse/chimeric antibody | QVQLQQPGAELVKPGASVKLSCKASGYSFTTYWMHWVKQ RPGQGLEWIGMIQPNSGGTKYNEKFKKKATLTVDKSSTTAS MELSSLTSEDSAVYYCARGAGTVDYFDYWGQGSTLTVSS | 79 |
| 23F11 LC in mouse/chimeric antibody | DIVLTHSPVSLAVSLGQRATISCRASESVDIYGNSFMHWYQQ KPGQPPKLLIYRASNLESGIPARFSGSGSRTDFTLTINPVEAD DVATYYCQQSTEDPYTFGGGTKLEIK | 80 |
| 4B6 H1 in CHO cells | QVQLVQSGAEVVKPGASVKISCKASGYVFTDYYMNWVKQ APGQGLEWIGDINPNNGGTSYNQKFQGRATVTVDKSTRTAY | 81 |

Figure 34 continued

| | | |
|---|---|---|
| | MELSRLRSDDTAVYYCVKWGDGPFAYWGQGTLVTVSS | |
| 4B6 L1 in CHO cells | DIQMTQSQSSLSASVGDRVTITCQASQNVGAAVAWYQQKPG KAPKLLIYSASNRYTGVPSRFSGSGSGTDFTLTISSMQPEDIA TYFCQQYSNYPTFGSGTKLGIK | 82 |
| 4B6 H2 in CHO cells | QVQLVQSGAEVKKPGASVKVSCKASGYVFTDYYMNWVRQ APGQGLEWIGDINPNNGGTSYNQKFQGRVTVTVDTSISTAY MELSRLRSDDTAVYYCVKWGDGPFAYWGQGTLVTVSS | 83 |
| 4B6 L2 in CHO cells | DIQMTQSPSSLSASVGDRVTITCQASQNVGAAVAWYQQKPG KAPKLLIYSASNLETGVPSRFSGSGSGTDFTLTISSLQPEDIAT YFCQQYSNYPTFGSGTKLGIK | 84 |
| 4B6 HC in mouse/chimeric antibody | EVQLQQSGPELVKPGASVKISCKASGYVFTDYYMNWVKQS HGKSLEWIGDINPNNGGTSYNHKFKGKATVTVDKSSRTAY MELLSLTSEDSAVYYCVKWGDGPFAYWGQGTLVTVSA | 85 |
| 4B6 LC in mouse/chimeric antibody | DIVMTQSQKFMSTSVGDRVSITCKASQNVGAAVAWYQQKP GQSPKLLIYSASNRYTGVPDRFTGSGSGTDFTLTISNMQSED LADYFCQQYSNYPTFGSGTKLGIK | 86 |
| 18G4 HC in mouse/chimeric antibody-DNA sequence | CAGGTCCAGCTGCAGCAGCCTGGGACTGCACTGGTGAAG CCTGGGGCTTCAGTGAAGCTGTCCTGCAAGGCTTCTGGCT ACACCTTCTCCAGCTACTACATACACTGGGTGAAACAGAG GCCTGGACAAGGCCTTGAGTGGATTGGAAATATTAATCCT TTCAATGGTGGTTCTATCTACAATGAGAAGTTCAAGAACA AGGCCTCGCTGACTGTAGACACATCCTCCAACACAGCCTA CATGCAGCTCAGCAGCCTGACATCTGAGGACTCTGCGGTC TATTATTGTGCAAGGTGGCACTTTGACTACTGGGGCCAAG GCACCTCTCTCACAGTCTCCTCA | 93 |
| 18G4 LC in mouse/chimeric antibody-DNA sequence | GACATTGTGATGACCCAGTCTCCATCCTCCCTGGCTGTGA CAGCAGGAGAGAAGGTCACTTTGAAATGCAAGTCCAGTC AGAGTCTTTTGTGGAGTGGAAACCAAAATAACTACTTATC CTGGTACCAGCAGAAACAAGGGCAGCCTCCTAAACTGCT TATCTATGGGGCATCCATTAGAGAATCTTGGGTCCCTGATC GATTCACAGGAAGTGGATCTGGGACAGACTTCACTCTTAC CATTGGCAATGTGTCTGCTGAAGACCTAGCAGTTTATTACT GTCAGCACAATCATGGCAGCTTTCTCCCCTACACGTTCGG AGGGGGGACCAGGCTGGAAATAAAA | 94 |
| 21F11 HC in mouse/chimeric antibody-DNA sequence | CAGGTCCAACTGCAGCAGCCTGGGGCTGAGCTGGTAAAG CCTGGGGCTTCAGTGAAGTTGTCCTGCAAGGCTTCTGGCT ACACTTTCACCAGCAACTGGATGCACTGGGTGAAGCAGA GGCCTGGACAAGGCCTTGAGTGGATTGGAATGATGCATCC TAATAGTGGTAGTATCAATTACAATGAGAAGTTCAAGAAC AAGGCCACACTGACTGCAGACAAATCCTCCAGCACAGCC TACATGCAACTCAGTAGCCTGACATCTGAGGACTCTGCGG TCTACTACTGTGCAAGATCCTACTACGGTAGTAGCCCGTAC TACTTTGACTACTGGGGCCAAGGCACCACTCTCACAGTCT CCTCA | 95 |
| 21F11 LC in mouse/chimeric antibody-DNA sequence | GATATCCAGATGACACAGACTACATCCTCCCTGTCTGCCTC TCTGGGAGACAGAGTCACCATCAGTTGCAGGGCAAGTCA GGACATTAGCAATTATTTAAACTGGTATCAGCAGAAACCA GATGGAACTGTTAAACTCCTGATCTACTACACATCAAGATT ACACTCAGGAGTCCCATCAAGGTTCAGTGGCAGTGGGTC TGGAACAGATTTTTCTCTCACCATTAGCAACCTGGAGGAA GAAGATATTGCCACTTACTTTTGCCAGCAGGGTGATACGC TTCCGTGGACGTTCGGTGGAGGCACCAAGCTGGAAATCA AA | 96 |
| 26F5 HC in mouse/chimeric antibody-DNA sequence | CAGGTCCAACTTCAGCAGCCTGGGGCTGAGCTGGTAAAG CCTGGGGCTTCAGTGAAGTTGTCCTGCAAGGCTTCTGGCT ACACTTTCCCCAGCTACTGGATGCACTGGATGAAGCAGAG GCCTGGACAAGGCCTTGAGTGGATTGGAATGATTCAGCCT | 97 |

Figure 34 continued

| | | |
|---|---|---|
| | AGTACTTCTGGTACTATCTACAATGAGAGATTCAAGAACC AGGTCACACTGACTGTAGACAAATCTTCCAGCACAGCCTA CATGCAACTCAGCAGCCAGACATCTGAGGACTCTGCGGT CTATTACTGTGCAAGAGGAACTGGGACGGTGGACTACTTT GATTACTGGGGCCAAGGCACCACTCTCACAGTCTCCTCA | |
| 26F5 LC in mouse/chimeric antibody-DNA sequence | GACATTGTGCTGACCCAATCTCCAGCTTCTTTGGCTGTGT CTCTAGGGCAGAGGGCCACCATATCCTGCAGAGCCAGCG AAAGTGTTGATAGTTATGGCAATAGTTTTATACACTGGTAC CAACAGAAGCCAGGACAGCCACCCAAACTCCTCATCCAT CGTGCATCCAACCTAGAATCTGGGATCCCTGCCACATTCA GCGGCAGTGGGTCTAGGACAGACTTCACCCTCACCATAAA TCCTGTGGAGGCTGATGATGTTGCAACCTATTACTGTCAA CAAAGTAAGGAGGACCCGTACACGTTCGGAGGGGGGACC AAGCTGGAAATAAAA | 98 |
| 4B6 H3 in CHO cells-DNA sequence | CAGGTGCAGCTGGTGCAGAGCGGCGCAGAAGTGGTCAA GCCAGGAGCCTCAGTGAAGATCAGCTGCAAGGCCAGCGG CTACGTGTTCACCGACTACTATATGAACTGGGTGAAACAG GCACCAGGACAGGGACTGGAGTGGATCGGGGATATTAAC CCTAACAATGGCGGAACAAGCTACAATCAGAAGTTTCAG GGCAGGGCAACCGTGACAGTGGACAAATCTACTAGTACC GCCTATATGGAACTGTCTCGGCTGAGAAGCGACGATACCG CTGTGTACTATTGTGTCAAGTGGGGCGACGGACCCTTCGC ATATTGGGGCCAGGGGACACTGGTGACTGTCAGCTCC | 99 |
| 4B6 L3 in CHO cells-DNA sequence | GACATTCAGATGACACAGTCTCAGAGTAGCCTGTCAGCCA GCGTGGGCGACCGAGTCACCATCACATGCCAGGCCAGTC AGAACGTGGGAGCCGCTGTCGCTTGGTACCAGCAGAAGC CAGGCAAAGCTCCCAAGCTGCTGATCTACTCCGCATCTAA TCGGTACACAGGGGTGCCCAGCAGATTCAGTGGCTCAGG GAGCGGAACTGACTTTACTCTGACCATCAGCTCCATGCAG CCTGAAGATATTGCCACCTACTTCTGCCAGCAGTACTCAA ACTATCCAACCTTTGGCAGCGGGACAAAACTGGGGATCA AG | 100 |
| 22C9 HC in mouse/chimeric antibody-DNA sequence | CAGGTCCAACTGCAGCAGTCTGGGGCTGAGTTGGTAAAG CCGGGGGCTTCAGTGAAGTTGTCCTGCAAGGCTTCTGGCT ACACTTTCACCAGCTACTGGATGCACTGGGTGTGGCAGAG GCCTGGACAAGGCCTTGAGTGGATTGGAATGATTCATCCT AATAGTGATATTACTAACTGCAATGAGAATTTCAAGCACAC GGTCACACTGACTGTTGACAAATCCTCCAGTACAGCCTAC ATGCAACTCAGCAGCCTGACATCTGAGGACTCTGCGGTCT TTTACTGTGCAAGATCGGACGGTAGTAGCTACTGGTACTT CGATGTCTGGGGCACAGGGACCACGGTCACCGTCTCCTC A | 101 |
| 22C9 LC in mouse/chimeric antibody-DNA sequence | AGTATTGTGATGACCCAGACTCCCAAATTCCTGTCTGTATC AGCAGGAGACAGGGTTACCATAACCTGCAAGGCCGGTCA GAGTGTGAATAATGATGTAGCTTGGTACCAACAGAAGCCA GGGCAGTCTCCTAAACTGCTGATATATTATGCATCCAATCG TTATACTGGAGTCCCTGATCGCTTCACTGGCAGTGGATATG GGACGGATTTCACTTTCACCATCAGCACTGTGCAGGCTGA AGACCTGGCAGTTTATTTCTGTCAGCAGGATTTTAGCTCTC CGCTCACGTTCGGTGCTGGGACCAAGCTGGAACTGAAAC | 102 |
| 23A11 H3 in 293 cells | AGTATTGTGATGACCCAGACTCCCAAATTCCTGTCTGTATC AGCAGGAGACAGGGTTACCATAACCTGCAAGGCCGGTCA GAGTGTGAATAATGATGTAGCTTGGTACCAACAGAAGCCA GGGCAGTCTCCTAAACTGCTGATATATTATGCATCCAATCG TTATACTGGAGTCCCTGATCGCTTCACTGGCAGTGGATATG GGACGGATTTCACTTTCACCATCAGCACTGTGCAGGCTGA AGACCTGGCAGTTTATTTCTGTCAGCAGGATTTTAGCTCTC | 103 |

Figure 34 continued

| | CGCTCACGTTCGGTGCTGGGACCAAGCTGGAACTGAAAC | |
|---|---|---|
| 23A11 L5 in 293 cells | GACATCGTGCTGACCCAGAGCCCCGCCAGCCTGGCCGTG AGCGTGGGCCAGAGAGCCACCATCACCTGCAGAGCCAGC GAGAGCGTGGACATCTACGGCAACAGCTTCATGCATTGGT ATCAACAGAAGCCCGGCCAGGCCCCCAAGCTGCTGATCTA TCGGGCCAGCAACCTGGAGAGCGGCATCCCCGCCAGATT CAGCGGCAGCGGCAGCAGAACCGACTTCACCCTGACCAT CAACCCCGTGGAGGCCAACGACACCGCCACCTACTACTG CCAACAGAGCAACGACGACCCCTACACCTTCGGCGGCGG CACCAAGCTGGAGACCAAG | 104 |
| 23F11 H4 in 293 cells | CAGGTGCAGCTGGTGCAGAGCGGCGCCGAGGTGAAGAA GCCCGGCGCCAGCGTGAAGCTGAGCTGCAAGGCCAGCGG CTACATCTTCACCACCTACTGGATGCACTGGGTGAAGCAG AGACCCGGCCAGGGCCTGGAGTGGATCGGCATGATCCAG CCCAACAGCGGCGGCACCAAGTACAACGAGAAGTTCAAG AAGAAGGCCACCCTGACCGTGGACAAGAGCATCAGCACC GCCTACATGGAGCTGAGCAGACTGACCAGCGACGACACC GCCGTGTACTACTGCGCCAGAGGCGCCGGCACCGTGGAC TACTTCGACTACTGGGGCCAGGGCAGCACCCTGACCGTCT CgagC | 105 |
| 23A11 L4 in 293 cells | GACATCGTGCTGACCCAGAGCCCCGCCAGCCTGGCCGTG AGCGTGGGCCAGAGAGCCACCATCACCTGCAGAGCCAGC GAGAGCGTGGACATCTACGGCAACAGCTTCATGCATTGGT ATCAACAGAAGCCCGGCCAGCCCCCCAAGCTGCTGATCTA TCGGGCCAGCAACCTGGAGAGCGGCATCCCCGCCAGATT CAGCGGCAGCGGCAGCAGAACCGACTTCACCCTGACCAT CAACCCCGTGGAGGCCAACGACACCGCCACCTACTACTG CCAGCAGAGCACCGAAGACCCCTACACCTTCGGCGGCGG CACCAAGCTGGAGATCAAG | 106 |

Figure 34 continued

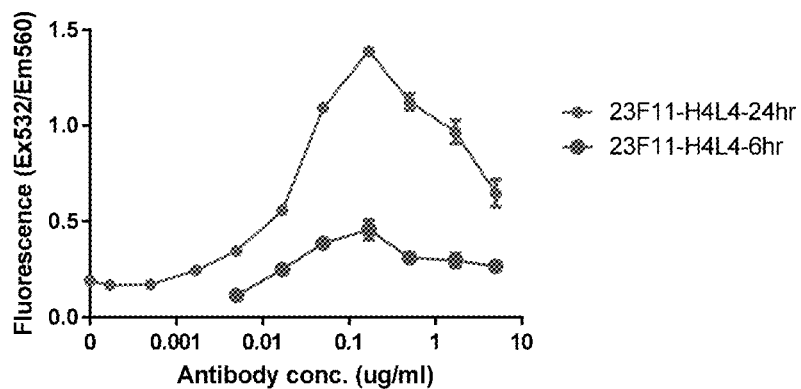

Figure 35

ANTI-PD-L1 ANTIBODIES

CROSS-REFERENCE TO RELATED APPLICATIONS

This application is a continuation of U.S. application Ser. No. 16/086,013, filed Sep. 18, 2018, which is a U.S. National Stage filing under 35 U.S.C. § 371 of International Application No. PCT/CN2017/073242, filed Feb. 10, 2017, which claims the benefit of priority to PCT Application No. PCT/CN2016/077082, filed Mar. 23, 2016, the contents of each of which applications are incorporated herein by reference in their entireties.

FIELD OF THE INVENTION

The present disclosure generally relates to novel anti-PD-L1 antibodies that specifically bind to human PD-L1.

BACKGROUND

PD-1, a member of the CD28 family, is an inhibitory receptor expressed on the surface of T cells which functions to physiologically limit T cell activation and proliferation. Its ligand, PD-L1 (B7-H1/CD274), is expressed on antigen presenting cells and tumor cells. Binding of PD-L1 to its receptor inhibits T cell activation and counterbalances T cell stimulatory signals, such as the binding of B7 to CD28.

PD-L1 is not expressed by normal epithelial tissues, but it is aberrantly expressed on a wide array of human cancers. In this context, PD-L1 may promote cancer progression by disabling the host anti-tumor response. Its expression on tumor cells has been associated with poorer prognosis in renal cell carcinoma, lung cancer, breast cancer, pancreatic cancer, ovarian cancer, urothelial cancer, gastric cancer, esophageal cancer, and hepatocellular carcinoma.

Multiple antibodies targeting PD-1 have been generated and showed efficacious in tumor growth and prolong overall survival in randomized controlled trials. Several PD-L1 targeting antibodies have been discovered and showed activities in inhibiting tumor growth. Because these antibodies are internalized by PD-L1 expressing cells and degraded in endosome and lysosome compartment quickly, these antibodies are quickly eliminated by PD-L1 expressing cells and thus the ability of these antibodies to inhibit tumor growth is limited by the amount of antibodies delivered. Sustained inhibition of tumor growth requires continuous infusion of large amount of antibodies to keep the concentration of antibody in the tumor site high enough to block the activity of PD-L1. Therefore the cost of providing these agents is expected to be very high as it requires injection of large amount of antibodies to the patient. More importantly, the ability to achieve complete response will also be limited. Thus, the generation of antibodies with significantly better efficacy than current anti-PD-L1 antibodies will be needed.

BRIEF SUMMARY OF THE INVENTION

The present disclosure provides novel monoclonal anti-PD-L1 antibodies (in particular chimeric and humanized antibodies), polynucleotides encoding the same, methods of using the same and binding epitopes thereof on the human PD-L1 protein.

In certain embodiments, an isolated PD-L1 antibody is provided herein comprising heavy chain HCDR1, HCDR2 and HCDR3 and light chain LCDR1, LCDR2 and LCDR3 sequences, wherein the HCDR1 sequence is TYWX$_1$H (SEQ ID NO: 1) or a homologue sequence of at least 80% (e.g. at least 85%, 88%, 90%, 91%, 92%, 93%, 94%, 95%, 96%, 97%, 98%, 99%) sequence identity thereof;

the HCDR2 sequence is MIQPNSGGTKYNX$_2$X$_3$FKX$_4$ (SEQ ID NO: 2) or a homologue sequence of at least 80% (e.g. at least 85%, 88%, 90%, 91%, 92%, 93%, 94%, 95%, 96%, 97%, 98%, 99%) sequence identity thereof;

the HCDR3 sequence is GAGTVDYFDY (SEQ ID NO: 3) or a homologue sequence of at least 80% (e.g. at least 85%, 88%, 90%, 91%, 92%, 93%, 94%, 95%, 96%, 97%, 98%, 99%) sequence identity thereof;

the LCDR1 sequence is RASESVDIYGNSFMH (SEQ ID NO: 4) or a homologue sequence of at least 80% (e.g. at least 85%, 88%, 90%, 91%, 92%, 93%, 94%, 95%, 96%, 97%, 98%, 99%) sequence identity thereof;

the LCDR2 sequence is RASNLES (SEQ ID NO: 5) or a homologue sequence of at least 80% (e.g. at least 85%, 88%, 90%, 91%, 92%, 93%, 94%, 95%, 96%, 97%, 98%, 99%) sequence identity thereof;

the LCDR3 sequence is X$_5$QSX$_6$X$_7$DPYT (SEQ ID NO: 6) or a homologue sequence of at least 80% (e.g. at least 85%, 88%, 90%, 91%, 92%, 93%, 94%, 95%, 96%, 97%, 98%, 99%) sequence identity thereof;

wherein X$_1$ is I or M; X$_2$ is D or E; X$_3$ is Q or K; X$_4$ is N or K; X$_5$ is Q or H; X$_6$ is N or T; X$_7$ is D or E.

In certain embodiments, X$_1$ is I or M; X$_2$ is D or E; X$_3$ is Q or K; X$_4$ is N or K; X$_5$ is Q; X$_6$ is N or T; X$_7$ is D or E. In certain embodiments, X$_1$ is I; X$_2$ is D; X$_3$ is Q; X$_4$ is N; X$_5$ is Q; X$_6$ is N, X$_7$ is D. In certain embodiments, X$_1$ is M; X$_2$ is E; X$_3$ is K; X$_4$ is K; X$_5$ is Q; X$_6$ is T; X$_7$ is E. In certain embodiments, X$_1$ is I; X$_2$ is D; X$_3$ is Q; X$_4$ is N; X$_5$ is H; X$_6$ is N; X$_7$ is D. In certain embodiments, X$_1$ is M; X$_2$ is E; X$_3$ is K; X$_4$ is K; X$_5$ is H; X$_6$ is T; X$_7$ is E.

In certain embodiments, the PD-L1 antibody provided herein comprises 1, 2, 3, 4, 5 or 6 CDRs selected from SEQ ID NOs: 7-12, or a homologue of at least 80% (e.g. at least 85%, 88%, 90%, 91%, 92%, 93%, 94%, 95%, 96%, 97%, 98%, 99%) sequence identity thereof. In certain embodiments, the PD-L1 antibody provided herein comprises 3 heavy chain CDRs selected from SEQ ID NOs: 7-9. In certain embodiments, the PD-L1 antibody provided herein comprises 3 light chain CDRs selected from SEQ ID NOs: 10-12. In certain embodiments, the PD-L1 antibody provided herein comprises 6 CDRs selected from SEQ ID NOs: 7-12.

In certain embodiments, the PD-L1 antibody provided herein comprises heavy chain framework sequences of HFR1, HFR2, HFR3 and HFR4 and light chain framework sequences of LFR1, LFR2, LFR3 and LFR4, wherein the sequences of heavy chain variable region is according to the formula: HFR1-HCDR1-HFR2-HCDR2-HFR3-HCDR3-HFR4, and the sequences of light chain variable region is according to the formula LFR1-LCDR1-LFR2-LCDR2-LFR3-LCDR3-LFR4.

In certain embodiments, wherein the HFR1 sequence is Xa$_1$VQLXa$_2$QXa$_3$GAEXa$_4$Xa$_5$KPGASVKXa$_6$SCKASGY Xa$_7$FT (SEQ ID NO: 13);

the HFR2 sequence is WVXa$_8$QXa$_9$PGQGLEWIG (SEQ ID NO: 14);

the HFR3 sequence is Xa$_{10}$Xa$_{11}$TLTVDXa$_{12}$SXa$_{13}$Xa$_{14}$TAXa$_{15}$MXa$_{16}$LSXa$_{17}$LX a$_{18}$SXa$_{19}$DXa$_{20}$AVYYCAR(SEQ ID NO: 15);

the HFR4 sequence is WGQGXa$_{21}$TLXa$_{22}$Xa$_{23}$SS (SEQ ID NO: 16);

the LFR1 sequence is DIVLTXa$_{24}$SPXa$_{25}$SLXa$_{26}$VSXa$_{27}$GQRATIXa$_{28}$C (SEQ ID NO: 17);

the LFR2 sequence is WYQQKPGQXa$_{29}$PKLLIY (SEQ ID NO: 18);

the LFR3 sequence is GIPARFSGSGSRTDFTLTINPVEAXa$_{30}$DXa$_{31}$ATYYC (SEQ ID NO: 19);

the LFR4 sequence is FGGGTKLEXa$_{32}$K (SEQ ID NO: 20);

wherein Xa$_1$ is Q or L; Xa$_2$ is Q or V; Xa$_3$ is S or P; Xa$_4$ is L or V; Xa$_5$ is V or K; Xa$_6$ is L or V; Xa$_7$ is T, S or I; Xa$_8$ is W, K or R; Xa$_9$ is R or A; Xa$_{10}$ is R or K; Xa$_{11}$ is V or A; Xa$_{12}$ is K or T; Xa$_{13}$ is S or I; Xa$_{14}$ is S or T; Xa$_{15}$ is Y or S; Xa$_{16}$ is Q or E; Xa$_{17}$ is S, G or R; Xa$_{18}$ is T or R; Xa$_{19}$ is E or D; Xa$_{20}$ is S or T; Xa$_{21}$ is T or S; Xa$_{22}$ is S or T; Xa$_{23}$ is V or I; Xa$_{24}$ is Q or H; Xa$_{25}$ is A or V; Xa$_{26}$ is A or T; Xa$_{27}$ is L, A or V; Xa$_{28}$ is S or T; Xa$_{29}$ is S, P or A; Xa$_{30}$ is D, N or Q; Xa$_{31}$ is V or T; Xa$_{32}$ is L, T or I; Xa$_{33}$ is F or Y; Xa$_{34}$ is T or Q; Xa$_{35}$ is V or L; Xa$_{36}$ is D or S; Xa$_{37}$ is M or L; Xa$_{38}$ is T or S; Xa$_{39}$ is F or S; Xa$_{40}$ is D or Q; Xa$_{41}$ is V or A; Xa$_{42}$ is V or I; Xa$_{43}$ is D or A; Xa$_{44}$ is T or S; Xa$_{45}$ is Y or S; Xa$_{46}$ is G or R; Xa$_{47}$ is F or L; Xa$_{48}$ is S or N; Xa$_{49}$ is T or P; Xa$_{50}$ is Q or E; Xa$_{51}$ is V or T; Xa$_{52}$ is F or Y; Xa$_{53}$ is A or G.

In certain embodiments, Xa$_1$ is Q; Xa$_2$ is V; Xa$_3$ is S; Xa$_4$ is V; Xa$_5$ is K; Xa$_6$ is L; Xa$_7$ is I; Xa$_8$ is K; Xa$_9$ is R; Xa$_{10}$ is R or K; Xa$_{11}$ is A; Xa$_{12}$ is K; Xa$_{13}$ is I; Xa$_{14}$ is S; Xa$_{15}$ is Y; Xa$_{16}$ is E; Xa$_{17}$ is R; Xa$_{18}$ is T; Xa$_{19}$ is D; Xa$_{20}$ is T; Xa$_{21}$ is T or S; Xa$_{22}$ is T or S; Xa$_{23}$ is I or V; Xa$_{24}$ is Q; Xa$_{25}$ is A; Xa$_{26}$ is A; Xa$_{27}$ is V; Xa$_{28}$ is T; Xa$_{29}$ is A or P; Xa$_{30}$ is Q; Xa$_{31}$ is T; Xa$_{32}$ is T or I; Xa$_{33}$ is Y; Xa$_{34}$ is Q; Xa$_{35}$ is L; Xa$_{36}$ is D; Xa$_{37}$ is L; Xa$_{38}$ is S; Xa$_{39}$ is S; Xa$_{40}$ is Q; Xa$_{41}$ is A; Xa$_{42}$ is I; Xa$_{43}$ is A; Xa$_{44}$ is S; Xa$_{45}$ is S; Xa$_{46}$ is R; Xa$_{47}$ is L; Xa$_{48}$ is N; Xa$_{49}$ is P; Xa$_{50}$ is E; Xa$_{51}$ is T; Xa$_{52}$ is Y; Xa$_{53}$ is G.

In certain embodiments, Xa$_1$ is Q; Xa$_2$ is V; Xa$_3$ is S; Xa$_4$ is V; Xa$_5$ is K; Xa$_6$ is L; Xa$_7$ is I; Xa$_8$ is K; Xa$_9$ is R; Xa$_{10}$ is R; Xa$_{11}$ is A; Xa$_{12}$ is K; Xa$_{13}$ is I; Xa$_{14}$ is S; Xa$_{15}$ is Y; Xa$_{16}$ is E; Xa$_{17}$ is R; Xa$_{18}$ is T; Xa$_{19}$ is D; Xa$_{20}$ is T; Xa$_{21}$ is T; Xa$_{22}$ is S; Xa$_{23}$ is I; Xa$_{24}$ is Q; Xa$_{25}$ is A; Xa$_{26}$ is A; Xa$_{27}$ is V; Xa$_{28}$ is T; Xa$_{29}$ is A; Xa$_{30}$ is Q; Xa$_{31}$ is T; Xa$_{32}$ is T; Xa$_{33}$ is Y; Xa$_{34}$ is Q; Xa$_{35}$ is L; Xa$_{36}$ is D; Xa$_{37}$ is L; Xa$_{38}$ is S; Xa$_{39}$ is S; Xa$_{40}$ is Q; Xa$_{41}$ is A; Xa$_{42}$ is I; Xa$_{43}$ is A; Xa$_{44}$ is S; Xa$_{45}$ is S; Xa$_{46}$ is R; Xa$_{47}$ is L; Xa$_{48}$ is N; Xa$_{49}$ is P; Xa$_{50}$ is E; Xa$_{51}$ is T; Xa$_{52}$ is Y; Xa$_{53}$ is G.

In certain embodiments, Xa$_1$ is Q; Xa$_2$ is V; Xa$_3$ is S; Xa$_4$ is V; Xa$_5$ is K; Xa$_6$ is L; Xa$_7$ is I; Xa$_8$ is K; Xa$_9$ is R; Xa$_{10}$ is K; Xa$_{11}$ is A; Xa$_{12}$ is K; Xa$_{13}$ is I; Xa$_{14}$ is S; Xa$_{15}$ is Y; Xa$_{16}$ is E; Xa$_{17}$ is R; Xa$_{18}$ is T; Xa$_{19}$ is D; Xa$_{20}$ is T; Xa$_{21}$ is S; Xa$_{22}$ is T; Xa$_{23}$ is V; Xa$_{24}$ is Q; Xa$_{25}$ is A; Xa$_{26}$ is A; Xa$_{27}$ is V; Xa$_{28}$ is T; Xa$_{29}$ is P; Xa$_{30}$ is Q; Xa$_{31}$ is T; Xa$_{32}$ is I; Xa$_{33}$ is Y; Xa$_{34}$ is Q; Xa$_{35}$ is L; Xa$_{36}$ is D; Xa$_{37}$ is L; Xa$_{38}$ is S; Xa$_{39}$ is S; Xa$_{40}$ is Q; Xa$_{41}$ is A; Xa$_{42}$ is I; Xa$_{43}$ is A; Xa$_{44}$ is S; Xa$_{45}$ is S; Xa$_{46}$ is R; Xa$_{47}$ is L; Xa$_{48}$ is N; Xa$_{49}$ is P; Xa$_{50}$ is E; Xa$_{51}$ is T; Xa$_{52}$ is Y; Xa$_{53}$ is G.

In certain embodiments, Xa$_1$ is L or Q; Xa$_2$ is V; Xa$_3$ is S; Xa$_4$ is V; Xa$_5$ is K; Xa$_6$ is L; Xa$_7$ is I; Xa$_8$ is K; Xa$_9$ is R; Xa$_{10}$ is R; Xa$_{11}$ is A; Xa$_{12}$ is K; Xa$_{13}$ is I; Xa$_{14}$ is S; Xa$_{15}$ is Y; Xa$_{16}$ is E; Xa$_{17}$ is R; Xa$_{18}$ is T; Xa$_{19}$ is D; Xa$_{20}$ is T; Xa$_{21}$ is T; Xa$_{22}$ is S; Xa$_{23}$ is I; Xa$_{24}$ is Q; Xa$_{25}$ is A; Xa$_{26}$ is A; Xa$_{27}$ is V; Xa$_{28}$ is T; Xa$_{29}$ is S; Xa$_{30}$ is N; Xa$_{31}$ is T; Xa$_{32}$ is T; Xa$_{33}$ is Y; Xa$_{34}$ is Q; Xa$_{35}$ is L; Xa$_{36}$ is D; Xa$_{37}$ is L; Xa$_{38}$ is S; Xa$_{39}$ is S; Xa$_{40}$ is Q; Xa$_{41}$ is A; Xa$_{42}$ is I; Xa$_{43}$ is A; Xa$_{44}$ is S; Xa$_{45}$ is S; Xa$_{46}$ is R; Xa$_{47}$ is L; Xa$_{48}$ is N; Xa$_{49}$ is P; Xa$_{50}$ is E; Xa$_{51}$ is T; Xa$_{52}$ is Y; Xa$_{53}$ is G.

In certain embodiments, Xa$_1$ is L; Xa$_2$ is V; Xa$_3$ is S; Xa$_4$ is V; Xa$_5$ is K; Xa$_6$ is V; Xa$_7$ is I; Xa$_8$ is R; Xa$_9$ is A; Xa$_{10}$ is R; Xa$_{11}$ is V; Xa$_{12}$ is T; Xa$_{13}$ is I; Xa$_{14}$ is S; Xa$_{15}$ is Y; Xa$_{16}$ is E; Xa$_{17}$ is R; Xa$_{18}$ is R; Xa$_{19}$ is D; Xa$_{20}$ is T; Xa$_{21}$ is T; Xa$_{22}$ is S; Xa$_{23}$ is I; Xa$_{24}$ is Q; Xa$_{25}$ is A; Xa$_{26}$ is A; Xa$_{27}$ is V; Xa$_{28}$ is T; Xa$_{29}$ is S; Xa$_{30}$ is N; Xa$_{31}$ is T; Xa$_{32}$ is T; Xa$_{33}$ is Y; Xa$_{34}$ is Q; Xa$_{35}$ is L; Xa$_{36}$ is D; Xa$_{37}$ is L; Xa$_{38}$ is S; Xa$_{39}$ is S; Xa$_{40}$ is Q; Xa$_{41}$ is A; Xa$_{42}$ is I; Xa$_{43}$ is A; Xa$_{44}$ is S; Xa$_{45}$ is S; Xa$_{46}$ is R; Xa$_{47}$ is L; Xa$_{48}$ is N; Xa$_{49}$ is P; Xa$_{50}$ is E; Xa$_{51}$ is T; Xa$_{52}$ is Y; Xa$_{53}$ is G.

In certain embodiments, Xa$_1$ is L; Xa$_2$ is V; Xa$_3$ is S; Xa$_4$ is V; Xa$_5$ is K; Xa$_6$ is V; Xa$_7$ is I; Xa$_8$ is R; Xa$_9$ is A; Xa$_{10}$ is R; Xa$_{11}$ is V; Xa$_{12}$ is T; Xa$_{13}$ is I; Xa$_{14}$ is S; Xa$_{15}$ is Y; Xa$_{16}$ is E; Xa$_{17}$ is R; Xa$_{18}$ is R; Xa$_{19}$ is D; Xa$_{20}$ is T; Xa$_{21}$ is T; Xa$_{22}$ is S; Xa$_{23}$ is I; Xa$_{24}$ is Q; Xa$_{25}$ is A; Xa$_{26}$ is A; Xa$_{27}$ is V; Xa$_{28}$ is T; Xa$_{29}$ is A; Xa$_{30}$ is Q or N; Xa$_{31}$ is T; Xa$_{32}$ is T; Xa$_{33}$ is Y; Xa$_{34}$ is Q; Xa$_{35}$ is L; Xa$_{36}$ is D; Xa$_{37}$ is L; Xa$_{38}$ is S; Xa$_{39}$ is S; Xa$_{40}$ is Q; Xa$_{41}$ is A; Xa$_{42}$ is I; Xa$_{43}$ is A; Xa$_{44}$ is S; Xa$_{45}$ is S; Xa$_{46}$ is R; Xa$_{47}$ is L; Xa$_{48}$ is N; Xa$_{49}$ is P; Xa$_{50}$ is E; Xa$_{51}$ is T; Xa$_{52}$ is Y; Xa$_{53}$ is G.

In certain embodiments, Xa$_1$ is Q; Xa$_2$ is V; Xa$_3$ is S; Xa$_4$ is V; Xa$_5$ is K; Xa$_6$ is V; Xa$_7$ is I; Xa$_8$ is R; Xa$_9$ is A; Xa$_{10}$ is K; Xa$_{11}$ is A; Xa$_{12}$ is T; Xa$_{13}$ is I; Xa$_{14}$ is S; Xa$_{15}$ is Y; Xa$_{16}$ is E; Xa$_{17}$ is R; Xa$_{18}$ is R; Xa$_{19}$ is D; Xa$_{20}$ is T; Xa$_{21}$ is S; Xa$_{22}$ is T; Xa$_{23}$ is V; Xa$_{24}$ is Q; Xa$_{25}$ is A; Xa$_{26}$ is A; Xa$_{27}$ is V; Xa$_{28}$ is T; Xa$_{29}$ is P; Xa$_{30}$ is N; Xa$_{31}$ is T; Xa$_{32}$ is I; Xa$_{33}$ is Y; Xa$_{34}$ is Q; Xa$_{35}$ is L; Xa$_{36}$ is D; Xa$_{37}$ is L; Xa$_{38}$ is S; Xa$_{39}$ is S; Xa$_{40}$ is Q; Xa$_{41}$ is A; Xa$_{42}$ is I; Xa$_{43}$ is A; Xa$_{44}$ is S; Xa$_{45}$ is S; Xa$_{46}$ is R; Xa$_{47}$ is L; Xa$_{48}$ is N; Xa$_{49}$ is P; Xa$_{50}$ is E; Xa$_{51}$ is T; Xa$_{52}$ is Y; Xa$_{53}$ is G.

In certain embodiments, Xa$_1$ is Q; Xa$_2$ is V; Xa$_3$ is S; Xa$_4$ is V; Xa$_5$ is K; Xa$_6$ is V; Xa$_7$ is I; Xa$_8$ is R; Xa$_9$ is A; Xa$_{10}$ is K; Xa$_{11}$ is A; Xa$_{12}$ is T; Xa$_{13}$ is I; Xa$_{14}$ is S; Xa$_{15}$ is Y; Xa$_{16}$ is E; Xa$_{17}$ is R; Xa$_{18}$ is R; Xa$_{19}$ is D; Xa$_{20}$ is T; Xa$_{21}$ is S; Xa$_{22}$ is T; Xa$_{23}$ is V; Xa$_{24}$ is Q; Xa$_{25}$ is A; Xa$_{26}$ is A; Xa$_{27}$ is V; Xa$_{28}$ is T; Xa$_{29}$ is P; Xa$_{30}$ is N or Q; Xa$_{31}$ is T; Xa$_{32}$ is I; Xa$_{33}$ is Y; Xa$_{34}$ is Q; Xa$_{35}$ is L; Xa$_{36}$ is D; Xa$_{37}$ is L; Xa$_{38}$ is S; Xa$_{39}$ is S; Xa$_{40}$ is Q; Xa$_{41}$ is A; Xa$_{42}$ is I; Xa$_{43}$ is A; Xa$_{44}$ is S; Xa$_{45}$ is S; Xa$_{46}$ is R; Xa$_{47}$ is L; Xa$_{48}$ is N; Xa$_{49}$ is P; Xa$_{50}$ is E; Xa$_{51}$ is T; Xa$_{52}$ is Y; Xa$_{53}$ is G.

In certain embodiments, Xa$_1$ is Q; Xa$_2$ is V; Xa$_3$ is S; Xa$_4$ is V; Xa$_5$ is K; Xa$_6$ is L; Xa$_7$ is I; Xa$_8$ is K; Xa$_9$ is R; Xa$_{10}$ is K; Xa$_{11}$ is A; Xa$_{12}$ is K; Xa$_{13}$ is I; Xa$_{14}$ is S; Xa$_{15}$ is Y; Xa$_{16}$ is E; Xa$_{17}$ is R; Xa$_{18}$ is T; Xa$_{19}$ is D; Xa$_{20}$ is T; Xa$_{21}$ is S; Xa$_{22}$ is T; Xa$_{23}$ is V; Xa$_{24}$ is Q; Xa$_{25}$ is A; Xa$_{26}$ is A; Xa$_{27}$ is V; Xa$_{28}$ is T; Xa$_{29}$ is P; Xa$_{30}$ is N; Xa$_{31}$ is T; Xa$_{32}$ is I; Xa$_{33}$ is Y; Xa$_{34}$ is Q; Xa$_{35}$ is L; Xa$_{36}$ is D; Xa$_{37}$ is L; Xa$_{38}$ is S; Xa$_{39}$ is S; Xa$_{40}$ is Q; Xa$_{41}$ is A; Xa$_{42}$ is I; Xa$_{43}$ is A; Xa$_{44}$ is S; Xa$_{45}$ is S; Xa$_{46}$ is R; Xa$_{47}$ is L; Xa$_{48}$ is N; Xa$_{49}$ is P; Xa$_{50}$ is E; Xa$_{51}$ is T; Xa$_{52}$ is Y; Xa$_{53}$ is G.

In certain embodiments, the PD-L1 antibody comprises a heavy chain variable region as set forth in SEQ ID NO: 61 and a light chain variable region as set forth in SEQ ID NO: 62. In certain embodiments, the PD-L1 antibody comprises a heavy chain variable region as set forth in SEQ ID NO: 71 and a light chain variable region as set forth in SEQ ID NO: 72. In certain embodiments, the PD-L1 antibody comprises a heavy chain variable region as set forth in SEQ ID NO: 71 and a light chain variable region as set forth in SEQ ID NO: 70. In certain embodiments, the PD-L1 antibody comprises a heavy chain variable region as set forth in SEQ ID NO: 69 and a light chain variable region as set forth in SEQ ID NO: 72. In certain embodiments, the PD-L1 antibody comprises a heavy chain variable region as set forth in SEQ ID NO: 69 and a light chain variable region as set forth in SEQ ID NO: 70. In certain embodiments, the PD-L1 antibody comprises a heavy chain variable region as set forth in SEQ ID NO: 73 and a light chain variable region as set forth in SEQ ID NO: 74.

In certain embodiments, the PD-L1 antibody comprises a heavy chain variable region as set forth in SEQ ID NO: 63 and a light chain variable region as set forth in SEQ ID NO: 64. In certain embodiments, the PD-L1 antibody comprises a heavy chain variable region as set forth in SEQ ID NO: 75 and a light chain variable region as set forth in SEQ ID NO: 76. In certain embodiments, the PD-L1 antibody comprises a heavy chain variable region as set forth in SEQ ID NO: 77 and a light chain variable region as set forth in SEQ ID NO: 78. In certain embodiments, the PD-L1 antibody comprises a heavy chain variable region as set forth in SEQ ID NO: 75 and a light chain variable region as set forth in SEQ ID NO: 78. In certain embodiments, the PD-L1 antibody comprises a heavy chain variable region as set forth in SEQ ID NO: 77 and a light chain variable region as set forth in SEQ ID NO: 76. In certain embodiments, the PD-L1 antibody comprises a heavy chain variable region as set forth in SEQ ID NO: 79 and a light chain variable region as set forth in SEQ ID NO: 80.

The present disclosure also provides PD-L1 antibodies that comprise 1, 2, 3, 4, 5 or 6 CDRs selected from SEQ ID NOs: 7-12. In certain embodiments, the antibodies comprise 3 heavy chain CDRs selected from SEQ ID NOs: 7-9. In certain embodiments, the antibodies comprise 3 light chain CDRs selected from SEQ ID NOs: 10-12. In certain embodiments, the antibodies comprise a heavy chain variable region as set forth in SEQ ID NO: 21, or a humanized version thereof. In certain embodiments, the antibodies comprise a light chain variable region as set forth in SEQ ID NO: 22, or a humanized version thereof. In certain embodiments, the antibodies comprise a heavy chain variable region as set forth in SEQ ID NO: 21 and a light chain variable region as set forth in SEQ ID NO: 22, or a humanized version thereof.

An isolated PD-L1 antibody, having a binding to PD-L1 at acidic pH measured by an assay testing and a binding to PD-L1 at neutral pH measured by the assay testing, wherein the binding to PD-L1 at acidic pH is substantially lower than the binding to PD-L1 at neutral pH. In certain embodiments, the binding of the PD-L1 antibody to PD-L1 at the acidic pH is no more than 80%, 70%, 60%, 50%, 40%, 30%, 20%, 10% or 5% of the binding to PD-L1 at the neutral pH at the same assay setting. In certain embodiments, the neutral pH is 7.4, and the acidic pH is 6.0, 5.5, 5.0, 4.5 or 4.0. In certain embodiments, the binding of the PD-L1 antibody provided herein to PD-L1 at acidic pH6.0, pH5.5 or pH5.0 is substantially lower than its binding to PD-L1 at pH7.4 at the same assay setting.

In certain embodiments, the assay setting is measured by binding or blocking activity via ELISA, FACS, surface plasmon resonance, GST pull down, epitope-tag, immunoprecipitation, Far-Western, fluorescence resonance energy transfer, time resolved fluorescence immunoassays (TR-FIA), radioimmunoassays (RIA), enzyme immunoassays, latex agglutination, Western blot, and immunohistochemistry and any of the combination thereof in vitro.

In certain embodiments, the disclosure also provides an isolated PD-L1 antibody that binds to the same epitope as or has competitive binding to the PD-L1 antibody. In certain embodiments, the epitope comprises at least one (e.g. at least two, three, four or five) of the following amino acid residues of PD-L1 E58, K62, N63, I64, S80 and Y81. In certain embodiments, the epitope further comprises at least one (e.g. at least two or three) of the following amino acid residues of PD-L: R113, M115, Y123, K124 and R125. In certain embodiments, the epitope comprises one of the following combinations of amino acid residues of PD-L: 1) E58, R113, M115, Y123 and K124; 2) E58, S80, R113 and R125. In certain embodiments, the epitope further comprises at least one (e.g. at least two or three) of the following amino acid residues of PD-L1: K62, N63, I64, Y81 and D122. In certain embodiments, the epitope comprises one of the following combinations of amino acid residues of PD-L: 1) E58, N63, I64, S80, Y81, R113 and R125; 2) E58, S80, R113, M115, D122, Y123, K124 and R125; 3) E58, K62, N63, S80, Y81, R113 and R125; 4) E58, N63, I64, S80, Y81, R113, K124 and R125.

A method of treating a PD-L1 associated condition in a subject in need thereof, comprising administering to the subject an isolated PD-L1 antibody whose binding to PD-L1 at acidic pH is substantially lower than its binding to PD-L1 at neutral pH at the same assay setting, thereby treating the condition is provided herein.

In certain embodiments, the antibody is administered at a dosage which is no more than 80%, 70%, 60%, 50%, 45%, 40%, 35%, 30%, 25%, 20%, 15% or 10% of a reference dosage, wherein the reference dosage is determined by a reference antibody to achieve a comparable in vivo therapeutic effect, wherein the reference antibody displays a similar binding to PD-L1 at both the acidic pH and the neutral pH, and wherein the reference antibody and the antibody have similar binding to PD-L1 at the neutral pH.

In certain embodiments, the antibody is administered at a dosing frequency less than that of a reference dosing frequency, wherein the reference dosing frequency is determined by a reference antibody to achieve a comparable in vivo therapeutic effect, wherein the reference antibody displays a similar binding to PD-L1 at both the acidic pH and the neutral pH, and wherein the reference antibody and the antibody have similar binding to PD-L1 at the neutral pH.

In certain embodiments, the antibody has an in vivo half life in a target organ longer than a reference in vivo half life, wherein the reference in vivo half life is determined by a reference antibody, wherein the reference antibody displays a similar binding to PD-L1 at both the acidic pH and the neutral pH, and wherein the reference antibody and the antibody have similar binding to PD-L1 at the neutral pH. In certain embodiments, the target organ comprises one or more of serum, kidney, lung, pancreas, liver, gallbladder, bladder, skin, esophagus, ovarian, breast, colon, rectum, stomach, spleen, or brain.

The present disclosure further provides herein an isolated PD-L1 antibody, comprising heavy chain HCDR1', HCDR2' and HCDR3' and light chain LCDR1', LCDR2' and LCDR3' sequences, wherein the HCDR1' sequence is selected from the group consisting of DYYMN (SEQ ID NO: 23), SEQ ID NO: 29, 35, 41, and a homologue sequence of at least 80% (e.g. at least 85%, 88%, 90%, 91%, 92%, 93%, 94%, 95%, 96%, 97%, 98%, 99%) sequence identity thereof;

the HCDR2' sequence is selected from the group consisting of DINPNNGGTSYNX'$_1$KFX'$_2$G (SEQ ID NO: 24), SEQ ID NO: 30, 36, 42, or a homologue sequence of at least 80% (e.g. at least 85%, 88%, 90%, 91%, 92%, 93%, 94%, 95%, 96%, 97%, 98%, 99%) sequence identity thereof;

the HCDR3' sequence is selected from the group consisting of VKWGDGPFAY (SEQ ID NO: 25), SEQ ID NO: 31, 37, 43, and a homologue sequence of at least 80% (e.g. at least 85%, 88%, 90%, 91%, 92%, 93%, 94%, 95%, 96%, 97%, 98%, 99%) sequence identity thereof;

the LCDR1' sequence is selected from the group consisting of X'$_3$ASQNVGAAVA (SEQ ID NO: 26), SEQ ID NO: 32, 38, 44, and a homologue sequence of at least 80% (e.g. at least 85%, 88%, 90%, 91%, 92%, 93%, 94%, 95%, 96%, 97%, 98%, 99%) sequence identity thereof;

the LCDR2' sequence is selected from the group consisting of SASNX'$_4$X'$_5$T (SEQ ID NO: 27), SEQ ID NO: 33, 39, 45, and a homologue sequence of at least 80% (e.g. at least 85%, 88%, 90%, 91%, 92%, 93%, 94%, 95%, 96%, 97%, 98%, 99%) sequence identity thereof;

the LCDR3' sequence is selected from the group consisting of QQYSNYPT (SEQ ID NO: 28), SEQ ID NO: 34, 40, 46, and a homologue sequence of at least 80% (e.g. at least 85%, 88%, 90%, 91%, 92%, 93%, 94%, 95%, 96%, 97%, 98%, 99%) sequence identity thereof;

wherein X'$_1$ is H or Q; X'$_2$ is K or Q; X'$_3$ is K or Q; X'$_4$ is R or L; X'$_5$ is Y or E.

In certain embodiments, X'$_1$ is Q; X'$_2$ is Q; X'$_3$ is Q; X'$_4$ is R; X'$_5$ is Y.

In certain embodiments, the PD-L1 antibody provided herein comprises heavy chain framework of HFR1', HFR2', HFR3' and HFR4' and light chain framework sequences of LFR1', LFR2', LFR3' and LFR4', wherein the sequences of heavy chain variable region is according to the formula: HFR1'-HCDR1'-HFR2'-HCDR1'-HFR3'-HCDR1'-HFR4', and the sequences of light chain variable region is according to the formula LFR1'-LCDR1'-LFR2'-LCDR1'-LFR3'-LCDR1'-LFR4'.

In certain embodiments, the HFR1' sequence is X'a$_1$VQLX'a$_2$QSGX'a$_3$EX'a$_4$X'a$_5$KPGASVKX'a$_6$SCKASGYVFT (SEQ ID NO: 47);

the HFR2' sequence is WVX'a$_7$QX'a$_8$X'a$_9$GX'a$_{10}$X'a$_{11}$LEWIG (SEQ ID NO: 48);

the HFR3' sequence is X'a$_{12}$X'a$_{13}$TVTVDX'a$_{14}$SX'a$_{15}$X'a$_{16}$TAYMELX'a$_{17}$X'a$_{18}$LX'a$_{19}$SX'a$_{20}$DX'a$_{21}$AVYY C (SEQ ID NO: 49);

the HFR4' sequence is WGQGTLVTVSX'a$_{22}$ (SEQ ID NO: 50);

the LFR1' sequence is DIX'a$_{23}$MTQSX'a$_{24}$X'a$_{25}$X'a$_{26}$X'a$_{27}$SX'a$_{28}$SVGDRVX'a$_{29}$ITC (SEQ ID NO: 51);

the LFR2' sequence is WYQQKPGX'a$_{30}$X'a$_{31}$PKLLIY (SEQ ID NO: 52);

the LFR3' sequence is GVPX'a$_{32}$RFX'a$_{33}$GSGSGTDFTLTISX'a$_{34}$X'a$_{35}$QX'a$_{36}$EDX'a$_{37}$AX'a$_{38}$YFC (SEQ ID NO: 53);

the LFR4' sequence is FGSGTKLGIK (SEQ ID NO: 54);

wherein X'a$_1$ is Q or E; X'a$_2$ is Q or V; X'a$_3$ is A or P; X'a$_4$ is L or V; X'a$_5$ is V or K; X'a$_6$ is I or V; X'a$_7$ is K or R; X'a$_8$ is S or A; X'a$_9$ is H or P; X'a$_{10}$ is Q or K; X'a$_{11}$ is S or G; X'a$_{12}$ is K or R; X'a$_{13}$ is A or V; X'a$_{14}$ is K or T; X'a$_{15}$ is S, T or I; X'a$_{16}$ is S or R; X'a$_{17}$ is L or S; X'a$_{118}$ is S or R; X'a$_{19}$ is R or T; X'a$_{20}$ is E or D; X'a$_{21}$ is S or T; X'a$_{22}$ is A or S; X'a$_{23}$ is Q or V; X'a$_{24}$ is Q or P; X'a$_{25}$ is K or S; X'a$_{26}$ is F or S; X'a$_{27}$ is M or L; X'a$_{28}$ is T or A; X'a$_{29}$ is S or T; X'a$_{30}$ is Q or K; X'a$_{31}$ is S or A; X'a$_{32}$ is S or D; X'a$_{33}$ is S or T; X'a$_{34}$ is S or N; X'a$_{35}$ is M or L; X'a$_{36}$ is S or P; X'a$_{37}$ is L or I; X'a$_{38}$ is D or T.

In certain embodiments, X'a$_1$ is Q; X'a$_2$ is V; X'a$_3$ is A; X'a$_4$ is V; X'a$_5$ is V; X'a$_6$ is I; X'a$_7$ is K; X'a$_8$ is A; X'a$_9$ is P; X'a$_{10}$ is Q; X'a$_{11}$ is G; X'a$_{12}$ is R; X'a$_{13}$ is A; X'a$_{14}$ is K; X'a$_{15}$ is T; X'a$_{16}$ is R; X'a$_{17}$ is S; X'a$_{18}$ is R; X'a$_{19}$ is R; X'a$_{20}$ is D; X'a$_{21}$ is T; X'a$_{22}$ is S; X'a$_{23}$ is Q; X'a$_{24}$ is Q; X'a$_{25}$ is S; X'a$_{26}$ is S; X'a$_{27}$ is L; X'a$_{28}$ is A; X'a$_{29}$ is T; X'a$_{30}$ is K; X'a$_{31}$ is A; X'a$_{32}$ is S; X'a$_{33}$ is S; X'a$_{34}$ is S; X'a$_{35}$ is M; X'a$_{36}$ is P; X'a$_{37}$ is I; X'a$_{38}$ is T.

In certain embodiments, X'a$_1$ is Q; X'a$_2$ is V; X'a$_3$ is A; X'a$_4$ is V; X'a$_5$ is K; X'a$_6$ is V; X'a$_7$ is R; X'a$_8$ is A; X'a$_9$ is P; X'a$_{10}$ is Q; X'a$_{11}$ is G; X'a$_{12}$ is R; X'a$_{13}$ is V; X'a$_{14}$ is T; X'a$_{15}$ is I; X'a$_{16}$ is R; X'a$_{17}$ is S; X'a$_{18}$ is R; X'a$_{19}$ is R; X'a$_{20}$ is D; X'a$_{21}$ is T; X'a$_{22}$ is S; X'a$_{23}$ is Q; X'a$_{24}$ is Q; X'a$_{25}$ is S; X'a$_{26}$ is S; X'a$_{27}$ is L; X'a$_{28}$ is A; X'a$_{29}$ is T; X'a$_{30}$ is K; X'a$_{31}$ is A; X'a$_{32}$ is S; X'a$_{33}$ is S; X'a$_{34}$ is S; X'a$_{35}$ is M; X'a$_{36}$ is P; X'a$_{37}$ is I; X'a$_{38}$ is T.

In certain embodiments, X'a$_1$ is Q; X'a$_2$ is V; X'a$_3$ is A; X'a$_4$ is V; X'a$_5$ is V; X'a$_6$ is I; X'a$_7$ is K; X'a$_8$ is A; X'a$_9$ is P; X'a$_{10}$ is Q; X'a$_{11}$ is G; X'a$_{12}$ is R; X'a$_{13}$ is A; X'a$_{14}$ is K; X'a$_{15}$ is T; X'a$_{16}$ is R; X'a$_{17}$ is S; X'a$_{18}$ is R; X'a$_{19}$ is R; X'a$_{20}$ is D; X'a$_{21}$ is T; X'a$_{22}$ is S; X'a$_{23}$ is Q; X'a$_{24}$ is P; X'a$_{25}$ is S; X'a$_{26}$ is S; X'a$_{27}$ is L; X'a$_{28}$ is A; X'a$_{29}$ is T; X'a$_{30}$ is K; X'a$_{31}$ is A; X'a$_{32}$ is S; X'a$_{33}$ is S; X'a$_{34}$ is S; X'a$_{35}$ is L; X'a$_{36}$ is P; X'a$_{37}$ is I; X'a$_{38}$ is T.

In certain embodiments, X'a$_1$ is Q; X'a$_2$ is V; X'a$_3$ is A; X'a$_4$ is V; X'a$_5$ is K; X'a$_6$ is V; X'a$_7$ is R; X'a$_8$ is A; X'a$_9$ is P; X'a$_{10}$ is Q; X'a$_{11}$ is G; X'a$_{12}$ is R; X'a$_{13}$ is V; X'a$_{14}$ is T; X'a$_{15}$ is I; X'a$_{16}$ is R; X'a$_{17}$ is S; X'a$_{18}$ is R; X'a$_{19}$ is R; X'a$_{20}$ is D; X'a$_{21}$ is T; X'a$_{22}$ is S; X'a$_{23}$ is Q; X'a$_{24}$ is P; X'a$_{25}$ is S; X'a$_{26}$ is S; X'a$_{27}$ is L; X'a$_{28}$ is A; X'a$_{29}$ is T; X'a$_{30}$ is K; X'a$_{31}$ is A; X'a$_{32}$ is A; X'a$_{33}$ is S; X'a$_{34}$ is S; X'a$_{35}$ is L; X'a$_{36}$ is P; X'a$_{37}$ is I; X'a$_{38}$ is T.

In certain embodiments, the PD-L1 antibody provided herein comprises a heavy chain variable region as set forth in SEQ ID NO: 65 and a light chain variable region as set forth in SEQ ID NO: 66. In certain embodiments, the PD-L1 antibody provided herein comprises a heavy chain variable region as set forth in SEQ ID NO: 67 and a light chain variable region as set forth in SEQ ID NO: 68. In certain embodiments, the PD-L1 antibody provided herein comprises a heavy chain variable region as set forth in SEQ ID NO: 65 and a light chain variable region as set forth in SEQ ID NO: 68. In certain embodiments, the PD-L1 antibody provided herein comprises a heavy chain variable region as set forth in SEQ ID NO: 67 and a light chain variable region as set forth in SEQ ID NO: 66. In certain embodiments, the PD-L1 antibody provided herein comprises a heavy chain variable region as set forth in SEQ ID NO: 85 and a light chain variable region as set forth in SEQ ID NO: 86.

The present disclosure further provided herein another isolated PD-L1 antibody that comprises at least 1, 2, 3, 4, 5 or 6 CDRs selected from SEQ ID NOs: 29-46. In certain embodiments, the isolated PD-L1 antibody that comprises 1) the heavy chain HCDR1' is SEQ ID NO: 29, HCDR2' is SEQ ID NO: 30 and HCDR3' is SEQ ID NO: 31; 2) the heavy chain HCDR1' is SEQ ID NO: 35, HCDR2' is SEQ ID NO: 36 and HCDR3' is SEQ ID NO: 37; or 3) the heavy chain HCDR1' is SEQ ID NO: 41, HCDR2' is SEQ ID NO: 42 and HCDR3' is SEQ ID NO: 43. In certain embodiments, the PD-L1 antibody comprises 1) the light chain LCDR1' is SEQ ID NO: 32, LCDR2' is SEQ ID NO: 33 and LCDR3' is SEQ ID NO: 34; 2) the light chain LCDR1' is SEQ ID NO: 38, LCDR2' is SEQ ID NO: 39 and LCDR3' is SEQ ID NO: 40; or 3) the light chain LCDR1' is SEQ ID NO: 44, LCDR2' is SEQ ID NO: 45 and LCDR3' is SEQ ID NO: 46. In certain embodiments, the PD-L1 antibody comprises 1) the heavy chain HCDR1' is SEQ ID NO: 29, HCDR2' is SEQ ID NO: 30 and HCDR3' is SEQ ID NO: 31, the light chain LCDR1' is SEQ ID NO: 32, LCDR2' is SEQ ID NO: 33 and LCDR3' is SEQ ID NO: 34; 2) the heavy chain HCDR1' is SEQ ID NO: 35, HCDR2' is SEQ ID NO: 36 and HCDR3' is SEQ ID NO: 37, the light chain LCDR1' is SEQ ID NO: 38, LCDR2' is SEQ ID NO: 39 and LCDR3' is SEQ ID NO: 40; or 3) the heavy chain HCDR1' is SEQ ID NO: 41, HCDR2' is SEQ ID NO: 42 and HCDR3' is SEQ ID NO: 43, the light chain LCDR1' is SEQ ID NO: 44, LCDR2' is SEQ ID NO: 45 and LCDR3' is SEQ ID NO: 46.

In certain embodiments, the PD-L1 antibody comprises a heavy chain variable region selected from SEQ ID NOs: 55, 57 and 59. In certain embodiments, the PD-L1 antibody comprises a light chain variable region selected from SEQ ID NOs: 56, 58 and 60.

In certain embodiments, the PD-L1 antibody comprises a heavy chain variable region of SEQ ID NO: 55, or a humanized version thereof and a light chain variable region of SEQ ID NO: 56, or a humanized version thereof. In certain embodiments, the PD-L1 antibody comprises a heavy chain variable region of SEQ ID NO: 57, or a humanized version thereof and a light chain variable region of SEQ ID NO: 58, or a humanized version thereof. In certain embodiments, the PD-L1 antibody comprises a heavy chain variable region of SEQ ID NO: 59, or a humanized version thereof and a light chain variable region of SEQ ID NO: 60, or a humanized version thereof.

The present disclosure also provides another isolated PD-L1 antibody that binds to the same epitope as or has competitive binding to the PD-L1 antibody provided herein. In certain embodiments, the epitope comprises at least the amino acid residue of E58 and S80. In certain embodiments, wherein the epitope further comprises at least one (e.g. at least two, three, or four) of the following amino acid residues of PD-L: Y56, R113, D122, Y123 and R125. In certain embodiments, the epitope comprises one of the following combinations of amino acid residues of PD-L: 1) E58, R113, D122, Y123 and R125; 2) Y56, E58 and R113; 3) E58, R113 and R125. In certain embodiments, wherein the epitope further comprises at least one (or at least two) of the following amino acid residues of PD-L: S80 and D122. In certain embodiments, the epitope comprises one of the following combinations of amino acid residues of PD-L: 1) E58, S80, R113, D122, Y123 and R125; 2) E58, S80, R113 and R125.

The present disclosure also provided herein an isolated PD-L1 antibody with a thermal transition midpoint (Tm) of more than 76 (e.g. more than 80, more than 85, or more than 90) degrees Celsius as measured by differential scanning calorimetry. In certain embodiments, the antibody herein is a bispecific antibody, humanized antibody, chimeric antibody, monoclonal antibody, recombinant antibody, labeled antibody, bivalent antibody, or anti-idiotypic antibody. In certain embodiments, the antibody is an antigen-binding fragment selected from the group consisting of camelized single domain antibody, a diabody, a scFv, an scFv dimer, a BsFv, a dsFv, a (dsFv)$_2$, a dsFv-dsFv', an Fv fragment, a Fab, a Fab', a F(ab')$_2$, a ds diabody, a nanobody, a domain antibody, an isolated CDR and a bivalent domain antibody.

In certain embodiments, the PD-L1 antibody provided herein (such as 4B6, 26F5, 21F11, 23A11, 23F11 and 22C9) bind to human and non-human primate PD-L1, but do not bind to mouse PD-L1. In certain embodiments, the PD-L1 antibody provided herein (such as 18G4) bind to both human and mouse PD-L1.

The present disclosure also relates to a pharmaceutical composition comprising the antibody provided herein.

The present disclosure also relates to a polynucleotide encoding the antibody provided herein. A vector comprising the polynucleotide is provided herein. An isolated host cell comprising the vector is also provided herein. In certain embodiments, the host cell produces the antibody encoded by the polynucleotide.

The present disclosure also relates to a kit comprising the antibody provided herein.

The present disclosure also relates to a method of producing the antibody provided herein, comprising culturing the host cell under the condition at which the polynucleotide is expressed.

The present disclosure also relates to a method of treating a PD-L1 associated condition in a subject in need thereof, comprising administering to the subject a therapeutically effective amount of the antibody provided herein. In certain embodiments, the second therapeutic agent is an agent used in a radiation therapy, chemotherapy, targeted therapies, gene therapy, immunotherapy, hormonal therapy, angiogenesis inhibition, palliative care, surgery or the combination thereof. In certain embodiments, the second therapeutic agent is VEGFR2 antibody.

Also provided in the present disclosure is a pharmaceutical composition comprising the PD-L1 antibody provided herein and a second therapeutic agent.

Further provided in the present disclosure is a method of treating a PD-L1 associated condition in a subject in need thereof, comprising administration to the subject a therapeutically effective amount of the pharmaceutical composition.

The present disclosure also provided an isolated non-human tumor cell that comprises a polynucleotide encoding human PD-L1 protein. In certain embodiments, the non-human tumor cell is a rodent (e.g. mouse, rat, or hamster, etc) tumor cell.

Also provided herein is a method of producing a non-human tumor cell comprising a polynucleotide encoding the human PD-L1 protein, including introducing a polynucleotide encoding the human PD-L1. In certain embodiments, the method further including inactivating endogenous non-human PD-L1 gene. In certain embodiments, the inactivation includes gene disruption of the protein-coding region, mutation, addition, gene silencing or gene deletion, thereby eliminating or minimizing the expression of the target gene or generating a functionally inactive/truncated protein. In certain embodiments, the human PD-L1 gene segment is operably inserted into the endogenous non-human PD-L1 gene locus. In certain embodiments, the human PD-L1 gene segment is inserted at a site other than the endogenous non-human PD-L1 gene locus. In certain embodiments, the human PD-L1 gene segment is in the form of episomal DNA segment.

A method of screening or evaluating the in vivo efficacy of an antibody against human PD-L1, including inoculating a non-human tumor cell comprising a polynucleotide encoding the human PD-L1 protein into a non-human animal, contacting the antibody with the non-human tumor cell in the non-human animal and determining tumor burden of the non-human tumor cell. The tumor cell can be solid tumor cell or non-solid tumor cell. In certain embodiments, the non-human cell is inoculated into a syngenic non-human animal to generate a syngenic tumor model. In certain embodiments, the non-human animal is a rodent (e.g. mouse, rat, or hamster, etc).

In one aspect, the present disclosure provides herein an isolated PD-L1 antibody that binds to or having competitive binding to the epitope comprises one of the following combinations of amino acid residues of PD-L: 1) E58 and S80; 2) E58 and R113; 3) E58 and D122; 4) E58 and R125. In certain embodiments, the epitope further comprises at least one of the following amino acid residues of PD-L1: Y56 and Y23. In certain embodiments, the epitope comprises one of the following combinations of amino acid residues of PD-L1: 1) E58, R113, M115, Y23 and K124; 2) E58, S80, R113 and R125; 3) E58, R113, D122, Y23 and R125; 4) Y56, E58, and R113; 5) E58, R113 and R125. In certain embodiments, the epitope further comprises at least one of the following amino acid residues of PD-L: K62, N63, I64 and Y81. In certain embodiments, the epitope comprises one of the following combinations of amino acid residues of PD-L: 1) E58, N63, I64, S80, Y81, R113 and R125; 2) E58, S80, R113, M115, D122, Y23, K124 and R125; 3) E58, K62, N63, S80, Y81, R113 and R125; 4) E58, N63, I64, S80, Y81, R113, K124 and R125; 5) E58, S80, R113, D122, Y23 and R125.

In one aspect, also provided herein is an isolated PD-L1 antibody that binds to or having competitive binding to an epitope consists of amino acid residue S80 of PD-L1.

In one aspect, the present disclosure provides an isolated PD-L1 antibody that has a duration of sustained PD-L1 receptor occupancy of at least 7 days (e.g. at least 8, 9, 10, 11, 12, 13, 14, 15, 16, 17, 18, 19, 20, 21, 22, 23, 24, 25, 30, 35, or 40 days).

An isolated PD-L1 antibody that binds to activated human T cells with an EC50 value of about 0.03 μg/ml as measured by ELISA (e.g. of 0.001 μg/ml-1 μg/ml (e.g. 0.001 μg/ml-0.5 μg/ml, 0.001 μg/ml-0.2 μg/ml, 0.001 μg/ml-0.1 μg/ml, 0.01 μg/ml-0.2 μg/ml, 0.01 μg/ml-0.1 μg/ml, 0.01 μg/ml-0.05 μg/ml, 0.01 μg/ml-0.03 μg/ml or 0.001 μg/ml-0.01 μg/ml) as measured by ELISA, or EC50 of 0.01 μg/ml-1 μg/ml (e.g. 0.01 μg/ml-0.5 μg/ml, 0.01 μg/ml-0.2 μg/ml, 0.02 μg/ml-1 μg/ml, 0.02 μg/ml-0.5 μg/ml, 0.02 μg/ml-0.2 μg/ml, or 0.02 μg/ml-0.1 μg/ml) as measured by FACS).

BRIEF DESCRIPTION OF FIGURES

FIG. 14A indicates the amino acid sequences of the germline and humanized heavy chain variable regions of 4B6 (4B6-germline, 4B6-Hzd-HC-V3 and 4B6-HC-V4) and FIG. 14B indicates the amino acid sequences of the germline and humanized light chain variable regions of 4B6 (4B6 LC germline, 4B6-Hzd-LC-V3 and 4B6-LC-V4).

FIG. 15A indicates the amino acid sequences of the germline and humanized heavy chain variable regions of 23A11 antibody (23A11-HC-germline, 23A11-HC-V3 and 23A11-HC-V5) and FIG. 15B indicates the amino acid sequences of the germline and humanized light chain variable regions of 23A11 antibody (23A11-LC-germline, 23A11-LC-V3 and 23A11-LC-V5).

FIG. 16A indicates the amino acid sequences of the germline and humanized heavy chain variable regions of 23F11 antibody (23F11 Germline HC, 23F11-HC-V4 and 23F11-HC-V6) and FIG. 16B indicates the amino acid sequences of the germline and humanized light chain variable regions of 23F11 antibody (23F11Germline LC, 23F11-LC-V4 and 23F11-LC-V6).

Mice (n=8 for each group) were IP injected 3 times/week for 3 weeks, the results of which are expressed as mean S.E.M.

Figure 27A:
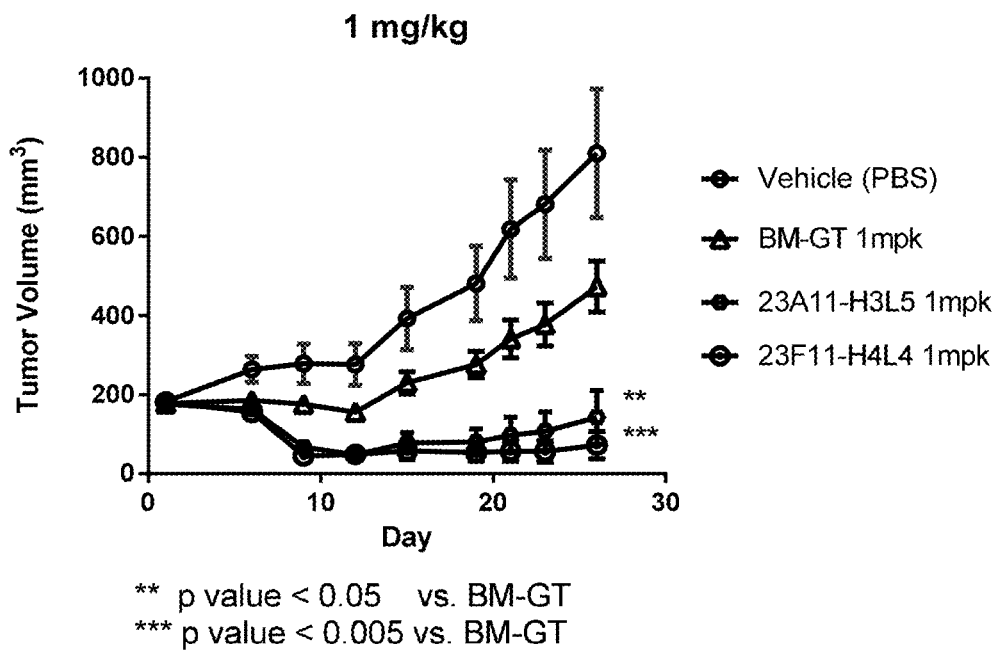
Figure 27B:
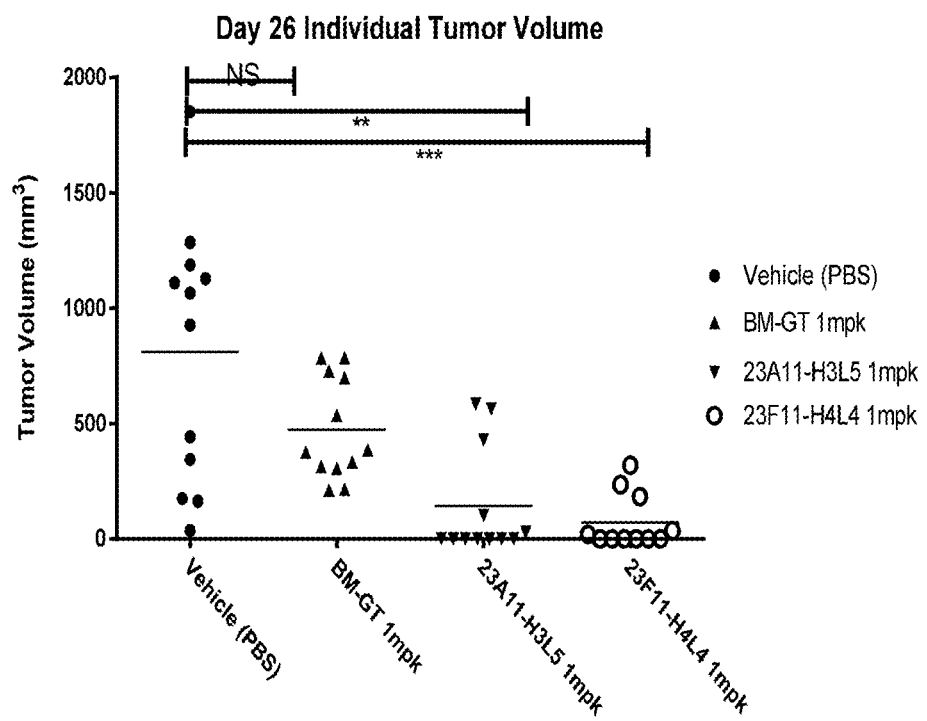

FIG. 27A shows the averaged tumor volume measured over time in MC38/Human-PD-L1 knock-in tumor model, indicating the in vivo anti-tumor activities of the antibodies (vehicle in open circle, BM-GT in open triangle, 23A11-H3L5 in open circle and 23F11-H4L4 in dotted open circle) in inhibiting the growth of tumor. FIG. 27B shows the averaged tumor volume at Day 26 with mice dosed with antibodies (vehicle in solid circle, BM-GT in solid triangle, 23A11-H3L5 in inverted solid triangle and 23F11-H4L4 in open circle). Mice (n=12 for each group) were IV injected with 1 mpk antibodies at day 0 and day 15, the results of which are expressed as mean±S.E.M.

Figure 28A:
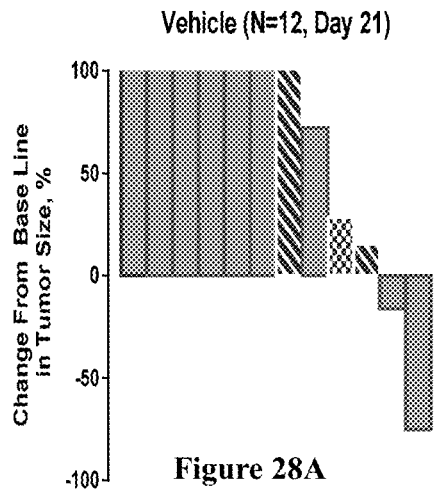
Figure 28B:
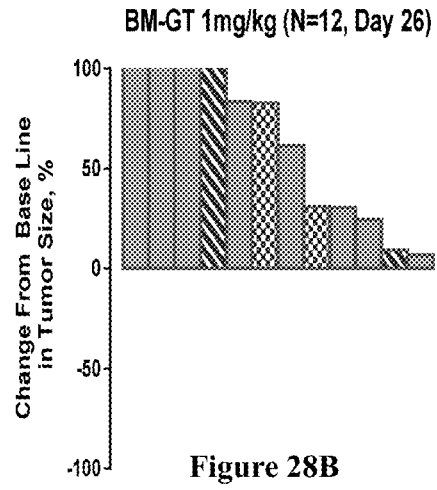
Figure 28C:
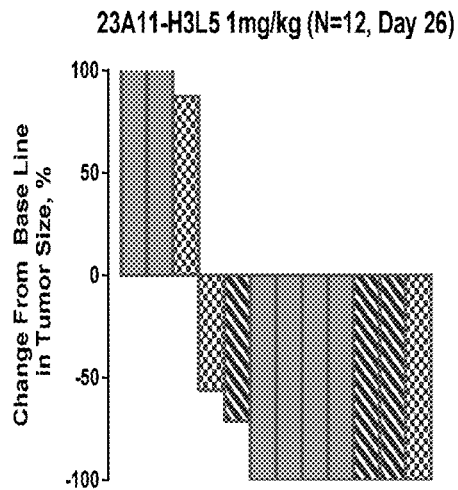
Figure 28D:
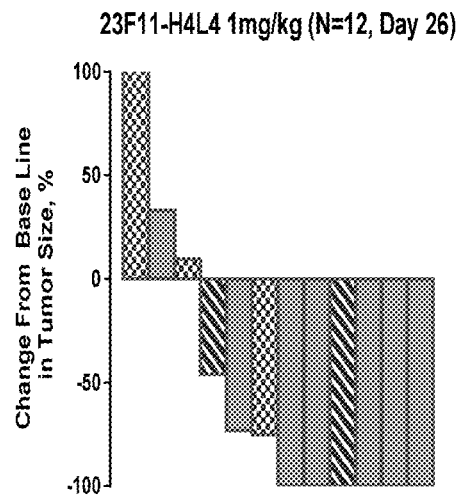

FIG. 28A to FIG. 28D are waterfall graphs showing the change of tumor size in mice normalized to the starting point treated with IV injection of 1 mg/kg PD-L1 antibodies (Vehicle (FIG. 28A), BM-GT (FIG. 28B), 23A11-H3L5 (FIG. 28C) and 23F11-H4L4 (FIG. 28D).

Figure 29A:
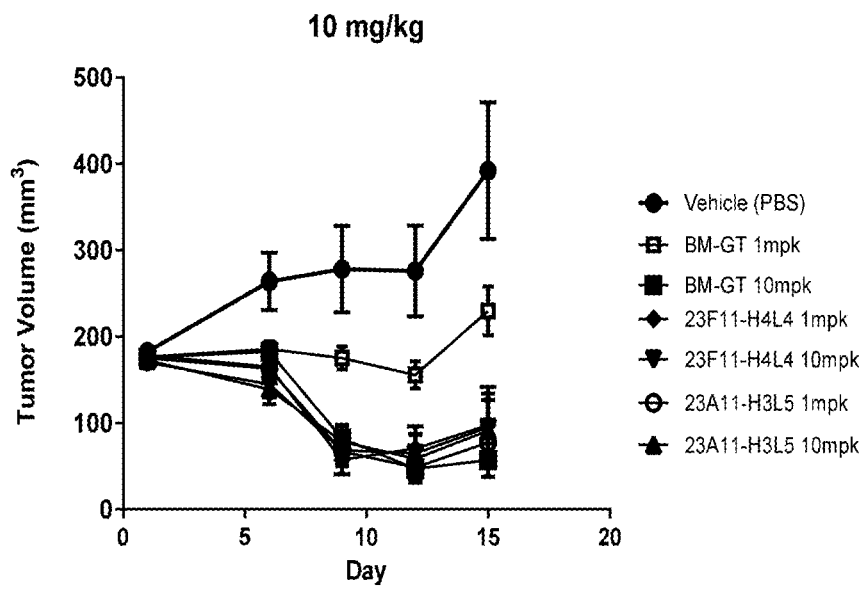
Figure 29B:
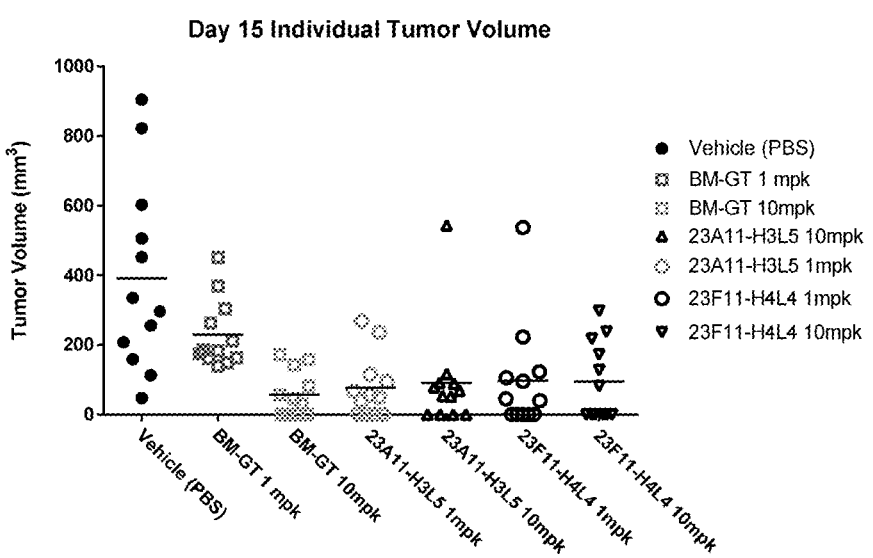

FIG. 29A shows the averaged tumor volume measured over time in inhibiting the growth of tumor in MC38/Human-PD-L1 knock-in tumor model IV dosing with different dosages of the PD-L1 antibodies (vehicle in solid circle, BM-GT 1 mpk in open square, BM-GT 10 mpk in solid square, 23F11-H4L4 1 mpk in solid diamond, 23F11-H4L4 10 mpk in inverted solid triangle, 23A11-H3L5 1 mpk in open circle, 23A11-H3L5 10 mpk in solid triangle), indicating the in vivo anti-tumor activities. FIG. 29B shows the averaged tumor volume at Day 15 with mice dosed with different antibodies (vehicle in solid circle, BM-GT 1 mpk in dark open square, BM-GT 10 mpk in light open square, 23A11-H3L5 1 mpk in light open circle, 23A11-H3L5 10 mpk in dark open triangle, 23F11-H4L4 1 mpk in dark open circle and 23F11-H4L4 10 mpk in inverted dark open triangle). Mice (n=12 for each group) were IV injected with antibodies at day 0, and the results are expressed as mean±S.E.M.

Figure 30:
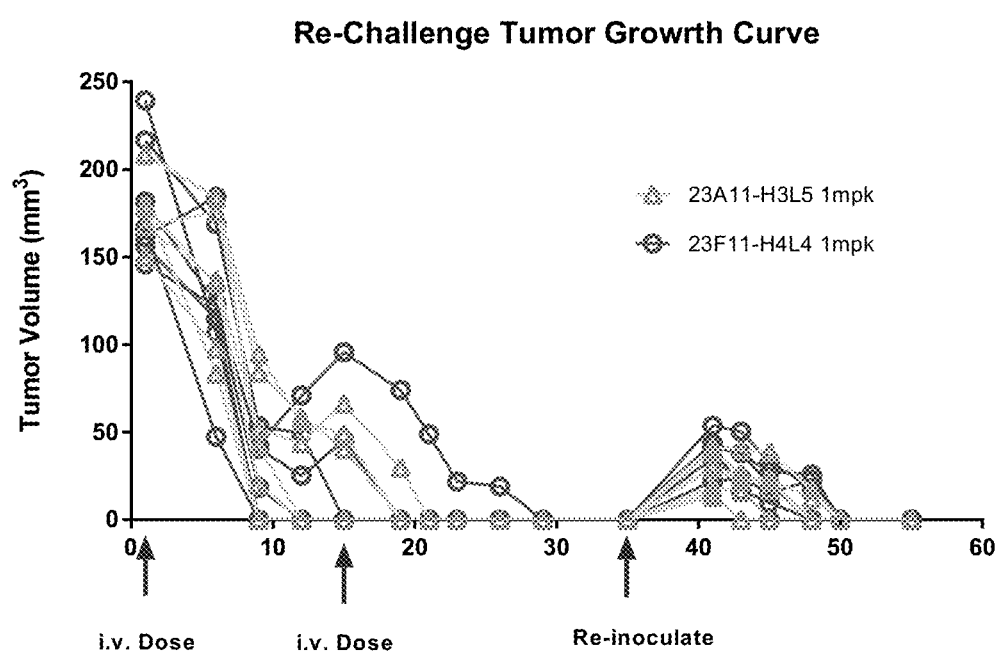

FIG. 30 shows the in vivo anti-tumor activities of the humanized PD-L1 antibodies 23A11-H3L5 (in triangle) and 23F11-H4L4 (in circle) in MC38/Human-PD-L1 knock-in tumor model re-challenged with tumor cells at Day 35.

Figure 31A:
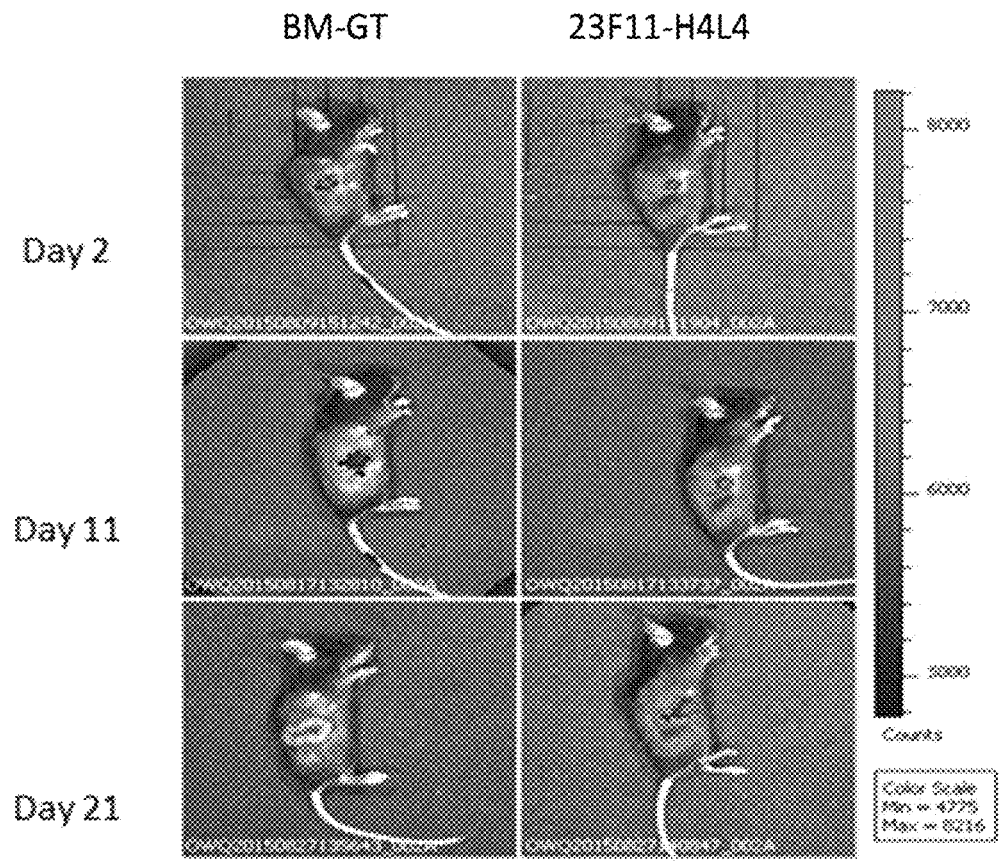
Figure 31B:
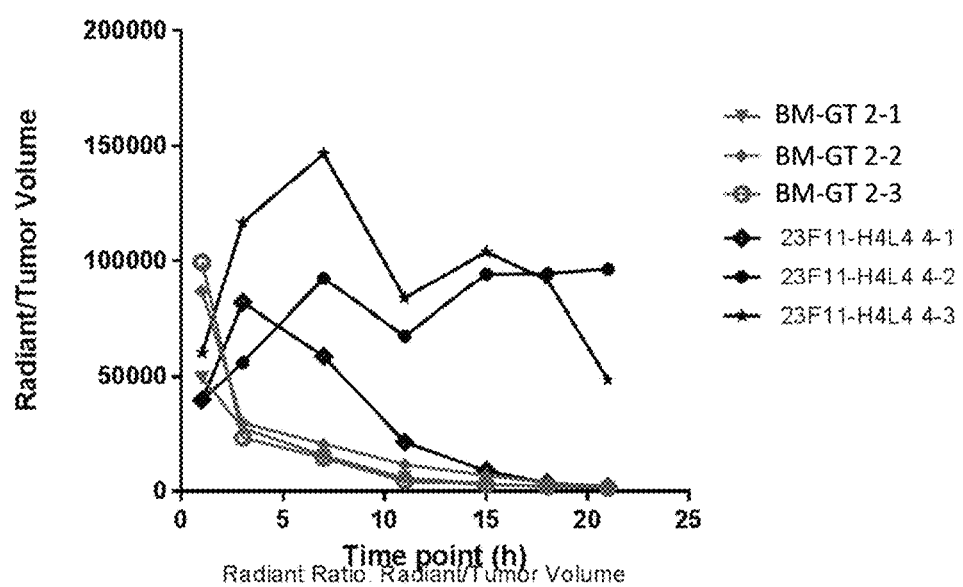
Figure 31C:
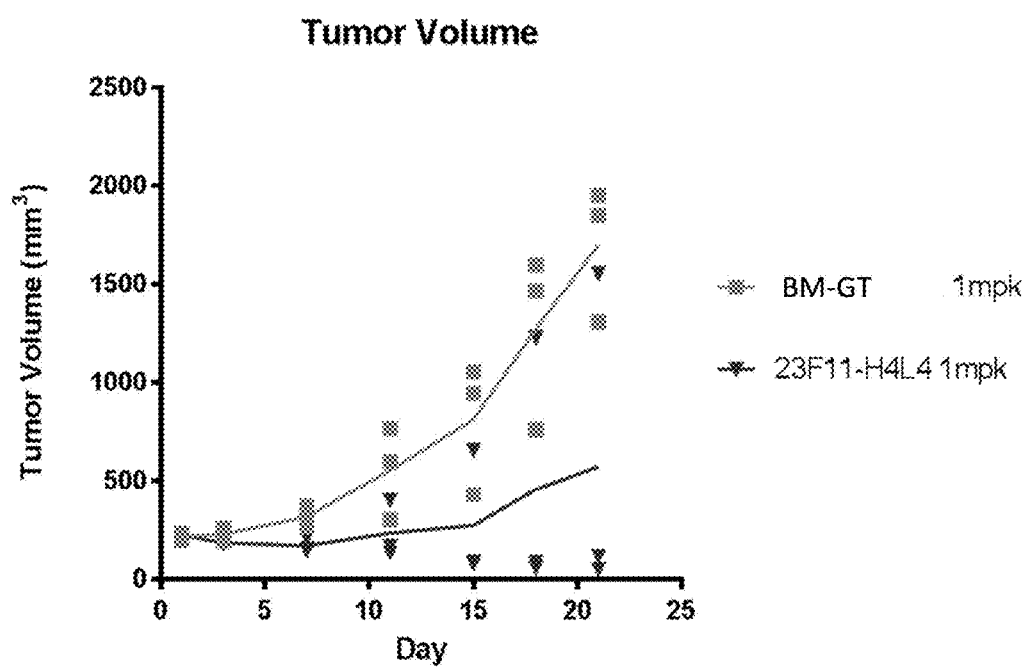

FIG. 31A shows the exemplary imaging of the radiant signal of labeled pH-dependent PD-L1 antibody 23F11-H4L4 and BM-GT that penetrate into the MC38/hPD-L1 tumor cells at different time points after dosing at 1 mg/kg intravenously; FIG. 31B shows the ratio of radiant/tumor volume measured over hours in each mouse (for BM-GT, 2-1 (inverted grey triangle), 2-2 (solid grey diamond), 2-3 (open grey circle) and for 23F11-H4L4, 4-1 (open dark diamond), 4-2 (solid dark diamond), 4-3 (dark star)); FIG. 31C shows tumor volume measured over days in each mouse dosed with BM-GT (in square) or 23F11-H4L4 (in inverted triangle) and the lines represent averaged values.

Figure 32A:
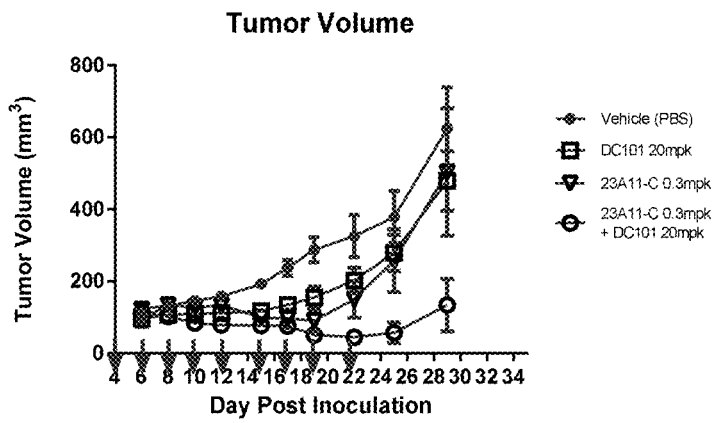
Figure 32B:
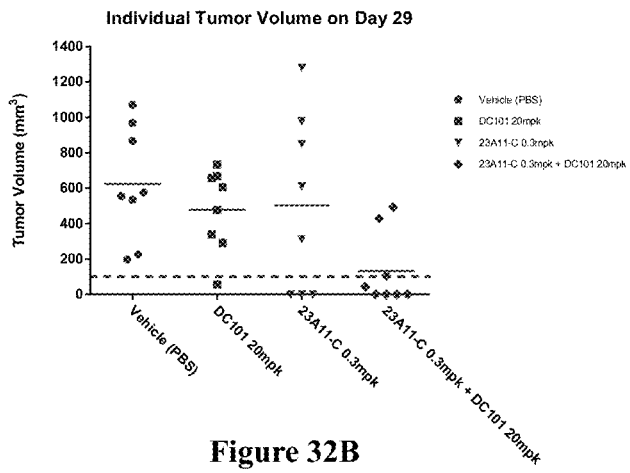
Figure 32C:
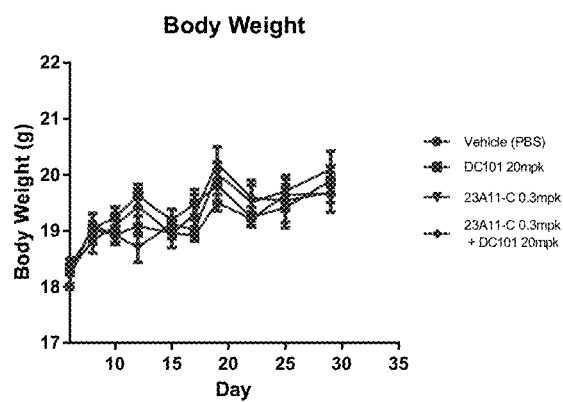
Figure 32D:
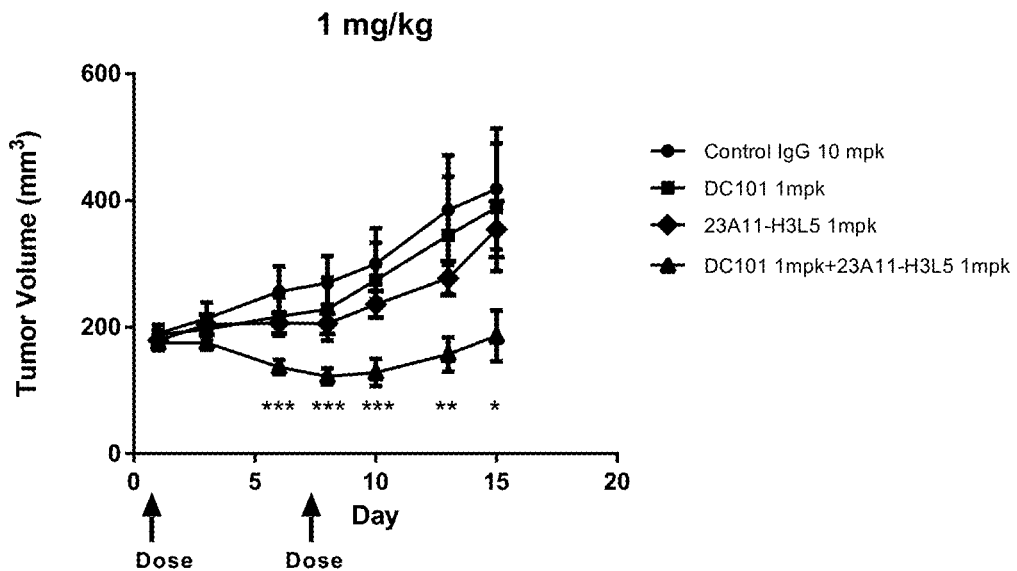
Figure 32E:
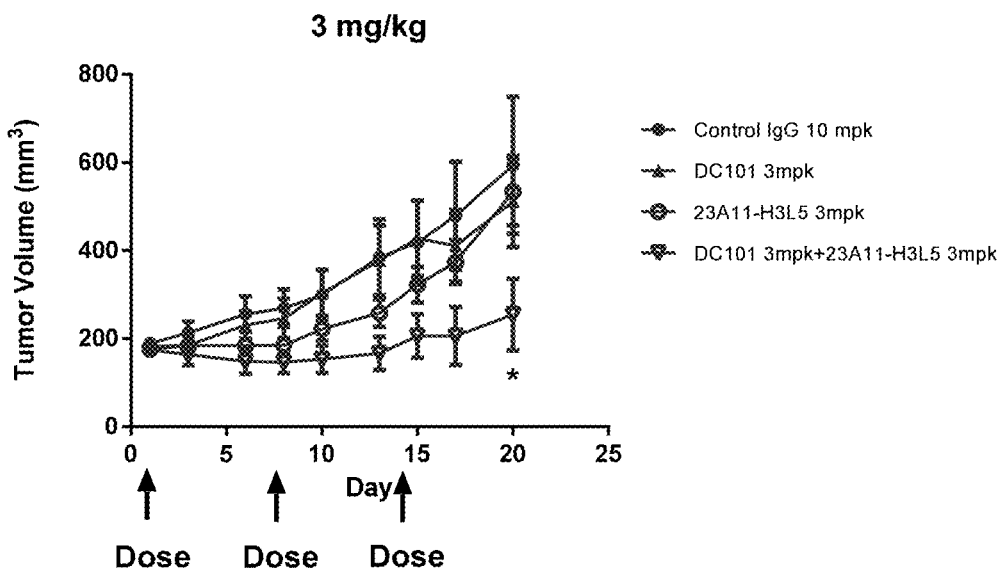

FIG. 32A shows the averaged tumor volume measured over time in the mice of hPD-L1/MC38 tumor model dosed with vehicle (solid circle), DC101 alone (an anti-VEGFR2 antibody in open square), 23A11-C alone (inverted open triangle), and the combination of 23A11-C and DC101 (open circle), respectively, showing the in vivo anti-tumor activities of the combination; FIG. 32B shows the averaged tumor volume at Day 29 with mice injected with vehicle (solid circle), DC101 alone (an anti-VEGFR2 antibody in solid square), 23A11-C alone (inverted solid triangle), and the combination of 23A11-C and DC101 (solid diamond), respectively; FIG. 32C shows the averaged mice body weight over time measured in the same test dosed with vehicle (solid circle), DC101 alone (an anti-VEGFR2 antibody in solid square), 23A11-C alone (inverted solid triangle), and the combination of 23A11-C and DC101 (solid diamond), respectively, and mice (n=8 for each group) were IV injected with 0.3 mpk of 23A11-C and/or 20 mpk of DC101 3 times a week for 3 weeks. FIG. 32D indicates the averaged tumor volume measured over time with mice dosed with 10 mpk control IgG (solid circle), 1 mpk DC101 alone (solid square), 1 mpk 23A11-H3L5 alone (solid diamond) and the combination of 1 mpk 23A11-H3L5 and 1 mpk DC101 (solid triangle), respectively; FIG. 32E shows the averaged tumor volume measured over time with mice dosed with 10 mpk control IgG (solid circle), 3 mpk DC101 alone (solid triangle), 3 mpk 23A11-H3L5 alone (open circle) and the combination of 3 mpk 23A11-H3L5 and 3 mpk DC101 (inverted open triangle), respectively. Mice (n=8 for each group) were IV injected with antibodies once a week for 2-3 weeks. Results are expressed as mean±S.E.M.

Figure 33A:
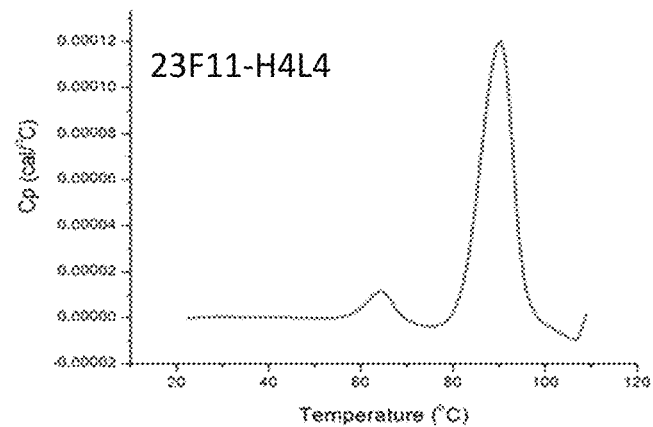
Figure 33B:
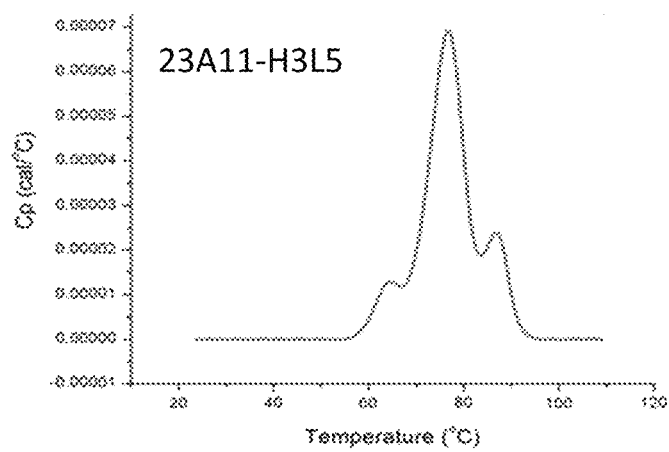

FIG. 33A shows a graph illustrating the thermal transition midpoint (Tm) of 23F11-H4L4 and FIG. 33B shows the thermal transition midpoint (Tm) of 23A11-H3L5, respectively, as measured by differential scanning calorimetry (DSC).

FIG. 34 shows the list of sequences described in the present disclosure.

FIG. 35 shows a graph for the internalization of 23F11-H4L4 into MC38/hPD-L1 cells. Y axis shows the fluorescence signal of 23F11-H4L4 in the cells at different antibody concentrations as measured by Varioskan Flash. Small grey circles represent 23F11-H4L4 tested after 24 hours, and big black circles represent 23F11-H4L4 tested after 6 hours.

Figure 36A:
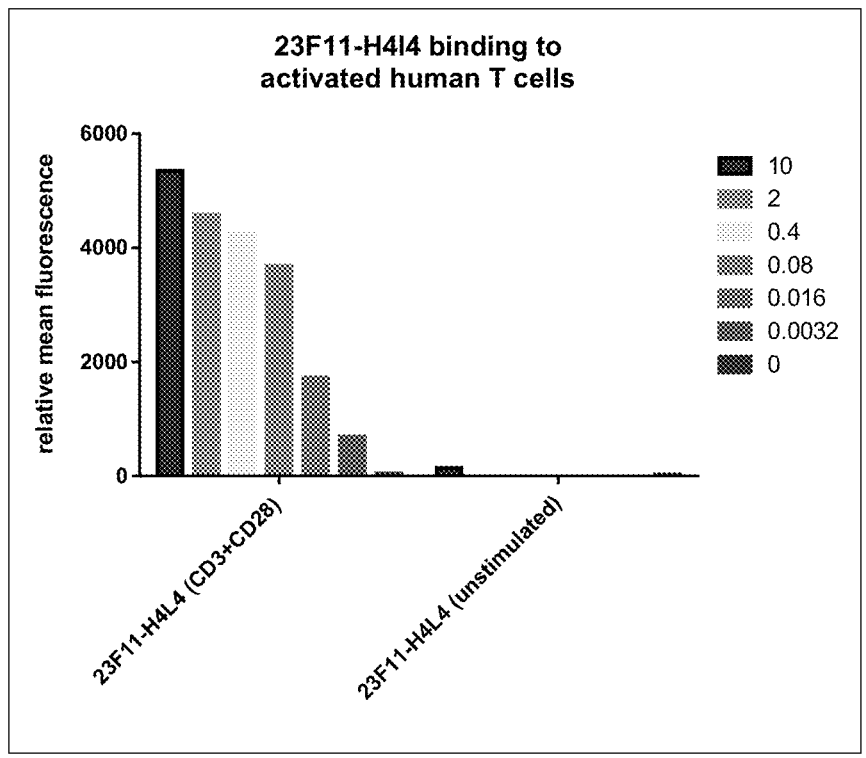
Figure 36B:
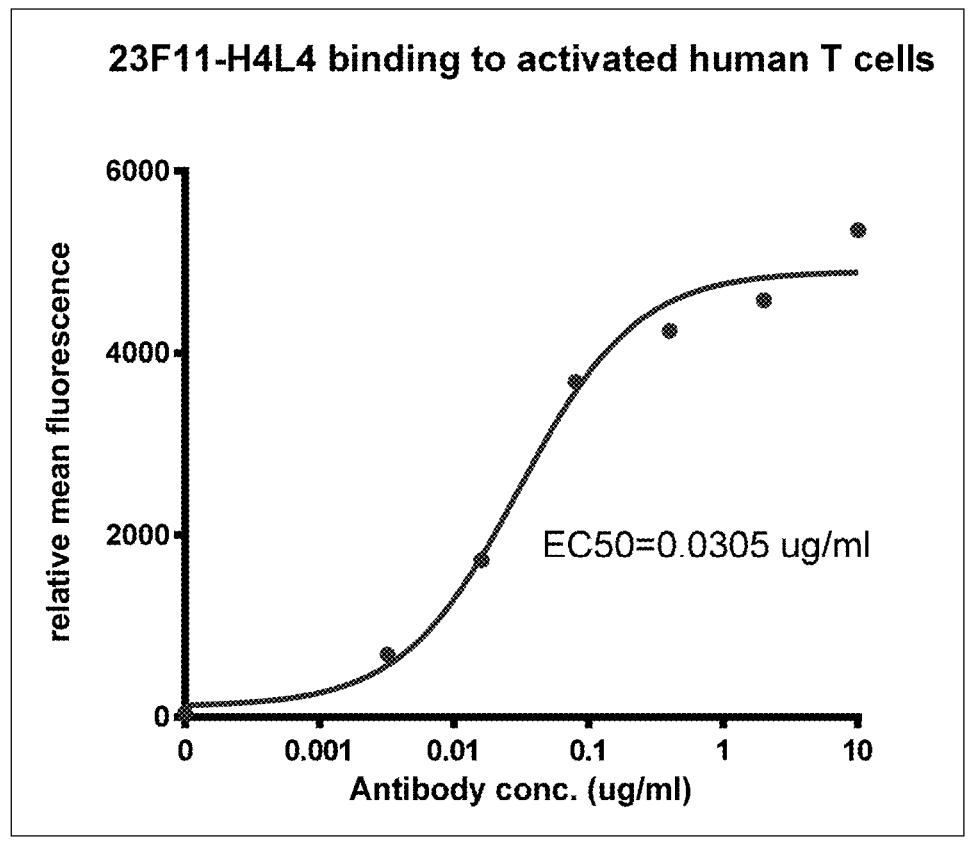

FIGS. 36A and 36B illustrate binding of 23F11-H4L4 to activated human T cells. FIG. 36A shows binding of 23F11-H4L4 to CD3 and CD28 positive monocytes, while very little binding was detected in CD3 and CD28 negative monocytes.

Figure 37A:
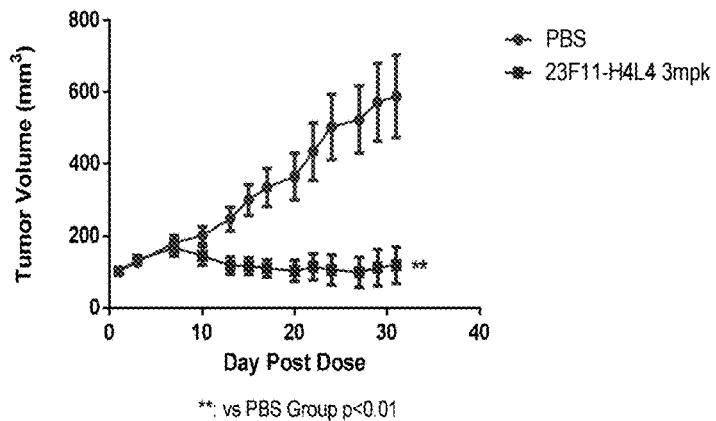
Figure 37B:
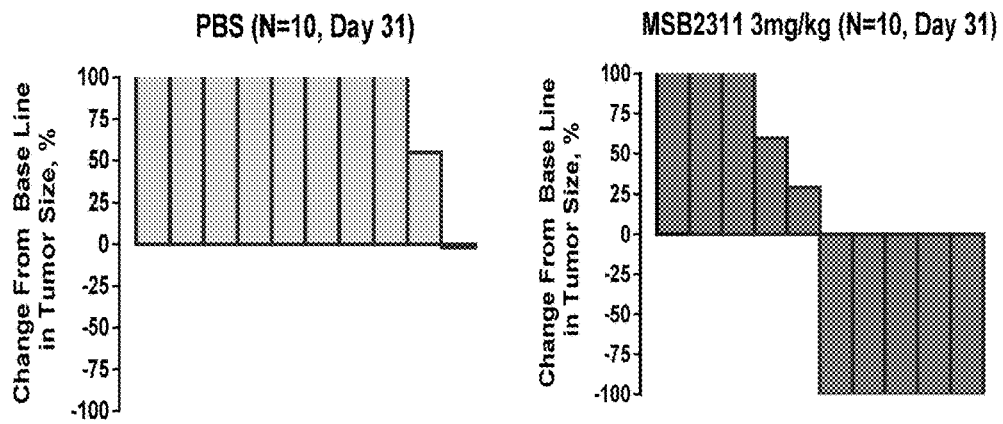
Figure 37C:
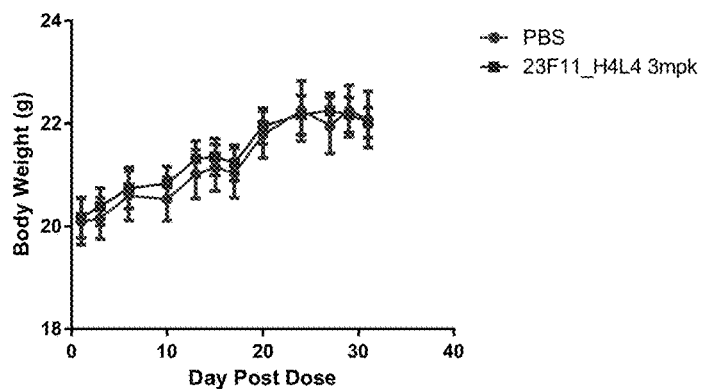

FIG. 37A-37C illustrate in vivo efficacy study of PD-L1 antibody in hPD-1 knock-in mouse model with MC38/hPD-L1 cells. FIG. 37A shows tumor volume overtime in human PD-1 Knock-in C57BL/6 mice administered with PBS and 23F11-H4L4, respectively. FIG. 37B shows the change of tumor size in individual mouse normalized to the starting point treated with IV injection of PBS or 3 mg/kg PD-L1 antibodies, respectively. FIG. 37C shows the averaged mice body weight over time measured in the same test dosed with PBS (solid circle), and 23F11-H4L4 (solid square), respectively.

Figure 38A:
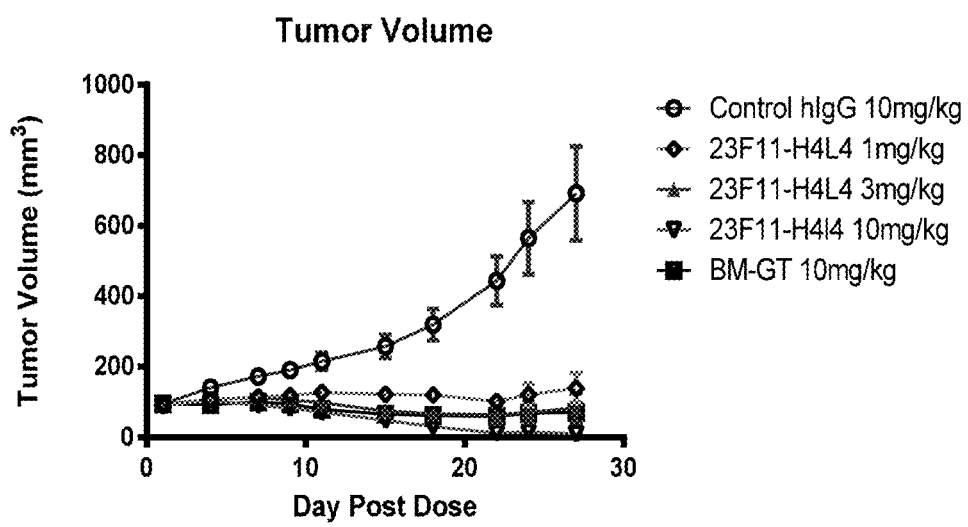
Figure 38B:
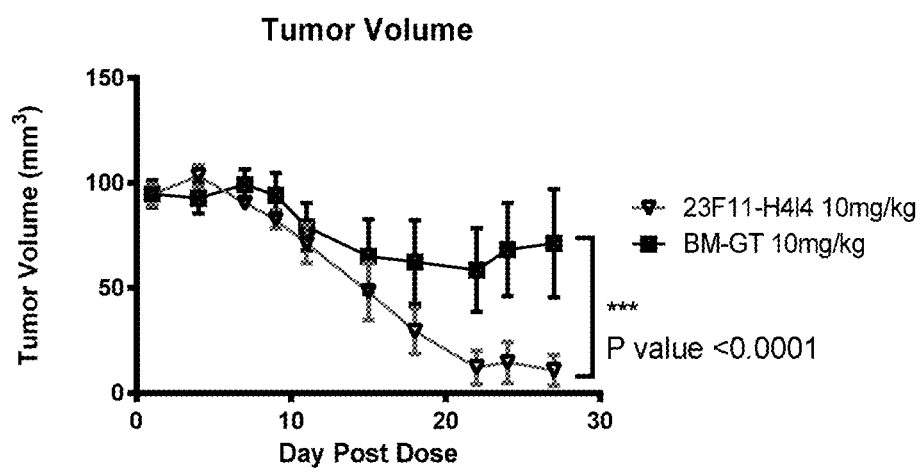
Figure 38C:
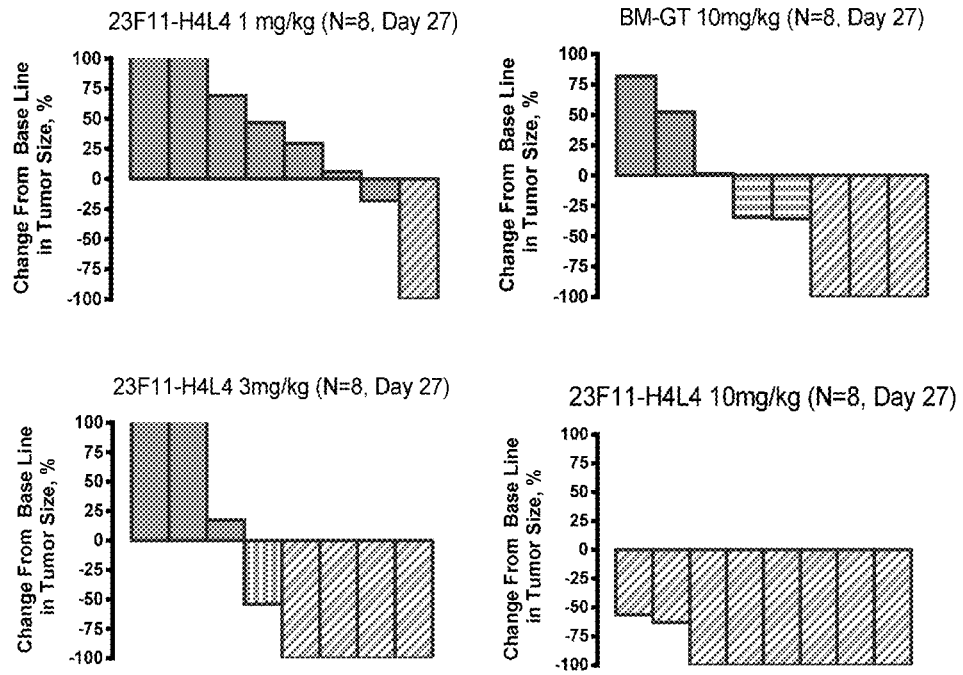

FIG. 38A-38C illustrate in vivo efficacy study of PD-L1 antibody in hPD-1 knock-in mouse model with MC38/hPD-L1 cells. FIGS. 38A and 38B show tumor volume overtime in human PD-1 Knock-in C57BL/6 mice administered with 23F11-H4L4 (1 mg/kg, 3 mg/kg and 10 mg/kg), control hIgG (AB160160, 10 mg/kg) and BM-GT (10 mg/kg), respectively. FIG. 37C shows the change of tumor size in individual mouse normalized to the starting point treated with IP injection of PD-L1 antibodies, control hIgG or BM-GT, respectively.

Figure 39:
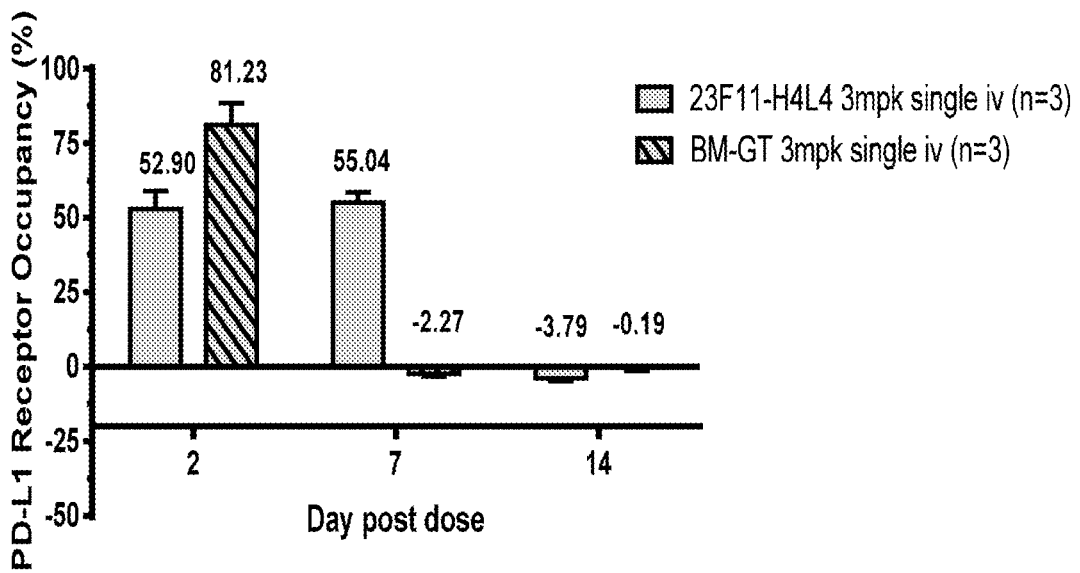

FIG. 39 shows the PD-L1 receptor occupancy for 23F11-H4L4 and BM-GT measured at day 2, 7 and 14 after IV administration in the mice with MC38/hPD-L1 tumors.

Figure 40:
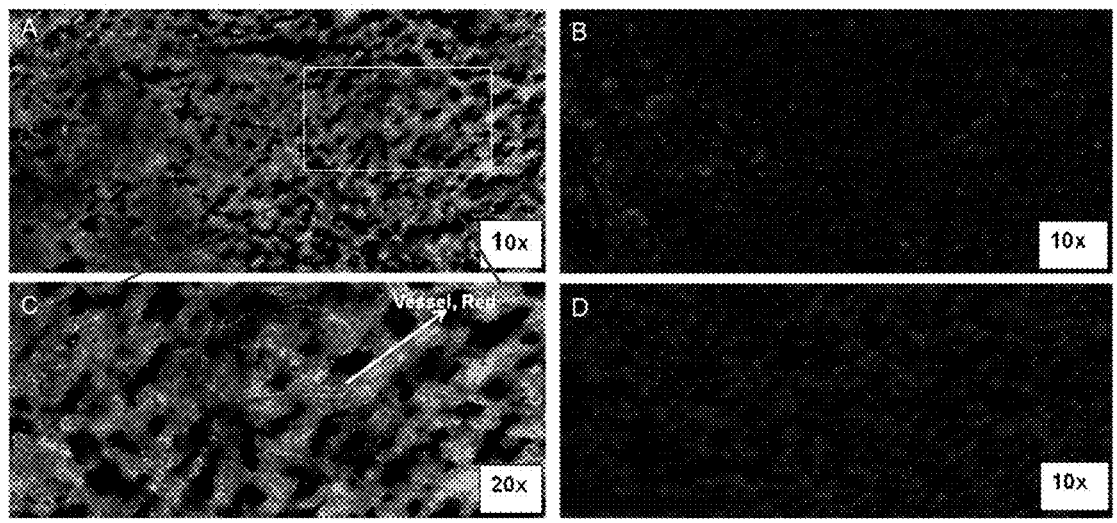

FIG. 40 shows representative image of 23F11-H4L4 penetration and TIL on Frozen MC38/hPD-L1 CDx tumor section on Day 7 after dosing at 10 mpk. Figure A: 23F11-H4L4 stained with Alexa Fluor 488 Goat anti-human IgG (H+L) second antibody (Green); Figure B: TIL stained with Alexa Fluor® 594 anti-mouse CD8b.2 (Red); Figure C:

Vessel stained with Alexa Fluor® 594 anti-mouse CD31 (Red); Figure D: Negative Control. Nucleus stained with DAPI (Blue).

DETAILED DESCRIPTION OF THE INVENTION

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

As used herein, "PD-L1" (also known as B7-H1/CD274) refers to programmed cell death ligand 1 (PD-L1, see, for example, Freeman et al. (2000) J. Exp. Med. 192:1027). It is expressed in placenta, spleen, lymph nodes, thymus, heart, fetal liver, and is also found on many tumor or cancer cells. "PD-L2" refers to programmed cell death ligand 2 (PD-L2, see, for example, Latchman et al. (2001) Nat. Immunol. 2:261). "PD-1" (also known as CD279) refers to programmed cell death 1, a member of the CD28 family, is encoded by the PDCD 1 gene and is an inhibitory receptor expressed on the surface of T cells which functions to physiologically limit T cell activation and proliferation. Representative amino acid sequence of human PD-1 is disclosed under the NCBI accession number: NP_005009.2, and the representative nucleic acid sequence encoding the human PD-1 is shown under the NCBI accession number: NM_005018.2. The "PD-1 ligand" includes either or both PD-L1 and PD-L2 and any variants or isoforms which are naturally expressed by cells, and/or fragments thereof having at least one biological activity of the full-length polypeptides. The sequence of human PD-L1 is disclosed under the NCBI accession number: NP_054862.1 (representative amino acid sequence) and NCBI accession number: NM_014143.3 (representative nucleic acid sequence).

The term "antibody" as used herein includes any immunoglobulin, monoclonal antibody, polyclonal antibody, multivalent antibody, multispecific antibody, or bispecific (bivalent) antibody or a functional portion thereof that binds to a specific antigen. A native intact antibody comprises two heavy chains (H) and two light (L) chains inter-connected by disulfide bonds. Each heavy chain consists of a variable region (VH) and a first, second, and third constant region (CH1, CH2 and CH3, respectively), while each light chain consists of a variable region (VL) and a constant region (CL). Mammalian heavy chains are classified as α, δ, ε, γ, and μ, and mammalian light chains are classified as λ or κ. The variable regions of the light and heavy chains are responsible for antigen binding. The variables region in both chains are generally subdivided into three regions of hypervariability called the complementarity determining regions (CDRs) (light (L) chain CDRs including LCDR1, LCDR2, and LCDR3, heavy (H) chain CDRs including HCDR1, HCDR2, HCDR3). CDR boundaries for the antibodies and antigen-binding fragments disclosed herein may be defined or identified by the conventions of Kabat, Chothia, or Al-Lazikani (Al-Lazikani, B., Chothia, C., Lesk, A. M., J. Mol. Biol., 273(4), 927 (1997); Chothia, C. et al., J Mol Biol. December 5; 186(3):651-63 (1985); Chothia, C. and Lesk, A. M., J. Mol. Biol., 196,901 (1987); Chothia, C. et al., Nature. December 21-28; 342(6252):877-83 (1989); Kabat E. A. et al., National Institutes of Health, Bethesda, Md. (1991)). The three CDRs are interposed between flanking stretches known as framework regions (FRs), which are more highly conserved than the CDRs and form a scaffold to support the hypervariable loops. Therefore, each VH and VL comprises of three CDRs and four FRs in the following order (amino acid residues N terminus to C terminus): FR1, CDR1, FR2, CDR2, FR3, CDR3, FR4. The constant regions of the heavy and light chains are not involved in antigen binding, but exhibit various effector functions. Antibodies are assigned to the five major classes based on the amino acid sequence of the constant region of their heavy chain: IgA, IgD, IgE, IgG, and IgM, which are characterized by the presence of α, δ, ε, γ, and μ heavy chains, respectively. Subclasses of several of the major antibody classes are such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

As used herein, the term "antigen-binding fragment" refers to an antibody fragment formed from a fragment of an antibody comprising one or more CDRs, or any other antibody portion that binds to an antigen but does not comprise an intact native antibody structure. In certain embodiments, the antibody provided herein is an antigen-binding fragment. Examples of antigen-binding fragment include, without limitation, a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, an isolated CDR and a bivalent domain antibody. An antigen-binding fragment is capable of binding to the same antigen to which the parent antibody binds. In certain embodiments, an antigen-binding fragment may comprise one or more CDRs from a particular human antibody.

"Fab" with regard to an antibody refers to a monovalent antigen-binding fragment of the antibody consisting of a single light chain (both variable and constant regions) bound to the variable region and first constant region of a single heavy chain by a disulfide bond. Fab can be obtained by papain digestion of an antibody at the residues proximal to the N-terminus of the disulfide bond between the heavy chains of the hinge region.

"Fab'" refers to a Fab fragment that includes a portion of the hinge region, which can be obtained by pepsin digestion of an antibody at the residues proximal to the C-terminus of the disulfide bond between the heavy chains of the hinge region and thus is different from Fab in a small number of residues (including one or more cysteines) in the hinge region.

"F(ab')$_2$" refers to a dimer of Fab' that comprises two light chains and part of two heavy chains.

"Fc" with regard to an antibody refers to that portion of the antibody consisting of the second and third constant regions of a first heavy chain bound to the second and third constant regions of a second heavy chain via disulfide bond. IgG and IgM Fc regions contain three heavy chain constant regions (second, third and fourth heavy chain constant regions in each chain). It can be obtained by papain digestion of an antibody. The Fc portion of the antibody is responsible for various effector functions such as ADCC, and CDC, but does not function in antigen binding.

"Fv" with regard to an antibody refers to the smallest fragment of the antibody to bear the complete antigen binding site. A Fv fragment consists of the variable region of a single light chain bound to the variable region of a single heavy chain. A "dsFv" refers to a disulfide-stabilized Fv fragment that the linkage between the variable region of a single light chain and the variable region of a single heavy chain is a disulfide bond.

"Single-chain Fv antibody" or "scFv" refers to an engineered antibody consisting of a light chain variable region and a heavy chain variable region connected to one another directly or via a peptide linker sequence (Huston J S et al. *Proc Natl Acad Sci USA*, 85:5879(1988)). A "scFv dimer" refers to a single chain comprising two heavy chain variable regions and two light chain variable regions with a linker. In certain embodiments, an "scFv dimer" is a bivalent diabody or bivalent ScFv (BsFv) comprising $V_H$—$V_L$ (linked by a peptide linker) dimerized with another $V_H$-$V_L$ moiety such that $V_H$'s of one moiety coordinate with the $V_L$'s of the other moiety and form two binding sites which can target the same antigens (or eptipoes) or different antigens (or eptipoes). In other embodiments, a "scFv dimer" is a bispecific diabody comprising $V_H$—$V_{L2}$ (linked by a peptide linker) associated with $V_L$-$V_{H1}$ (also linked by a peptide linker) such that $V_{H1}$ and $V_{L1}$ coordinate and $V_{H2}$ and $V_L$ coordinate and each coordinated pair has a different antigen specificity.

"Single-chain Fv-Fc antibody" or "scFv-Fc" refers to an engineered antibody consisting of a scFv connected to the Fc region of an antibody.

"Camelized single domain antibody," "heavy chain antibody," "nanobody" or "HCAb" refers to an antibody that contains two $V_H$ domains and no light chains (Riechmann L. and Muyldermans S., *J Immunol Methods*. December 10; 231(1-2):25-38 (1999); Muyldermans S., *J Biotechnol*. June; 74(4):277-302 (2001); WO94/04678; WO94/25591; U.S. Pat. No. 6,005,079). Heavy chain antibodies were originally obtained from Camelidae (camels, dromedaries, and llamas). Although devoid of light chains, camelized antibodies have an authentic antigen-binding repertoire (Hamers-Casterman C. et al., *Nature*. June 3; 363(6428):446-8 (1993); Nguyen V K. et al. "Heavy-chain antibodies in Camelidae; a case of evolutionary innovation," Immunogenetics. April; 54(1):39-47 (2002); Nguyen V K. et al. *Immunology*. May; 109(1):93-101 (2003)). The variable domain of a heavy chain antibody (VHH domain) represents the smallest known antigen-binding unit generated by adaptive immune responses (Koch-Nolte F. et al., *FASEB J*. November; 21(13):3490-8. Epub 2007 Jun. 15 (2007)). "Diabodies" include small antibody fragments with two antigen-binding sites, wherein the fragments comprise a $V_H$ domain connected to a $V_L$ domain in a single polypeptide chain ($V_H$—$V_L$ or $V_L$—$V_H$) (see, e.g., Holliger P. et al., *Proc Natl Acad Sci USA*. July 15; 90(14):6444-8 (1993); EP404097; WO93/11161). The two domains on the same chain cannot be paired, because the linker is too short, thus, the domains are forced to pair with the complementary domains of another chain, thereby creating two antigen-binding sites. The antigen-binding sites may target the same of different antigens (or epitopes).

A "domain antibody" refers to an antibody fragment containing only the variable region of a heavy chain or the variable region of a light chain. In certain embodiments, two or more $V_H$ domains are covalently joined with a peptide linker to form a bivalent or multivalent domain antibody. The two $V_H$ domains of a bivalent domain antibody may target the same or different antigens.

In certain embodiments, a "(dsFv)$_2$" comprises three peptide chains: two $V_H$ moieties linked by a peptide linker and bound by disulfide bridges to two $V_L$ moieties.

In certain embodiments, a "bispecific ds diabody" comprises $V_{H1}$-$V_{L2}$ (linked by a peptide linker) bound to $V_L$-$V_{H2}$ (also linked by a peptide linker) via a disulfide bridge between $V_{H1}$ and $V_L$.

In certain embodiments, a "bispecific dsFv" or "dsFv-dsFv'" comprises three peptide chains: a $V_{H1}$-$V_{H2}$ moiety wherein the heavy chains are bound by a peptide linker (e.g., a long flexible linker) and paired via disulfide bridges to $V_{L1}$ and $V_{L2}$ moieties, respectively. Each disulfide paired heavy and light chain has a different antigen specificity.

The term "humanized" or "humanized version" as used herein, with reference to antibody or antigen-binding fragment, refers to the antibody or the antigen-binding fragment comprises CDRs derived from non-human animals (e.g. a rodent, rabbit, dog, goat, horse, or chicken), FR regions derived from human, and when applicable, the constant regions derived from human. In certain embodiments, the constant regions from a human antibody are fused to the non-human variable regions. A humanized antibody or antigen-binding fragment is useful as human therapeutics. In certain embodiments because it has reduced immunogenicity or is less likely to induce an immune response in human, as compared to the non-human species antibody. In some embodiments, the non-human animal is a mammal, for example, a mouse, a rat, a rabbit, a goat, a sheep, a guinea pig, a hamster, or a non-human primate (for example, a monkey (e.g., cynomolgus or rhesus monkey) or an ape (e.g., chimpanzee, gorilla, simian or affen)). In some embodiments, the humanized antibody or antigen-binding fragment is composed of substantially all human sequences except for the CDR sequences which are non-human. In some embodiments, the humanized antibody or antigen-binding fragment is modified to improve the antibody performance, such as binding or binding affinity. For example, one or more amino acid residues in one or more non-human CDRs are altered to reduce potential immunogenicity in human, wherein the altered amino acid residues either are not critical for immunospecific binding or the alterations are conservative changes, such that the binding of the humanized antibody to the antigen is not significantly affected. In some embodiments, the FR regions derived from human may comprise the same amino acid sequence as the human antibody from which it is derived, or it may comprise some amino acid changes, for example, no more than 10, 9, 8, 7, 6, 5, 4, 3, 2, or 1 changes of amino acid. In some embodiments, such change in amino acid could be present in heavy chain FR regions only, in light chain FR regions only, or in both chains. In some preferable embodiments, the humanized antibodies comprise human FR1-3 and human JH and Jκ.

The term "chimeric" as used herein refers to an antibody or antigen-binding fragment that has a portion of heavy and/or light chain derived from one species, and the rest of the heavy and/or light chain derived from a different species. In an illustrative example, a chimeric antibody may comprise a constant region derived from human and a variable region derived from a non-human species, such as from mouse.

"Anti-PD-L1 antibody" as used herein refers to an antibody that is capable of specific binding to PD-L1 (e.g. human or non-human primate PD-1) with an affinity which is sufficient to provide for diagnostic and/or therapeutic use.

"Substantially", "substantially the same" as used herein refer to a high degree of similarity between two numeric values, and those skilled in the art would not recognize or consider a significant difference between the two values or of little difference with regard to statistics and/or biological activity as indicated by the values. In contrast, "substantially lower" means that a numeric value is less than about 50%, less than about 40%, less than about 30%, less than about 20%, less than about 10% as a function of the reference value.

The term "specific binding" or "specifically binds" as used herein refers to a non-random binding reaction between two molecules, such as for example between an antibody and an antigen. In certain embodiments, the antibodies or antigen-binding fragments provided herein specifically bind human and/or non-human primate PD-1 with a binding affinity ($K_D$) of about 0.01 nM to about 100 nM, about 0.1 nM to about 100 nM, 0.01 nM to about 10 nM, about 0.1 nM to about 10 nM, 0.01 nM to about 1 nM, about 0.1 nM to about 1 nM or about 0.01 nM to about 0.1 nM) at pH 7.4. $K_D$ as used herein refers to the ratio of the dissociation rate to the association rate ($k_{off}/k_{on}$), may be determined using surface plasmon resonance methods for example using instrument such as Biacore.

The ability to "block binding" or "compete for the same epitope" as used herein refers to the ability of an antibody or antigen-binding fragment to inhibit the binding interaction between two molecules (e.g. human PD-L1 and an anti-PD-L1 antibody) to any detectable degree. In certain embodiments, an antibody or antigen-binding fragment that blocks binding between two molecules inhibits the binding interaction between the two molecules by at least 50%. In certain embodiments, this inhibition may be greater than 60%, greater than 70%, greater than 80%, or greater than 90%.

The term "epitope" as used herein refers to the specific group of atoms (e.g. sugar side chains, phosphoryl groups, sulfonyl groups) or amino acids on an antigen bound by an antigen binding protein, such as an antibody. An epitope can be conformational or linear. A conformational epitope can comprise non-contiguous but spatially juxtaposed amino acid residues due to the three dimensional tertiary folding of a protein, wherein those residues directly contribute to the affinity of the interaction and will lose the ability of interaction when exposed to denaturing solvents. In contrast, all the points of interaction of a linear epitope are arranged linearly along the primary amino acid residues on the protein and the small segments of the contiguous amino acids can be digested from an antigen binding with major histocompatibility complex (MHC) molecules or retained on exposure to denaturing solvents (Salmerón A et al., *J Immunol.* 1991 Nov. 1; 147(9):3047-52; Goldsby et al., *Immunology* (Fifth ed.). New York: W. H. Freeman and Company. pp. 57-75. ISBN 0-7167-4947-5). In one embodiments of the present disclosure, the epitopes bound by the PD-L1 antibodies provided herein is conformational. In another embodiments of the present disclosure, the epitopes bound by the PD-L1 antibodies provided herein is linear. Two antibodies may bind the same epitope within an antigen if they exhibit competitive binding for the antigen. For example, if an antibody or antigen-binding fragment blocks binding of the exemplary antibodies of the present disclosure, such as 21F11, 18G4, 4B6, 26F5, 23A11, 23F11, 22C9, chimeric antibodies thereof, humanized 4B6, humanized 23A11 and humanized 23F11, to human PD-1, then the antibody or antigen-binding fragment may be considered to bind the same epitope as those exemplary antibodies.

A particular amino acid residue within the epitope can be mutated, e.g. by alanine scanning mutagenesis, and mutations that reduce or prevent protein binding are identified. An "alanine scanning mutagenesis" is a method that can be performed for identifying certain residues or regions of a protein that affect the interaction of the epitope with another compound or protein that binds to it. A residue or group of target residues within the protein is replaced by a neutral or negatively charged amino acid (most preferably alanine or polyalanine, or a conservative amino acid substitution). Any mutation of the amino acid residues or codons encoding the same that reduces binding of the protein more than a threshold or reduces binding of the protein to the maximal degree than other mutations is likely to be within the epitope bound by the protein. In certain embodiments of the present disclosure, the epitope that is critical for the pH-dependent PD-L1 antibody comprises at least one of the amino acid residues of E58, N63, S80, Y81 and 164.

The sequences described below can be found in FIG. 34.

"18G4" as used herein refers to a mouse monoclonal antibody having a heavy chain variable region of SEQ ID NO: 55 (corresponding encoding DNA sequences SEQ ID NO: 93), light chain variable region of SEQ ID NO: 56 (corresponding encoding DNA sequences SEQ ID NO: 94). The chimeric antibody thereof (i.e. 18G4-C/18G4-chimeric) comprises a human constant region of IgG1 isotype fused to the mouse variable region.

"4B6" as used herein refers to a mouse monoclonal antibody having a heavy chain variable region of SEQ ID NO: 85, light chain variable region of SEQ ID NO: 86. The chimeric antibody thereof (i.e. 4B6-C/4B6-chimeric) comprises a human constant region of IgG1 isotype fused to the mouse variable region. The heavy chain and light chain of the antibody are humanized to generate humanized heavy chains (H1 corresponds to sequence SEQ ID NO:81; H2 corresponds to sequence SEQ ID NO:83; H3 corresponds to sequence is SEQ ID NO:65 (with encoding DNA sequences SEQ ID NO: 99); and H4 corresponds to sequence SEQ ID NO:67) and light chains (L1 corresponds to sequence SEQ ID NO:82, L2 corresponds to sequence is SEQ ID NO:84, L3 corresponds to sequence SEQ ID NO:66 (with encoding DNA sequences SEQ ID NO: 100) and L4 corresponds to sequence SEQ ID NO:68), thereby producing humanized antibodies, such as 4B6-H3L3, 4B6-H3L4, 4B6-H4L3 and 4B6-H4L4. The humanized antibody can also be produced in CHO cells for small/large scale production with a mutation of N to A at position 297 in the Fc region.

"26F5" as used herein refers to a mouse monoclonal antibody having a heavy chain variable region of SEQ ID NO: 59 (with encoding DNA sequences SEQ ID NO: 97), light chain variable region of SEQ ID NO: 60 (with encoding DNA sequences SEQ ID NO: 98). The chimeric antibody thereof (i.e. 26F5-C/26F5-chimeric) comprises a human constant region of IgG1 isotype fused to the mouse variable region.

"21F11" as used herein refers to a mouse monoclonal antibody having a heavy chain variable region of SEQ ID NO: 57 (with encoding DNA sequences SEQ ID NO: 95), light chain variable region of SEQ ID NO: 58 (with encoding DNA sequences SEQ ID NO: 96). The chimeric antibody thereof ((i.e. 21F11-C/21F11-chimeric) comprises a human constant region of IgG1 isotype fused to the mouse variable region.

"23A11" as used herein refers to a mouse monoclonal antibody having a heavy chain variable region of SEQ ID NO: 73, light chain variable region of SEQ ID NO: 74. The chimeric antibody thereof (i.e. 23A11-C/23A11-chimeric)

comprises a human constant region of IgG1 isotype fused to the mouse variable region. The heavy chain and light chain of the antibody are humanized to generate humanized heavy chains (H3 corresponds to sequence SEQ ID NO:71 (with encoding DNA sequences SEQ ID NO: 103); H5 corresponds to sequence SEQ ID NO:69) and light chains (L3 corresponds to sequence SEQ ID NO:72, L5 corresponds to sequence SEQ ID NO:70 (with encoding DNA sequences SEQ ID NO: 104)), thereby producing humanized antibodies in 293 cells, such as 23A11-H3L5, 23A11-H5L3, 23A11-H3L3 and 23A11-H5L5. The antibody can also be produced in CHO cells for small/large scale production, such as 23A11-H3L5 (the corresponding sequences of H3 and L5 are SEQ ID NO: 61 and SEQ ID NO: 62, respectively) with a mutation of N to A at position 297 in the Fc region.

"23F11" as used herein refers to a mouse monoclonal antibody having a heavy chain variable region of SEQ ID NO: 79, light chain variable region of SEQ ID NO: 80. The chimeric antibody thereof (i.e. 23F11-C/23F11-chimeric) comprises a human constant region of IgG1 isotype fused to the mouse variable region. The heavy chain and light chain of the antibody are humanized to generate humanized heavy chains (H4 corresponds to sequence SEQ ID NO:75 (with encoding DNA sequences SEQ ID NO: 105); H6 corresponds to sequence SEQ ID NO:77) and light chains (L4 corresponds to sequence SEQ ID NO:76 (with encoding DNA sequences SEQ ID NO: 106), L6 corresponds to sequence SEQ ID NO:78), thereby producing humanized antibodies in 293 cells, such as 23F11-H4L4, 23F11-H6L4, 23F11-H4L6, 23F11-H6L6. The antibody can also be produced in CHO cells for small/large scale production, such as 23F11-H4L4 (the corresponding sequences of H4 and L4 are SEQ ID NO: 63 and SEQ ID NO: 64, respectively) with a mutation of N to A at position 297 in the Fc region.

"22C9" as used herein refers to a mouse monoclonal antibody having a heavy chain variable region of SEQ ID NO: 21 (with encoding DNA sequences SEQ ID NO: 101), light chain variable region of SEQ ID NO: 22 (with encoding DNA sequences SEQ ID NO: 102). The chimeric antibody thereof (i.e. 22C9-C/22C9-chimeric) comprises a human constant region of IgG1 isotype fused to the mouse variable region.

A "conservative substitution" with reference to amino acid sequence refers to replacing an amino acid residue with a different amino acid residue having a side chain with similar physiochemical properties or substitution of those amino acids that are not critical to the activity of the polypeptide. For example, conservative substitutions can be made among amino acid residues with nonpolar side chains (e.g. Met, Ala, Val, Leu, and Ile, Pro, Phe, Trp), among residues with uncharged polar side chains (e.g. Cys, Ser, Thr, Asn, Gly and Gln), among residues with acidic side chains (e.g. Asp, Glu), among amino acids with basic side chains (e.g. His, Lys, and Arg), among amino acids with beta-branched side chains (e.g., Thr, Val and Ile), among amino acids with sulfur-containing side chains (e.g., Cys and Met), or among residues with aromatic side chains (e.g. Trp, Tyr, His and Phe). In certain embodiments, substitutions, deletions or additions can also be considered as "conservative substitution". The number of amino acids that are inserted or deleted can be in the range of about 1 to 5. As known in the art, conservative substitution usually does not cause significant change in the protein conformational structure, and therefore could retain the biological activity of a protein.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum correspondence. Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

As used herein, a "homologue sequence" and "homologous sequence" are used interchangeable and refer to polynucleotide sequences (or its complementary strand) or amino acid sequences that have sequences identity of at least 80% (e.g. at least 85%, 88%, 90%, 91%, 92%, 93%, 94%, 95%, 96%, 97%, 98%, 99%) to another sequences when optionally aligned.

"T cell" as used herein refers to a type of lymphocyte that plays a critical role in the cell-mediated immunity, including helper T cells (e.g. $CD4^+$ T cells, T helper 1 type T cells, T helper 2 type T cells, T helper 3 type T cells, T helper 17 type T cells), cytotoxic T cells (e.g. $CD8^+$ T cells), memory T cells (e.g. central memory T cells (TCM cells), effector memory T cells (TEM cells and TEMRA cells) and resident memory T cells (TRM) that are either CD8+ or CD4+), natural killer T (NKT) cells and inhibitory T cells.

"Effector functions" or "antibody effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and C1q on the C1 complex; antibody-dependent cell-mediated cytotoxicity (ADCC) induced by binding of Fc region of an antibody to Fc receptor on an effector cell; and phagocytosis. "Reduce or deplete effector functions" refers to the antibody effector function is reduced by at least 50% (e.g. 60%, 70%, 80%, 90%, 95%, 96%, 97%, 98%, 99%) from the parent antibody. In certain embodiments, the effector function is eliminated through a mutation in the Fc region to eliminate glycosylation, e.g. N297A or D265A (see Shields et al., *J. Biol. Chem.* 276 (9): 6591-6604 (2001)), K322A, L234A/L235A. "Fc region" as used herein refers to a C-terminal region of an immunoglobulin heavy chain.

"Cancer" or "cancerous condition" as used herein refers to any medical condition characterized by malignant cell growth or neoplasm, abnormal proliferation, infiltration or metastasis, and includes both solid tumor cancers and non-solid cancers (hematologic malignancies) such as leukemia. Solid tumors include sarcomas and carcinomas. Sarcomas are non-epithelial tumors in a blood vessel, bone, fat tissue, ligament, lymph vessels, muscle or tendon, whereas carcinomas are epithelial tumors in the skin, glands and the linings of organs. "Tumor" as used herein refers to a solid mass of neoplastic and/or malignant cells.

"Treating", "treatment" or "therapy" of a condition as used herein can be used interchangeably, and includes therapeutic treatment, prophylactic or preventative measures, such as preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof. With regard to cancer, "treating", "treatment" or "therapy" may refer to inhibiting or slowing neoplastic or malignant cell growth (such as reducing the tumor volume as compared to a control), proliferation, infiltration into other organs or metastasis, preventing, delaying or halting the development of neoplastic or malignant cell growth, proliferation, or metastasis, or some combinations thereof. With regard to a tumor, "treating" or "treatment" includes eradicating all or part of a tumor, inhibiting or slowing tumor growth and metastasis, preventing or delaying the development of a tumor, or some combinations thereof. An "isolated" substance has been altered by the hand of man from the natural state. If an "isolated" composition or substance occurs in nature, it has been changed or removed from its original environment, or both. For example, an "isolated" polynucleotide or polypeptide is a polynucleotide or a polypeptide that is free of other polynucleotides or polypeptides, respectively, and is not associated with naturally components that accompany the polynucleotide or a polypeptide in the native state. In certain embodiments, an "isolated" antibody is purified by at least one step to a purity of at least 90%, 91%, 92%, 93%, 94%, 95%, 96%, 97%, 98%, 99% as determined by electrophoretic methods (such as SDS-PAGE using Coomassie blue or silver stain, isoelectric focusing, capillary electrophoresis), chromatographic methods (such as ion exchange chromatography or reverse phase HPLC) or Lowry method.

The term "vector" as used herein refers to a vehicle into which a polynucleotide encoding a protein may be operably inserted and transported so as to express that protein in a host cell. A vector may be used to transform, transduce, or transfect a host cell so as to bring about the expression of the genetic element it carries within the host cell. Exemplary types of vectors includes, but not limited to, plasmids (e.g. phagemids, cosmids, yeast artificial chromosome (YAC), bacterial artificial chromosome (BAC) or P1-derived artificial chromosome (PAC)), viral vector (bacteriophages such as lambda phage or M13 phage, or animal viruses), bacterial vector, or non-episomal mammalian vectors. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector (e.g. a bacterial vector or episomal mammalian vector) may contain an origin of replication. A vector may also include materials to aid in its entry into the cell, including but not limited to a viral particle, a liposome, or a protein coating.

The "host cell" as used herein refers to a cell into which an exogenous polynucleotide and/or a vector has been introduced to express one or more exogenous proteins. It intends to refer to both the particular subject cell and the progeny thereof. A host cell can be a prokaryote, a eukaryote, a plant cell, an animal cell or a hybridoma. It can be a cell that does not express a protein at a desired level but comprises the nucleic acid, unless a regulatory agent is introduced into the cell or a regulatory sequence is introduced into the host cell so that it is operably linked with the nucleic acid.

A "PD-L1 associated condition" as used herein refers to any condition that is caused by, exacerbated by, or otherwise linked to increased or decreased expression or activities of PD-L1 (e.g. a human PD-L1).

The term "therapeutically effective amount" or "effective dosage" as used herein refers to the dosage or concentration of a drug effective to treat a disease or condition associated with human PD-L1. For example, with regard to the use of the antibodies or antigen-binding fragments disclosed herein to treat cancer, a therapeutically effective amount is the dosage or concentration of the antibody or antigen-binding fragment capable of reducing the tumor volume, eradicating all or part of a tumor, inhibiting or slowing tumor growth or cancer cell infiltration into other organs, inhibiting growth or proliferation of cells mediating a cancerous condition, inhibiting or slowing tumor cell metastasis, ameliorating any symptom or marker associated with a tumor or cancerous condition, preventing or delaying the development of a tumor or cancerous condition, or some combination thereof.

The term "pharmaceutically acceptable" indicates that the designated carrier, vehicle, diluent, excipient(s), and/or salt are generally chemically and/or physically compatible with the other ingredients comprising the formulation, and physiologically compatible with the recipient thereof.

The term "receptor occupancy" refers to the ratio of receptors occupied by a ligand at equilibrium and the total number of receptors available, usually expressed as a percentage of the total number of receptors. The duration of receptor occupancy can be evaluated by measuring and comparing the receptor occupancy at different time points. Measurement of receptor occupancy are known in the art, such as FACS, Positron Emission Computed Tomography (PET), autoradiography, etc.

Anti-PD-L1 Antibody

The present disclosure provides anti-PD-L1 antibodies and the antigen-binding fragments thereof. In certain embodiments, the present disclosure provides exemplary monoclonal antibodies 21F11, 18G4, 4B6, 26F5, 23A11, 23F11, 22C9, the chimeric antibodies thereof, humanized 4B6, humanized 23A11 and humanized 23F11.

In certain embodiments, the anti-PD-L1 antibodies and the antigen-binding fragments thereof are pH-dependent in binding to the antigen (e.g. human PD-L1). The antigen binding exhibited by the pH-dependent antibodies at physiological neutral pH (i.e. pH 7.4) is greater than acidic pH 5.5 or 6.0 (e.g. at endosomal pH). Such pH-dependent antibodies preferentially dissociate from the antigen in the endosome. This can increase antibody halflife when the antigen undergoes antigen-mediated clearance, because the pH-dependent antibody can escape the antigen-mediated degradation in the lysozome by dissociating from the antigen in endosome and recycling out of the cell. Advantages of the pH-dependent antibodies include lower dosage of the therapeutic pH-dependent antibody (no more than 80%, 70%, 60%, 50%, 40%, 30%, 20% or 10% of the dosage that would otherwise be required for a reference PD-L1 antibody to achieve a comparable in vivo therapeutic effect) or less dosing frequency due to the improved recyclability and enhanced serum half-life, as compared to a reference PD-L1 antibody, both of which achieve a comparable in vivo therapeutic effect. The reference antibody is non-pH dependent, such that it binds to PD-L1 similarly at both acidic and neutral pH and has a similar binding at neutral pH as compared to the pH-dependent antibodies. In certain embodiments, the pH-dependent antibodies possess the above advantages when compared to its non-pH-dependent version that has the same binding to PD-L1.

In certain embodiments, the specific binding of the pH-dependent anti-PD-L1 antibody and the antigen-binding fragments thereof to human PD-L1 is greater at neutral pH (e.g. pH7.4) than that at acidic pH (e.g. pH6.0, 5.5, 5.0, 4.5 or 4.0). In certain embodiments, the binding of the antibody to PD-L1 at acidic pH5.5 is substantially lower than its binding to PD-L1 at pH7.4 at the same assay setting. In certain embodiments, the binding of the PD-L1 antibody and the antigen-binding fragments thereof provided herein at acidic pH is at most 2%, 5%, 10%, 25%, 30%, 35%, 40%, 45%, 50%, 55%, 60%, 65%, 70%, 75%, 80%, or 85% of that at neutral pH (i.e. 7.4) as measured by ELISA. In certain embodiments, the $K_D$ ratio, and/or Koff ratio of the pH-dependent anti-PD-L1 antibody to human PD-L1 at acidic pH/neutral pH is 2, 3, 4, 5, 8, 10, 15, 20, 30, 40, or 100 or more. In certain embodiments, the dissociative half-life (t 1/2) of the pH-dependent anti-PD-L1 antibody to human PD-L1 is less than 5, 4, 3, 2, 1, 0.5, 0.2 or 0.1 min at acidic pH at 25° C. or 37° C. In certain embodiments, the pH-dependent anti-PD-L1 antibody and the antigen-binding fragments thereof to human PD-L1 described herein has a decrease in dissociative half-life (t.sub.1/2) at acidic pH as compared to that of a reference PD-L1 antibody at neutral pH of at least about 2, 3, 5, 8, 10, 15, 20, 30, 50, or 100-fold. In certain embodiments, the reduction of the in vivo amount of PD-1 protein is prolonged when exposed to the pH-dependent anti-PD-L1 antibody as compared to a reference PD-L1 antibody that has a similar binding to PD-L1 at neutral pH. In certain embodiments, the pH-dependent anti-PD-L1 antibody and the antigen-binding fragments thereof bind to human PD-L1 has an increased target organ half life upon administration of a certain dose as compared to that of a reference PD-L1 antibody of the same dose. In certain embodiments, the antibody and the antigen-binding fragments thereof have an in vivo half life in a target organ that would otherwise be shorter for the antibody, if it displayed similar binding to PD-L1 at both acidic pH and neutral pH. In certain embodiments, the target organ includes but not limited to, blood or serum, kidney, lung, pancreas, liver, gallbladder, bladder, skin, esophagus, ovarian, breast, colon, rectum, stomach, spleen or brain.

A skilled artisan will understand that the CDR sequences provided herein can be modified to contain one or more substitutions (or insertion or deletion) of amino acid residues, such that the resulting antibody is improved in one or more properties (such as improved binding or binding affinity, increased pharmacokinetic half-life, pH sensitivity, compatibility to conjugation reduced risk of glycosylation and/or deamination on a CDR residue, and reduced immunogenicity), and is otherwise comparable to the parent antibody (i.e. antibody having otherwise the same set of CDR sequences except for the above-mentioned modification or change), or at least substantially retains the antigen-binding property of the parent antibody. For example, a library of antibody variants (such as Fab or scFv variants) can be generated and expressed with phage display technology, and then screened for the binding or binding affinity to human PD-L1. For another example, computer software can be used to virtually simulate the binding of the antibodies to human PD-L1, and identify the amino acid residues on the antibodies which form the binding interface. Such residues may be either avoided in the substitution so as to prevent reduction in binding or binding affinity, or targeted for substitution to provide for a stronger binding. In certain embodiments, at least one (or all) of the substitution(s) in the CDR sequences is conservative substitution.

In certain embodiments, the antibodies and the antigen-binding fragments thereof comprise one or more CDR sequences having at least 80% (e.g. at least 85%, 88%, 90%, 91%, 92%, 93%, 94%, 95%, 96%, 97%, 98%, 99%) sequence identity to that (or those) provided herein, and in the meantime retain the binding activity or binding affinity to human PD-L1 at a level similar to or even higher than its parental antibody having substantially the same sequence except that the corresponding CDR sequence is in 100% sequence identity to that (or those) provided herein.

In certain embodiments, the anti-PD-L1 antibodies and the antigen-binding fragments thereof are chimeric. The chimeric antibody contains one or more regions from an antibody and one or more regions from other antibodies or species. In certain embodiments, at least one CDR of the chimeric anti-PD-L1 antibody is derived from one species. In certain embodiments, all of the CDRs are derived from another species. In certain embodiments, a variable region of the chimeric anti-PD-L1 antibody is derived from one species and is linked to a constant region of an antibody of another species. The chimeric antibody retains the binding activity or binding affinity of the parent antibody.

In certain embodiments, the anti-PD-L1 antibodies and the antigen-binding fragments thereof are humanized. In certain embodiments, the humanized antibody originated from non-human species, and several amino acid residues in the framework and constant regions of the heavy and light chains have been mutated to reduce or avoid an immunogenicity in humans. In certain embodiments, the variable regions of a non-human species is fused to the constant regions of a human antibody. In certain embodiments, the humanized antibody is created by CDR grafting, i.e. replacing the CDR of a human antibody with the corresponding CDR of a non-human antibody. Thus, the immunogenicity of the humanized antibody in human is low. In certain embodiments, the human framework regions are substituted with one or more amino acid residues from the non-human antibody (e.g. mouse framework region) from which the CDR sequences are derived, for example, to improve or retain the binding activity or binding affinity. In certain embodiments, the humanized antibody retains or increases the binding activity or binding affinity of the parent antibody.

In some embodiments, the chimeric or humanized anti-PD-L1 antibodies and the antigen-binding fragments thereof comprise a heavy chain variable region selected from the group consisting of: SEQ ID NO: 21, 47, 55, 57, 59, 61, 63, 65, 67, 69, 71, 73, 75, 77, 79, 81, 83 and 85, and a homologous sequence thereof having at least 80% (e.g. at least 85%, 88%, 90%, 91%, 92%, 93%, 94%, 95%, 96%, 97%, 98%, 99%) sequence identity; and/or a light chain variable region selected from the group consisting of: SEQ ID NO: 22, 48, 56, 58, 60, 62, 64, 66, 68, 70, 72, 74, 76, 78, 80, 82, 84 and 86, and a homologous sequence thereof having at least 80% (e.g. at least 85%, 88%, 90%, 91%, 92%, 93%, 94%, 95%, 96%, 97%, 98%, 99%) sequence identity. These humanized antibodies retain the binding activity or binding affinity to human PD-L1, preferably at a level similar to one of the exemplary antibodies: 4B6, 18G4, 26F5, 21F11, 23A11, 23F11, 22C9, and the chimeric antibodies thereof, humanized 4B6, humanized 23F11 and humanized 23A11.

In certain embodiments, the PD-L1 antibodies of 4B6, 26F5, 21F11, 23A11, 23F11, 22C9, and the chimeric antibodies thereof, humanized 4B6, humanized 23F11 and humanized 23A11 bind to human and non-human primate PD-L1, but not to mouse PD-L1. In certain embodiments, the PD-L1 antibodies (e.g. 18G4), the chimeric antibodies thereof and the antigen-binding fragments thereof can bind to both human and mouse PD-L1. The binding activity or binding affinity are determined based on a competition assay such as ELISA assays, radio-ligand competition binding assays, and FACS analysis.

In some embodiments, the anti-PD-L1 antibodies and the antigen-binding fragments thereof provided herein are capable of specifically binding to human PD-L1 with a binding affinity (Kd) of about $10^{-7}$ M or less (e.g. $10^{-8}$ M, $10^{-9}$ M, $10^{-10}$ M, $10^{-11}$ M, $10^{-12}$ M) as measured by plasmon resonance binding assay. The binding affinity can be represented by $K_D$ value, which is calculated as the ratio of dissociation rate to association rate ($k_{off}/k_{on}$) when the binding between the antigen and the antigen-binding molecule reaches equilibrium. The antigen-binding affinity (e.g. $K_D$) can be appropriately determined using suitable methods known in the art, including, for example, plasmon resonance binding assay using instruments such as Biacore (see, for example, Murphy, M. et al, Current protocols in protein science, Chapter 19, unit 19.14, 2006).

In certain embodiments, the PD-L1 antibody and the antigen-binding fragments thereof are capable of binding to hPD-L1 with EC50 (i.e. 50% binding concentration) of 0.001 µg/ml-1 µg/ml (e.g. 0.001 µg/ml-0.5 µg/ml, 0.001 µg/ml-0.2 µg/ml, 0.001 µg/ml-0.1 µg/ml, 0.01 µg/ml-0.2 µg/ml, 0.01 µg/ml-0.1 µg/ml, 0.01 µg/ml-0.05 µg/ml, 0.01 µg/ml-0.03 µg/ml or 0.001 µg/ml-0.01 µg/ml) as measured by ELISA, or EC50 of 0.01 µg/ml-1 µg/ml (e.g. 0.01 µg/ml-0.5 µg/ml, 0.01 µg/ml-0.2 µg/ml, 0.05 µg/ml-1 µg/ml, 0.05 µg/ml-0.5 µg/ml or 0.05 µg/ml-0.2 µg/ml) as measured by FACS. Binding of the antibodies to human PD-L1 can be measured by methods known in the art, for example, ELISA, FACS, surface plasmon resonance, GST pull down, epitope-tag, immunoprecipitation, Far-Western, fluorescence resonance energy transfer, time resolved fluorescence immunoassays (TR-FIA), radioimmunoassays (RIA), enzyme immunoassays, latex agglutination, Western blot, and immunohistochemistry or other binding assay. In an illustrative example, the test antibody (i.e. first antibody) is allowed to bind to immobilized human PD-L1 or cells expressing human PD-L1, after washing away the unbound antibody, and a labeled secondary antibody is introduced which can bind to and thus allow the detection of the bound first antibody. The detection can be conducted with a microplate reader when immobilized PD-L1 is used, or by using FACS analysis when the cells expressing human PD-L1 are used.

In certain embodiments, the antibodies and the fragments thereof provided herein inhibit the binding of human PD-1 to human PD-L1 at an $IC_{50}$ of 0.05 µg/ml-1 µg/ml (e.g. 0.05 µg/ml-0.8 µg/ml, 0.05 µg/ml-0.5 µg/ml or 0.05 µg/ml-0.3 µg/ml) as measured in FACS or an $IC_{50}$ of 0.001 µg/ml-0.5 µg/ml (e.g. 0.001 µg/ml-0.2 µg/ml, 0.001 µg/ml-0.1 µg/ml, 0.001 µg/ml-0.05 µg/ml, 0.001 µg/ml-0.02 µg/ml, 0.005 µg/ml-0.05 µg/ml, 0.005 µg/ml-0.02 µg/ml or 0.005 µg/ml-0.01 µg/ml) as measured in ELISA.

In certain embodiments, the antibodies and the fragments thereof provided herein block the binding of human PD-L1 to its receptor (i.e. human PD-1) and thereby provide biological activity including, for example, inducing cytokine production from the activated T cells (such as CD4+ T cells and CD8+ T cells), inducing proliferation of activated T cells (such as CD4+ T cells and CD8+ T cells), and reversing T reg's suppressive function. Exemplary cytokines include TL-2 and IFNγ. The term "IL-2" refers to interleukin 2, a type of cytokine signaling molecule in the immune system that regulates the activities of white blood cells (e.g. leukocytes). The term "Interferon gamma (IFNγ)" is a cytokine that is produced by natural killer (NK), NK T cells, CD4+ and CD8+ T cells, which are critical activators of macrophages and inducers of major histocompatibility complex (MHC) molecule expression. The cytokine production can be determined using methods known in the art, for example, by ELISA. Methods can also be used to detect proliferation of T cells, including [$^3$H] thymidine incorporation assay and luminescent cell viability assay.

The anti-PD-L1 antibodies and the antigen-binding fragments thereof are specific for human PD-L1 and/or non-human primate. In certain embodiments, the antibodies and antigen-binding fragments thereof do not bind to PD-L2 (e.g. human PD-L2). For example, the binding affinity with PD-L2 is less than 15%, 10%, 9%, 8%, 7%, 6%, 5%, 4%, 3%, 2%, or 1% of that with human PD-L1.

In certain embodiments, the antibodies and antigen-binding fragments thereof bind to non-human primate PD-L1 at an EC50 of 0.001 µg/ml-0.5 µg/ml (e.g. 0.001 µg/ml-0.2 µg/ml, 0.001 µg/ml-0.1 µg/ml, 0.001 µg/ml-0.05 µg/ml, 0.001 µg/ml-0.02 µg/ml, 0.005 µg/ml-0.05 µg/ml, 0.005 µg/ml-0.02 µg/ml or 0.005 µg/ml-0.01 µg/ml) as measured in ELISA.

The anti-PD-L1 antibodies and the antigen-binding fragments thereof are specific for human PD-L1 and/or non-human primate PD-L1. In certain embodiments, the antibodies and antigen-binding fragments thereof do not bind to mouse PD-L1. For example, the binding affinity with mouse PD-L1 is less than 15%, 10%, 9%, 8%, 7%, 6%, 5%, 4%, 3%, 2%, or 1% of that with human PD-L1.

In certain embodiments, the antibodies and antigen-binding fragments thereof do not bind to mouse PD-L1 but bind to non-human primate PD-L1 with a binding activity or binding affinity similar to that of human PD-L1. For example, the binding of the exemplary antibodies 4B6, 26F5, 21F11, 23A11, 23F11, 22C9, and the chimeric antibodies thereof, humanized 4B6, humanized 23F11 and humanized 23A11 to mouse PD-L1 is very low in conventional binding assays such as ELISA, or FACS analysis, whereas the binding of these antibodies to non-human primate PD-L1 is similar to that of human PD-L1 as measured by ELISA or FACS. In certain embodiments, the antibodies and antigen-binding fragments thereof (such as 18G4) bind to mouse PD-L1 as well as to non-human primate PD-L1 with a binding activity or binding affinity similar to that of human PD-L1.

In certain embodiments, the anti-PD-L1 antibodies and antigen-binding fragments thereof provided herein can be used in combination with immunogenic agents, such as tumor cells, purified tumor antigen, and cells transfected with genes encoding immune stimulating cytokines, tumor vaccines. In addition, the anti-PD-L1 antibodies and antigen-binding fragments thereof can be included in combination therapies, including standard chemo- and radio-therapies (e.g. radiotherapy, X-ray therapy), target based small molecule therapies (e.g. tyrosine kinase inhibitors imatinib, gefitinib; monoclonal antibodies, photodynamic therapy), immune therapy (e.g. antibodies against tumor markers, such as carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb Band p155, DLL4, Notch1, Notch2/3, Fzd7, or Wnt, r-spondin (RSPO) 1, RSPO2, RSPO3 or RSPO4), emerging other immune checkpoint modulator therapies (e.g. vaccine), hormonal therapy, angiogenesis inhibition (angiogenesis inhibitor), gene therapy (inducers of cellular proliferation, inhibitors of cellular proliferation, or regulators of programmed cell death), palliative care (i.e. treatment directed to improving the quality of care to reduce pain (e.g. morphine and oxycodone), nausea, vomiting (e.g. ondansetron and aprepitant), diarrhea and hemorrhage) and surgery. In certain embodiments, the antibodies and antigen-binding fragments thereof can be used as the base of antibody-drug conjugates, bispecific or multivalent antibodies.

The anti-PD-L1 antibodies and antigen-binding fragments thereof provided herein can be a monoclonal antibody, polyclonal antibody, humanized antibody, chimeric antibody, recombinant antibody, bispecific antibody, labeled antibody, bivalent antibody, or anti-idiotypic antibody. A recombinant antibody is an antibody prepared in vitro using recombinant methods rather than in animals. A bispecific or bivalent antibody is an artificial antibody having fragments of two different monoclonal antibodies and can bind to two different antigens. An antibody or antigen-binding fragment thereof that is "bivalent" comprises two antigen-binding sites. The two antigen binding sites may bind to the same antigen, or they may each bind to a different antigen, in which case the antibody or antigen-binding fragment is characterized as "bispecific."

In some embodiments, the anti-PD-L1 antibodies and antigen-binding fragments thereof provided herein are humanized or chimeric antibodies. In certain embodiments, the humanized or chimeric antibodies are prepared using recombinant methods. For example, a non-human animal can be immunized with proper antigen such as human PD-L1 protein. Gene fragments encoding the antibody variable regions that bind to the antigen are cut out from the gene of a monoclonal antibody of the mouse, and this portion is operably linked to a gene of the constant region of an antibody derived from human IgG1. The recombinant gene fragment is incorporated into an expression vector, which is then introduced into a host cell for the production of a chimeric antibody (see U.S. Pat. Nos. 4,816,397; 4,816,567; 5,807,715).

A "humanized antibody" is an antibody obtained by grafting a non-human derived antibody CDR gene onto a human antibody gene, so that the variable region framework and constant regions are, if present, entirely or substantially from human antibody sequences. The methods for preparing a humanized antibody are known in the art (see, for example, U.S. Pat. Nos. 5,225,539, 5,530,101, 6,407,213; 5,859,205; 6,881,557 EP239400, EP125023, WO90/07861, and WO96/02576). In certain embodiments, a humanized antibody comprises a humanized heavy chain and a humanized light chain. In certain embodiments, the sequence of a grafted CDR in the humanized PD-L1 antibody is at least 60%, 70%, 80%, 82%, 85%, 88%, 90%, 95% or 100% identical to the corresponding CDR. In certain embodiments, no more than 3 conservative amino acid substitutions occurs in a CDR of the humanized PD-L1 antibody. In certain embodiments, the amino acid residues of the variable region framework of the humanized PD-L1 antibody are substituted for sequence optimization. In certain embodiments, the variable region framework sequences of the humanized PD-L1 antibody chain are at least 65%, 70%, 75%, 80%, 85%, 90%, 95% or 100% identical to the corresponding human variable region framework sequences.

In some embodiments, the anti-PD-L1 antibody and the antigen-binding fragment thereof is a camelized single domain antibody, a diabody, a scFv, an scFv dimer, a BsFv, a dsFv, a (dsFv)$_2$, a dsFv-dsFv', an Fv fragment, a Fab, a Fab', a F(ab')$_2$, a ds diabody, a nanobody, a domain antibody, an isolated CDR or a bivalent domain antibody.

In some embodiments, the anti-PD-L1 antibodies and the antigen-binding fragments thereof further comprise an immunoglobulin constant region. In some embodiments, an immunoglobulin constant region comprises a heavy chain and/or a light chain constant region. The heavy chain constant region comprises CH1, CH1-CH2, or CH1-CH3 regions. In some embodiments, the constant region may further comprise one or more modifications to confer desirable properties. For example, the constant region may be modified to reduce or deplete one or more effector functions, to improve FcRn receptor binding, or to introduce one or more cysteine residues.

In certain embodiments, the anti-PD-L1 antibodies and the antigen-binding fragments thereof are thermostability improved. The term "thermostability" or "thermotolerance" as used herein refers to the functional stability of the anti-PD-L1 antibody instead of the thermodynamic properties and to the antibody's resistance to irreversible denaturation caused by thermal and/or physical/chemical manipulations including, but not limited to, heating, cooling, freezing, freeze-thaw cycle, vibration, vortex, ultrasonication, chemical denaturants, pH, detergents, salts, additives, proteases or temperature. Irreversible denaturation leads to the irreversible unfolding of the functional conformations of the antibody, loss of biological activity and aggregation of the denaturated protein. The increase of stability to heat can be determined by measuring ligand binding or by using spectroscopic methods such as fluorescence, circular dichroism (CD) or light scattering that are sensitive to unfolding at increasing temperatures. The PD-L1 antibody provided herein is capable of increasing the stability as measured by an increase in the thermalstability in a functional conformational state with at least 2° C., at least 5° C., at least 8° C., at least 10° C., at least 15° C., at least 20° C. or at least 30° C. The thermostability of the antibodies provided herein can be measured, for example, by differential scanning fluorimetry (DSF) or differential scanning calorimetry (DSC) (see He F et al., J Pharm Sci. 2011 April; 100(4):1330-40.), wherein the thermal transition midpoint (Tm) is measured and indicates the relative stability of the protein in liquid. In certain embodiments, the Tm of a PD-L1 antibody is more than 74° C., more than 76° C., more than 78° C., more than 80° C., more than 82° C., more than 84° C., more than 86° C., more than 88° C., more than 90° C., or more than 92° C., more than 94° C., more than 96° C., or more than 98° C. In certain embodiments, the PD-L1 antibody with improved thermostability is 23F11 (e.g. 23F11-H4L4, 23A11-H6L4, 23A11-H4L6, or 23A11-H6L6), which has the thermal transition midpoint (Tm) of more than 90° C.

In some embodiments, the anti-PD-L1 antibodies and the antigen-binding fragments thereof further form an antibody-drug-conjugates (ADC's). It is contemplated that a variety of payload may be linked to the antibodies or antigen-binding fragments provided herein (see, for example, "Conjugate Vaccines", Contributions to Microbiology and Immunology, J. M. Cruse and R. E. Lewis, Jr. (eds.), Carger Press, New York, (1989)). The term of "payload (s)" are used interchangeable with "drug (s)", and these payloads may be linked to the antibodies or antigen-binding fragments by covalent binding, affinity binding, intercalation, coordinate binding, complexation, association, blending, or addition, among other methods. In certain embodiments, the antibodies and antigen-binding fragments disclosed herein may be engineered to contain specific sites outside the epitope binding portion that may be utilized for binding to one or more payloads, such as peptides, nucleic acid molecules, drugs, cytotoxins, polypeptides, proteins, fusion proteins, antibodies, haptens, small molecules, mimetic agents, synthetic drugs, inorganic molecules, organic molecules, radioisotopes and reporter groups. For example, such a site may include one or more reactive amino acid residues, such as for example cysteine or histidine residues, to facilitate covalent linkage to a payload. In certain embodiments, the antibodies may be linked to a payload indirectly via a linker, or through another payload. For example, the antibody or antigen-binding fragments may be conjugated to biotin, then indirectly conjugated to a second payload that is conjugated to avidin. The payload can be a reporter group or a detectable label, a pharmacokinetic modifying moiety, a purification moiety, or a cytotoxic moiety. Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luceriferases, glucoamylase, lysozyme, saccharide oxidases or β-D-galactosidase), radioisotopes (e.g. 123I, 124I, 125I, 131I, 35S, 3H, 111In, 112In, 14C, 64Cu, 67Cu, 86Y, 88Y, 90Y, 177Lu, 211At, 186Re, 188Re, 153Sm, 212Bi, and 32P, other lanthanides, luminescent labels), chromophoric moiety, digoxigenin, biotin/avidin, a DNA molecule or gold for detection. In certain embodiments, the payload can be a pharmacokinetic modifying moiety such as PEG which helps increase half-life of the antibody. Other suitable polymers include, such as, carboxymethylcellulose, dextran, polyvinyl alcohol, polyvinyl pyrrolidone, copolymers of ethylene glycol/propylene glycol, and the like. In certain embodiments, the payload can be a purification moiety such as a magnetic bead. A payload of "cytotoxic" moiety can be any agent that is detrimental to cells or that can damage or kill cells. Examples of cytotoxic moiety include, without limitation, a chemotherapeutic agent, an anti-tumor agent, a growth inhibitor, a drug, a toxin, such as, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, platiniums (e.g., cisplatin and oxaliplatin), plant alkaloids (e.g., topoisomerase inhibitors, *vinca* alkaloids, taxanes, and epipodophyllotoxins) and anthramycin (AMC)), and anti-mitotic agents (e.g., vincristine and vinblastine). The term "loading" or "drug loading" or "payload loading" as used herein refers to the average number of drugs/payloads per antibody. The drug loading can be within the range from 1 to 20 (e.g. from 1 to 15, 1 to 10, 2 to 10, 1 to 8, 2 to 8, 2 to 6, 2 to 5 or 2 to 4) drugs per antibody (also as drug to antibody ratio), as determined by suitable methods in the art, such as mass spectrometry, UV/visible spectroscopy, ELISA assay, and HPLC. In certain embodiments, the drug loading is 1, 2, 3, 4, 5, 6, 7, 8, 9 or 10.

Polynucleotides and Recombinant Methods

The present disclosure provides isolated polynucleotides that encode the anti-PD-L1 antibodies and the antigen-binding fragments thereof. In certain embodiments, the isolated polynucleotides comprise one or more nucleotide sequences encoding the CDR sequences provided in the present disclosure.

The process of producing the monoclonal anti PD-L1 antibody or the antigen-binding fragments thereof includes: Immunizing a suitable animal with human PD-L1 protein or hPD-L1 producing cells. The animal can be mouse, rat, sheep, goat, rabbit, or guinea pig. Generate hybridoma using the spleen or the lymph node or gathering B cells of the immunized animal and measuring the PD-L1 antibodies titer. Clone the polynucleotides encoding the PD-L1 antibodies or the antigen-binding fragments thereof with suitable titer from the hybridoma or B cell clones from the immunized animal. The cloned or modified (e.g. chimeric, humanized) polynucleotides are incorporated into a suitable vector, which is then introduced into host cells to produce of the antibody of the disclosure. The antibody and the antigen-binding fragments thereof provided herein can be obtained in a substantially pure and homogeneous form by culturing the host cells, followed by separation and purification of the host cells or the culture liquid (e.g. supernatant). For the separation and purification of the antibody or the antigen-binding fragments thereof, an ordinary method used for polypeptide purification can be employed.

In some embodiments, the isolated polynucleotides encodes a heavy chain variable region and comprise a sequence selected from the group consisting of: SEQ ID NO: 93, 95, 97, 99, 101, 103 and 105, and a homologous sequence thereof having at least 80% (e.g. at least 85%, 88%, 90%, 91%, 92%, 93%, 94%, 95%, 96%, 97%, 98%, 99%) sequence identity. In some embodiments, the isolated polynucleotides encode a light chain variable region and comprise a sequence selected from the group consisting of: SEQ ID NO: 94, 96, 98, 100, 102, 104 and 106, and a homologous sequence thereof having at least 80% (e.g. at least 85%, 88%, 90%, 91%, 92%, 93%, 94%, 95%, 96%, 97%, 98%, 99%) sequence identity. In certain embodiments, the percentage identity is due to genetic code degeneracy, while the encoded protein sequence remains unchanged.

The isolated polynucleotide that encodes the anti-PD-L1 antibodies and the antigen-binding fragments thereof can be inserted into a vector for further cloning (amplification of the DNA) or for expression, using recombinant techniques known in the art. In another embodiment, the antibody may be produced by homologous recombination known in the art. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence (e.g. translation signals or leader sequence), an origin of replication, one or more selectable marker genes, an enhancer element, a promoter (e.g. SV40, CMV, EF-1α), and a transcription termination sequence.

In some embodiments, the vector system includes mammalian, bacterial, yeast systems, etc, and comprises plasmids such as, but not limited to, pALTER, pBAD, pcDNA, pCal, pL, pET, pGEMEX, pGEX, pCI, pCMV, pEGFP, pEGFT, pSV2, pFUSE, pVITRO, pVIVO, pMAL, pMONO, pSE- LECT, pUNO, pDUO, Psg5L, pBABE, pWPXL, pBI, p15TV-L, pProl8, pTD, pRS420, pLexA, pACT2.2, pCDM8, pCDNA1.1/amp, pcDNA3.1, pRc/RSV, pEF-1, pCMV-SCRIPT®, pFB, pSG5, pXT1, pCDEF3, pSVS-PORT, pEF-Bos, etc, and other laboratorial and commercially available expression vectors. Suitable vectors may include, plasmid, or viral vectors (e.g., replication defective retroviruses, adenoviruses and adeno-associated viruses). The vectors can be maintained in single copy or multiple copies, or integrated into the host cell genome. Vectors comprising the polynucleotide sequence encoding the antibody or antigen-binding fragment can be introduced to a host cell for replication or gene expression. Suitable host cells for cloning or expressing the DNA in the vectors herein are the prokaryote, yeast, insect cells or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis*, *Pseudomonas* such as *P. aeruginosa*, and *Streptomyces, Bacillus, Streptococcus, Streptomyces, Staphylococcus, Enterococcus, Lactobacillus, Lactococcus, Clostridium, Geobacillus, Oceanobacillus, Pseudomonas, Salmonella, Campylobacter, Helicobacter, Flavobacterium, Fusobacterium, Ilyobacter, Neisseria*, and *Ureaplasma*. Suitable insect cells includes *Drosophila* Schnieder S2 cells and Sf9). Suitable yeast includes *P. methanolica, P. pastoris, S. cerevisiae* or common baker's yeast. Preferable mammalian cells include CHO cells, HEK293 cells, lymphocytes and myelomas. In certain embodiments, when glycosylation and Fc effector function for an antibody are not needed, the antibody may be produced in bacteria.

In addition to the above examples, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

However, vertebrate cells have drawn the greatest interest, and the propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatocellular carcinoma cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; PC12; mouse embryo fibroblast cell line (3T3); NSO myeloma cells (a murine myeloma cell line that does not endogenously produce any functional immunoglobulin chains). Different host cells have various characteristic and mechanisms for the post-translational processing and modification of proteins and gene products. Therefore, suitable cell lines can be chosen as host cells to ensure the correct modification and processing (such as primary transcript, glycosylation, and phosphorylation) of the antibody expressed. In some preferable embodiments, the host cell is HEK293T cell. In some preferable embodiments, the host cell is CHO cell.

Host cells are transformed with the above-described expression or cloning vectors for anti-PD-L1 antibody production and cultured in conventional nutrient media modified as appropriate for inducing promoters, selecting transformants, or amplifying the genes encoding the desired sequences. In certain embodiments, the vectors can be transferred into the host cell by methods known in the art such as transformation, electroporation, calcium phosphate treatment, lipofection. In certain embodiments, transfection of a vector into a eukaryote includes calcium phosphate co-precipitates, microinjection, electroporation, lipofection and viral infection. The eukaryotic host cell may be co-transformed with a second polynucleotide encoding the antibody. In certain embodiments, the host cell containing the transferred vector can transiently express the anti-PD-L1 antibody.

The host cells used to produce the antibodies or antigen-binding fragments provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma), Luria broth (LB), and Terrific broth (TB) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody and the antigen-binding fragments thereof can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody and the antigen-binding fragments thereof are secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody prepared from the cells can be purified using, for example, hydroxylapatite chromatography, hydrophobic chromatography, reverse-phase chromatography, absorption chromatography, filtration, ultrafiltration, solvent precipitation, solvent extraction, distillation, SDS-polyacrylamide gel electrophoresis, dialysis, DEAE-cellulose ion exchange chromatography, ammonium sulfate precipitation, salting out, immnoprecipitation, isoelectric focusing, recrystallization and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human .gamma.1, .gamma.2, or .gamma.4 heavy chains (Lindmark et al., J. Immunol. Meth. 62:1-13 (1983)). Examples of protein A columns include Hyper D, POROS, and Sepharose FF (GE Healthcare Biosciences). Protein G is recommended for all mouse isotypes and for human .gamma.3 (Guss et al., EMBO J. 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Kits

The present disclosure provides kits comprising the anti-PD-L1 antibodies or the antigen-binding fragments thereof, or the pharmaceutical composition comprising the anti-PD-L1 antibodies or the antigen-binding fragments thereof provided herein. In some embodiments, the kits are useful for detecting the presence or the level of PD-L1 in a biological sample. The biological sample can comprise a cell or a tissue.

In some embodiments, the anti-PD-L1 antibody or the antigen-binding fragment thereof which is comprised in the kit is conjugated with a detectable label (for example, fluorescent, radioactive or enzymatic label). In certain other embodiments, the kit comprises an unlabeled anti-PD-L1 antibody or antigen-binding fragments thereof or a pharmaceutical composition containing the unlabeled anti-PD-L1 antibody or antigen-binding fragments thereof, and further comprises a secondary labeled antibody which is capable of binding to the unlabeled anti-PD-L1 antibody. The kit may further include means of detecting a label (for example, filter sets to detect fluorescent labels, enzyme substrates for enzymatic labels, etc). The kit may comprise additional reagents and buffers used for the performance of a particular method. The kit may further comprise an instruction of use, and a package that separates each of the components in the kit. In certain embodiments, the kit comprises an immunoassay for detecting the PD-L1 antibody.

In certain embodiments, the anti-PD-L1 antibody or the antigen-binding fragment thereof that are comprised in the kit is associated with a substrate or a device useful in a sandwich assay such as ELISA, or in an immunographic assay. Useful substrate or device can be, for example, microtiter plate and test strip.

In certain embodiments, the kit is provided for detecting PD-L1 protein level. In some embodiments, the kit is used for predicting, diagnosing, preventing or treating PD-L1 associated conditions.

Pharmaceutical Composition and Method of Treatment

The present disclosure further provides pharmaceutical compositions comprising the anti-PD-L1 antibodies or the antigen-binding fragments thereof and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, humectants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment and conjugates as provided herein decreases oxidation of the antibody or antigen-binding fragment. This reduction in oxidation prevents or reduces loss of binding activity or binding affinity, thereby improving antibody stability and maximizing shelf-life. Therefore, in certain embodiments compositions are provided that comprise one or more antibodies or antigen-binding fragments as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine. Suitable humectants include, ethylene glycol, glycerin, or sorbitol. Suitable lubricants include, for example, cetyl esters wax, hydrogenated vegetable oil, magnesium stearate, methyl stearate, mineral oil, polyoxyethylene-polyoxypropylene copolymer, polyethylene glycol, polyvinyl alcohol, sodium lauryl sulfate or white wax, or a mixture of two or more thereof. Suitable emulsifiers include carbomer, polyoxyethylene-20-stearyl ether, cetostearyl alcohol, cetyl alcohol, cholesterol, diglycol stearate, glyceryl stearate, hydroxypropyl cellulose, hydroxypropylmethyl cellulose, lanolin, polyoxyethylene lauryl ether, methyl cellulose, polyoxyethylene stearate, polysorbate, propylene glycol monostearate, sorbitan esters or stearic acid.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, lotion, foam, pill, capsule, tablet, sustained release formulation, ointment, cream, paste, gel, spray, aerosol, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-PD-L1 antibody or antigen-binding fragment thereof or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Therapeutic methods for treating a PD-L1 associated condition are also provided, comprising: administering to a subject a therapeutically effective amount of the PD-L1 antibody or the antigen-binding fragments thereof as provided herein, thereby treating or preventing a condition or a disorder associated with related to PD-L1. In another embodiment, methods are provided to treat a condition in a subject that would benefit from upregulation of immune response, comprising administering a therapeutically effective amount of the PD-L1 antibody as provided herein to a subject in need thereof.

The therapeutically effective amount (when used alone or in combination with other agents such as chemotherapeutic agents) of an antibody or antigen-binding fragment as provided herein will depend on various factors known in the art, such as for example type of disease to be treated, the type of antibody, body weight, age, past medical history, present medications, state of health of the subject, immune condition and potential for cross-reaction, allergies, sensitivities and adverse side-effects, as well as the administration route and the type, the severity and development of the disease and the discretion of the attending physician or veterinarian. In certain embodiments, an antibody or antigen-binding fragment as provided herein may be administered at a therapeutically effective dosage of about 0.01 mg/kg to about 100 mg/kg one or more times per day (e.g., about 0.01 mg/kg, about 0.3 mg/kg, about 0.5 mg/kg, about 1 mg/kg, about 3 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg one or more times per day). In certain embodiments, the antibody or antigen-binding fragment is administered at a dosage of about 50 mg/kg or less, and in certain the dosage is 20 mg/kg or less, 10 mg/kg or less, 3 mg/kg or less, 1 mg/kg or less, 0.3 mg/kg or less, or 0.1 mg/kg or less. In certain embodiments, the administration dosage may change over the course of treatment. For example, in certain embodiments the initial administration dosage may be higher than the subsequent administration dosages. In certain embodiments, the administration dosage may vary over the course of treatment depending on the reaction of the subject.

Dosage regimens may be adjusted to provide the optimum desired response (e.g., a therapeutic response). In certain embodiments, antibody or antigen-binding fragment as provided herein is administered to the subject at one time or over a series of treatments. In certain embodiments, antibody or antigen-binding fragment as provided herein is administered to the subject by one or more separate administrations, or by continuous infusion depending on the type and severity of the disease. Guidance can be found in for example, U.S. Pat. Nos. 4,657,760; 5,206,344; 5,225,212.

The antibodies and antigen-binding fragments disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

In certain embodiments, the antibodies and antigen-binding fragments disclosed herein may be administered in a controlled-release manner. A controlled-release parenteral preparations can be made as implants, oily injections or particulate systems (e.g. microspheres, microparticles, microcapsules, nanocapsules, nanospheres, and nanoparticles) (see Banga, A. J., Therapeutic Peptides and Proteins: Formulation, Processing, and Delivery Systems, Technomic Publishing Company, Inc., Lancaster, Pa., (1995); Kreuter, J., Colloidal Drug Delivery Systems, J. Kreuter, ed., Marcel Dekker, Inc., New York, N.Y., pp. 219-342 (1994); Tice & Tabibi, Treatise on Controlled Drug Delivery, A. Kydonieus, ed., Marcel Dekker, Inc. New York, N.Y., pp. 315-339, (1992)). In certain embodiments, the PD-L1 antibodies and antigen-binding fragments disclosed herein may be administered in degradable or nondegradable polymeric matrices (see Langer, *Accounts Chem. Res.* 26:537-542, 1993).

Conditions associated with PD-L1 can be immune related disease or disorder. In certain embodiments, the condition is solid tumors, hematological disorders, infectious diseases, autoimmune diseases or fibrotic diseases. In certain embodiments, the solid tumors include, for example, non-small cell lung cancer (squamous/nonsquamous), small cell lung cancer, renal cell cancer, colorectal cancer, colon cancer, ovarian cancer, breast cancer (including basal breast carcinoma, ductal carcinoma and lobular breast carcinoma), pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, melanoma, myelomas, mycoses fungoids, merkel cell cancer, hepatocellular carcinoma (HCC), fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, lymphoid malignancy, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, hepatoma, bile duct carcinoma, choriocarcinoma, Wilms' tumor, cervical cancer, testicular tumor, seminoma. The hematologic disorders include such as classical Hodgkin lymphoma (CHL), primary mediastinal large B-cell lymphoma, T-cell/histiocyte-rich B-cell lymphoma, acute lymphocytic leukemia, acute myelocytic leukemia, acute myelogenous leukemia and myeloblastic, promyelocytic, myelomonocytic, monocytic and erythroleukemia, chronic myelocytic (granulocytic) leukemia, chronic myelogenous leukemia, chronic lymphocytic leukemia, polycythemia vera, mast cell derived tumors, EBV-positive and –negative PTLD, and diffuse large B-cell lymphoma (DLBCL), plasmablastic lymphoma, extranodal NK/T-cell lymphoma, nasopharyngeal carcinoma, and HHV8-associated primary effusion lymphoma, non-Hodgkin's lymphoma, multiple myeloma, Waldenstrom's macroglobulinemia, heavy chain disease, myelodysplastic syndrome, hairy cell leukemia and myelodysplasia, neoplasm of the central nervous system (CNS), such as primary CNS lymphoma, spinal axis tumor, brain stem glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma. In certain embodiments, the tumors and cancers are metastatic, especially metastatic tumors expressing PD-L1. In certain embodiments, a tumor is melanoma or colon cancer.

In certain embodiments, the PD-L1 associated conditions and disorders include autoimmune or inflammatory diseases, such as systemic lupus erythematosus (SLE), intestinal mucosal inflammation, wasting disease associated with colitis, multiple sclerosis, viral infections, rheumatoid arthritis, osteoarthritis, Cohn's disease, and inflammatory bowel disease, psoriasis, systemic scleroderma, autoimmune diabetes and the like. In certain embodiments, the PD-L1 associated conditions and disorders include infectious disease such as fungus infection, parasite/protozoan infection or chronic viral infection, for example, coccidioiodmycosis immitis, histoplasmosis, onychomycosis, aspergilosis, blastomycosis, candidiasis albicans, paracoccidioiomycosis, microsporidiosis, *Acanthamoeba keratitis*, Amoebiasis, Ascariasis, Babesiosis, Balantidiasis, Baylisascariasis, Chagas disease, Clonorchiasis, Cochliomyia, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, Trichuriasis, Trypanosomiasis, helminth infection, viral infection of hepatitis B (HBV), hepatitis C (HCV), herpes virus, Epstein-Barr virus, HIV, cytomegalovirus, herpes simplex virus type I, herpes simplex virus type II, human papilloma virus, adenovirus, human immunodeficiency virus I, human immunodeficiency virus II, Kaposi West sarcoma associated herpes virus epidemics, thin ring virus (Torquetenovirus), human T lymphotrophic viruse I, human T lymphotrophic viruse II, varicella zoster, JC virus or BK virus. In certain embodiments, the PD-L1 associated conditions include fibrotic diseases, such as glomerulonephritis, neural scarring, dermal scarring, pulmonary fibrosis, lung fibrosis, radiation induced fibrosis, hepatic fibrosis, myelofibrosis.

Methods of Use

The present disclosure further provides methods of using the anti-PD-L1 antibodies or the antigen-binding fragments thereof.

In some embodiments, the present disclosure provides methods of treating a PD-L1 associated condition in a subject, comprising administering to the subject a therapeutically effective amount of the antibody or the antigen-binding fragments thereof. In certain embodiments, the subject has been identified as having a disorder or condition likely to respond to a PD-L1 antagonist. In certain embodiments, the present disclosure provides methods of preventing, detecting, or diagnosing PD-L1 associated condition, comprising contacting the PD-L1 antibody or the antigen-binding fragments thereof provided herein with a biological sample obtained from a subject suspect of or having or at risk of having the PD-L1 associated condition and determining the level of PD-L1 antibody or the antigen-binding fragments thereof that binds to PD-L1 in the biological sample.

For the treatment of the PD-L1 associated condition, the subject is tested as positive for PD-L1 expression, or tested as having elevated level of PD-L1 expression. Various methods can be used to determine the presence or level of PD-L1 in a test biological sample from the individual. For example, the test biological sample can be exposed to anti-PD-L1 antibody or antigen-binding fragment thereof, which binds to and detects the expressed PD-L1 protein. Alternatively, PD-L1 can also be detected at nucleic acid expression level, using methods such as qPCR, reverse transcriptase PCR, microarray, SAGE, FISH, and the like. In some embodiments, the test sample is derived from a cancer cell or tissue (e.g. biopsied tissue from an organ), tumor infiltrating immune cells, or bodily fluid (e.g. blood or serum). In certain embodiments, the presence or upregulated level of the PD-L1 in the test biological sample indicates the likelihood of responsiveness. The term "upregulated" as used herein, refers to an overall increase of no less than 10%, 15%, 20%, 25%, 30%, 35%, 40%, 45%, 50%, 55%, 60%, 65%, 70%, 75%, 80% or greater, in the protein level of PD-L1 in the test sample as detected using the antibodies or antigen-binding fragments provided herein, as compared to the PD-L1 protein level in a reference sample as detected using the same antibody. The reference sample can be a control sample obtained from a healthy or non-diseased individual, or a healthy or non-diseased sample obtained from the same individual from whom the test sample is obtained, or a sample obtained from the same individual at an earlier time point during the treatment of the condition. For example, the reference sample can be a non-diseased sample adjacent to or in the neighborhood of the test sample (e.g. tumor).

The antibodies or antigen-binding fragments disclosed herein may be administered alone or in combination with one or more additional therapeutic means or agents. For example, the antibodies or antigen-binding fragments disclosed herein may be administered in combination with a second therapy, such as radiation therapy, chemotherapy, targeted therapies, gene therapy, immunotherapy, hormonal therapy, angiogenesis inhibition, palliative care, surgery for the treatment of cancer (e.g., tumorectomy), one or more anti-emetics or other treatments for complications arising from chemotherapy, or a second therapeutic agent for use in the treatment of cancer or any medical disorder mediated by PD-L1, for example, another antibody, therapeutic polynucleotide, chemotherapeutic agent(s), anti-angiogenic agent, cytokines, other cytotoxic agent(s), growth inhibitory agent(s). In certain of these embodiments, an antibody or antigen-binding fragment as disclosed herein that is administered in combination with one or more additional therapeutic agents may be administered simultaneously with the one or more additional therapeutic agents, and in certain of these embodiments the antibody or antigen-binding fragment and the additional therapeutic agent(s) may be administered as part of the same pharmaceutical composition. However, an antibody or antigen-binding fragment administered "in combination" with another therapeutic agent does not have to be administered simultaneously with or in the same composition as the agent. An antibody or antigen-binding fragment administered prior to or after another agent is considered to be administered "in combination" with that agent as the phrase is used herein, even if the antibody or antigen-binding fragment and second agent are administered via different routes. Where possible, additional therapeutic agents administered in combination with the antibodies or antigen-binding fragments disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art. In certain embodiments, an anti-angiogenic agent administered in combination with the PD-L1 antibody provided herein is monoclonal antibody for anti-vasculogenic therapy, such as Bevacizumab (VEGF antibody), IMC-1C11 or DC101 (VEGFR-2 antibody), mF4-31C1 (VEGFR-3 antibody), and Vitaxin (integrin $\alpha_v\beta_3$ antibody).

In certain embodiments, the therapeutic agents can induce or boost immune response against cancer. For example, a tumor vaccine can be used to induce immune response to certain tumor or cancer. Cytokine therapy can also be used to enhance tumor antigen presentation to the immune system. Examples of cytokine therapy include, without limitation, interferons such as interferon-$\alpha$, -$\beta$, and -$\gamma$, colony stimulating factors such as macrophage-CSF, granulocyte macrophage CSF, and granulocyte-CSF, insulin growth factor (IGF-1), vascular endothelial growth factor (VEGF), transforming growth factor (TGF), fibroblast growth factor (FGF), interleukins such IL-1, IL-la, IL-2, IL-3, IL-4, IL-5, IL-6, IL-7, IL-8, IL-9, IL-10, IL-11, and IL-12, tumor necrosis factors such as TNF-$\alpha$ and TNF-$\beta$ or any combination thereof. Agents that inactivate immunosuppressive targets can also be used, for example, IL-1-antagonist (IL-1A), VEGFR2 antagonist (e.g. Vatalanib, Sunitinib, Sorafenib, Pazopanib), TGF-beta inhibitors, FGFR antagonist, platelet-derived growth factor receptor (PDGFR) antagonist (e.g. Imatinib, Sunitinib, Sorafenib, Pazopanib), epidermal growth factor receptor (EGFR, ErbB) antagonist (e.g. Gefitinib, Lapatinib, Canertinib), IL-10 inhibitors, and Fas ligand inhibitors, or any combination thereof. Another group of agents include those that activate immune responsiveness to tumor or cancer cells, for example, those enhance T cell activation (e.g. agonist of T cell costimulatory molecules such as CTLA-4, ICOS and OX-40), and those enhance dendritic cell function and antigen presentation.

Screening and Evaluating the In Vivo Efficacy of Anti-PD-L1 Antibody

In order to screen and/or evaluate the in vivo efficacy (e.g. binding activity or binding affinity) of the PD-L1 antibody or the antigen-binding fragments thereof, a non-human tumor cell that expresses the human PD-L1 protein being inoculated into a non-human animal is generated. In certain embodiments, the non-human tumor cell is a rodent (e.g. mouse, rat, or hamster, etc) cell. In certain embodiments, the non-human tumor cell is a melanoma cell line (B16) or a mouse colon cancer cell line (MC38). The non-human tumor cell can comprise a polynucleotide encoding the human PD-L1 protein with inactivation of the endogenous non-human PD-L1 gene segment. The inactivation of the target gene can be caused by gene disruption of the protein-coding sequence, mutation, addition, gene silencing (e.g. RNAi gene antisense) or gene deletion (e.g. partially or entirely deletion of the coding sequence, or the coding sequence including flanking regions) at the endogenous gene locus, thereby eliminating or minimizing the expression of the non-human target gene or generating a functionally inactive/truncated polypeptide that is not bound by its ligands. The flanking region of the encoding sequence can be within the range of about 1 bp to about 500 bp at both the 5' and 3' ends, or the flanking region can be larger than 500 bp but will not include inactivation of other genes according to the disclosure. "Gene disruption" as used herein refers to addition of one or more nucleotides or amino acids to the naturally occurring sequence. The gene disruption can be addition or insertion of a marker/reporter gene into the protein-coding sequence. In certain embodiments, the inactivation is non-revertible. In certain embodiments, inactivation results in a cell having no detectable activity for the target gene or gene product. The inactivation of a target gene is performed using suitable means in the art, for example, homologous recombination, RNA interference (RNAi) or CRISPR/Cas9 system. In certain embodiments, the human PD-L1 gene segment encoding the human PD-L1 protein is operably inserted into the endogenous non-human PD-L1 gene locus (gene replacement). In certain embodiments, the inserted polynucleotide encoding the human PD-L1 is integrated in a random, non-specific location (gene augmentation). In yet further embodiments, the polynucleotide encoding the human PD-L1 can be stably maintained in the cell as episomes, e.g. in the form of a separate, episomal segment of DNA, and the replication of the episomal DNA is independent of or in synchronization with the host cell cycle.

The non-human tumor cells with complete inactivation of the target gene can be identified by FACS analysis of the cell surface expression or detecting the target gene transcription. The polynucleotide encoding the human PD-L1 protein can be introduced into the tumor cell, by any suitable method known in the art, such as homologous recombinant and transgenic method, via any suitable expression vector as described in the present disclosure (such as a lentivirus vector). The tumor cells with complete inactivation of the target gene and/or expression of introduced gene of interest can be identified by FACS analysis of the cell surface expression or detecting the target gene transcription by any suitable method in the art.

A method of screening or evaluating the in vivo efficacy of an antibody or the antigen-binding fragments thereof against human PD-L1, including inoculating a tumor cell comprising a polynucleotide encoding the human PD-L1 protein into a non-human animal, contacting the antibody with the tumor cell in the non-human animal and determining tumor burden of the tumor cell. As used herein, the "tumor burden" is the amount of tumor cells in an individual that can be determined by the tumor volume, number, or weight. A tumor cell can be a solid tumor cell or non-solid tumor cell (such as hematologic cells). The tumor cell can be a human tumor cell or a non-human tumor cell. In certain embodiments, the tumor cell is inoculated into a syngenic non-human animal to generate a syngenic tumor model. In certain embodiments, the tumor cell is cultured several passages before being inoculated into the non-human animal. In certain embodiments, the non-human animal has a human-immune system. In certain embodiments, the in vivo efficacy of the PD-L1 antibody or the antigen-binding fragments thereof is determined by the growth inhibition of the tumor volume in the non-human animal dosed with PD-L1 antibodies, as compared with control.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1: Preparation and Characterization of PD-L1 Protein

Human PD-L1/CD274 Protein: Recombinant Human PD-L1/CD274 Protein (Accession #NP_054862.1) (hPD-L1-his) was expressed in human 293 cells (HEK293). Briefly the coding region of the human PD-L1 gene from Phe19-Arg238 with 6×his tag at C-terminus was used for transfection. The supernatant was purified using His-tag affinity column. The resulting purified protein was characterized using SDS page gel. This protein was purchased from ACRO Biosystem (PD1-H5229).

Human PD-L1/CD274 with C-Fc Tag: Recombinant Human PD-L1/CD274 (Accession #NP_054862.1) with C-Fc Tag (hPD-L1-Fc) was expressed in human 293 cells (HEK293). Briefly the coding region of the human PD-L1 gene from Phe19-Arg238 fused with Fc fragment of human IgG1 at C-terminus was used for transfection. The supernatant was purified using Fc-tag affinity column. The resulting purified protein was characterized using SDS page gel. This protein was purchased from ACRO Biosystem (PD1-H5258).

Mouse PD-L1/CD274 Protein: Recombinant Mouse PD-L1/CD274 Protein (mPD-L1-his) Phe19-Arg238 (Accession #NP_068693) was fused with 6×his tag at C-terminus and produced in human 293 cells (HEK293). The transfection supernatant from HEK293 cells was purified using His-tag affinity column. The resulting purified protein was characterized using SDS page gel. This protein was purchased from ACRO Biosystem (PD1-M5220).

Mouse PD-L1/CD274 with C-Fc Tag: Recombinant Mouse PD-L1/CD274 Protein (mPD-L1-Fc) Phe19-Arg238 (Accession #NP_068693) with C-Fc Tag was fused with Fc fragment of human IgG1 at C-terminus and produced in human 293 cells (HEK293). The transfection supernatant from HEK293 cells was purified using Fc-tag affinity column. The resulting purified protein was characterized using SDS page gel. This protein was purchased from ACRO Biosystem (PD1-M5251).

Cynomolgus PD-L1/CD274 with His tag: Recombinant Cynomolgus PD-L1/CD274 Protein (cPD-L1-His) Phe19-Arg238 (Accession #F6VEW6) was fused with polyhistidine tag at C-terminus and produced in human 293 cells (HEK293). The transfection supernatant from HEK293 cells was purified using His-tag affinity column. The resulting purified protein was characterized using SDS page gel. This protein was purchased from ACRO Biosystem (PD1-C52H4).

Cynomolgus PD-L1/CD274 with C-Fc Tag: Recombinant Cynomolgus PD-L1/CD274 Protein (cyno PD-L1-Fc) Phe9-Arg238 (Accession #F6VEW6) with C-Fc Tag was fused with Fc fragment of human IgG1 at C-terminus and produced in human 293 cells (HEK293). The transfection supernatant from HEK293 cells was purified using Fc-tag affinity column. The resulting purified protein was characterized using SDS page gel. This protein was purchased from ACRO Biosystem (PD1-C5253).

The above PD-L1 proteins were used in the following experiments.

Example 2: Antibody Generation

1. Antigen Conjugation and Immunization

For immunization, the recombinant hPD-L1-Fc (or mPD-L1-Fc) protein was conjugated with various MabSpace immune-enhancing peptides. Briefly 2-8 fold molar excess of the peptide was mixed with Sulfo-SMCC (sulfosuccinimidyl 4-[N-maleimidomethyl]cyclohexane-1-carboxylate, Peirce #22322)-activated hPD-L1-Fc protein and incubated for one hour at room temperature. The reaction was stopped and the conjugated protein was analyzed and QCed using SDS-PAGE gel.

Above conjugated hPD-L1-Fc and mPD-L1-Fc protein was emulsified in a 1:1 ratio using Complete Freund's Adjuvant (Pierce), respectively, and then immunized subcutaneously and intraperitoneally into C57B/L6 mice. Additional immunizations were carried out using CpG and Alum to preserve native conformation of the protein. Immunization occurred at least every 2 weeks and anti-serum from the mice was taken after the 1st immunizations for anti-PD-L1 titer analysis by ELISA assay. For determining the serum titer, 20 µl of mouse serum was prepared from each immunized mice. High-binding clear polystyrene 96 well plates (Nunc) were coated with 100 µl/well of a 1 ug/ml solution consisting of mouse or human PD-L1-his in high pH coating buffer (0.16% Na2CO3, 0.3% NaHCO$_3$, pH9.8). The plates were incubated overnight at 4° C., and then washed once on an automatic plate washer using washing buffer PBS+0.1% Tween 20 (Sigma). 200 µl of blocking buffer (PBS+1% BSA+1% Goat serum+0.05% Tween 20) was added to each well and incubated for 2 hours at room temperature. The blocking buffer was then aspirated and 100 µl of serially diluted serum in dilution buffer (PBS+1% BSA+1% Goat serum+0.01% Tween 20) was transferred to each well of the ELISA plate and allowed to incubate for 60 min at room temp. The plates were then washed 3 times using the method described above. 100 µl/well of solution of HRP conjugated goat anti-mouse Fc antibody (Abcam) diluted in dilution buffer was then added to each well of the plate. After that the ELISA plates were allowed to incubate for 60 min at RT, the plates were washed 3 times with 250 µl/well washing buffer. Finally, 100 µl/well of TMB was added to each well and the reaction was terminated using 0.64M H$_2$SO$_4$. The plates were read on a Thermo Multiscan FC at 450 nM.

2. Fusions

Four days prior to fusion, each mouse was boosted intraperitoneally with unconjugated hPD-L1-Fc and mPD-L1-Fc protein in PBS. On the fusion day, the spleens were removed aseptically and the organs were processed into a single cell suspension. The red blood cells were lysed and the spleenocytes were washed with DMEM (Gibco). Viable, log-phase growth myeloma cells (SP2/0) were mixed with the murine spleenocytes in a 1:4 ratio. The cells were then washed 2 times before the fusion with PEG. The post fusion cells were washed with DMEM and suspended in cell growth media supplemented with 10% FBS+HFCS+OPI+1×HAT. 200 µl per well of this cell suspension was plated into 96-well cell culture plates and incubated overnight in a 37° C. humidified 10% CO$_2$ incubator. The cultures were incubated for 7 days and then the growth media was aspirated out of the wells and exchanged for fresh growth media. Screening of hybridoma supernatants commenced 2-3 days after the media change.

Example 2: Antibody Screening

1. Screening for PD-L1 Binders by ELISA Assay

High-binding clear polystyrene 96 well plates (Nunc) were coated with 100 µl/well of 0.5 ug/ml hPD-L1-his or mPD-L1-his in high pH coating buffer and were incubated overnight at 4° C. Then the plates were washed once on an automatic plate washer using washing buffer (PBS+0.1% Tween 20 (Sigma)). 200 µl of blocking buffer (PBS+1% BSA+1% normal goat serum+0.05% Tween-20) was added to each well and was incubated for 2 hours at room temperature. 100 µl of hybridoma supernatant was transferred to each well of the ELISA plate and was allowed to incubate for 60 min at room temperature. The plates were then washed 3 times using the method described above. 100 µl/well of a solution of HRP conjugated goat anti-mouse Fc antibody (Abcam) diluted in blocking solution was then added to each well of the plate. After that the ELISA plates were allowed to incubate for 60 min at RT then plates were washed 3 times with 250 µl/well washing buffer. Finally, 100 µl/well of TMB was added to each well and the reaction was terminated using 0.64M H$_2$SO$_4$. The plates were read on a Thermo Multiscan FC at 450 nM. Cells from the ELISA positive hybridoma wells were subsequently expanded in cell culture for further characterization studies.

Figure 1A:
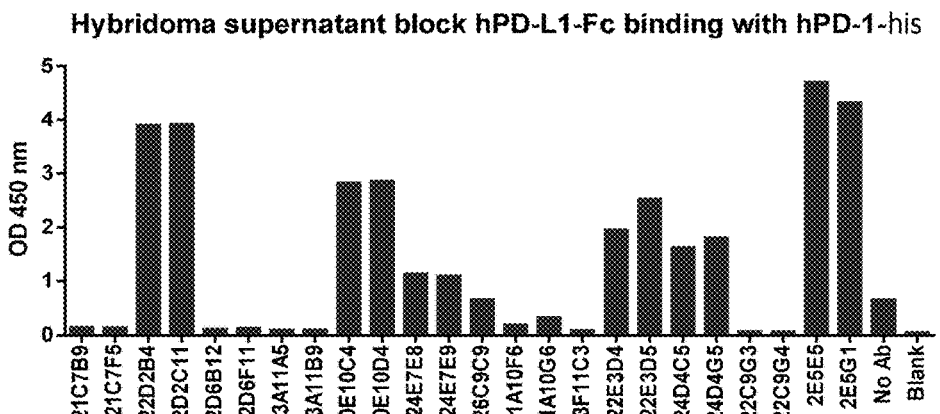
FIG. 1A is a bar chart presenting the ability of mouse anti-PD-L1 antibodies in the hybridoma supernatant to block the binding of hPD-L1-Fc to hPD-1-his coated on the plate.
Figure 1B:
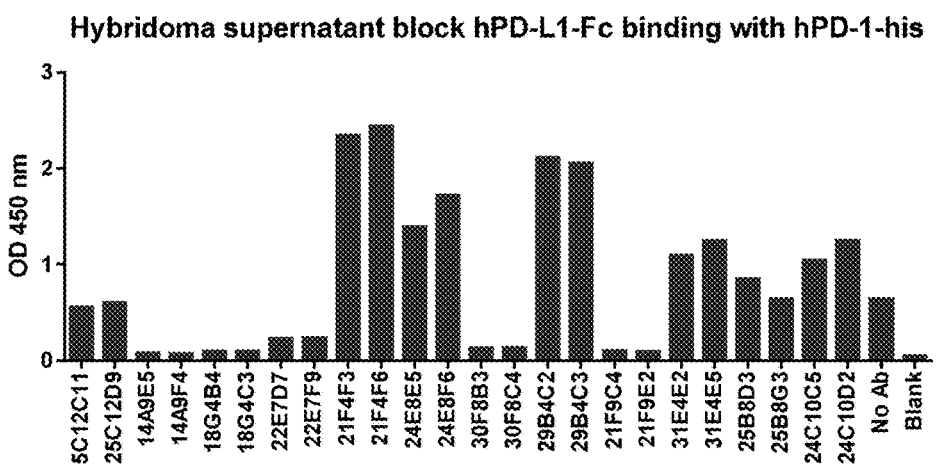
FIG. 1B is a bar chart presenting the ability of mouse anti-PD-L1 antibodies in the hybridoma supernatant to block the binding of hPD-L1-Fc to hPD-1-his coated on the plate and FIG. 1C is also a bar chart presenting the ability of mouse anti-PD-L1 antibodies in the hybridoma supernatant to block the binding of hPD-L1-Fc to hPD-1-his coated on the plate, as measured by ELISA analysis.
Figure 1C:
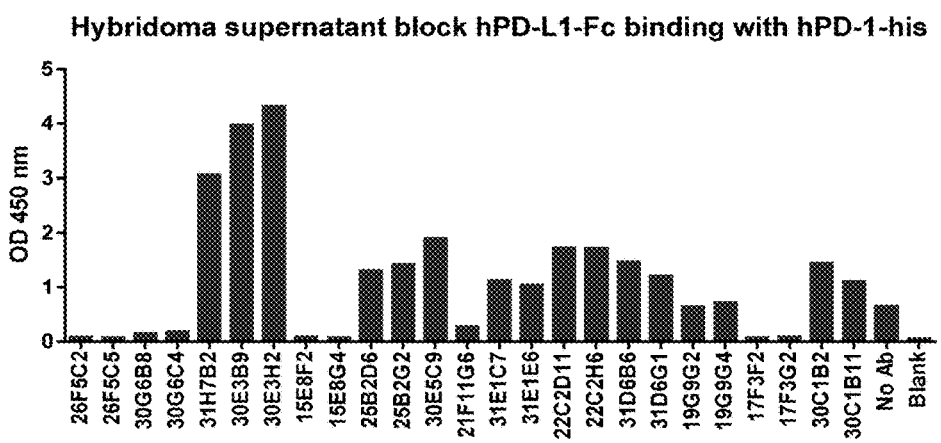

2. Evaluation of Blocking Activities of Hybridoma Supernatants to Inhibit Binding of PD-1 to PD-L1 in ELISA High-binding clear polystyrene 96-well plates (Nunc) were coated with 100 µl/well of 2 µg/ml hPD-L1-Fc (Acrobiosystems, Cat #PD1-H5258) in high pH coating buffer and were incubated overnight at 4° C. Then the plates were washed once on an automatic plate washer using washing buffer (PBS+0.1% Tween 20 (Sigma)). 200 µl of blocking buffer (PBS+1% BSA+1% normal goat serum+0.05% Tween-20) was added to each well and incubated 2 hours at room temp. 100 µl of hybridoma supernatant was transferred to each well of the ELISA plate and was allowed to incubate for 60 min at room temperature. The plates were then washed 3 times using the method described above. 80 µl 1 µg/ml hPD-1-his (ACRO Biosystems, Cat #PD1-H5221) was added to each well with dilution buffer. 100 µl/well of a solution of Anti-his-HRP (1:4000 dilution, CWBIO, Cat #CW0285) antibody diluted in blocking solution was then added to each well of the plate. After that the ELISA plates were allowed to incubate for 60 min at RT, and then the plates were washed 3 times with 250 µl/well washing buffer. Finally, 100 µl/well of TMB was added to each well and reaction was terminated using 0.64M $H_2SO_4$. The plates were read on a Thermo Multiscan FC at 450 nM. Cells from the ELISA positive hybridoma wells were subsequently expanded in cell culture for further characterization studies (see FIG. 1A-C).

3. Evaluation of Blocking Activities of Hybridoma Supernatants to Inhibit Binding of PD-1 to PD-L1 on Tumor Cells by FACS Log phase IFN-r stimulated (500 U/ml for 2 days) HCC827 cells were collected and resuspended in blocking buffer (5% BSA+PBS). 2×10^5 cells were added to each tube and then washed once with PBS (1500 rpm, 5 mins, RT). The 100 µl/tube hybridoma supernatants with blocking buffer were added into corresponding tubes and incubated at 4° C. for 1 hr. The cells were then washed twice with 1 ml PBS, followed by adding 100 µl/tube 3 µg/ml biotinylated hPD-1-Fc-N297A (ACRObiosystems) and incubated at 4° C. for 1 hr. After being washed for three times with PBS, 100 µl/tube streptavidin-PE (EBiosciences) 1:200 in blocking buffer was added to each tube. The cells were incubated at 4° C. for 1 hr and then washed twice with PBS, followed by resuspending cells in 150 µl PBS for each sample. The cells were then transferred into FACS tube and the binding of the antibodies to the cells were detected using flow cytometry (ACEA Bioscience Novocyte).

4. Screening for pH-Dependent PD-L1 Binding by ELISA

Figure 2A:
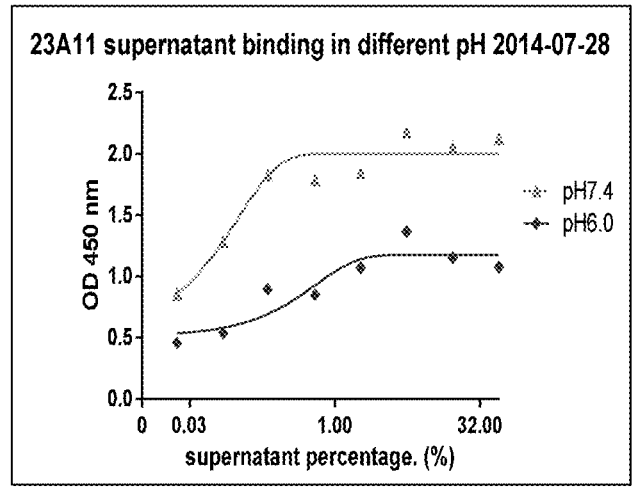
FIG. 2A is a graphic illustration showing the pH-dependent binding of mouse anti-PD-L1 antibody 23A11 in the hybridoma supernatant to hPD-L-his with higher binding at pH7.4 (triangle) and lower binding at pH6.0 (diamond), as measured by ELISA analysis.
Figure 2B:
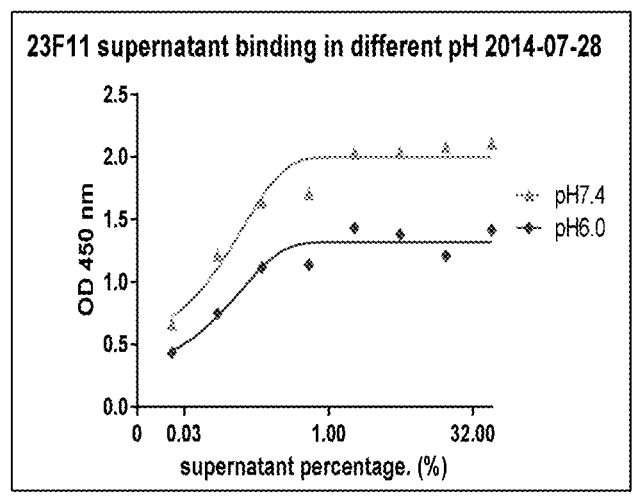
FIG. 2B shows the pH-dependent binding of mouse antibody clone 23F11 in the hybridoma supernatant to hPD-L1 with higher binding at pH7.4 (triangle) and lower binding at pH6.0 (diamond) as measured by ELISA analysis.

High-binding clear polystyrene 96 well plates (Nunc) were coated with 100 µl/well of 0.5 ug/ml hPD-L1-his in high pH coating buffer and were incubated overnight at 4° C. Then the plates were washed once on an automatic plate washer using washing buffer PBS+0.1% Tween 20 (Sigma). 200 µl of blocking buffer (PBS+1% BSA+1% normal goat serum+0.05% Tween-20) was added to each well and incubated 2 hours at room temp. 100 µl of hybridoma supernatant was transferred to each well of the ELISA plate and allowed to incubate for 60 min at room temp in either pH7.4 or pH6.0. The plates were then washed 3 times using the method described above with buffer either at pH7.4 or pH6.0. Afterwards 100 µl/well of a solution of HRP conjugated goat anti-mouse Fc antibody (Abcam) diluted in blocking solution in pH7.4 was then added to each well of the plate. After that the ELISA plates were allowed to incubate for 60 min at RT, and then the plates were washed 3 times with 200 µl/well pH7.4 or pH6.0 washing buffer. Finally, 100 µl/well of TMB was added to each well and the reaction was terminated using 0.64M $H_2SO_4$. The plates were read on a Thermo Multiscan FC at 450 nM. Cells from the ELISA positive hybridoma wells were subsequently expanded in cell culture for further characterization studies. The result for clone 23A11 (FIG. 2A) and clone 23F11 (FIG. 2B) are shown.

Examples 3: Subcloning of Positive Hybridoma Clones and Small Scale Antibody Production 1. Subcloning of Positive Hybridoma Clones Cells from the ELISA positive hybridoma wells with the desired binding profile and blocking activity were selected and each plated using limited dilution in 96 well plates. These cells were allowed to grow for 7 days. Once the adequate cell mass was reached, supernatant from each well was collected and re-screened for antigen binding ability (see screening in Example 2).

From each 96 well plate, clones with highest antigen binding activity were identified and expanded with limited dilution further into 96-well plates with 2001 of hybridoma growth medium per well. After 7 days, cells from 96-well plates were tested for antigen binding. The subcloning was done more than 2 times. When more than 90 of the wells display positive binding signal, two clones with the highest antigen binding activity were identified and transferred to 24-well plates with medium and was allowed to grow for 2 additional days. Once 24 well plates were confluent, cells were transferred to 6-well plates. After 5 days of incubation, a portion of the cells were frozen down. The remainder of the cells were transferred into a flask and allowed to expand. Once the flasks were confluent, half of cells were frozen down (3 vials per clone) for additional backup. The other half was allowed to expand further in flasks with medium for antibody production. Isotypes were determined using standard methodologies.

2. Small Scale Antibody Production

Hybridoma cells were inoculated to roller bottle and cultured for 14 days with 200-300 ml of hybridoma culture medium (Invitrogen). PD-L1 monoclonal antibodies (mAbs) were purified from hybridoma cell culture as follows. All purification processes were carried out at room temperature. One purification scheme was used to purify various mAbs and used affinity chromatography.

The host cell culture fluid (CCF) was centrifuged to remove cell debris. The CCF supernatant was then filtered, diluted and then loaded onto Protein G chromatography media in the form of a column, Protein G High Performance (Bio-Rad) and equilibrated.

After loading, the Protein G column was washed until the absorbance at 280 nm of the flow-through returned to baseline. The PD-L1 mAb was then eluted from the column using glycine, pH 2.5 and immediately neutralized by adding 50 µL of a stock solution of 1 M Tris Base per mL of elution volume. The absorbance at 280 nm of the eluate was monitored and fractions containing protein were collected to make the Protein A pool.

Following purification, the PD-L1 mAbs were formulated in PBS by dialysis using 10,000 MWCO membranes (Pierce Slide-A-Lyzer or dialysis tubing). Following formulation, the PD-L1 mAbs were filtered.

Example 4: Analysis of Purified PD-L1 Binding Antibody

Figure 3:
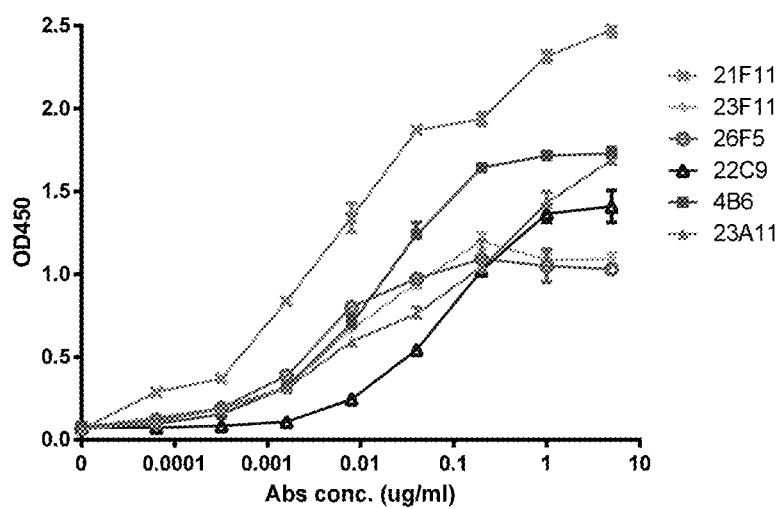
FIG. 3 shows the binding of serially diluted purified mouse monoclonal PD-L1 antibodies (21F11 (cross), 23F11 (diamond), 26F5 (open circle), 22C9 (open triangle), 4B6 (solid square), 23A11 (solid triangle)) of various clones to hPD-L1 as measured by ELISA analysis.

High-binding clear polystyrene 96 well plates (Nunc) were coated with 100 µl/well of a 0.5 µg/ml hPD-L1-his in high pH coating buffer and incubated overnight 4° C. Then plates were washed once on an automatic plate washer using washing buffer (PBS+0.1% Tween 20 (Sigma)). 200 µl of blocking buffer (PBS+1% BSA+1% normal goat serum+ 0.05% Tween-20) was added to each well and incubated 2 hours at room temp. Then add serially diluted purified antibodies with dilution buffer (PBS+1% BSA+1% normal goat serum+0.01% Tween-20) and incubate for 1 hour at RT. The plates were then washed 3 times using the method described above. 100 µl/well of a solution of HRP conjugated goat anti-mouse Fc antibody (Abcam) in dilution buffer was then added to each well of the plate. After that the ELISA plates were allowed to incubate for 60 min at RT then plates were washed 3 times with 250 µl/well washing buffer. Finally, 100 µl/well of TMB was added to each well and was terminated using 0.64M $H_2SO_4$. The plates were read on a Thermo Multiscan FC at 450 nM (see FIG. 3).

Example 5: Evaluation of Blocking Activities of Purified Antibodies to Inhibit Binding of PD-1 to PD-L1

1. Evaluation in ELISA

Figure 4A:
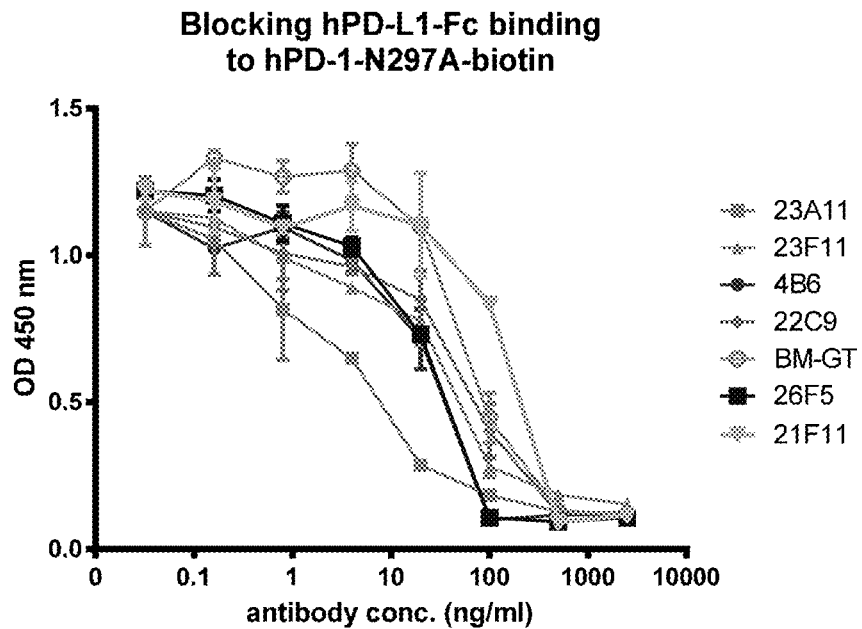
FIG. 4A shows the activities of the serially diluted purified mouse monoclonal PD-L1 antibodies (23A11 (light grey solid square), 23F11 (solid triangle), 4B6 (solid circle), 22C9 (solid diamond), 26F5 (dark solid square), 21F11 (inverted triangle) and BM-GT (open circle)) in blocking the binding of hPD-1-Fc to hPD-1-N297A-biotin as measured by ELISA.

High-binding clear polystyrene 96 well plates (Nunc) were coated with 100 µl/well of coating solution consisting of 0.5 µg/ml hPD-L1-Fc overnight at 4° C. Then washed once on an automatic plate washer using washing buffer PBS+0.1% Tween 20 (Sigma). 200 µl of blocking buffer (PBS+1% BSA+1% normal goat serum+0.05% Tween-20) was added to each well and incubated for 2 hours at room temperature. Then add serial diluted antibodies (from 10 µg/ml to 0.0006 µg/ml) with dilution buffer (PBS+1% BSA+1% normal goat serum+0.01% Tween-20) and incubate for 1 hour at RT. The plates were then washed 3 times using the method described above. 1 µg/ml biotinylated hPD-1-Fc-N297A (Acrobiosystem) were added and incubated for 1 hour at RT. After the plates were washed 3 times, 100 µl/well of a solution of HRP conjugated Neutravidin antibody (Pierce) diluted in dilution buffer was then added to each well of the plate. After that the ELISA plates were allowed to incubate for 60 min at RT then plates were washed 3 times with 250 µl/well washing buffer. Finally, 100 µl/well of TMB was added to each well and reaction was terminated using 0.64M $H_2SO_4$. The plates were read on a Thermo Multiscan FC at 450 nM (see FIG. 4A). BM-GT is a benchmark antibody (MPDL-3280A) disclosed in the U.S. Pat. No. 8,217,849.

2. Evaluation on Tumor Cells by FACS

Figure 4B:
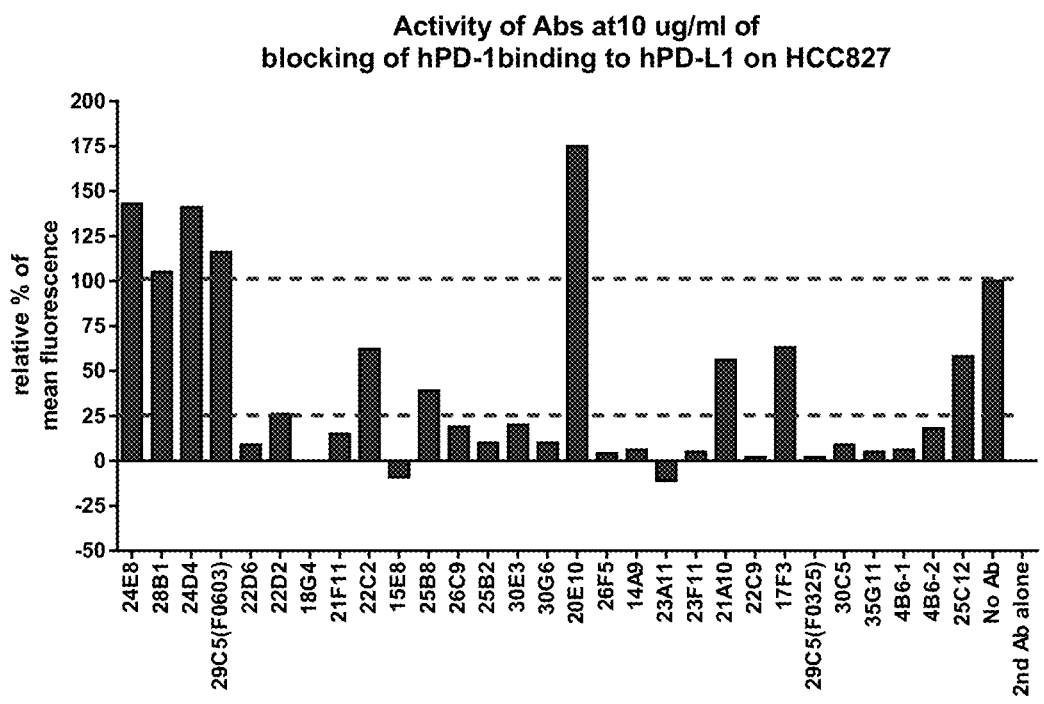
FIG. 4B shows the activities of the PD-L1 antibodies at 10 μg/ml in blocking the binding of hPD-1-Fc N297A to hPD-L1 expressed on HCC827 aa measured by FACS analysis.

Log phase IFN-r stimulated (500 U/ml for 2 days) HCC827 cells were collected and resuspended in blocking buffer (5% BSA+PBS). 2×10^5 cells were added to each tube and then washed once with PBS (1500 rpm, 5 mins, RT). The 100 µl/tube diluted antibodies in blocking buffer were added into corresponding tubes to contain a final concentration of 10 µg/ml and incubate at 4° C. for 1 hr. The cells were then washed twice with 1 ml PBS, followed by adding 100 µl/tube 3 µg/ml biotinylated hPD-1-Fc-N297A (Acrobiosystem) and incubated at 4° C. for 1 hr. After being washed for three times with PBS, 100 µl/tube streptavidin-PE (EBiosciences) diluted 1:200 in blocking buffer was added to each tube. The cells were incubated at 4° C. for 1 hr and then washed twice with PBS, followed by resuspending cells in 150 µl PBS for each sample. The cells were then transferred into FACS tube and the binding of the antibodies to the cells were detected using flow cytometry (ACEA Bioscience Novocyte) (see FIG. 4B).

Example 6: Dose-Dependent Response of Purified PD-L1 Antibodies

Figure 5A:
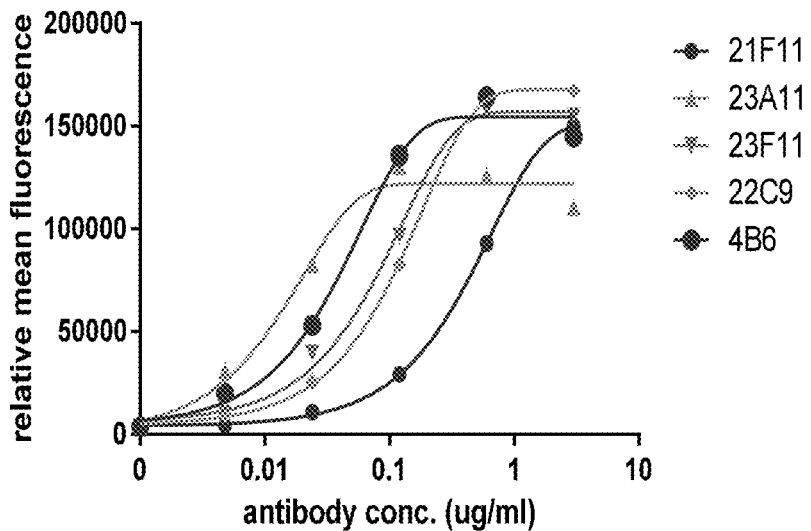
FIG. 5A shows the dose-dependent binding of the mouse purified PD-L1 antibodies to hPD-L1 expressed on HCC827.

1. Dose-Dependent Response of Binding of Purified PD-L1 Antibodies to HCC827 Measured by FACS Log phase IFN-γ stimulated (500 U/ml for 2 days) HCC827 cells were collected and resuspended in blocking buffer (5% BSA+PBS). 2×10^5 cells were added to each tube and then washed once with PBS (1500 rpm, 5 mins, RT). The 100 µl/tube serial diluted PD-L1 antibodies purified from hybridoma supernatant in blocking buffer were added into corresponding tubes and were incubated at 4° C. for 1 hr. The cells were then washed twice with 1 ml PBS, followed by adding 100 µl/tube of $2^{nd}$ antibody (1:400 anti-mIgG (H+L)-PE, Cell signaling) in blocking buffer. The cells were incubated at 4° C. for 1 hr and then washed twice with PBS, followed by resuspending cells in 150 µl PBS for each sample. The cells were then transferred into FACS tube and the bindings of the antibodies to the cells were detected using flow cytometry (BD Accuri C6) (see FIG. 5A).

Figure 5B:
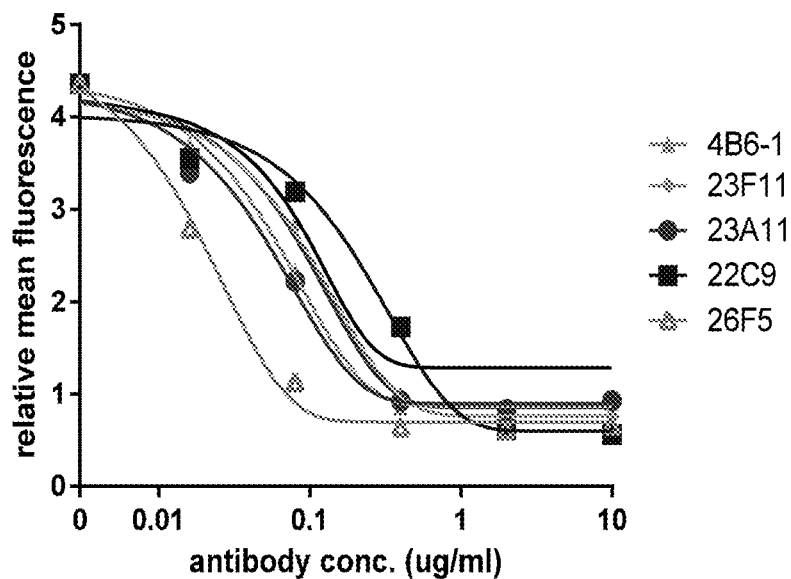
FIG. 5B illustrates the dose-dependent activities of the mouse purified PD-L1 antibodies in blocking the binding of hPD-1-N297A to hPD-L1 expressed on HCC827. 21F11 (circle), 23A11 (triangle), 23F11 (inverted triangle), 22C9 (diamond) and 4B6 (big circle).

2. Dose-Dependent Activities of Purified PD-L1 Antibodies to Block hPD-1 Binding to hPD-L1 on HCC827 Measured by FACS Log phase IFN-γ stimulated (500 U/ml for 2 days) HCC827 cells were collected and resuspended in blocking buffer (5% BSA+PBS). 2×10^5 cells were added to each tube and then washed once with PBS (1500 rpm, 5 mins, RT). The 100 µl/tube serial diluted PD-L1 antibodies purified from hybridoma supernatant with blocking buffer were added into corresponding tubes and were incubate at 4° C. for 1 hr. The cells were then washed twice with 1 ml PBS, followed by adding 100 µl/tube 3 µg/ml biotinylated hPD-1-N297A and being incubated at 4° C. for 1 hr. After being washed for three times with PBS, 100 µl/tube of 1:200 diluted (rabbit anti-hIgG-PE, Santa Cruz) in blocking buffer was added to each tube. The cells were incubated at 4° C. for 1 hr and then washed twice with PBS, followed by resuspending cells in 150 µl PBS for each sample. The cells were then transferred into FACS tube and the bindings of the antibodies to the cells were detected using flow cytometry (BD Accuri C6) (see FIG. 5B).

Example 7: Cloning and Sequence of Hybridoma Antibodies

The sequences of the mouse anti-human PD-L1 antibody light chain and heavy chain variable regions were obtained by the polymerase chain reaction (PCR) amplification technique known as 5' RACE (rapid amplification of cDNA ends). Total RNA from 4B6/23A11/23F11/22C9/26F5/21F11/18G4 antibody producing hybridoma cell was isolated using Trizol (Invitrogen) and cDNA was synthesized using Superscript first strand synthesis system (Invitrogen) with Oligo (DT) 12-18 primer (Invitrogen). The variable regions of mouse IgG gene were cloned by PCR with MuIgG VH3'-2 and MuIg-5' leader primers for heavy chain variable region and MuIgK VL3'-1 and MuIg-5" leader primer for light chain variable region (NOVAGEN). The resulting band for each antibody was cloned into TOPO TA cloning vector and DNAs from more than 10 clones were submitted for sequencing and determined using ABI DNA sequencing instruments (Perkin Elmer). Consensus sequences were determined using Vector NTI Advance 10 software (Invitrogen).

Generation of chimeric antibodies: After sequencing analysis and confirmation, the variable region of the each above mentioned genes were cloned into a recombinant expression vector, e.g. the sequence of the light chain variable region (VL) was cloned into pCP-hIgG1, and the sequence of the heavy chain variable region (VH) was cloned into pCP-hIgG1, respectively, for antibody production and purification.

Example 8: Recombinant Chimeric Antibody Expression and Purification

The expression and purification of the recombinant chimeric antibody protein produced above were conducted by following methods: HEK293E cells cultured in Freestyle 293 Expression Medium with 10% of Pluronic F-68 at 1×10^6 cell/ml were transfected with equal amount of heavy chain vector and light chain vector DNA with final concentration of 0.5 µg/ml and PEI (Polyethylenimine-linear, Polyscience) of 1.0 µg/ml. DNA to PEI ratio was 1:2. DNA and PEI complexes formed period with Optimal MEM should be 15 minutes at the room temperature. Transfected cells were cultured in the flasks with 5% $CO_2$, at 37° C. and at 125 rpm shaking speed. 1% Peptone medium was added at 22 to 26 hours post transfection. Conditioned medium was harvested on day 6 and supernatant was centrifuged at 3,000 rpm for 30 minutes. The clarified conditioned medium was then loaded onto ProteinA column (G.E. Healthcare), washed with PBS plus 0.1% triton-X100 and finally the bound IgG was eluted with a solution containing 0.1M glycine at pH 3.5. The eluted antibody protein was dialyzed to PBS and stored at −80° C. To remove endotoxin, the purified protein was further processed by passing through Hitrap DEAE Sepharose F.F. column and the resulting antibody was analyzed to determine the level of purity using size exclusion chromatography (Superdex 200 5/150 GL, G.E. Healthcare).

Example 9: Cross-Reactivity of Purified PD-L1 Antibodies to Cynomolgus and Rodent PD-L1 Protein and Binding Selectivity of hPD-L1 to hPD-L2

1. Cross-Species Binding to Cynomolgus PD-L1 Proteins

High-binding clear polystyrene 96-well plates (Nunc) were coated with 100 μl/well of a 0.5 μg/ml human or cynomolgus (cyno) PD-L1-his in high pH coating buffer and incubated overnight at 4° C. Then plates were washed once on an automatic plate washer using washing buffer (PBS+0.1% Tween 20 (Sigma)). 200 μl of blocking buffer (PBS+1% BSA+1% normal goat serum+0.05% Tween-20) was added to each well and incubated for 2 hours at room temperature. Then add serial diluted antibodies with dilution buffer (PBS+1% BSA+1% normal goat serum+0.01% Tween-20) and incubated for 1 hour at RT. The plates were then washed 3 times using the method described above. 100 μl/well of a solution of HRP conjugated goat anti-mouse Fc antibody (Abcam) for mouse hybridoma antibodies or Goat anti-human IgG Fc-HRP preadsorbed (Abcam) for 4B6 chimeric antibody in dilution buffer was then added to each well of the plate. After that the ELISA plates were allowed to incubate for 60 min at RT then plates were washed 3 times with 250 μl/well washing buffer. Finally, 100 μl/well of TMB was added to each well and the reaction was terminated using 0.64M $H_2SO_4$. The plates were read on a Thermo Multiscan FC at 450 nM (see FIG. 6A to 6E).

The chimeric antibody 4B6-C has similar binding affinity to its parent antibody 4B6. The binding affinity of 4B6 to human and monkey antigen is similar to that of 4B6-C as in FIG. 6A, and the binding affinity of 4B6-C in mouse is similar to that of 4B6 as in FIG. 6E.

2. Cross-Species Binding to Mouse PD-L1 Proteins

Figure 6A:
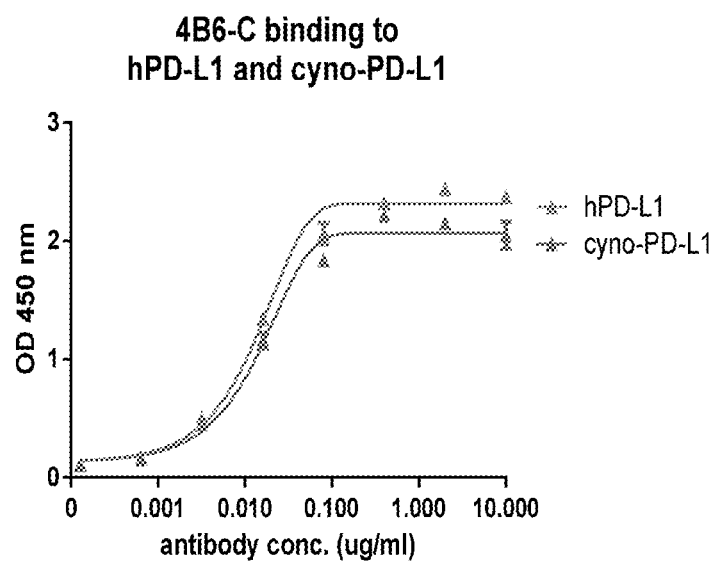
FIG. 6A (4B6-C), FIG. 6B (23A11), FIG. 6C (23F11), FIG. 6D (22C9) and FIG. 6E (21F11) show the mouse and/or chimeric PD-L1 antibodies bind to huma and cynomolgis PD-L1-his similarly, whereas those specifically binding to human and cynomolgus PD-L1 do not bind to mouse PD-L1-his as measured by ELISA, except that 18G4 binds both the human and mouse PD-L1 (FIG. 6F).
Figure 6B:
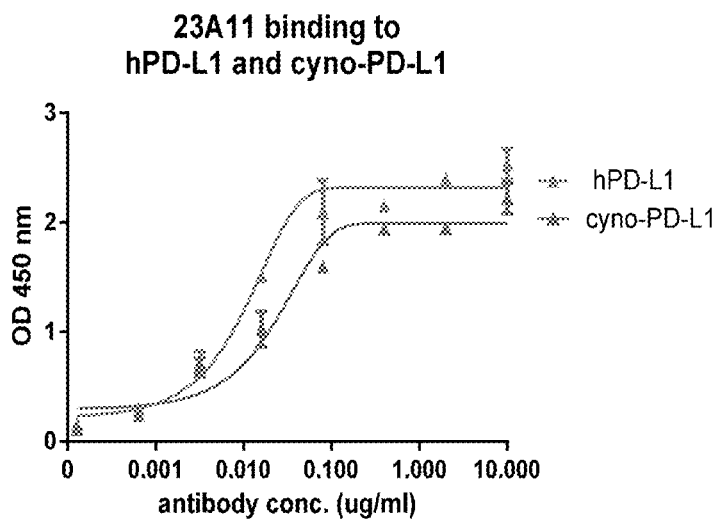
FIG. 6G shows that all the antibodies can bind to hPD-L1, but not to hPD-L2, as measured by ELISA.
Figure 6C:
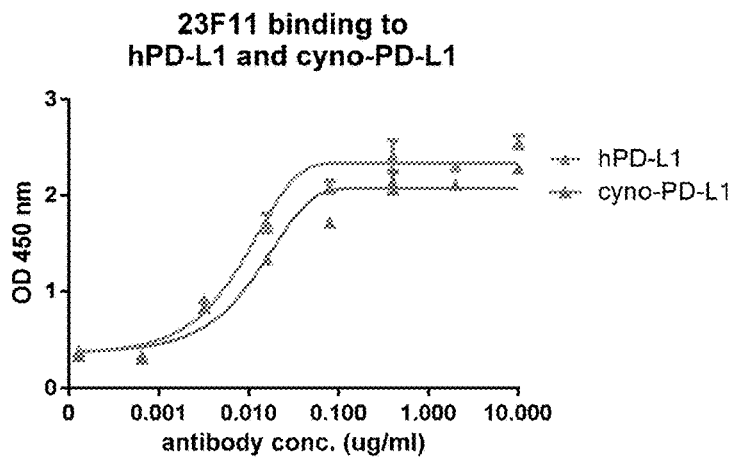
Figure 6D:
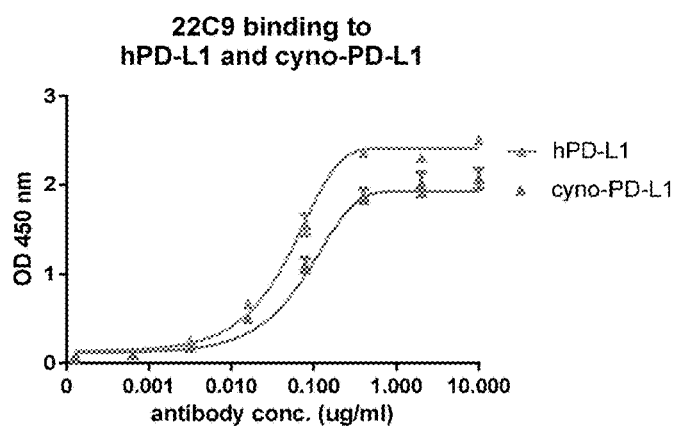
Figure 6E:
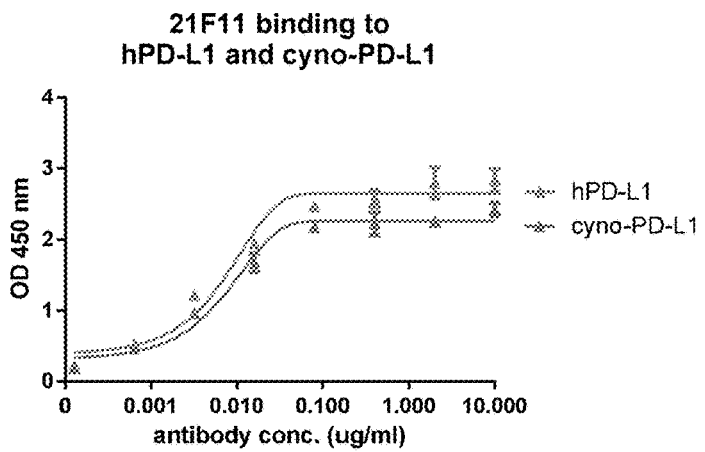
Figure 6F:
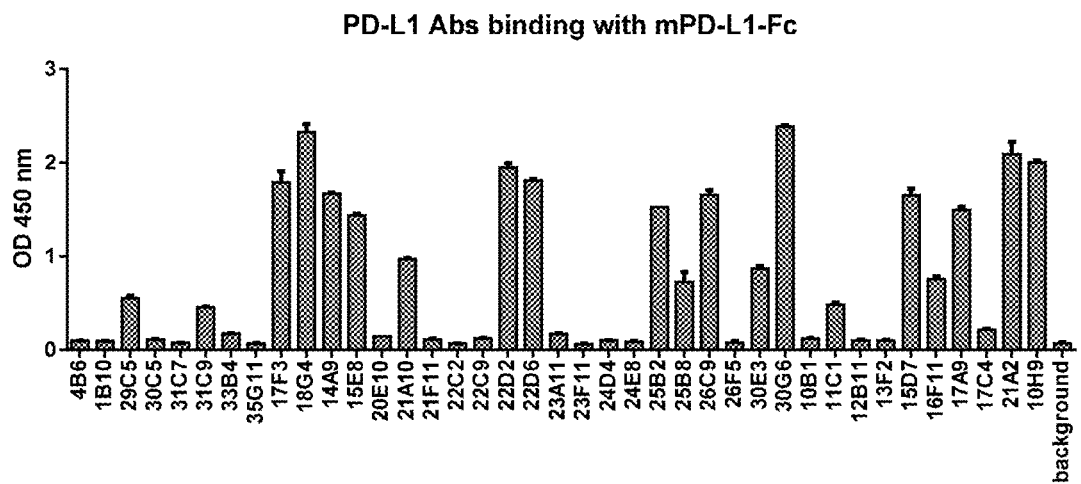

High-binding clear polystyrene 96 well plates (Nunc) were coated with 100 μl/well of 1 μg/ml mouse PD-L1-his in high pH coating buffer and incubated overnight at 4° C. Then plates were washed once on an automatic plate washer using washing buffer (PBS+0.1% Tween 20 (Sigma)). 200 μl of blocking buffer (PBS+1% BSA+1% normal goat serum+ 0.05% Tween-20) was added to each well and incubated for 2 hours at room temp. Then add 20 μg/ml purified hybridoma mouse antibodies in dilution buffer (PBS+1% BSA+1% normal goat serum+0.01% Tween-20) and incubate for 1 hour at RT. The plates were then washed 3 times with 250 μl/well washing buffer. 100 μl/well of a solution of HRP conjugated goat anti-mouse Fc antibody (Abcam) in dilution buffer was then added to each well of the plate. After that the ELISA plates were allowed to incubate for 60 min at RT then plates were washed 3 times with 250 μl/well washing buffer. Finally, 100 μl/well of TMB was added to each well and the reaction was terminated using 0.64M $H_2SO_4$. The plates were read on a Thermo Multiscan FC at 450 nM (see FIG. 6F).

3. Cross-Family Binding to hPD-L2 Protein

The bindings of purified antibodies (4B6, 23A11, 26F5, 23F11 and 22C9) to human PD-L2 protein were evaluated by ELISA similarly as described above for the cross-species binding. Briefly, high-binding clear polystyrene 96 well plates (Nunc) were coated with 100 μl/well of a 0.5 μg/ml human PD-L1-Fc (Acrobiosystems, Cat #PD1-H5258) or 100 μl/well of a 1 μg/ml hPD-L2-Fc (Acrobiosystems, Cat #PD2-H5251), respectively, in high pH coating buffer (0.16% Na2CO3+0.3% NaHCO3, pH 9.8) and incubated overnight at 4° C. Then the plates were washed once on an automatic plate washer using washing buffer (PBS+0.1% Tween 20 (Amresco)). 200 μl of blocking buffer (PBS+1% BSA+1% normal goat serum+0.05% Tween-20) was added to each well and incubated for 2 hours at room temp. Then add 100 μl 2 μg/ml purified PD-L1 antibodies with dilution buffer (PBS+1% BSA+1% normal goat serum+0.01% Tween-20) and incubate for 1 hour at RT. The plates were then washed 3 times with washing buffer. 100 μl/well of a solution of HRP conjugated goat anti-mouse IgG antibody (1:20000, Abcam) in dilution buffer was then added to each well of the plate. After that the ELISA plates were allowed to incubate for 60 min at RT then the plates were washed 3 times with 250 μl/well washing buffer. Finally, 100 μl/well of TMB was added to each well for 15 min and the reaction was terminated using 50 ul/well of 0.16 M/L sulfuric acid. The plates were read on a Thermo Multiscan FC at 450 nM (see FIG. 6G).

Figure 6G:
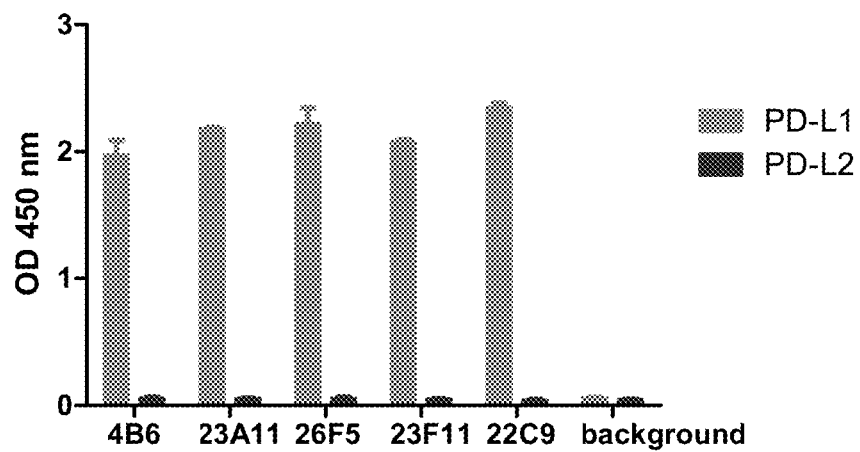

As shown in FIG. 6G, all of the tested antibodies can bind to hPD-L1 but not to hPD-L2.

Example 10: Characterization of Binding of Purified Anti-PD-L1 Antibodies to PD-L1 on Tumor Cells: FACS Binding Assay (HCC827 Cell)

Figure 7:
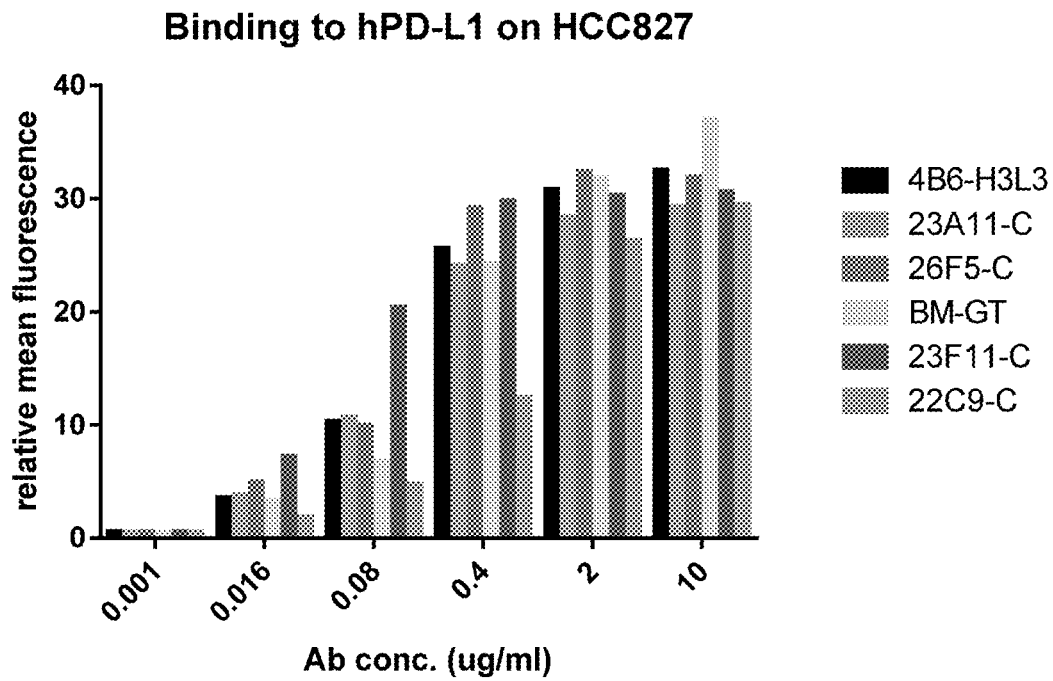
FIG. 7 illustrates the binding of chimeric and/or humanized PD-L1 antibodies to hPD-L1 expressed on HCC827 as measured by FACS.

Log phase IFN-γ stimulated (500 U/ml for 2 days) HCC827 cells were collected and resuspended in blocking buffer (5% BSA+PBS). 2×10^5 cells were added to each tube and then washed once with PBS (1500 rpm, 5 mins, RT). The 100 μl/tube serial diluted biotinylated PD-L1 antibodies with blocking buffer were added into corresponding tubes and incubate at 4° C. for 1 hr. The cells were then washed twice with 1 ml PBS, followed by adding 100 μl/tube of $2^{nd}$ antibody (or 1:200 rabbit anti-human IgG-PE (Santa Cruz) in blocking buffer. The cells were incubated at 4° C. for 1 hr and then washed twice with PBS, followed by resuspending cells in 150 μl PBS for each sample. The cells were then transferred into FACS tube and the binding of the antibodies to the cells were detected using flow cytometry (ACEA Bioscience Novocyte) (see FIG. 7). The antibodies with "C" represent chimeric antibodies, and antibody "4B6-H3L3" refers to humanized 4B6 with the combination of heavy chain H3 and light chain L3, as produced in Example 15.

Example 11: Evaluation of Blocking Activities of Purified Anti-PD-L Antibodies to Inhibit Binding of PD-1 to PD-L1 on Tumor Cells Log phase IFN-γ stimulated (500 U/ml for 2 days) HCC827 cells were collected and resuspended in blocking buffer (5% BSA+PBS). 2×10^5 cells were added to each tube and then washed once with PBS (1500 rpm, 5 mins, RT). The 100 μl/tube serial diluted PD-L1 antibodies (see FIG. 8) with blocking buffer were added into corresponding tubes and incubate at 4° C. for 1 hr. The cells were then washed twice with 1 ml PBS, followed by adding 100 μl/tube 3 μg/ml biotinylated hPD-1-N297A and incubated at 4° C. for 1 hr. After washing for three times with PBS, 100 μl/tube streptavidin-PE 1:200 (EBiosciences) in blocking buffer was added to each tube. The cells were incubated at 4° C. for 1 hr and then washed twice with PBS, followed by resuspending cells in 150 μl PBS for each sample. The cells were then transferred into FACS tube and the binding of the antibodies to the cells were detected with flow cytometry (ACEA Bioscience Novocyte).

Figure 8:
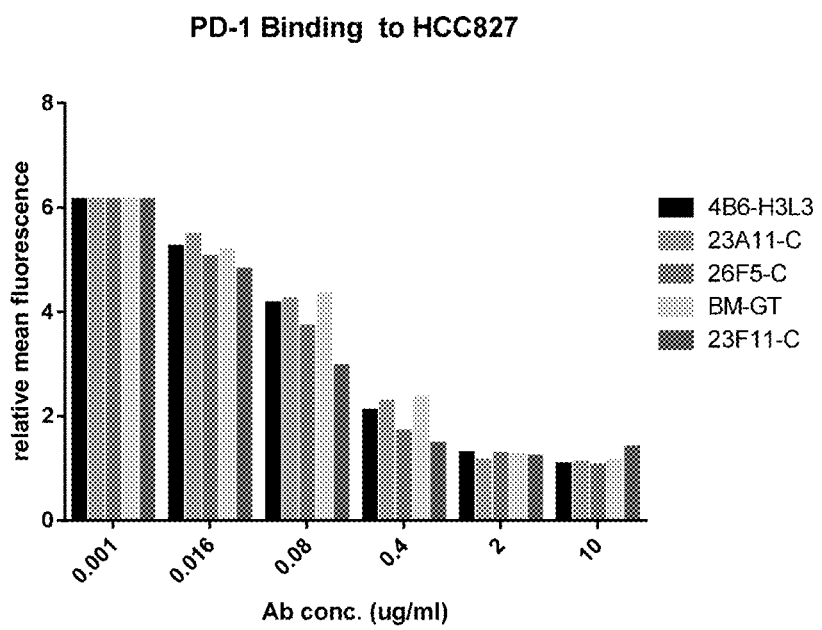
FIG. 8 presents the activities of the chimeric and/or humanized PD-L1 antibodies in blocking the binding of PD-1 to the hPD-L1 expressed on HCC827 as measured by FACS.

As shown in FIG. 8, the FACS result showed that the anti-PD-L1 antibodies exhibit concentration-dependent activities of inhibiting the binding of hPD-1 to hPD-L1 on tumor cell HCC827.

Example 12: Epitope Binning of Selected Anti-PD-L1 Via Competition ELISA

Figure 9A:
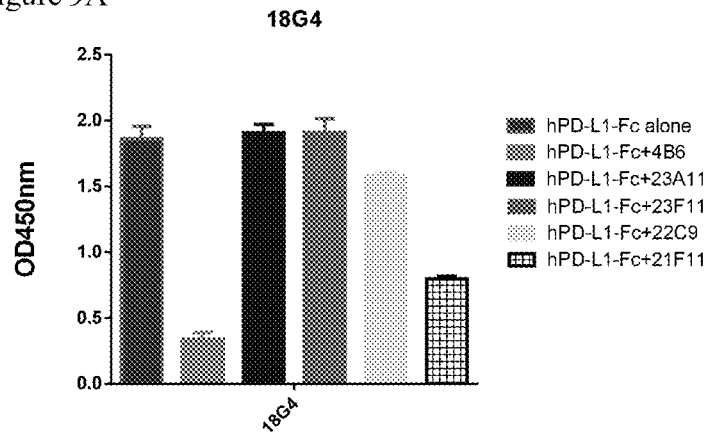
FIG. 9A (18G4), FIG. 9B (4B6) and FIG. 9C (23A11) are bar charts showing the results of epitope binding of the PD-L1 antibodies to hPD-L1-Fc in the presence of competitive antibodies 4B6, 23A11, 23F11, 22C9 and 21F11, as measured by competition ELISA, respectively.
Figure 9B:
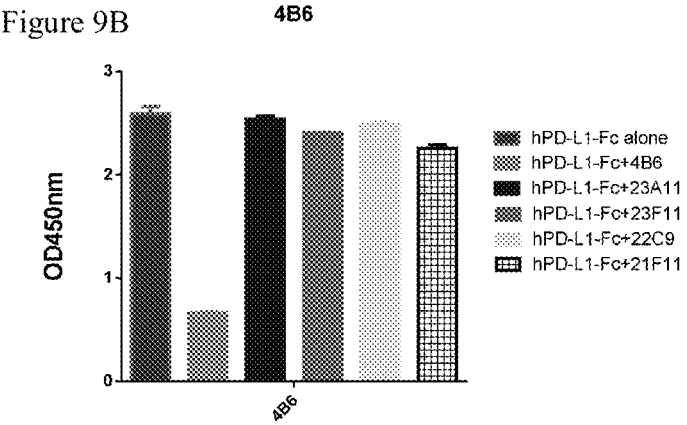
Figure 9C:
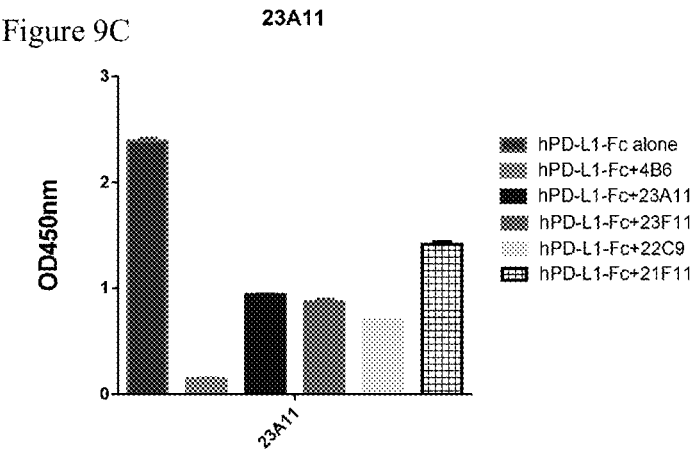
Figure 10A:
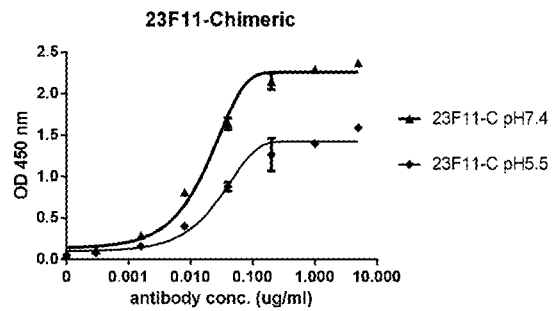
FIG. 10A (23F11-C), FIG. 10B (23A11-C), FIG. 10C (22C9-C), FIG. 10D (21F11-C), FIG. 10E (4B6-C), and FIG. 10F (26F5-C) are graphs showing the pH-dependent binding of the chimeric PD-L1 antibodies to hPD-L1-his at pH7.4 and pH5.5 as measured by ELISA analysis, respectively.
Figure 10D:
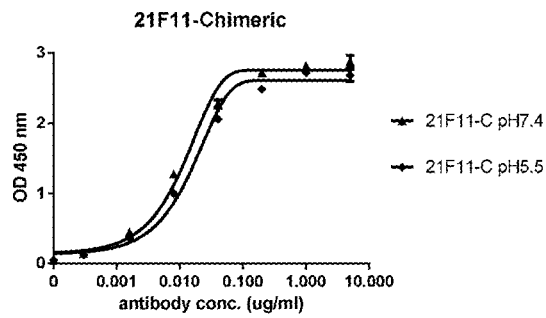
Figure 10B:
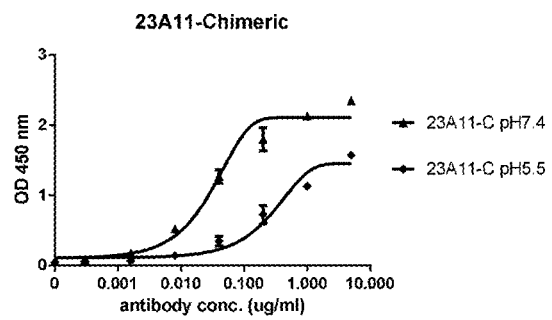
Figure 10E:
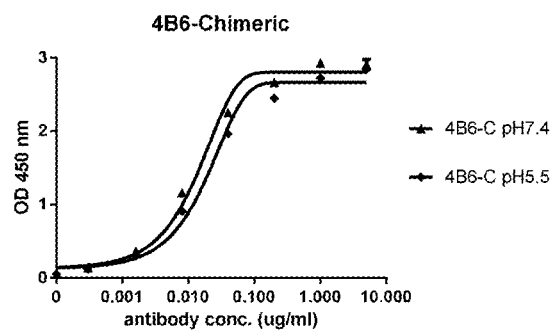
Figure 10C:
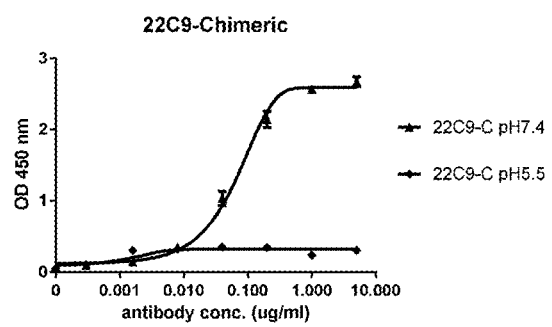
Figure 10F:
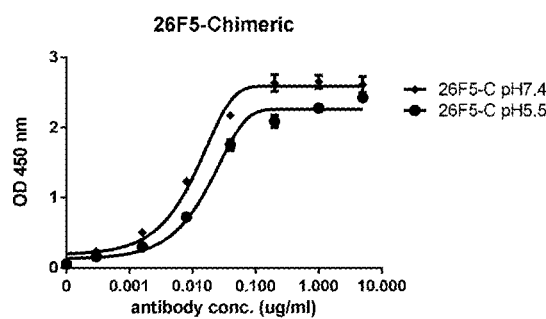

High-binding clear polystyrene 96 well plates (Nunc) were coated with 100 μl/well of coating solution consisting of 0.5 μg/ml hPD-L1-Fc overnight at 4° C. Then plates were washed once on an automatic plate washer using washing buffer (PBS+0.1% Tween 20 (Sigma)), followed by adding 200 μl of blocking buffer (PBS+1% BSA+1% normal goat serum+0.05% Tween-20) to each well. The plates were incubated for two hours at room temperature. Then serial diluted competitive antibodies 4B6, 23A11, 23F11, 22C9 and 21F11, at 20 μg/ml in dilution buffer (PBS+1% BSA+ 1% normal goat serum+0.01% Tween-20) were added and the plates were incubated for 1 hour at RT. The plates were then washed 3 times using the washing buffer. Biotinylated anti-PD-L1 antibodies (e.g. 18G4, 23A11, 4B6) at various concentrations yielding 80% of maximal binding signal were added and incubated for 1 hour at RT. After the plates were washed 3 times, 100 μl/well of a solution of HRP conjugated Neutravidin antibody (Pierce) diluted in dilution buffer was then added to each well of the plate. Afterwards the ELISA plates were incubated for 60 min at room temperature and then were washed three times with 250 μl/well washing buffer. Finally, 100 μl/well of TMB was added to each well and the reaction was terminated using 0.64M H$_2$SO$_4$. The plates were read on a Thermo Multiscan FC at 450 nM (see FIG. 9A to FIG. 9C).

Example 13: Characterization of pH-Dependent Binding of Recombinant Chimeric Antibodies High-binding clear polystyrene 96 well plates were coated with 100 μl/well of a 0.5 μg/ml hPD-L1-his (Acrobiosystems) in high pH coating buffer and incubated overnight at 4° C. Then the coated plates were washed once on an automatic plate washer with PBS+0.1% Tween 20 (Sigma). Then 200 μl of blocking buffer was added to each well and the plates were then incubated for 2 hours at room temperature. After aspirating the blocking buffer, serial diluted chimeric antibodies in dilution buffer with pH7.4 were added and the plates were incubated for 40 minutes at RT. The plates were then washed once with 250 μl/well washing buffer with pH of 7.4 or 5.5 and then 100 μl of pH 7.4 or pH 5.5 antibody dilution buffer was added and incubation continued for 2 hr at RT. Afterwards the plates were washed 3 times with 250 μl of washing buffer (shake for 10 s for every wash) and 100 μl/well of a solution of 1:20000 diluted HRP conjugated goat anti-human Fc antibody (Abcam) in pH7.4 dilution buffer was then added to each well of the plate and incubated for 1 hour at RT. Then the plates were washed 3 times with 250 ul of washing buffer (shake for 10 s for every wash). Finally, 100 μl/well of TMB was added to each well and the reaction was terminated using 0.64M H$_2$SO$_4$. The plates were read on a Thermo Multiscan FC at 450 nM (see FIG. 10A-F).

As shown in FIG. 10A to 10F, chimeric antibodies 23F11, 23A11 and 22C9 (FIG. 10A to 10C) showed pH-dependent binding to hPD-L1 (e.g. higher binding at pH7.4 than at pH 5.5), while chimeric antibodies 21F11, 4B6, 26F5 (FIG. 10D to 1° F.) showed no pH-dependent binding to hPD-L1 (similar binding affinity at pH5.5/pH7.4).

Example 14: In Vivo Evaluation of Anti-PD-L1 Antibodies

The in vivo activities of the above obtained anti-PD-L1 antibodies were evaluated using a modified syngeneic mouse Xenograft tumor model. The mice were inoculated subcutaneously with mouse tumor cells in which the mouse PD-L1 gene has been replaced with human PD-L1, including mouse colon cancer cell line MC38, and melanoma cell line B16. Anti-human PD-L1 antibodies were injected intraperitoneal (IP) 3 mg/kg, 10 mg/kg and/or 30 mg/kg three times a week or intravenously at doses of 1, 3 or 10 mg/kg once a week. Reference PD-L1 antibodies BM-GT (i.e. YW243.55.S70 or MPDL3280A as disclosed in the U.S. Pat. No. 8,217,149 (Genentech)) and BM-ME (i.e. 2.14H90P of the U.S. Pat. No. 8,779,108) were used as positive control. The effect of antibody on tumor growth was evaluated when tumors of the vehicle group reach volume of 1000 mm$^3$. Tumor volume and body weight were measured twice a week as described below and the effect of antibodies on tumor growth were calculated as tumor growth inhibition (TGI) relative to vehicle group.

1. Generation of Human PD-L1 Expressing Murine Tumor Cell Lines.

Endogenous CD274/PD-L1 in mouse tumor cell lines (B16 and MC38 were purchased from ATCC, respectively) was knocked out using a high efficient CRISPR/Cas9 system we recently developed. Briefly, sgRNAs targeting the first coding exon of mouse CD274/PD-L1 gene was designed, and the cells were transfected by hit-and-run CRISPR/Cas9+ sgRNA constructs and selected for knockout cells. The cells with complete knock out of endogenous CD274/PD-L1 were identified by FACS analysis for cell surface expression of CD274/PD-L1 in steady state or stimulated by interferon gamma, and subsequently verified by TA cloning and sequencing of the targeted genomic region. To generate human CD274/PD-L1 replacement cell lines, the coding sequence of human CD274/PD-L1 cDNA was cloned into a FG12 derived lentiviral vector. The mouse CD274/PD-L1 knockout cells were then infected with the human CD274/PD-L1 expressing lentivirus and high level and the stable expression of human CD274/PD-L1 in the established cell lines was confirmed by FACS analysis. The engineered cells of B16 and MC38 were named as B16-hPD-L1 KI, MC38-hPD-L1 KI, respectively.

2. Anti-Tumor Activities of PD-L1 Antibodies in the B16/Human-PD-L1 Knock-in Tumor Model The B16 cell was engineered to replace the mouse PD-L1 gene with the human PD-L1 and is named as B16-hPD-L1 KI. Prior to study, the B16-hPD-L1 KI cells were subcultured within 5 passages before inoculated into the mice. $2\times10^6$ cells/0.2 mL was injected via S.C. to each of the 10 female SPF grade C57BL/6 mice. The first dose (3 mpk or 10 mpk) of antibody (e.g. BM-GT, 4B6-C and 23A11) was injected one day after the tumor cells were injected. Tumor size was measured twice weekly in two dimensions using a caliper (INSIZE). Tumor growth inhibition (TGI) % was calculated based on the value measured at day 29. Results were analyzed using Prism GraphPad and expressed as mean±S.E.M. Comparisons between two groups were made by T-test, and the difference is considered significant if P is <0.05 (see Table 1).

TABLE 1

Study design to test the anti-tumor activities of PD-L1 antibodies in the treatment of B16/hPDL1 syngeneic murine tumor model

| Group | Treatment | Animal No. | Dosage | Dose Route | Schedule | Tumor Growth Inhibition (%) |
|---|---|---|---|---|---|---|
| 1 | Control (PBS) | 1-10 | — | i.p. | 3 times/week*3 | |
| 2 | BM-GT | 1-10 | 3 mpk | i.p. | 3 times/week*3 | 15.54 |
| 3 | BM-GT | 1-10 | 10 mpk | i.p. | 3 times/week*3 | 33.92 |
| 4 | 4B6-C | 1-10 | 3 mpk | i.p. | 3 times/week*3 | 34.00 |
| 5 | 4B6-C | 1-10 | 10 mpk | i.p. | 3 times/week*3 | 37.79 |
| 6 | 23A11 | 1-10 | 3 mpk | i.p. | 3 times/week*3 | 37.63 |
| 7 | 23A11 | 1-10 | 10 mpk | i.p. | 3 times/week*3 | 51.06**, $p < 0.05$ |

3. Anti-Tumor Activities of PD-L1 Antibodies in the MC38/Human-PD-L1 Knock-in (KI) Tumor Model MC-38 cells engineered to replace the mouse PD-L1 gene with the human PD-L1 is named as MC38-hPD-L1 KI. The MC38/hPDL1-KI tumor cells were maintained in vitro as a monolayer culture in RPMI1640 medium (Thermo Fisher) supplemented with 10% heat inactivated fetal bovine serum (ExCell Biology), 100 U/ml penicillin and 100 μg/ml streptomycin (Hyclone) at 37° C. in an atmosphere with 5% $CO_2$ in air. The tumor cells were routinely sub-cultured twice weekly by trypsin-EDTA treatment (Hyclone). The cells growing in an exponential growth phase were harvested and counted for tumor inoculation. Each female SPF grade C57BL/6 mouse was inoculated with 2×10^6 cells by S.C. injection on the right flank. Approximate 10 days after inoculation, 40 mice with the tumor volume around 100 mm^3 were selected and randomized into 5 groups (see the scheme in Table 2). Then the mice were treated with PBS, 10 mg/kg of body weight by TP injection of each purified antibody hybridoma derived mouse antibodies 4B6, 23A11, 23F11, 26F5 formulated in PBS at 1 mg/ml. Treatment continued three times a week for 4 weeks from first injection. Animal were sacrificed at the end of the study with $CO_2$ inhalation. Tumor size was measured twice weekly in two dimensions using a caliper (INSIZE), and the volume was expressed in $mm^3$ using the formula: V=0.5 a×b$^2$ where a and b are the long and short diameters of the tumor, respectively. Results were analyzed using Prism GraphPad and expressed as mean±S.E.M. Comparisons between two groups were made by T-test, and the difference is considered significant if P is *<0.05 and **<0.01 (see Table 3).

TABLE 2

Study design to test the anti-tumor activities of PD-L1 antibodies in the treatment of MC38/hPDL1 syngeneic murine tumor model

| Group | Treatment | Animal No. | Dosage | Dose Route | Schedule |
|---|---|---|---|---|---|
| 1 | Control (PBS) | 1-8 | — | i.p. | 3 times/week*3 |
| 2 | 4B6 | 1-8 | 10 mpk | i.p. | 3 times/week*3 |
| 3 | 23A11 | 1-8 | 10 mpk | i.p. | 3 times/week*3 |
| 4 | 23F11 | 1-8 | 10 mpk | i.p. | 3 times/week*3 |
| 5 | 26F5 | 1-8 | 10 mpk | i.p. | 3 times/week*3 |

TABLE 3

Tumor volume

| Treatment | Tumor Size (mm$^3$) at day 29 | TGI (%) | p value vs. PBS |
|---|---|---|---|
| PBS | 677.1 ± 203.2 | — | — |
| 4B6 10 mpk | 71.7 ± 45.5 | 89.4 | 0.0084* |
| 23A11 10 mpk | 295.9 ± 199.8 | 56.3 | 0.2054 |
| 26F5 10 mpk | 194.4 ± 194.4 | 71.3 | 0.1102 |
| 23F11 10 mpk | 27.6 ± 27.6 | 95.9 | 0.0048** |

Note:
a. Mean ± SEM,
*P < 0.05,
**P < 0.01

Figure 11A:
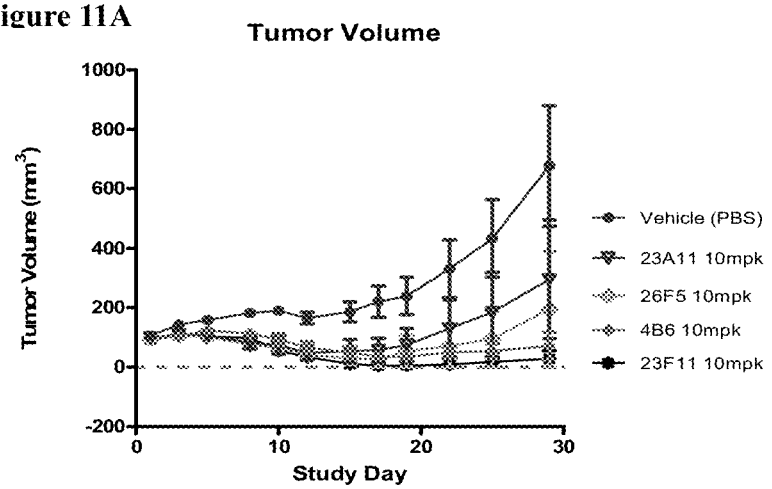
FIG. 11A shows the averaged tumor volume measured over time in MC38/Human-PD-L1 knock-in tumor model, which indicates the in vivo anti-tumor activities of the purified mouse anti-PD-L1 antibodies (4B6 (solid diamond), 23A11 (inverted open triangle), 23F11 (solid striped diamond) and 26F5 (open diamond)) and vehicle (solid circle) in inhibiting the growth of tumor.
Figure 11B:
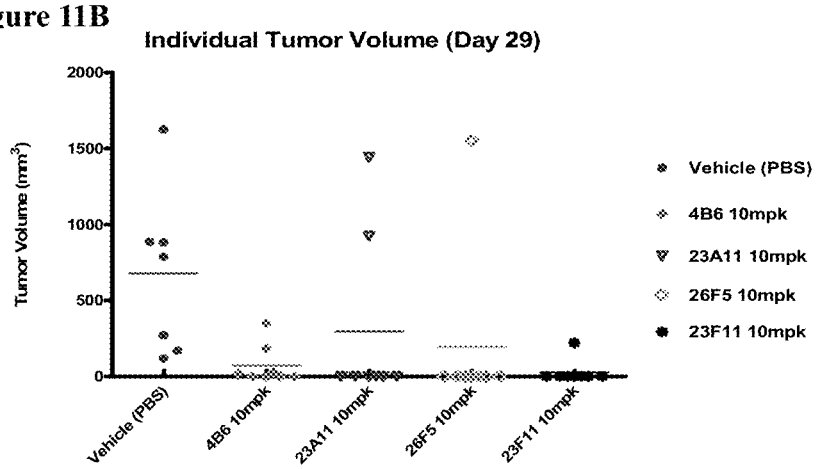
FIG. 11B shows the averaged tumor volume at Day 29 for the same antibodies.
Figure 11C:
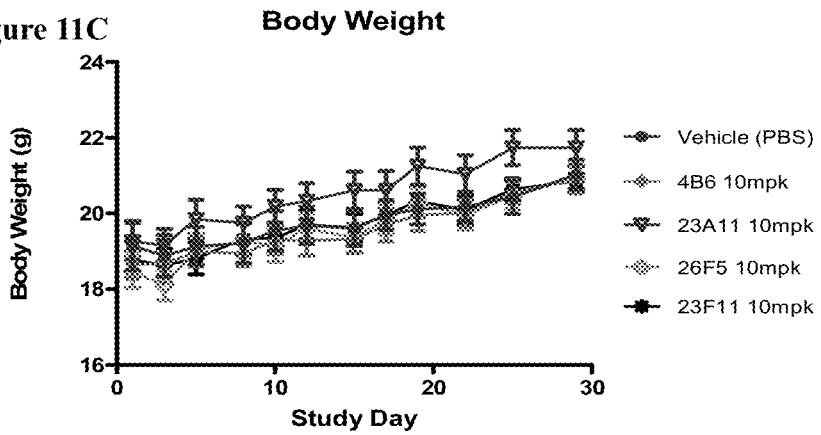
FIG. 11C shows the averaged body weight measured over time for the same antibodies. Mice (n=8 for each group) were IP injected with 10 mg/kg (i.e. mpk) antibodies 3 times/week for 3 weeks, results of which are expressed as mean±S.E.M.

As shown in Table 3 and FIG. 11A-11C, at the end of study, the average tumor volume in the control group is 6.7 times bigger than the volume at the starting point. 4/8, 6/8, 7/8 and 7/8 of the mice treated with antibody 4B6, 23A11, 25F5 and 23F11 respectively had no detectable tumor and thus can be considered complete responses. 2/8 of the mice in 4B6 treated group had >70% tumor reduction (see FIG. 11B). These data showed that these antibodies are very potent inhibitor of growth of established tumor and has the ability to clear tumor in majority of the mice.

4. Anti-Tumor Activities of PH-Dependent PD-L1 Antibodies in the MC38/Human-PD-L1 Knock-in Tumor Model To evaluate whether pH-dependent antibodies have any advantage in vivo in tumor inhibition, we compared the activity of one of the pH dependent antibodies 23F11 and one of the non-pH-dependent binding antibodies 4B6-C (see FIGS. 12A and 12B). These antibodies have potent neutralizing activities and can also inhibit tumor at high doses. To reveal potential advantage of the pH-dependent antibodies we test the antibodies at low dose: 1 mg/kg via IP injection. Briefly, each female SPF grade C57BL/6 mouse were inoculated with 2×10^6 cells (i.e. MC38-hPD-L1 KI) by S.C. injection on the right flank. Approximate 10 days after the inoculation, 40 mice with the tumor volume around 200 mm^3 were selected and randomized into 5 groups. Then the mice were treated with PBS, 4B6-chimeric (4B6-C), 23F11, benchmark antibodies BM-GT (also named as YW243.55.570 or MPDL3280A in U.S. Pat. No. 8,217,149) and BM-ME (also named as 2.14H90PT in U.S. Pat. No. 8,779,108) at 1 mg/kg of body weight by IP injection of each purified antibody formulated in PBS at 1 mg/ml. Treatment was given three times each week and continued for 3 weeks after the first injection. Animals were sacrificed at the end of the study by $CO_2$ inhalation. Tumor size was measured twice weekly in two dimensions using a caliper (INSIZE), and the volume was expressed in mm$^3$ using the formula: V=0.5 a×b$^2$ where a and b are the long and short diameters of the tumor, respectively. Results were analyzed using Prism GraphPad and expressed as mean±S.E.M. Comparisons between two groups were made by T-test, and the difference is considered significant if P is <0.05.

Figure 12A:
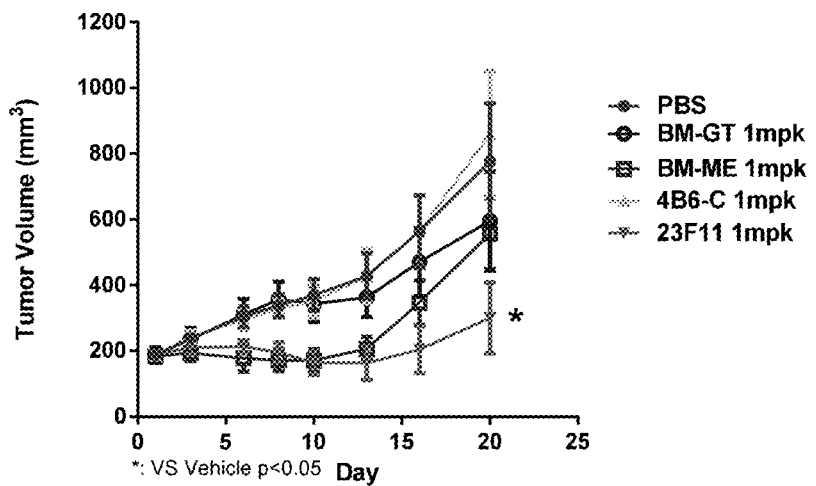
FIG. 12A shows the averaged tumor volume measured over time in MC38/Human-PD-L1 knock-in tumor model injected with the purified mouse/chimeric PD-L1 antibodies (4B6-C (light grey solid triangle), 23F11 (inverted dark solid triangle)) and benchmark antibodies of BM-GT (open circle) and BM-ME (open square) or control PBS (solid circle) in inhibiting the growth of tumor, which indicates the in vivo anti-tumor activities of the antibodies.
Figure 12B:
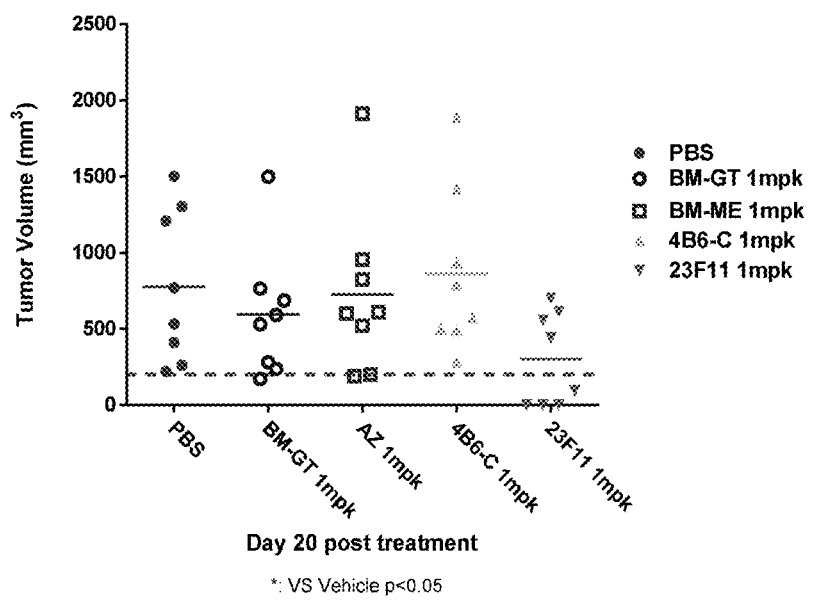
FIG. 12B shows the averaged tumor volume at Day 20, respectively, for mice (n=8 for each group) IP injected with 1 mpk (mg/kg) of said antibodies 3 times/week for 3 weeks.

The data in FIGS. 12A and 12B showed that the antibodies with pH-dependent binding property inhibited tumor growth much more potently than the antibodies without pH-dependent binding property. Treatment with antibody 23F11 at 1 mg/kg dose resulted in complete elimination of tumor in 3 out of 8 mice and 1 out 8 had more than 70% decrease in tumor volume compared to PBS treated group. Treatment with the non-pH-dependent binding antibody 4B6-C resulted in no-significant decrease in tumor volume and every mouse had a tumor larger than its volume at the starting point. Thus, antibody with pH-dependent binding can work at lower doses than non-pH-dependent binding antibodies in inhibiting tumor growth.

Figure 12C:
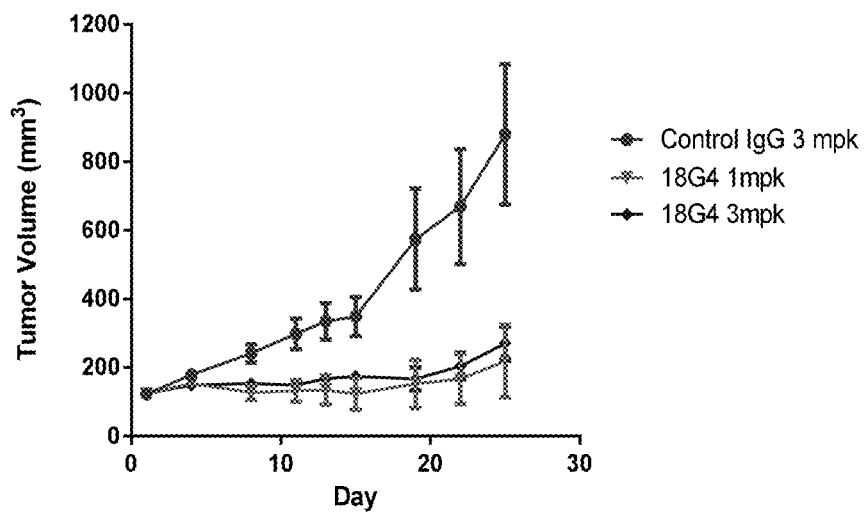
FIG. 12C shows the averaged tumor volume measured over time and FIG. 12D shows the averaged tumor volume at Day 25, for mice (n=8 for each group) IV injected with 1 mpk (light grey inverted solid triangle) or 3 mpk (solid diamond) mouse antibody 18G4.
Figure 12D:
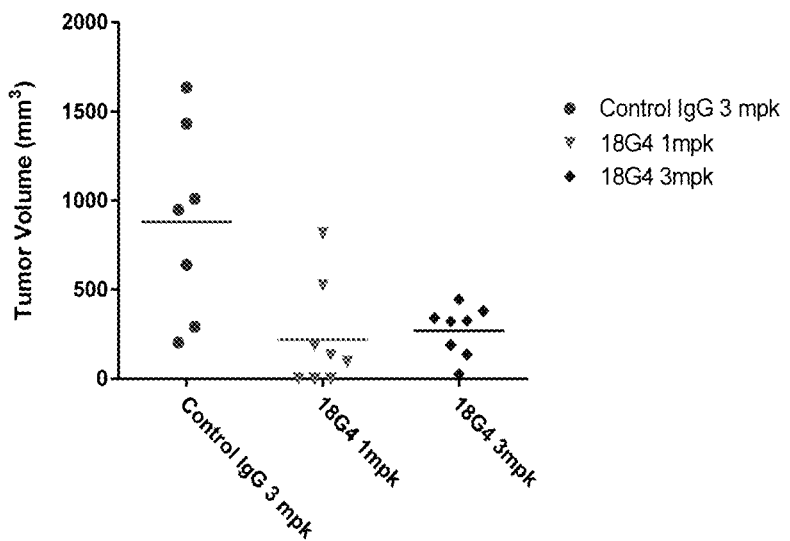
Figure 12E:
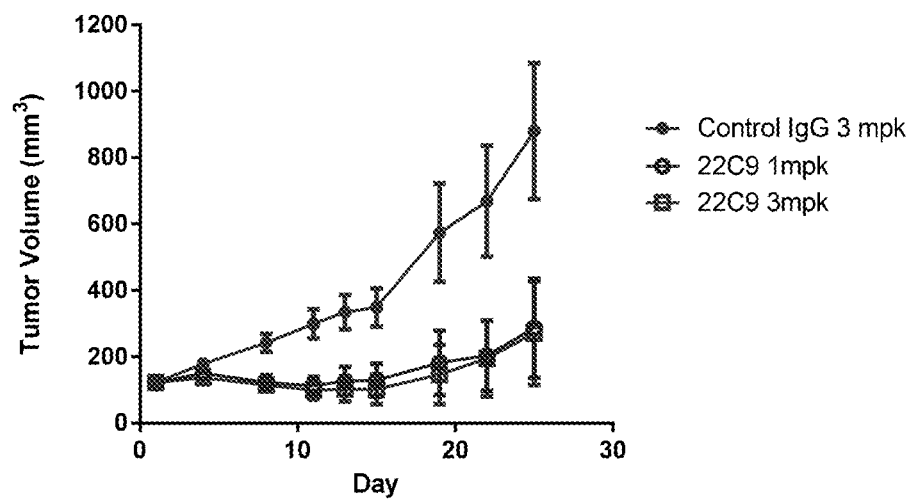
FIG. 12E shows the averaged tumor volume measured over time and FIG. 12F shows the averaged tumor volume at Day 25, respectively, for mice (n=8 for each group) IV injected with 1 mpk (open circle) or 3 mpk (open square) mouse 22C9; results are expressed as mean±S.E.M.
Figure 12F:
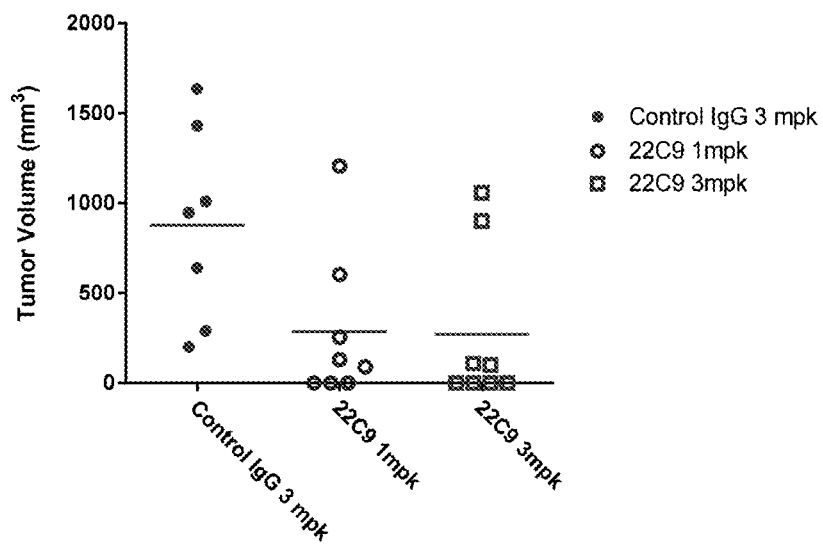

The inhibition of tumor growth of antibody 18G4 (see FIGS. 12C and 12D) and 22C9 (see FIGS. 12E and 12F) in MC38/Human-PD-L1 KI tumor model was also tested when delivered intravenously. Briefly, MC38/hPD-L1 tumor cells were inoculated as previously in C57/BL6 mice and allowed to grow for 6 days. At that time, mice with average tumor volume of around 120 mm$^3$ were selected and randomized into groups of 8 mice each. Each testing antibodies were dosed IV at 1 or 3 mg/kg of purified antibodies 18G4 and 22C9 purified from hybridoma culture in equal volume to individual mouse on day 0 and followed up to day 25. Animals were sacrificed at the end of the study with $CO_2$ inhalation. Tumor size was measured twice weekly in two dimensions using a caliper (INSIZE), and the volume was expressed in mm$^3$ using the formula: V=0.5 a×b$^2$ where a and b are the long and short diameters of the tumor, respectively (see Table 4 and FIG. 12C-12F). Record tumor regressions as partial (PR) if the tumor volume decreased to <50% of the tumor volume at the start of treatment, without dropping below measurable size, or as complete (CR) if the tumor burden has become unpalpable (see Table 5). Results in FIG. 12C-12F were analyzed using Prism GraphPad and expressed as mean±S.E.M. Comparisons between two groups were made by T-test, and the difference is considered significant if P is <0.05. The data showed that at 1 or 3 mg/kg dose, 18G4 (see Table 4 and 5, and FIGS. 12C and 12D) and 22C9 (see Table 4 and 5, and FIGS. 12E and 12F) were very active in inhibiting tumor growth under identical conditions.

TABLE 4

Tumor Growth Inhibition of 18G4 and 22C9 in MC38/hPD-L1 Syngeneic Tumor Model

| Group No. (n = 8) | Treatment | PR | CR | ORR % |
|---|---|---|---|---|
| 1 | Control IgG 3 mpk | 0 | 1 | 12.5 |
| 2 | 18G4 1 mpk | 0 | 3 | 37.5 |
| 3 | 18G4 3 mpk | 1 | 0 | 12.5 |
| 4 | 22C9 1 mpk | 0 | 3 | 37.5 |
| 5 | 22C9 3 mpk | 0 | 4 | 50 |

Note:
* p < 0.05;
Mean ± SD,
n = 8

TABLE 5

Tumor Regression on Day 25

| Group No. (n = 8) | Treatment | Tumor Size on Day 25 (mm3) | TGI (%) on Day 25 |
|---|---|---|---|
| 1 | Control IgG 3 mpk | 769.64 ± 590.08 | — |
| 2 | 18G4 1 mpk | 218.80 ± 296.83 | 71.57* |
| 3 | 18G4 3 mpk | 270.44 ± 140.37 | 64.86* |
| 4 | 22C9 1 mpk | 285.82 ± 423.96 | 62.86 |
| 5 | 22C9 3 mpk | 278.53 ± 418.35 | 63.81 |

Note:
CR: Complete Regression;
PR: Partial Regression;
ORR: Objective Response Rate 5. Anti-Tumor Activities of Chimeric pH-Dependent PD-L1 Antibodies in the MC38/Human-PD-L1 Knock-in Tumor Model To further validate that antibodies with pH dependent antigen binding property can inhibit tumor growth in vivo better than those without pH-dependent binding and eliminate the potential impact of Fc domain, we retested chimeric antibodies (i.e. 23A11-C and 23F11-C) produced with the same IgG isotype (i.e. human IgG1) as the benchmark antibodies in HEK293 cells (i.e. BM-GT).

Briefly, MC38/hPD-L1 KI cells were inoculated and treatment of antibodies at 1 mg/kg via IP injection was initiated when tumor volume was 100 mm$^3$ and antibodies were given IP injection three times a week. Results were analyzed using Prism GraphPad and expressed as mean±S.E.M. Comparisons between two groups (test vs. vehicle) were made by T-test, and the difference is considered significant if P is <0.05.

Figure 13A:
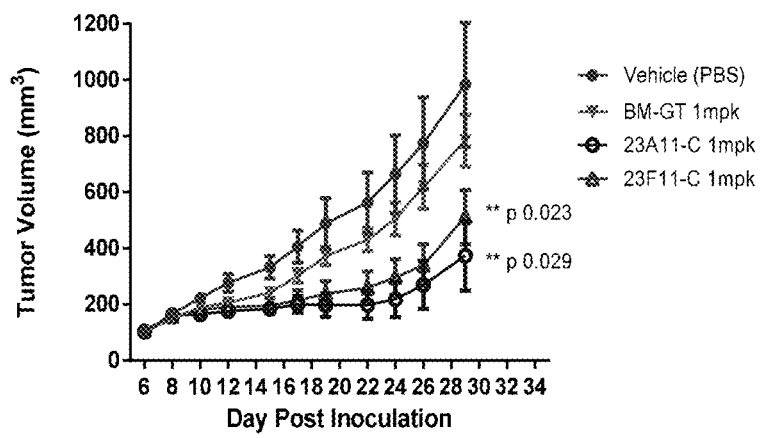
FIG. 13A shows the averaged tumor volume measured over time in the MC38/Human-PD-L1 knock-in tumor model, which indicates that the in vivo anti-tumor activities of the purified pH-dependent chimeric PD-L1 antibodies (23A11-C in open circle, 23F11-C in open triangle) in inhibiting the growth of tumor.
Figure 13B:
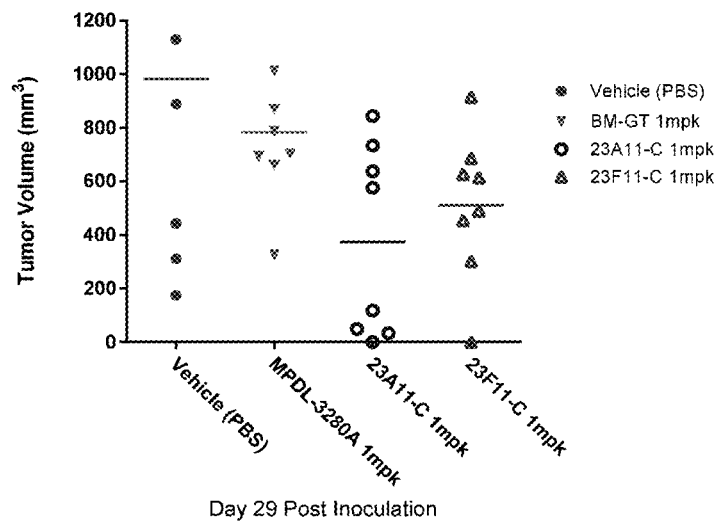
FIG. 13B shows the averaged tumor volume at Day 29; Mice (n=8 for each group) were IP injected with 1 mpk antibodies 3 times/week for 3 weeks, results expressed as mean±S.E.M, P is <0.05. Vehicle is depicted in solid circle and benchmark GT is in inverted solid triangle.

As shown in FIGS. 13A and 13B, the tumor volumes in the MC38/Human-PD-L1 mouse tumor model injected with 1 mpk of the chimeric pH-dependent antibodies (i.e. 23A11-C and 23F11-C) were smaller than that of 1 mpk of the benchmark antibody (i.e. BM-GT).

Example 15: Generation and Characterization of Humanized Antibodies

1. Generation, Expression and Purification of Humanzied Antibodies

The sequences of the variable domains of mouse antibodies 4B6, 23A11 and 23F11 were used to identify the germline sequence with the highest homology to the murine framework. Computer-modelling was used to design humanzied variants with CDR grafting and back mutation.

4B6

Human germline framework sequence VK/1D-13 for light chain and VH/1-2 for heavy chain were used for CDR grafting, respectively.

Figures 14A, 14B, 15A, 15B:
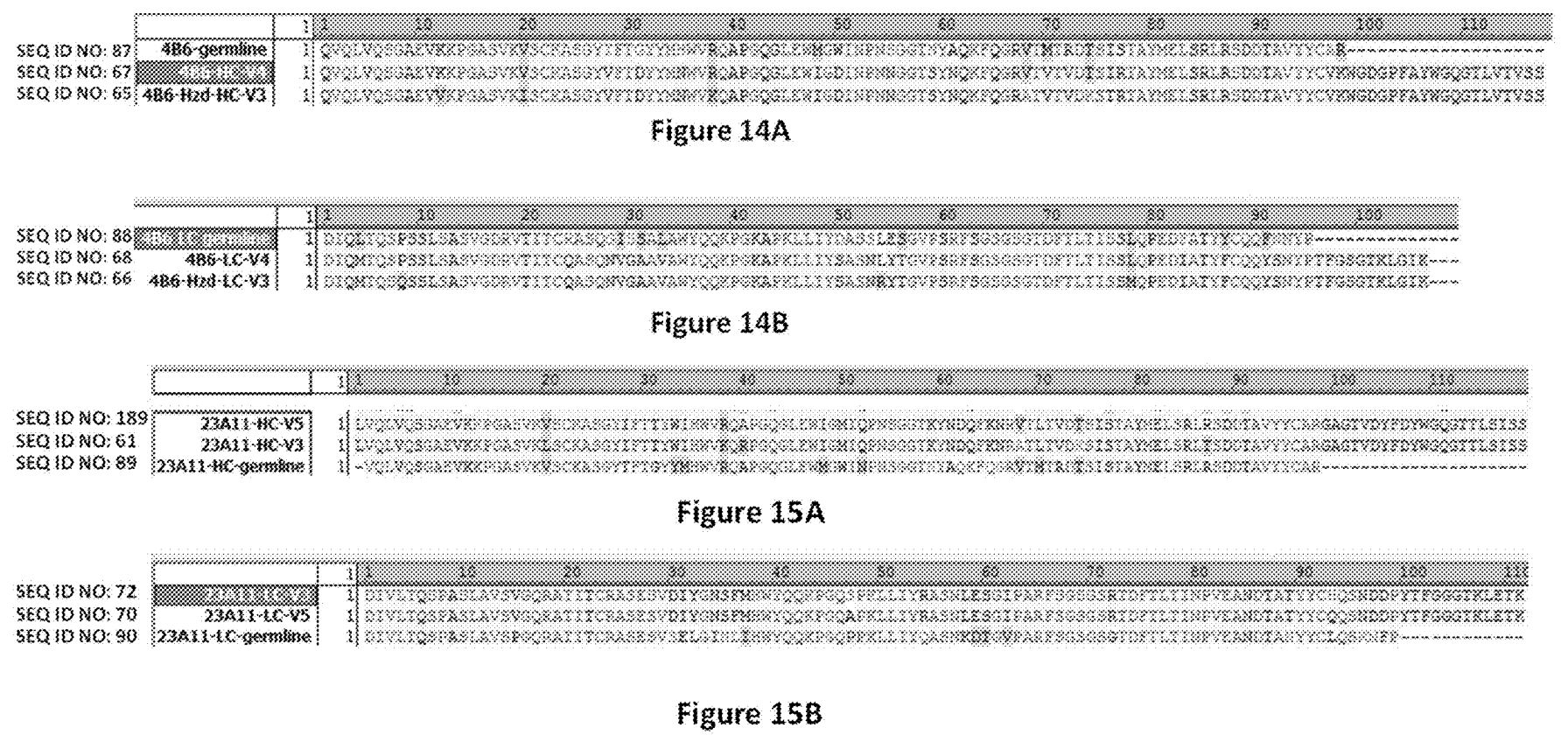

Heavy chain (HC) variants 3 and 4 were obtained by direct grafting the three CDRs to the germline sequence (SEQ ID NO: 87) and back mutation of K12V, T28V, V68A, R72V, T74K, S77R for HC variant 3 (SEQ ID NO: 65) and T28V, R72V, S77R for HC variant 4 (SEQ ID NO: 67), respectively (see FIG. 14A).

```
Germline sequence for 4B6 HC:
VH/1-2 (4B6-germline, SEQ ID NO: 87):
QVQLVQSGAEVKKPGASVKVSCKASGYTFTGYYMHWVRQAPGQGLEW

MGWINPNSGGTNYAQKFQGRVTMTRDTSISTAYMELSRLRSDDTAVY

YCAR

VH/1-2 variant 3 (4B6-Hzd-HC-V3, SEQ ID NO: 65):
QVQLVQSGAEVVKPGASVKISCKASGYVFTDYYMNWVKQAPGQGLEW

IGDINPNNGGTSYNQKFQGRATVTVDKSTRTAYMELSRLRSDDTAVY

YCVKWGDGPFAYWGQGTLVTVSS

VH/1-2 variant 4 (4B6-HC-V4, SEQ ID NO: 67):
QVQLVQSGAEVKKPGASVKVSCKASGYVFTDYYMNWVRQAPGQGLEW

IGDINPNNGGTSYNQKFQGRVTVTVDTSIRTAYMELSRLRSDDTAVY

YCVKWGDGPFAYWGQGTLVTVSS
```

Light chain (LC) variant 3 and 4 were obtained by direct grafting the three CDRs to germline sequence (SEQ ID NO: 88) and back mutation of L4M, P8Q, L78M, Y87F for LC variant 3 (SEQ ID NO: 66) and L4M, Y87F for LC variant 4 (SEQ ID NO: 68), respectively (see FIG. 14B).

```
Germline sequence for 4B6 LC:
VK/1D-13 (4B6 LC germline, SEQ ID NO: 88)
DIQLTQSPSSLSASVGDRVTITCRASQGISSALAWYQQKPGKAPKWY

DASSLESGVPSRFSGSGSGTDFTLTISSLQPEDFATYYCQQFNNYP

VK/1D-13 variant 3 (4B6-Hzd-LC-V3, SEQ ID NO: 66)
DIQMTQSQSSLSASVGDRVTITCQASQNVGAAVAWYQQKPGKAPKLL

IYSASNRYTGVPSRFSGSGSGTDFTLTISSMQPEDIATYFCQQYSNY

PTFGSGTKLGIK

VK/1D-13 variant 4 (4B6-LC-V4, SEQ ID NO: 68)
DIQMTQSPSSLSASVGDRVTITCQASQNVGAAVAWYQQKPGKAPKLL

IYSASNLYTGVPSRFSGSGSGTDFTLTISSLQPEDIATYFCQQYSNY

PTFGSGTKLGIK
```

23A11

Human germline framework sequence VH/1-2 for heavy chain and VK/7-3 for light chain were used for CDR grafting, respectively.

Heavy chain (HC) variant 3 and 5 were obtained by direct grafting the three CDRs to germline sequence (SEQ ID NO: 89) and back mutation of V20L, M48I, V68A, M70L, R72V, T75K, R87T for HC variant 3 (SEQ ID NO: 71) and M48I, M70L, R72V for HC variant 5 (SEQ ID NO: 189, the first amino acid L in SEQ ID NO: 69 is converted to Q), respectively (see FIG. 15A).

```
Germline sequence for 23A11 HC:
VH/1-2 (23A11-HC-germline, SEQ ID NO: 89):
QVQLVQSGAEVKKPGASVKVSCKASGYTFTGYYMHWVRQAPGQGLEW

MGWINPNSGGTNYAQKFQGRVTMTRDTSISTAYMELSRLRSDDTAVY

YCAR

VH/1-2 variant 3 (23A11-HC-V3, SEQ ID NO: 61):
QVQLVQSGAEVKKPGASVKLSCKASGYIFTTYWMWVKQRPGQGLEWI

GMIQPNSGGTKYNDQFKNRATLTVDKSISTAYMELSRLTSDDTAVYY

CARGAGTVDYFDYWGQGTTLSISS

VH/1-2 variant 5 (23A11-HC-V5, SEQ ID NO: 189):
QVQLVQSGAEVKKPGASVKVSCKASGYIFTTYWMWVRQAPGQGLEWI

GMIQPNSGGTKYNDQFKNRVTLTVDTSISTAYMELSRLRSDDTAVYY

CARGAGTVDYFDYWGQGTTLSISS
```

Light chain variant 3 and 5 were obtained by direct grafting three CDRs to germline sequence (SEQ ID NO: 90) and back mutation of P15V, P47S, Q54R, V62I, G72R, N89T, L93H for HC variant 3 (SEQ ID NO: 72) and P15V, P47A, Q54R, V62I, G72R, N89T, L93Q for HC variant 5 (SEQ ID NO: 70), respectively (see FIG. 15B).

```
Germline sequence for 23A11 LC
VK/7-3 (23A11-LC-germline, SEQ ID NO : 90):
DIVLTQSPASLAVSPGQRATITCRASESVSELGINLIHWYQQKPGQP

PKLLIYQASNKDTGVPARFSGSGSGTDFTLTINPVEANDTANYYCLQ

SKNFP

VK/7-3 variant 3 (23A11-LC-V3, SEQ ID NO: 72):
DIVLTQSPASLAVSVGQRATITCRASESVDIYGNSFMHWYQQKPGQS

PKLLIYRASNLESGIPARFSGSGSRTDFTLTINPVEANDTATYYCHQ

SNDDPYTFGGGTKLETK

VK/7-3 variant 5 (23A11-LC-V5, SEQ ID NO: 70):
DIVLTQSPASLAVSVGQRATITCRASESVDIYGNSFMHWYQQKPGQA

PKLLIYRASNLESGIPARFSGSGSRTDFTLTINPVEANDTATYYCQQ

SNDDPYTFGGGTKLETK
```

23F11

Human germline framework sequence VH/1-2 for heavy chain and VK/7-3 for light chain were used for CDR grafting, respectively.

Figures 16A, 16B:
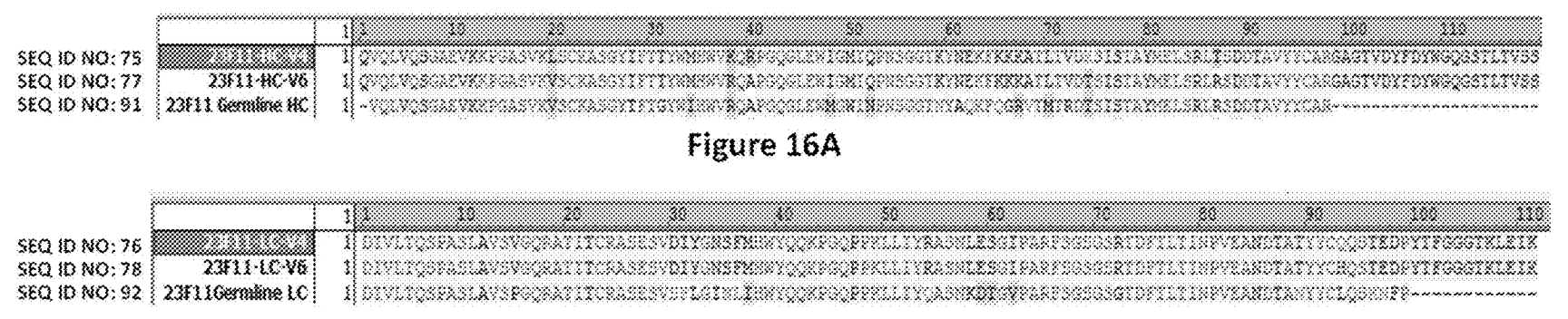

Heavy chain (HC) variant 4 and 6 were obtained by direct grafting three CDRs to germline sequence (SEQ ID NO: 91) and back mutation of V20L, M48I, R67K, V68A, M70L, R72V, T74K, R87T for HC variant 4 (SEQ ID NO: 75) and M48I, R67K, V68A, M70L, R72V for HC variant 6 (SEQ ID NO: 77), respectively (see FIG. 16A).

```
Germline sequence for 23F11 HC:
VH/1-2 (23F11 Germline HC, SEQ ID NO: 91):
VQLVQSGAEVKKPGASVKVSCKASGYTFTGYYMHWVRQAPGQGLEWM

GWINPNSGGTNYAQKFQGRVTMTRDTSISTAYMELSRLRSDDTAVYY

CAR

VH/1-2 variant 4 (23F11-HC-V4, SEQ ID NO: 75):
QVQLVQSGAEVKKPGASVKLSCKASGYIFTTYWMHWVKQRPGQGLEW

IGMIQPNSGGTKYNEKFKKKATLTVDKSISTAYMELSRLTSDDTAVY

YCARGAGTVDYFDYWGQGSTLTVSS

VH/1-2 variant 6 (23F11-HC-V6, SEQ ID NO: 77):
QVQLVQSGAEVKKPGASVKVSCKASGYIFTTYWMHWVRQAPGQGLEW

IGMIQPNSGGTKYNEKFKKKATLTVDTSISTAYMELSRLRSDDTAVY

YCARGAGTVDYFDYWGQGSTLTVSS
```

Light chain variant 4 and 6 were obtained by direct grafting three CDRs to germline sequence (SEQ ID NO: 92) and back mutation of P15V, Q54R, V62I, N89T, L93Q for LC variant 4 (SEQ ID NO: 76) and P15V, Q54R, V62I, N89T, L93H for LC variant 6 (SEQ ID NO: 78), respectively (see FIG. 16B).

```
Germline sequence for 23F11 LC
VK/7-3 (23F11 Germline LC, SEQ ID NO : 92):
DIVLTQSPASLAVSPGQRATITCRASESVSELGINLIHWYQQKPGQP

PKLLIYQASNKDTGVPARFSGSGSGTDFTLTINPVEANDTANYYCLQ

SKNFP
VK/7-3 variant 4 (23F11-LC-V4, SEQ ID NO: 76):
DIVLTQSPASLAVSVGQRATITCRASESVDIYGNSFMHWYQQKPGQP

PKLLIYRASNLESGIPARFSGSGSRTDFTLTINPVEANDTATYYCQQ

STEDPYTFGGGTKLEIK

VK/7-3 variant 6 (23F11-LC-V6, SEQ ID NO: 78):
DIVLTQSPASLAVSVGQRATITCRASESVDIYGNSFMHWYQQKPGQP

PKLLIYRASNLESGIPARFSGSGSRTDFTLTINPVEANDTATYYCHQ

STEDPYTFGGGTKLEIK
```

The above heavy chain and light chain cDNAs were synthesized and fused with the constant region of human IgG1 with N297A mutation in the Fc region (The numbering of the heavy chain residues described herein are according to the EU index of Kabat (see Kabat et al., "Proteins of Immunological Interest", US Dept. of Health & Human Services (1983))) to reduce or minimize the effector function of the Fc region, as well known in the art. The variable regions of the heavy chain and light chain of the selected antibody genes were synthesized and cloned into an expression vector and the large scale DNA was prepared using PureYield™ Plasmid Maxiprep System from Promega. Transfection was carried out using the ExpiFectamine™ 293 Reagent from Invitrogen according to the manufacturer's protocol. Supernatants were harvested when the cell viability was around 50%. Protein A beads and clean supernatants were incubated at 4° C. for 2 hr with rocking before going through a column. The Protein A beads inside the column were washed with PBS, and 100 mM Glycine buffer (pH3.0) was used to elute the antibody, which was dialyzed against the PBS buffer (137 mM NaCl, 2.7 mM KCl 10 mM $Na_2HPO_4$, 2 mM $KH_2PO_4$, pH7.4) overnight at 4° C. Finally, endotoxin was removed using Pierce High Capacity Endotoxin Removal Resin (Invitrogen, Catalog number: 88271). The purified antibody was characterized by SDS-PAGE and SEC-HPLC.

2. Binding of Humanized Antibodies to hPD-L1 in ELISA

Figure 17A:
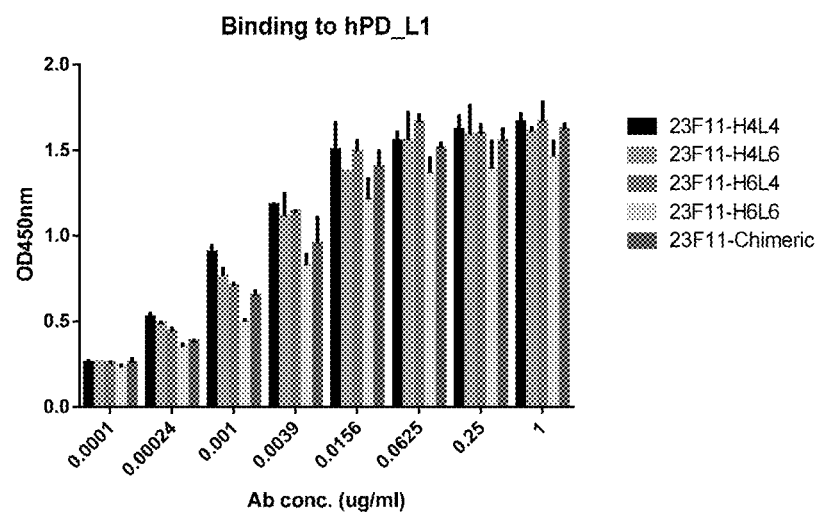
FIG. 17A is a bar chart illustrating the binding of 23F11 antibody (H4L4, H4L6, H6L4, H6L6 and chimeric)
Figure 17B:
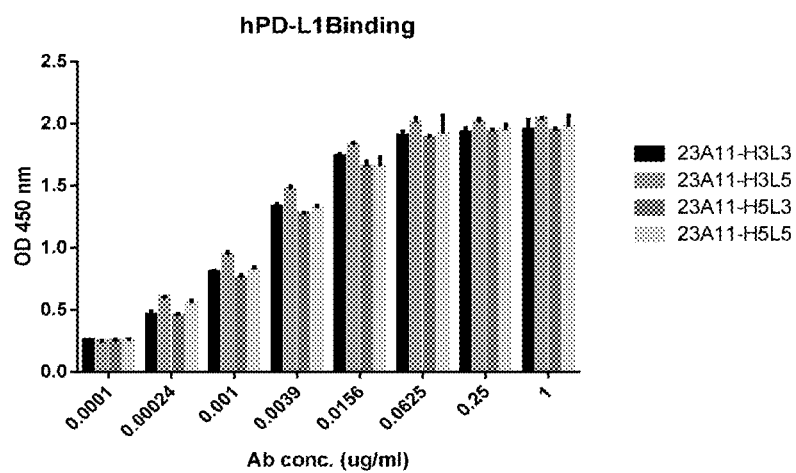
FIG. 17B shows the binding of humanized 23A11 antibody (H3L3, H3L5, H5L3 and H5L5) to hPD-L1-his, as measured by ELISA.
Figure 18A:
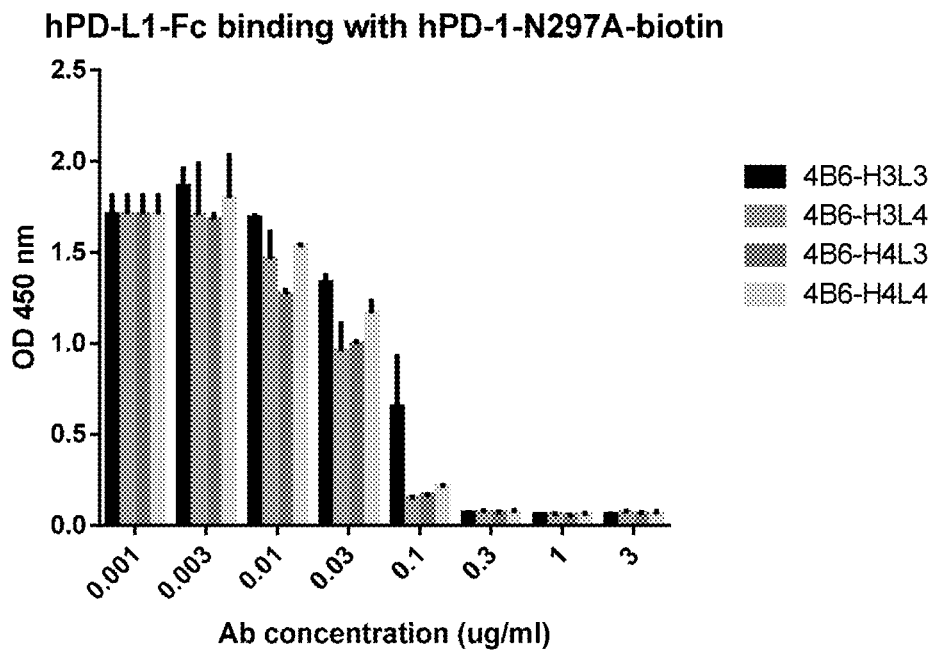
FIG. 18A to FIG. 18D are bar charts showing the activities of humanized PD-L1 antibodies in blocking the binding of hPD-L1-Fc to hPD-1-N297A as measured by ELISA. The results of humanized 4B6 (H3L3, H3L4, H4L3 and H4L4, FIG. 18A), 23F11 (H4L4, H4L6, H6L4, H6L6 and chimeric (C), FIG. 18B), humanized 23A11 (H3L3, H3L5, H5L3 and H5L5, FIG. 18C), and humanized 23A11 (H3L3 and H3L5) and humanized 23F11 (H4L4) with benchmark antibodies (BM-GT and BM-ME, see FIG. 18D) were shown, respectively.
Figure 18B:
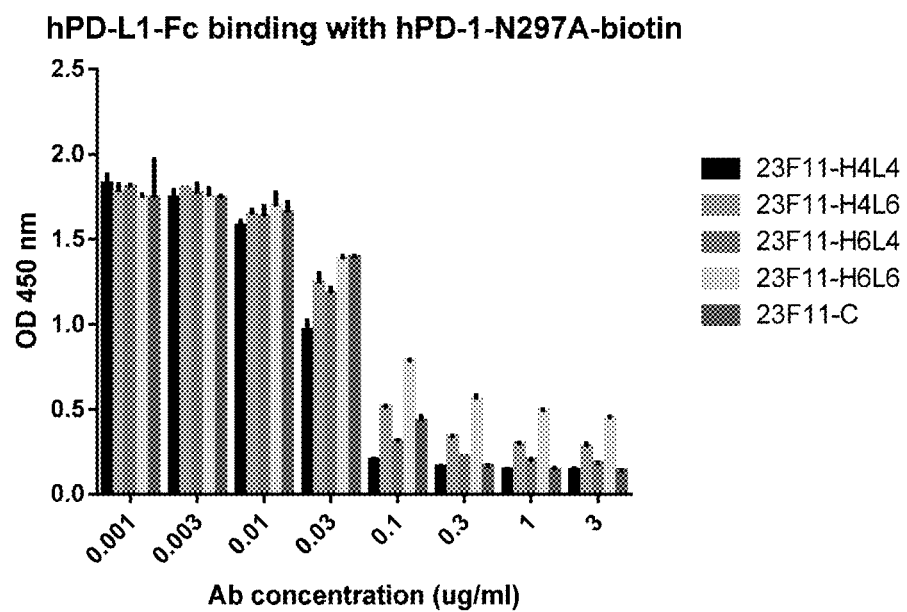
Figure 18C:
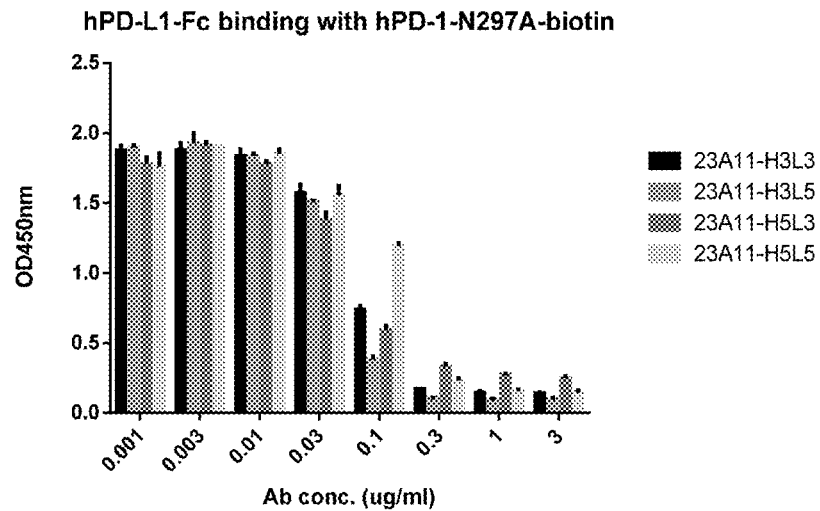
Figure 18D:
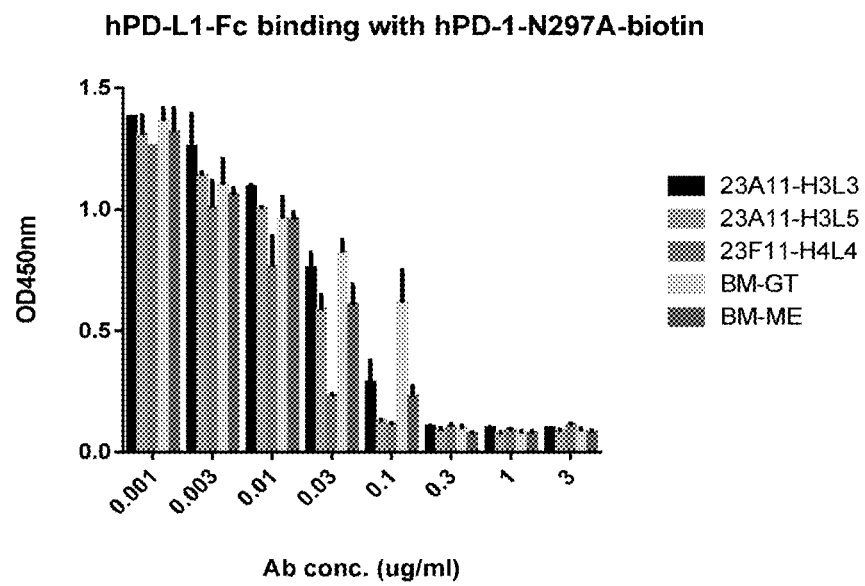

High-binding clear polystyrene 96 well plates (Nunc) were coated with 100 μl/well of a 0.5 μg/ml human PD-L1-his (Acrobiosystems, Cat #PD1-H5229) in high pH coating buffer and incubated overnight at 4° C. Then the plates were washed once on an automatic plate washer using washing buffer (PBS+0.1% Tween 20 (Sigma)). 200 μl of blocking buffer (PBS+1% BSA+1% normal goat serum+0.05% Tween-20) was added to each well and incubated for 2 hours at room temperature. Then add serial diluted humanized antibodies (produced in 293 cells) with dilution buffer (PBS+1% BSA+1% normal goat serum+0.01% Tween-20) and incubate for 1 hour at RT. The plates were then washed 3 times using the washing buffer. 100 μl/well of a solution of HRP conjugated goat anti-human Fc antibody (Abcam) in dilution buffer was then added to each well of the plate. After that the ELISA plates were allowed to incubate for 60 min at RT then the plates were washed 3 times using 200 μl/well pH7.4 washing buffer. Finally, 100 μl/well of TMB was added to each well and the reaction was terminated using 0.64M $H_2SO_4$. The plates were read on a Thermo Multiscan FC at 450 nM (see FIGS. 17A and 17B).

3. Blocking of hPD-1 Binding to hPD-L1 in ELISA

High-binding clear polystyrene 96 well plates (Nunc) were coated with 100 μl/well of coating solution consisting of 1 μg/ml hPD-L1-Fc overnight at 4° C. Then the plates were washed once on an automatic plate washer using washing buffer (PBS+0.1% Tween 20 (Sigma)). 200 μl of blocking buffer (PBS+1% BSA+1% normal goat serum+0.05% Tween-20) was added to each well and incubated 2 hours at room temp. Then add serial diluted antibodies (i.e. humanized 4B6, 23F11, 23A11 produced in 293 cells and benchmark antibodies BM-GT and BM-ME also produced in 293 cells) with dilution buffer (PBS+1% BSA+1% normal goat serum+0.01% Tween-20) and incubate for 1 hour at RT. The plates were then washed 3 times using the method described above. 1 μg/ml biotinylated hPD-1-N297A (Acrobiosystem) were added and incubated for 1 hour at RT. After the plates were washed 3 times, 100 μl/well of a solution of 1:5000 diluted HRP conjugated Neutravidin antibody (Pierce) in dilution buffer was then added to each well of the plate. After that the ELISA plates were allowed to incubate for 60 min at RT, then the plates were washed 3 times with 250 μl/well washing buffer. Finally, 100 μl/well of TMB was added to each well and the reaction was terminated using 0.64M $H_2SO_4$. The plates were read on a Thermo Multiscan FC at 450 nm (see FIG. 18A to 18D).

The data in FIG. 18A to 18D showed that some of the humanized antibodies are significantly more potent than others in inhibiting human PD-L1 binding to human PD-1.

4. Bindings of hPD-L1 Antibodies to hPD-L1 on HCC827 Measured by FACS

Figure 19:
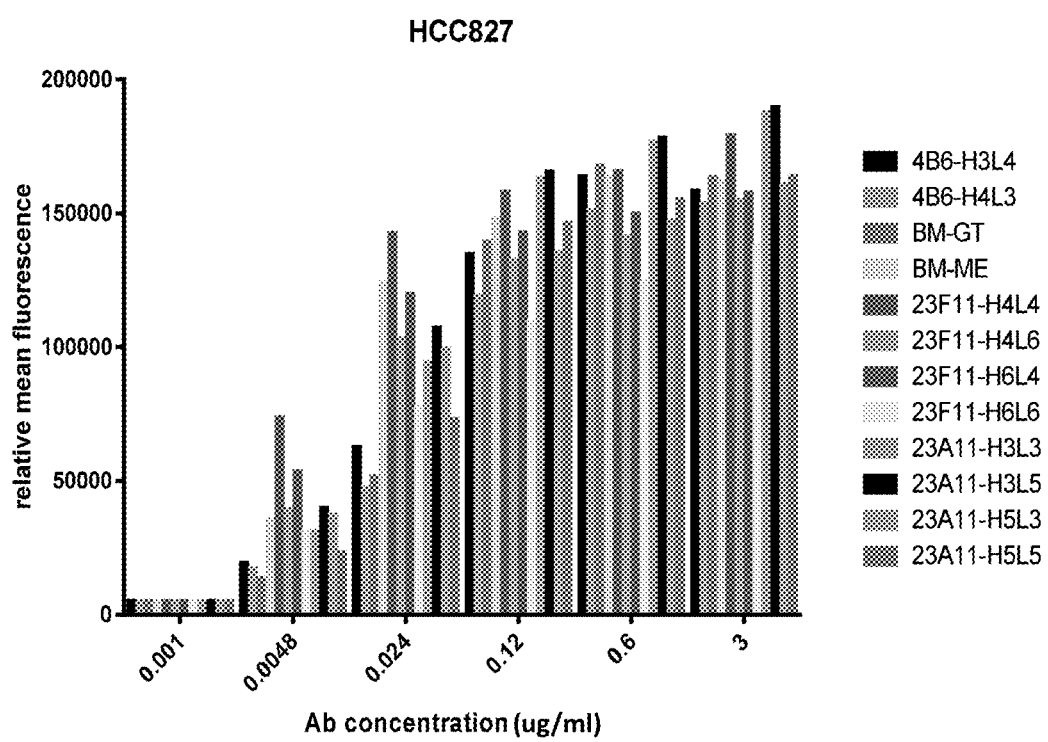
FIG. 19 shows the binding of humanized PD-L1 antibodies (BM-GT, BM-ME, 4B6-H3L4, 4B6-H4L3, 23F11-H4L4, 23F11-H4L6, 23F11-H6L4, 23F11-H6L6, 23A11-H3L3, 23A11-H3L5, 23A11-H5L3 and 23A11-H5L5) to hPD-L1 expressed on HCC827 as measured by FACS.

Log phase IFN-γ stimulated (500 U/ml for 2 days) HCC827 cells were collected and resuspended in blocking buffer (5% BSA+PBS). 2×10^5 cells were added to each tube and then washed once with PBS (1500 rpm, 5 mins, RT). The 100 μl/tube serial diluted humanized PD-L1 antibodies (produced in 293 cells) with blocking buffer were added into corresponding tubes and incubated at 4° C. for 1 hr. The cells were then washed twice with 1 ml PBS, followed by adding 100 μl/tube of $2^{nd}$ antibody (1:200 rabbit anti-human IgG-PE) in blocking buffer. The cells were incubated at 4° C. for 1 hr and then washed twice with PBS, followed by resuspending cells in 150 μl PBS for each sample. The cells were then transferred into FACS tubes and the bindings of the antibodies to the cells were detected with flow cytometry (ACEA Bioscience Novocyte) (see FIG. 19).

5. Blocking of hPD-1 Binding to hPD-L1 on HCC827 Measured by FACS

Figure 20A:
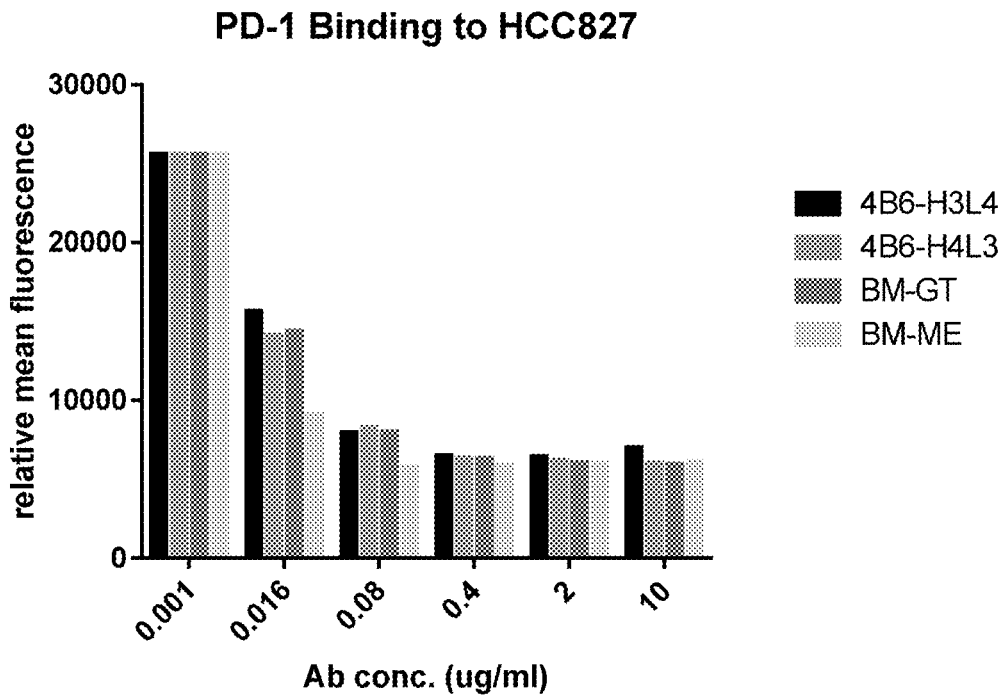
FIG. 20A is the bar charts showing the activities of humanized 4B6 (H3L4 and H4L3) and benchmark antibodies (BM-GT and BM-ME) in blocking the binding of hPD-1-N297A to hPD-L1 expressed on HCC827 as measured by FACS.
Figure 20B:
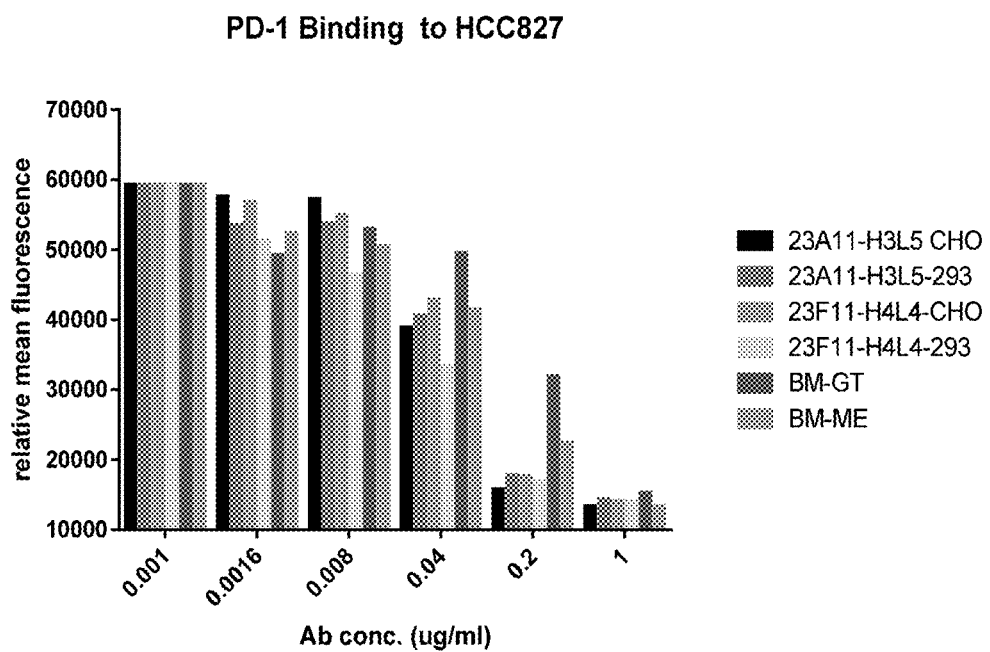
FIG. 20B shows the blocking activities of humanized 23A11 H3L5 (produced in CHO and 293, respectively), humanized 23F11 H4L4 (produced in CHO and 293, respectively) and benchmark antibody (BM-GT and BM-ME) to the binding of hPD-1-N297A to hPD-L1 expressed on HCC827 as measured by FACS.

Log phase IFN-γ stimulated (500 U/ml for 2 days) HCC827 cells were collected and resuspended in blocking buffer (5% BSA+PBS). 2×10^5 cells were added to each tube and then washed once with PBS (1500 rpm, 5 mins, RT). The 100 μl/tube serial diluted humanized PD-L1 antibodies (The antibodies expressed in 293 cells were named as "old", and that produced in CHO cells were named as "new" for small scale production in the following experiments. That is, 4B6-H3L4, 4B6-H4L3, 23A11-H3L5 293 and 23F11 H4L4 293 were produced in 293 cells; 23A11-H3L5 CHO and 23F11 H4L4 CHO were produced in CHO cells) with blocking buffer were added into corresponding tubes and incubate at 4° C. for 1 hr. The cells were then washed twice with 1 ml PBS, followed by adding 100 μl/tube 3 μg/ml biotinylated hPD-1-N297A and incubated at 4° C. for 1 hr. After washing for three times with PBS, 100 μl/tube streptavidin-PE 1:200 in blocking buffer was added to each tube. The cells were incubated at 4° C. for 1 hr and then washed twice with PBS, followed by resuspending cells in 150 μl PBS for each sample. The cells were then transferred into FACS tube and the binding of the antibodies to the cells were detected with flow cytometry (ACEA Bioscience Novocyte) (see FIGS. 20A and 20B).

Example 16: Evaluation of the Ability of the Purified Humanized Antibodies to Stimulate T Cell Activation in Mixed Lymphocyte Reaction (MLR)

Figure 21A:
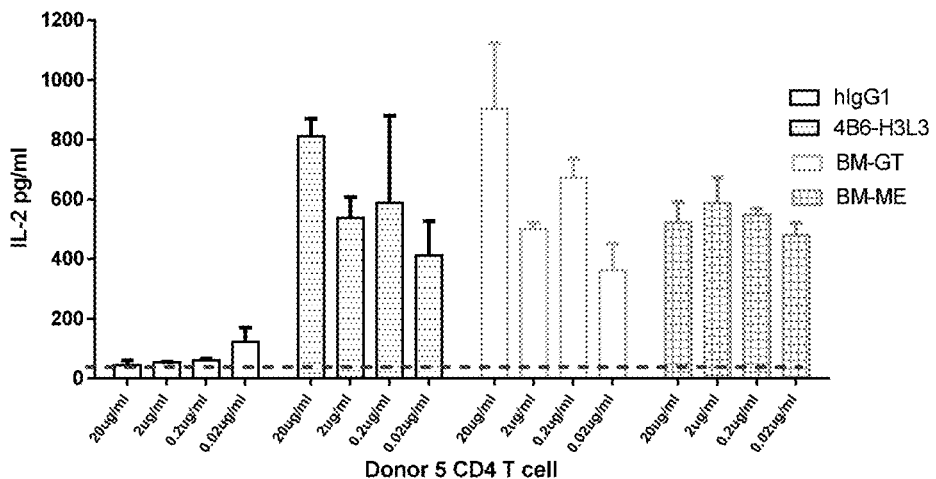
FIG. 21A is a bar chart illustrating the IL-2 produced in activated Donor 5 CD4 T cell stimulated by the humanized 4B6-H3L3 antibody, hIgG1, BM-GT and BM-ME in mixed lymphocyte reaction (MLR).
Figure 21B:
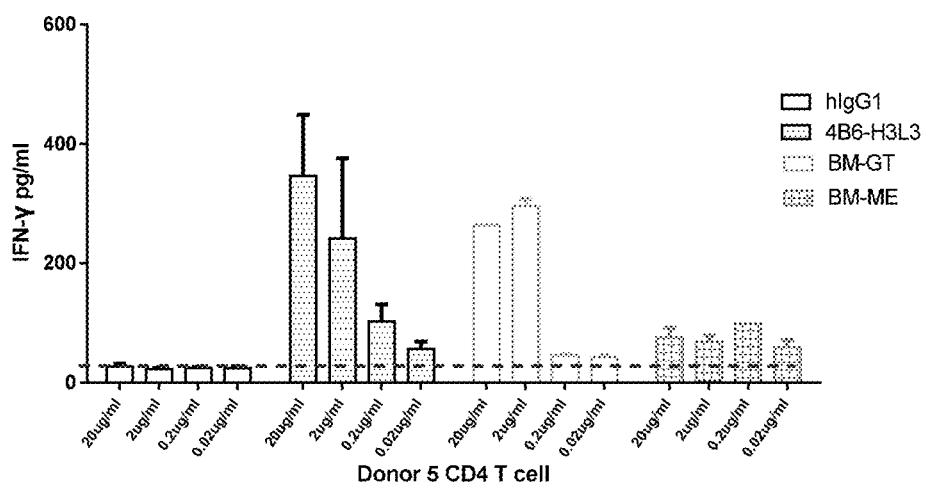
FIG. 21B shows the IFN-γ produced in the activated Donor 5 CD4 T cells stimulated by the humanized 4B6-H3L3 antibody, hIgG1, BM-GT and BM-ME in the same test.

To assess the ability of the anti-PD-L1 antibodies in relieving inhibition of PD-1/PD-L1 mediated T cell activation, we performed mixed lymphocyte reaction (MLR) assay. In the first experiment, DCs were derived from adherent peripheral blood mononuclear cells (PBMCs) which were isolated from fresh human blood. PBMCs were plated at density of 2×10^6/ml with serum-free medium in 6-well plate. 2 hours later, suspension cells were discarded and adherent cells were treated with 10 ng/ml GM-CSF and 30 ng/ml IL-4. Medium were changed every 3 days and 20 ng/ml TNFα were added on the $6^{th}$ day to make DC cells mature. The phenotype of DCs was detected by FACS using anti-CD11c-PE (Biolegend) and anti-HLA-DR-APC (Biolegend) at the $7^{th}$ day. CD4$^+$ T cells were separated from fresh blood of another donor using CD4$^+$ T cell enrichment kit (Stem Cell Inc.). After DCs being treated by mitomycin C (10 μg/ml for 2 hours), the DCs and CD4$^+$ T cells and PD-L1 antibodies were added to 200 μl/well at ratio of DCs 1: CD4$^+$ T 10 and incubated for 5 days in 37° C., 5% $CO_2$ incubator. Then IL-2 and IFN-γ of supernatant were detected using IL-2 duo-set (R&D) and IFN-γ detection kit (Peprotech) (see FIGS. 21A and 21B). The proliferation of T cells was measured by CellTiter-Glo luminescent cell viability assay kit (Promega).

Figure 21C:
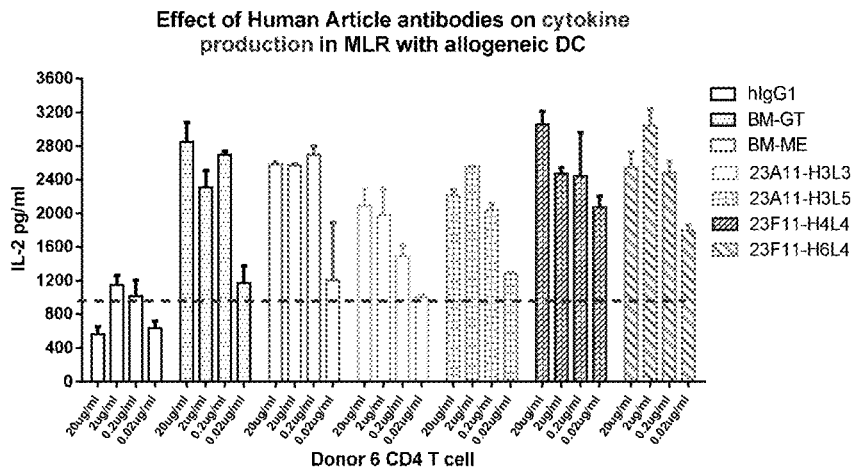
FIG. 21C shows the IL-2 produced in the activated Donor 6 CD4 T cells stimulated by the humanized 23A11-H3L3, 23A11-H3L5, 23F11-H4L4 and 23F11-H6L4, hIgG1, BM-GT and BM-ME in the same test.
Figure 21D:
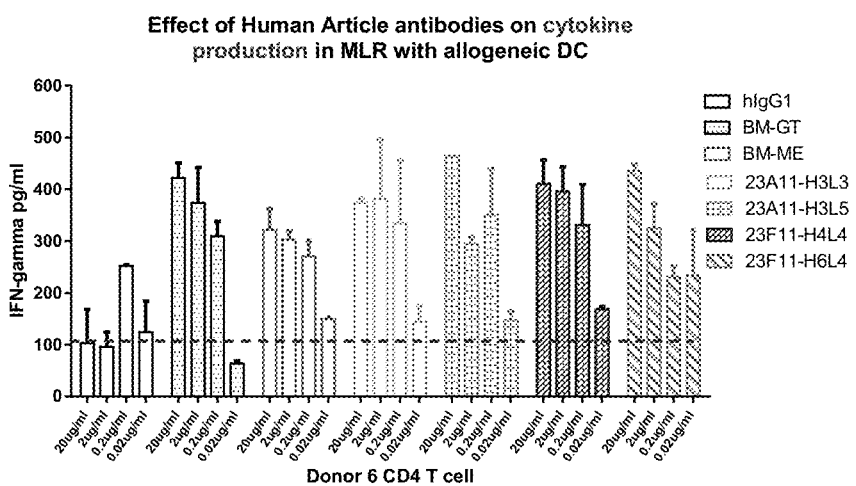
FIG. 21D shows the IFN-γ produced in the activated Donor 6 CD4 T cells stimulated by the humanized antibodies of 23A11-H3L3, 23A11-H3L5, 23F11-H4L4 and 23F11-H6L4, hIgG1, BM-GT and BM-ME in the same test.
Figure 22A:
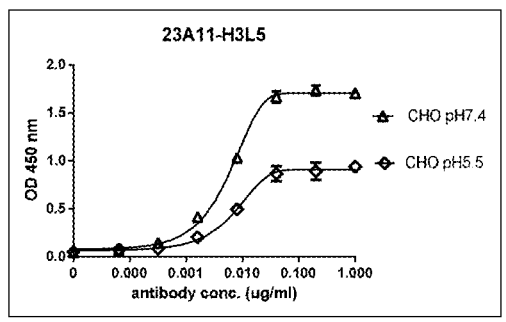
FIGS. 22A and 22C show the pH-dependent binding of humanized 23A11-H3L5 produced in CHO cells and 293 cells to hPD-L1-his at pH7.4 (triangle) and pH5.5 (diamond), respectively, as measured by ELISA analysis.
Figure 22B:
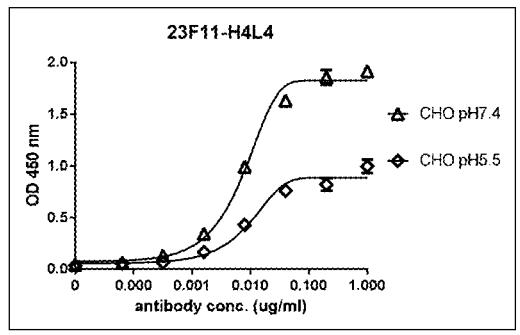
FIGS. 22B and 22D show the same of humanized 23F11-H4L4 to hPD-L1-his at pH7.4 (triangle) and pH5.5 (diamond), as measured by ELISA analysis.
Figure 22C:
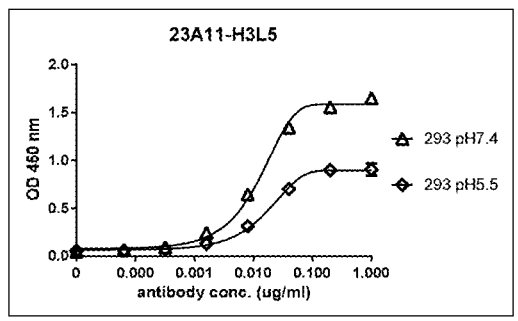
Figure 22D:
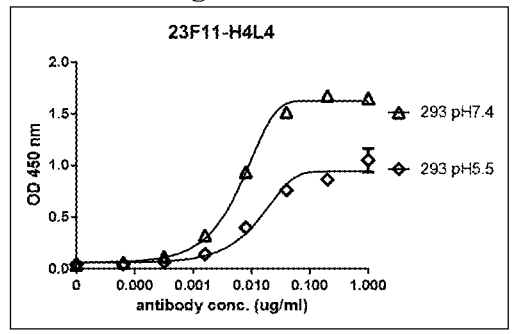
Figure 22E:
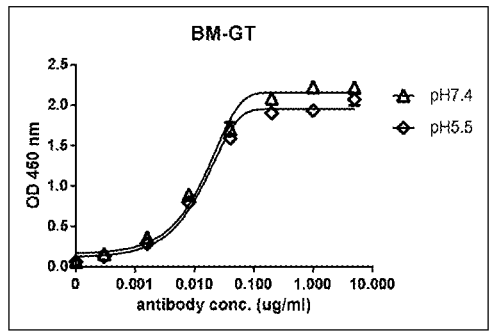
FIG. 22E shows the same test for the benchmark antibody BM-GT to hPD-L1-his at pH7.4 (triangle) and pH5.5 (diamond), respectively, as measured by ELISA analysis.
Figure 23A:
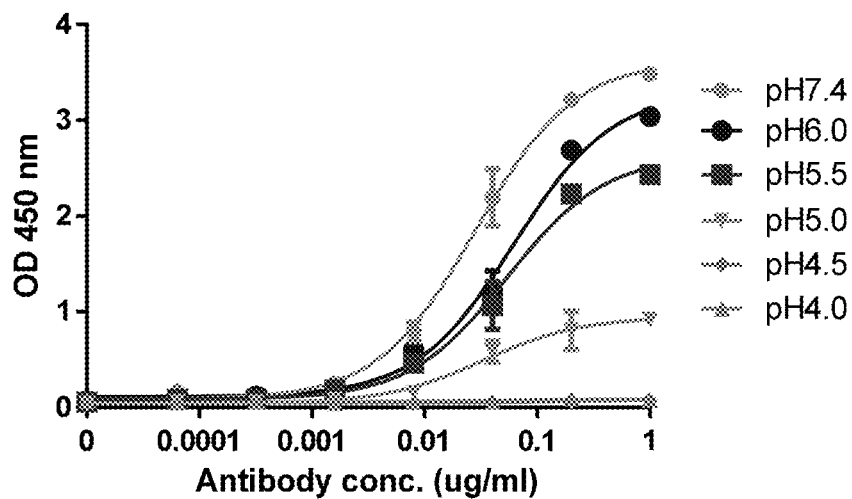
FIG. 23A presents the pH-dependent binding of 23A11-H3L5 to hPD-L1-his at neutral pH (i.e. 7.4) and acidic pH (i.e. 6.0, 5.5, 5.0, 4.5, 4.0) as measured by ELISA analysis.
Figure 23B:
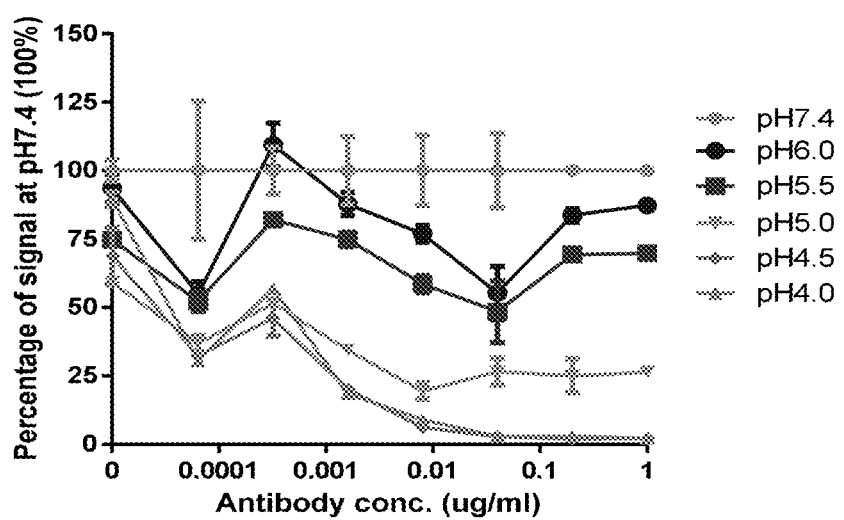
FIG. 23B shows the same results represented by the percentage of signal normalized to that of pH 7.4.
Figure 23C:
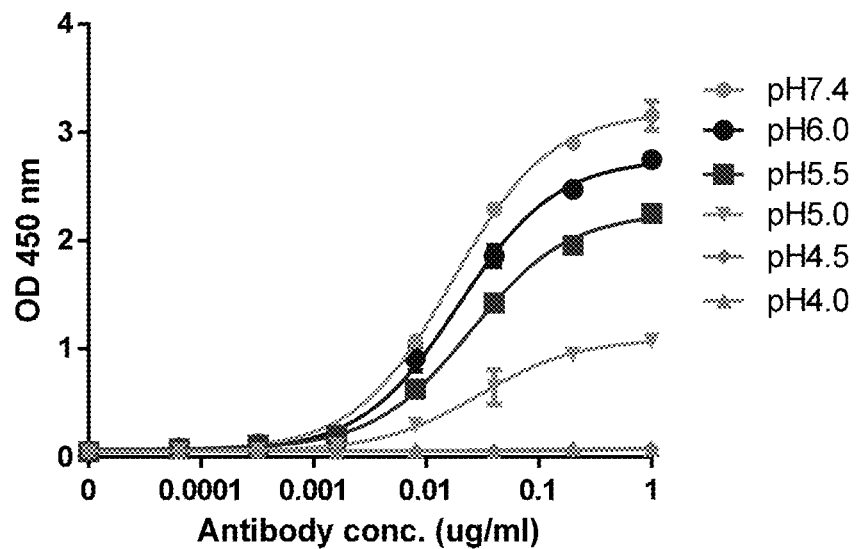
FIG. 23C presents the pH-dependent binding of 23F11-H4L4 to hPD-L1-his at neutral pH (i.e. 7.4) and acidic pH (i.e. 6.0, 5.5, 5.0, 4.5, 4.0) as measured by ELISA analysis.
Figure 23D:
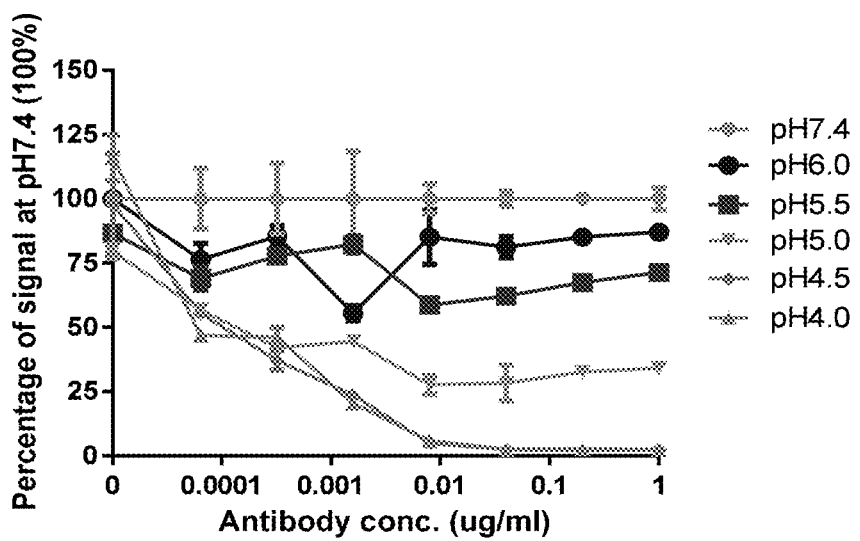
FIG. 23D shows the same results represented by the percentage of signal normalized to that of pH 7.4.
Figure 23E:
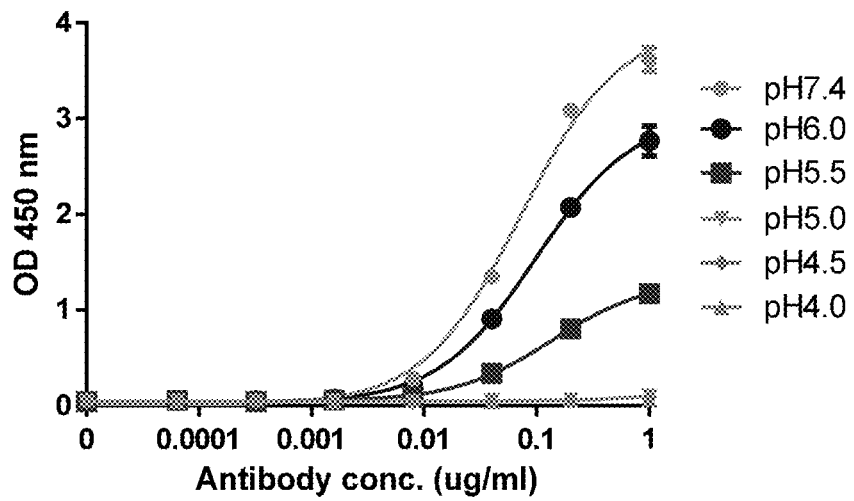
FIG. 23E presents the pH-dependent binding of 22C9-C to hPD-L1-his at neutral pH (i.e. 7.4) and acidic pH (i.e. 6.0, 5.5, 5.0, 4.5, 4.0) as measured by ELISA analysis.
Figure 23F:
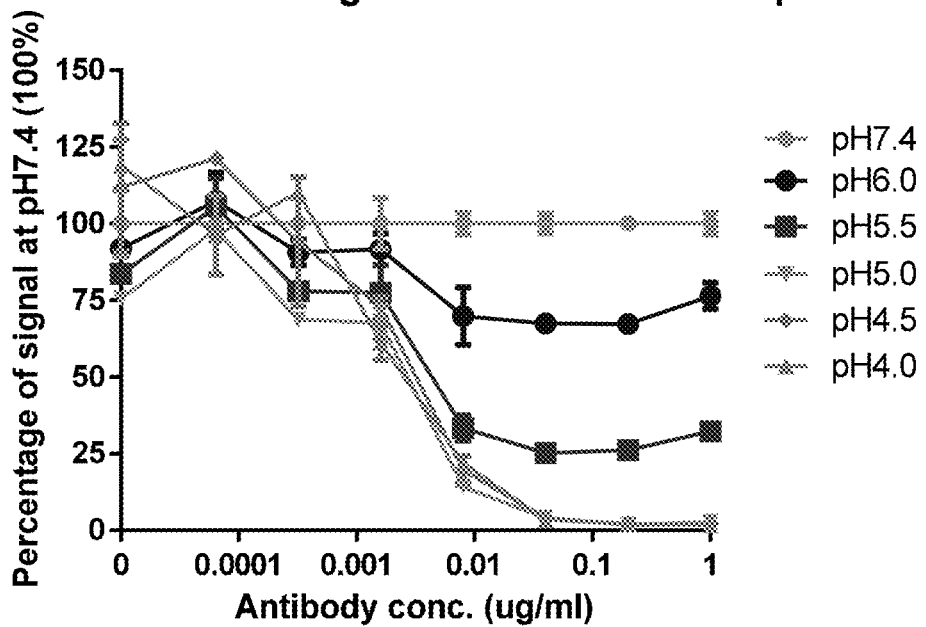
FIG. 23F shows the same results represented by the percentage of signal normalized to that of pH 7.4. In all figures of FIG. 23, pH7.4 (grey circle), pH6.0 (dark circle), pH 5.5 (dark square), pH 5.0 (inverted grey triangle), pH 4.5 (grey diamond), pH 4.0 (grey triangle).
Figure 24A:
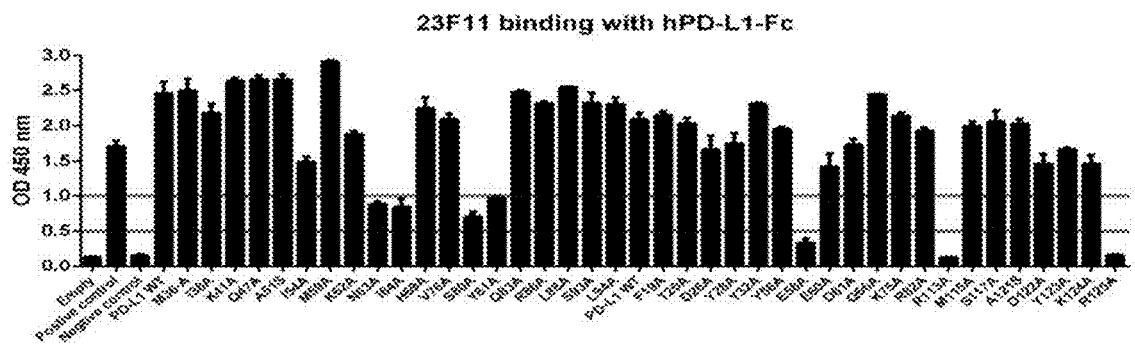
FIG. 24A to FIG. 24I are bar charts showing the binding of PD-L1 antibodies (23F11 (FIG. 24A), 23A11 (FIG. 24B), 26F5 (FIG. 24C), 18G4 (FIG. 24D), 4B6 (FIG. 24E), 21F11 (FIG. 24F), 22C9 (FIG. 24G), 23F11-H4L4 (FIG. 24H) and 23A11-H3L5 (FIG. 24I)) to the Alanine mutant hPD-L1-Fcs (generated in Example 18A) as measured by ELISA.
Figure 24B:
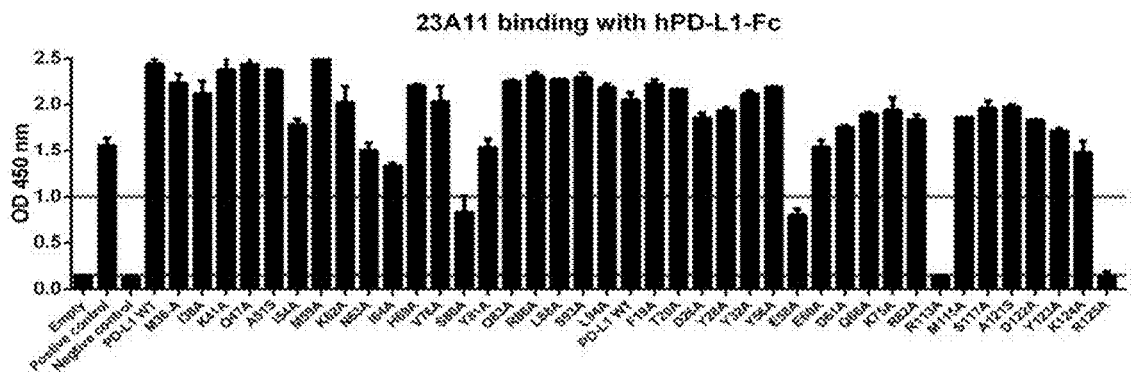
Figure 24C:
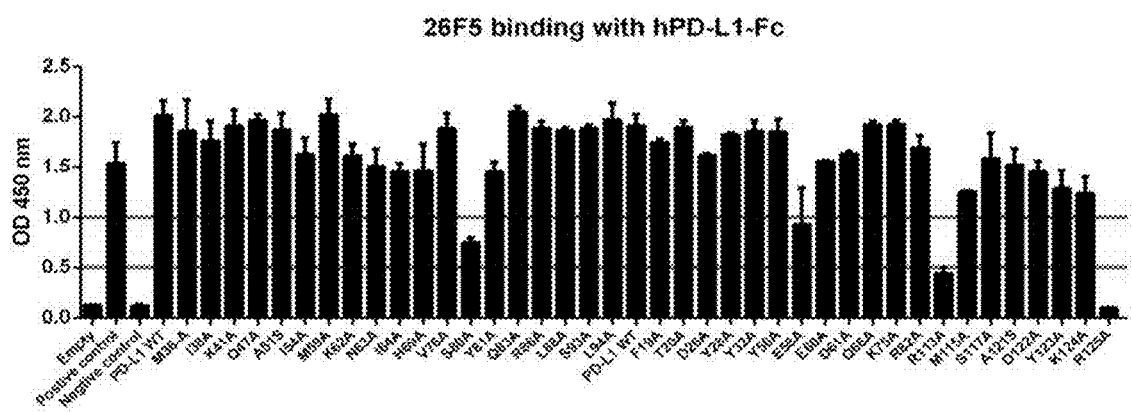
Figure 24D:
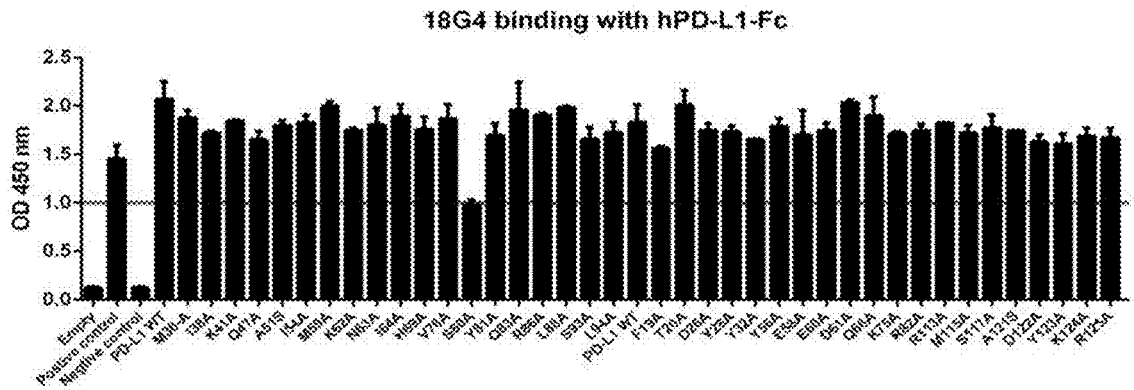
Figure 24E:
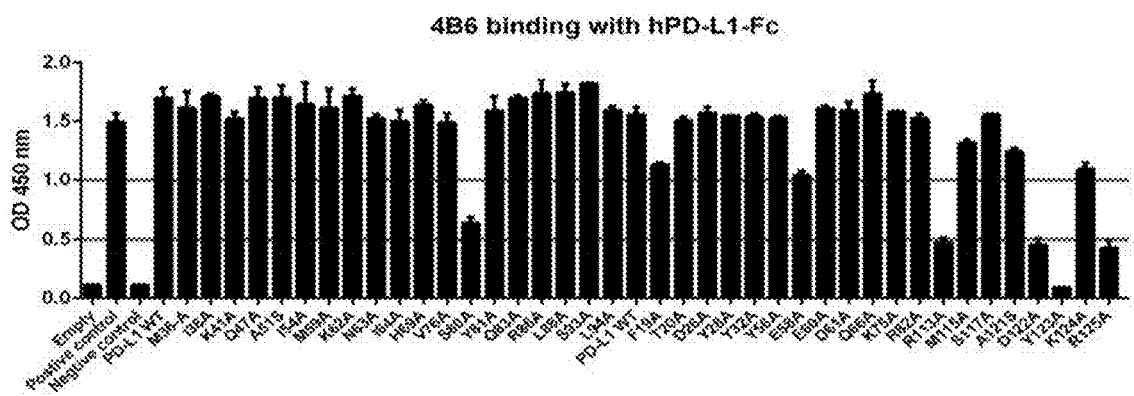
Figure 24F:
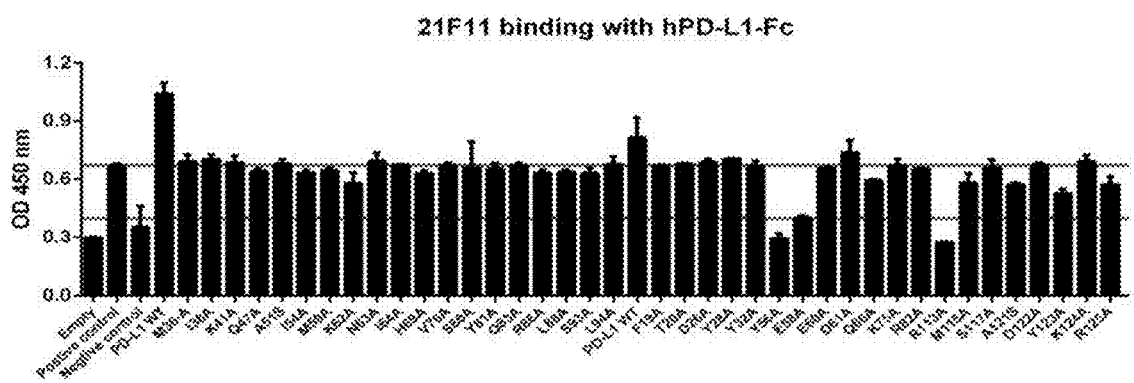
Figure 24G:
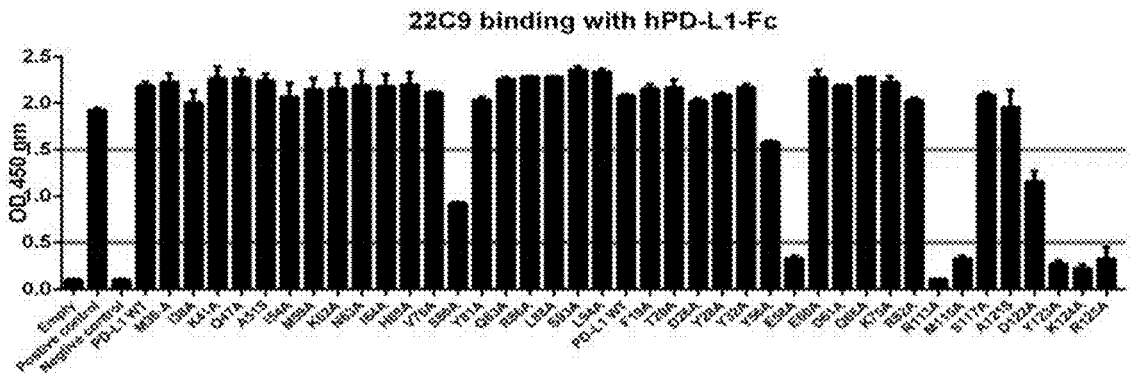
Figure 24H:
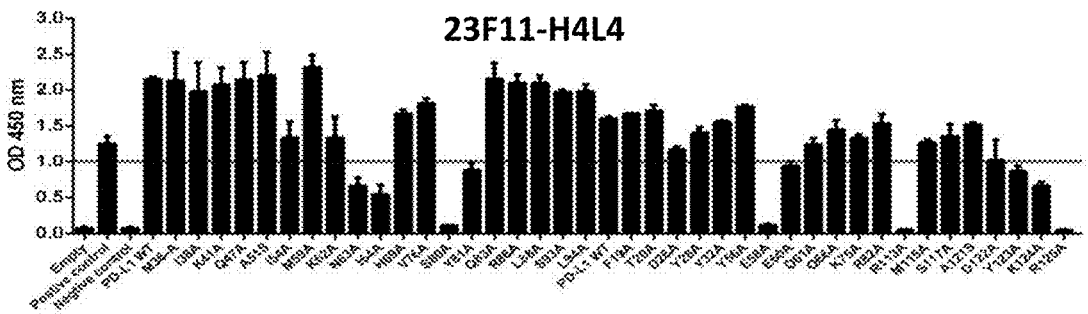
Figure 24I:
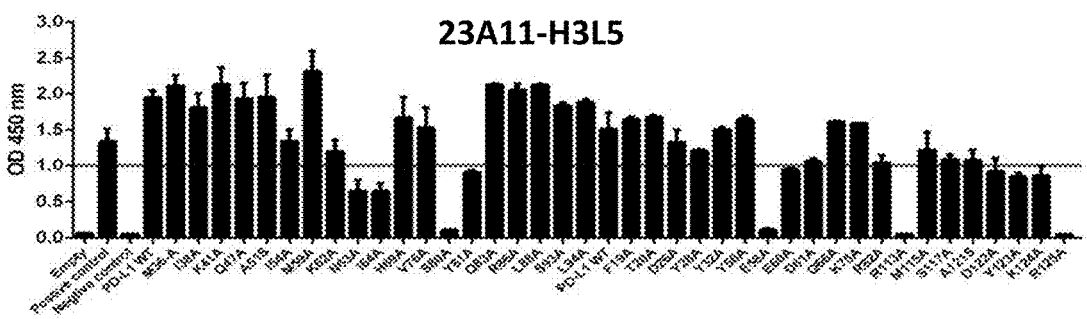

In the second experiment, peripheral blood was harvested and PBMC was isolated after adding 1:1 volume of Ficoll solution, followed by centrifuging for 30 minutes. The PBMC was used to isolate monocyte and T cells using CD14 coated magnetic beads and CD4 negative magnatic beads. The above obtained monocytes were differentiated by culturing for 7 days in the presence of 500 U/ml IL-4 (R&D) and 250 U/ml of GM-CSF (R&D) and followed by adding 100 ng/ml TNFα (R&D) and continue the culture for 3 more days. The above obtained DC cells were countered and 10,000 DC cells in 100 μl volume per well were mixed with 100,000 T cells in 50 μl volume, the testing antibodies or control IgG were then added in 50 μl volume and cultured for five days in duplicate either with or without extra added human PD-L1(1 μg/ml final concentration). The supernatant was harvested and the concentration of IL-2 and IFNγ was quantified using ELISA (R&D) (see FIGS. 21C and 21D).

Example 17: Evaluation of the Binding Affinity of Select Humanized Anti-PD-L1 Antibodies Via Biacore A CM5 sensor chip was activated in each flow cell by 7-min injection (10 μl/min) of freshly prepared 1:1 50 mM N-hydroxysuccinimide (NHS): 200 mM 1-ethyl-3-(3-dimethylaminopropyl)-carbodiimide (EDC). Then anti-human Fc antibody (GE Healthcare) in a concentration of 10 μg/ml in 10 mM sodium acetate buffer PH 5.0 was injected onto the activated chip at 10 μl/min (HBS-EP running buffer: 10 mM HEPES, 150 mM NaCl, 3.4 mM EDTA, 0.005% surfactant P20, pH 7.4). The remaining active coupling sites were blocked by 7 min injection of 1M ethanolamine at 10 μl/min. The immobilization level of each flow cell is ~9000RU. Antibodies were captured in FC2 by anti-human Fe IgG (GE Healthcare) to 200~300RU. FC1 was used as the reference cell. Antigen was injected at varying concentrations after capture of antibody. The association time for antibody binding antigen is 180 s. Surface Regeneration condition is 120 s at 10 μl/min in Gly pH1.5. The signals with captured antibody subtracted from those without captured antibody were calculated with Biacore X100 evaluation software ver. 2.0 (Biacore).

TABLE 6

Affinity parameters of antibodies binding to antigen

| Antibody | $k_a$ (1/Ms) | $k_d$ (1/s) | KD (M) |
| --- | --- | --- | --- |
| 4B6-H3L3 | 1.495E+5 | 9.270E−4 | 6.355E−9 |
| 4B6-H4L3 | 1.317E+5 | 1.484E−3 | 1.127E−8 |
| 23A11-H3L3 | 7.318E+5 | 5.421E−2 | 7.409E−8 |
| 23A11-H3L5 | 5.171E+5 | 2.232E−2 | 4.317E−8 |
| 23F11-H4L4 | 4.649E+5 | 3.042E−2 | 6.543E−8 |
| 23F11-H6L4 | 4.353E+5 | 4.481E−2 | 1.029E−7 |
| 18G4-chimeric | 4.500E+5 | 5.155E−3 | 1.133E−8 |
| BM-GT | 5.321E+5 | 1.158E−4 | 2.177E−10 |
| BM-ME | 6.605E+5 | 4.040E−4 | 6.177E−10 |

It is known that the interaction between human PD-1/hPD-L1 is weak and has a $K_D$ of about 7500+/−2200 nM (N=6, Cheng X et al., Structure and interactions of the human programmed cell death 1 receptor, J Biol Chem. 2013; 288(17):11771-85). Thus, our antibodies as shown in Table 6 have about 100 fold higher affinities than PD-1 of prior art to bind to hPD-L1.

Example 18: Evaluation of pH Dependent Bindings of Select PD-L1 Neutralizing Humanized Antibodies High-binding clear polystyrene 96 well plates were coated with 100 μl/well of a 0.5 μg/ml PD-L1-his in high pH coating buffer and incubated overnight 4° C. Then the coated plates were washed once on an automatic plate washer with PBS+0.1% Tween 20 (Sigma). Then 200 μl of blocking buffer was added to each well and the plates were then incubated for 2 hours at room temperature. After aspirating the blocking buffer serial diluted antibodies (i.e. 23A11 H3L5, 23F11 H4L4 produced by CHO or 293 cells) in dilution buffer with pH7.4 were added and the plates were incubated for 40 minutes at RT. The plates were then washed once with 250 μl/well washing buffer at pH7.4 and then 100 μl/well pH7.4 or pH5.5 washing buffer was added and the incubation was continued for 2 hours at RT with shaking. Afterwards, the plates was washed 3 times using washing buffer at pH7.4 and 100 μl/well of a solution of HRP conjugated goat anti-human Fc antibody (Abcam) in pH7.4 dilution buffer was then added to each well of the plate. After that the plates were allowed to incubate for 60 min at room temperature followed by washing three times with 200l/well pH7.4 washing buffer. Finally, 100 μl/well of TMB was added to each well and the reaction was terminated using 0.64M $H_2SO_4$. The plates were read on a Thermo Multiscan FC at 450 nm (see FIG. 22A to FIG. 22E).

Characterization of pH Dependent hPD-L1 Bindings Over a Wild Range of pH

The pH-dependent binding affinity was further measured at various pH values, such as pH4, pH4.5, pH5.0, pH5.5, pH6.0, pH7.4. The measurement by ELISA was conducted similarly to the method described above. High-binding clear polystyrene 96 well plates were coated with 100 μl/well of a 0.5 μg/ml hPD-L1-his in high pH coating buffer and incubated overnight at 4° C. Then the coated plates were washed 3 times with shaking for 10 s on an automatic plate washer with PBS+0.1% Tween 20 (Amresco). Then 200 µl of blocking buffer (1% BSA (Solarbio)+1% normal goat serum (Solarbio)+0.05% Tween 20 (Amresco)) was added to each well and the plates were then incubated for 2 hours at room temperature and washed 3 times as above. After aspirating the blocking buffer, 100 µl serial diluted antibodies (i.e. 23A11 H3L5, 23F11 H4L4 and 22C9-C produced by 293 cells) in dilution buffer (1% BSA (Solarbio)+1% normal goat serum (Solarbio)+0.01% Tween 20 (Amresco)) with pH7.4 were added and the plates were incubated for 40 minutes at RT. The plates were then washed once with 250 µl/well washing buffer at pH7.4, pH6.0, pH5.5, pH5.0, pH4.5 or pH4.0 and then 100 µl/well pH7.4 or pH5.5 washing buffer was added and the incubation was continued for 2 hours at RT with shaking. Afterwards, the plates was washed 3 times washing buffer at pH7.4 and 100 µl/well of a solution of HRP conjugated goat anti-hIgG HRP antibody (1:20000, Abcam) in pH7.4 dilution buffer was then added to each well of the plate. After that the plates were allowed to incubate for 60 min at room temperature followed by washing 3 times with 250 µl/well pH7.4 washing buffer. Finally, 100 µl/well of TMB was added to each well for 15 min and the reaction was terminated using 50 µl/well of 0.16M/L sulfuric acid. The plates were read on a Thermo Multiscan FC at 450 nm (see FIG. 23A-23F). The measurements were performed in triplicate.

For each antibody the binding signal at low pH was lower relative to that of at pH7.4. The lower the pH, the lower the binding signal is at a particular concentration of the antibody. At pH5, the binding signal of the three antibodies tested at high concentration e.g. 0.1, 0.3 or 1 µg/ml was less than 50% of their signal at pH7.4; at pH5.5, the signal of the three tested antibodies is less than 75% of that at pH7.4.

Example 18A: Epitope Binning of Select Anti-PD-L1 Via Alanine Scan

1. Generation of Mutant Human PD-L1 Recombinant Proteins

The cDNA coding for extracellular human PD-L1 (amino acid 19-238) and Fc fragment of human IgG1 was synthesized in vitro (SEQ ID NO: 107 is the amino acid sequence, and SEQ ID NO: 108 is the corresponding DNA sequence). Variants of human PD-L1 with single amino acid change at designated position as listed below were amplified by overlapping PCR as described below and using primers (Dr. Oligo BLP-192, Biolytic) as shown in (Table 7). The resulting fragment was digested with restriction enzymes for Hind III and BamH I at 5' and 3' ends respectively. The PCR product was then cloned into the pcDNA3.1 (+) vector by method of homologous recombination using Syno assembly mix reagent (Synbio) following manufacturer's instructions. Plasmid was purified QIAGEN Plasmid Mega Kit (QIAGEN).

```
Amino acid sequence
                                      (SEQ ID NO: 107)
METDTLLLWVLLLWVPGSTGFTVTVPKDLYVVEYGSNMTIECKFPVEKQL

DLAALIVYWEMEDKNIIQFVHGEEDLKVQHSSYRQRARLLKDQLSLGNAA

LQITDVKLQDAGVYRCMISYGGADYKRITVKVNAPYNKINQRILVVDPVT

SEHELTCQAEGYPKAEVIWTSSDHQVLSGKTTTTNSKREEKLFNVTSTLR

INTTTNEIFYCTFRRLDPEENHTAELVIPELPLAHPPNERENLYFQGAPE
```

```
-continued
LLGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALH

NHYTQKSLSLSPGK

DNA sequence (SEQ ID NO: 108):
AAGCTTgccgccaccATGGAAACCGACACTCTGCTGCTGTGGGTGCTGCT

GCTGTGGGTGCCAGGGTCAACCGGGTTCACCGTGACAGTGCCCAAGGACC

TGTACGTGGTGGAGTACGGCAGCAACATGACCATCGAGTGCAAGTTCCCC

GTGGAGAAGCAGCTGGATCTGGCCGCCCTGATCGTGTATTGGGAGATGGA

GGACAAGAACATCATCCAGTTCGTGCACGGCGAAGAGGACCTGAAGGTGC

AGCACAGCAGCTACAGGCAGAGGGCCAGACTGCTGAAGGACCAGCTGTCT

CTGGGAAACGCAGCTCTGCAGATCACCGACGTGAAGCTGCAGGACGCAGG

AGTCTACCGCTGCATGATCAGCTACGGCGGAGCCGACTACAAGAGGATCA

CCGTGAAGGTCAACGCCCCCTACAACAAGATCAACCAGAGAATCCTGGTG

GTGGACCCCGTGACCAGCGAGCACGAGCTGACTTGTCAGGCAGAGGGCTA

CCCCAAGGCCGAAGTGATTTGGACCAGCAGCGACCATCAGGTGCTGAGCG

GAAAGACCACCACCACCAACAGCAAGCGGGAGGAGAAGCTGTTCAACGTG

ACCAGCACCCTGCGGATCAACACCACCACCAACGAGATCTTCTACTGCAC

CTTCCGGAGACTGGACCCAGAGGAGAACCACACAGCCGAGCTGGTCATCC

CAGAACTGCCTCTGGCTCACCCTCCTAACGAGAGAGAGAATCTGTATTTT

CAGGGAGCACCAGAACTGCTGGGAGGACCATCCGTGTTCCTGTTTCCACC

CAAACCTAAGGACACCCTGATGATTAGCAGAACACCAGAAGTCACTTGCG

TGGTCGTGGACGTGTCCCACGAGGACCCCGAAGTCAAATTCAACTGGTAC

GTGGATGGCGTCGAGGTGCATAATGCTAAGACCAAACCAAGAGAGGAACA

GTACAACAGCACCTATAGGGTCGTGTCCGTCCTGACAGTGCTGCACCAGG

ACTGGCTGAACGGAAAGGAGTATAAATGCAAGGTGTCTAACAAGGCCCT

GCCAGCTCCCATCGAGAAGACTATTAGTAAAGCTAAGGGCCAGCCCCGCG

AACCTCAGGTGTACACCCTGCCTCCATCCCGAGACGAGCTGACCAAGAAC

CAGGTCTCTCTGACTTGTCTGGTGAAGGGATTCTATCCATCAGATATCGC

AGTGGAGTGGGAAAGCAATGGCCAGCCCGAGAACAATTACAAGACTACCC

CCCCTGTGCTGGACTCCGATGGCTCTTTCTTTCTGTATTCTAAACTGACC

GTGGATAAGAGTCGGTGGCAGCAGGGGAATGTCTTTTCATGCAGCGTGAT

GCACGAGGCACTGCACAATCATTACACTCAGAAGTCCCTGTCACTGTCAC

CTGGAAAGtagGGATCC
```

Using wild-type PD-L1 plasmid generated above (SEQ ID NOs: 107 and 108) as template, two segments of an integrated sequence were generated with mega primers (Tables 7), and ligation was accomplished by homologous recombination. The product was then cloned into the pcDNA3.1 (+) vector, after screening the individual positive colony through sequencing to identify the variants, PD-L1 mutants had been proved to be generated successfully. PCR procedure and conditions as follows:

| Step 1: to generate two mega fragments of variants | |
|---|---|
| | μl |
| ddH2O | 35 |
| 5 × S15 PCR buffer | 10 |
| 10 mM dNTP | 1 |
| F primer | 1 |
| R primer | 1 |
| PCR product | 1 |
| S15 polymerase | 1 |
| | 50 |

| Initial denaturation: | 98° C. | 1 min | |
|---|---|---|---|
| denaturation: | 98° C. | 15 s | |
| Annealing: | 58° C. | 30 s | |
| Extension: | 72° C. | 30 s per Kb | |
| Eventually extension: | 72° C. | 3 mins | 30 cycles |

| Step 2: to join the two pieces together | |
|---|---|
| Set up the following reaction on ice (homologous recombination): | |
| Syno assembly mix | 10 μl |
| Sequence products 1 | 2 μl |
| Sequence products 2 | 2 μl |
| Deionized H2O | 6 μl |
| Total Volume | 20 μl |

TABLE 7

Variants mutant primers sequence

| Wild type | 1-F | TATAGGGAGACCCAAGCTGGCTAGCGTTTAAACTTA AGCTTGCCGCCACCATGGAAACCGACACT | SEQ ID NO: 109 |
|---|---|---|---|
| Wild type | 1-R | TGGATATCTGCAGAATTCCACCACACTGGACTAGTG GATCCCTACTTTCCAGGTGACAGTGACAGGGACT | SEQ ID NO: 110 |
| M36-A | 2-AR | CACGGGGAACTTGCACTCGATGGTGGCGTTGCTGC CGTACTCCACCACGTACAGGTCCTTGG | SEQ ID NO: 111 |
| | 2-BF | TACGTGGTGGAGTACGGCAGCAACGCCACCATCGA GTGCAAGTTCCCCGTGGAGAAGCAGCT | SEQ ID NO: 112 |
| I38A | 3-AR | CTTCTCCACGGGGAACTTGCACTCGGCGGTCATGTT GCTGCCGTACTCCACCACGTACAGG | SEQ ID NO: 113 |
| | 3-BF | GTGGAGTACGGCAGCAACATGACCGCCGAGTGCAA GTTCCCCGTGGAGAAGCAGCTGGATCT | SEQ ID NO: 114 |
| K41A | 4-AR | ATCCAGCTGCTTCTCCACGGGGAAGGCGCACTCGA TGGTCATGTTGCTGCCGTACTCCACCA | SEQ ID NO: 115 |
| | 4-BF | GGCAGCAACATGACCATCGAGTGCGCCTTCCCCGT GGAGAAGCAGCTGGATCTGGCCGCCCT | SEQ ID NO: 116 |
| Q47A | 5-AR | CACGATCAGGGCGGCCAGATCCAGGGCCTTCTCCA CGGGGAACTTGCACTCGATGGTCATGT | SEQ ID NO: 117 |
| | 5-BF | GAGTGCAAGTTCCCCGTGGAGAAGGCCCTGGATCT GGCCGCCCTGATCGTGTATTGGGAGAT | SEQ ID NO: 118 |
| A51S | 6-AR | CATCTCCCAATACACGATCAGGGCGCTCAGATCCAG CTGCTTCTCCACGGGGAACTTGCACT | SEQ ID NO: 119 |
| | 6-BF | CCCGTGGAGAAGCAGCTGGATCTGAGCGCCCTGAT CGTGTATTGGGAGATGGAGGACAAGAA | SEQ ID NO: 120 |
| I54A | 7-AR | TCTTGTCCTCCATCTCCCAATACACGGCCAGGGCGG CCAGATCCAGCTGCTTCTCCACGGGG | SEQ ID NO: 121 |
| | 7-BF | AAGCAGCTGGATCTGGCCGCCCTGGCCGTGTATTG GGAGATGGAGGACAAGAACATCATCCA | SEQ ID NO: 122 |
| M59A | 8-AR | GAACTGGATGATGTTCTTGTCCTCGGCCTCCCAATA CACGATCAGGGCGGCCAGATCCAGCT | SEQ ID NO: 123 |
| | 8-BF | GCCGCCCTGATCGTGTATTGGGAGGCCGAGGACAA GAACATCATCCAGTTCGTGCACGGCGA | SEQ ID NO: 124 |
| K62A | 9-AR | GCCGTGCACGAACTGGATGATGTTGGCGTCCTCCAT CTCCCAATACACGATCAGGGCGGCCA | SEQ ID NO: 125 |
| | 9-BF | ATCGTGTATTGGGAGATGGAGGACGCCAACATCATC CAGTTCGTGCACGGCGAAGAGGACCT | SEQ ID NO: 126 |
| N63A | 10-AR | TTCGCCGTGCACGAACTGGATGATGGCCTTGTCCTC CATCTCCCAATACACGATCAGGGCGG | SEQ ID NO: 127 |
| | 10-BF | GTGTATTGGGAGATGGAGGACAAGGCCATCATCCA GTTCGTGCACGGCGAAGAGGACCTGAA | SEQ ID NO: 128 |
| I64A | 11-AR | CTCTTCGCCGTGCACGAACTGGATGGCGTTCTTGTC CTCCATCTCCCAATACACGATCAGGG | SEQ ID NO: 129 |
| | 11-BF | TATTGGGAGATGGAGGACAAGAACGCCATCCAGTT CGTGCACGGCGAAGAGGACCTGAAGGT | SEQ ID NO: 130 |
| H69A | 12-AR | CTGCACCTTCAGGTCCTCTTCGCCGGCCACGAACT GGATGATGTTCTTGTCCTCCATCTCCC | SEQ ID NO: 131 |

TABLE 7-continued

| | | Variants mutant primers sequence | |
|---|---|---|---|
| | 12-BF | GACAAGAACATCATCCAGTTCGTGGCCGGCGAAGA GGACCTGAAGGTGCAGCACAGCAGCTA | SEQ ID NO: 132 |
| V76A | 13-AR | CCTCTGCCTGTAGCTGCTGTGCTGGGCCTTCAGGTC CTCTTCGCCGTGCACGAACTGGATGA | SEQ ID NO: 133 |
| | 13-BF | GTGCACGGCGAAGAGGACCTGAAGGCCCAGCACA GCAGCTACAGGCAGAGGGCCAGACTGCT | SEQ ID NO: 134 |
| S80A | 14-AR | CAGCAGTCTGGCCCTCTGCCTGTAGGCGCTGTGCT GCACCTTCAGGTCCTCTTCGCCGTGCA | SEQ ID NO: 135 |
| | 14-BF | GAGGACCTGAAGGTGCAGCACAGCGCCTACAGGC AGAGGGCCAGACTGCTGAAGGACCAGCT | SEQ ID NO: 136 |
| Y81A | 15-AR | CTTCAGCAGTCTGGCCCTCTGCCTGGCGCTGCTGTG CTGCACCTTCAGGTCCTCTTCGCCGT | SEQ ID NO: 137 |
| | 15-BF | GACCTGAAGGTGCAGCACAGCAGCGCCAGGCAGA GGGCCAGACTGCTGAAGGACCAGCTGTC | SEQ ID NO: 138 |
| Q83A | 16-AR | CTGGTCCTTCAGCAGTCTGGCCCTGGCCCTGTAGCT GCTGTGCTGCACCTTCAGGTCCTCTT | SEQ ID NO: 139 |
| | 16-BF | AAGGTGCAGCACAGCAGCTACAGGGCCAGGGCCA GACTGCTGAAGGACCAGCTGTCTCTGGG | SEQ ID NO: 140 |
| R86A | 17-AR | CAGAGACAGCTGGTCCTTCAGCAGGGCGGCCCTCT GCCTGTAGCTGCTGTGCTGCACCTTCA | SEQ ID NO: 141 |
| | 17-BF | CACAGCAGCTACAGGCAGAGGGCCGCCCTGCTGAA GGACCAGCTGTCTCTGGGAAACGCAGC | SEQ ID NO: 142 |
| L88A | 18-AR | GTTTCCCAGAGACAGCTGGTCCTTGGCCAGTCTGG CCCTCTGCCTGTAGCTGCTGTGCTGCA | SEQ ID NO: 143 |
| | 18-BF | AGCTACAGGCAGAGGGCCAGACTGGCCAAGGACC AGCTGTCTCTGGGAAACGCAGCTCTGCA | SEQ ID NO: 144 |
| S93A | 19-AR | GATCTGCAGAGCTGCGTTTCCCAGGGCCAGCTGGT CCTTCAGCAGTCTGGCCCTCTGCCTGT | SEQ ID NO: 145 |
| | 19-BF | GCCAGACTGCTGAAGGACCAGCTGGCCCTGGGAA ACGCAGCTCTGCAGATCACCGACGTGAA | SEQ ID NO: 146 |
| L94A | 20-AR | GGTGATCTGCAGAGCTGCGTTTCCGGCAGACAGCT GGTCCTTCAGCAGTCTGGCCCTCTGCC | SEQ ID NO: 147 |
| | 20-BF | AGACTGCTGAAGGACCAGCTGTCTGCCGGAAACGC AGCTCTGCAGATCACCGACGTGAAGCT | SEQ ID NO: 148 |

Note:
AR-reverse primer, BF-forward primer

Other 20 variants are constructed by another company, Genewiz (Suzhou, China). Similar methods with Synbio Tech are performed to synthesize PD-L1 variants. And mega primers used for mutant sites are described in Table 8.

TABLE 8

| | | Variants mutant primers sequence | |
|---|---|---|---|
| F19A | 1-BF | CTGTGGGTGCCAGGGTCAACCGGGGCCACCGTGACA GTGCCCAAGGACCTGTACGTGGTGGA | SEQ ID NO: 149 |
| | 1-AR | CAGGTCCTTGGGCACTGTCACGGTGGCCCCGGTTGA CCCTGGCACCCACAGCAGCAGCACCC | SEQ ID NO: 150 |
| T20A | 2-BF | TGGGTGCCAGGGTCAACCGGGTTCGCCGTGACAGTG CCCAAGGACCTGTACGTGGTGGAGTA | SEQ ID NO: 151 |
| | 2-AR | GTACAGGTCCTTGGGCACTGTCACGGCGAACCCGGT TGACCCTGGCACCCACAGCAGCAGCA | SEQ ID NO: 152 |
| D26A | 3-BF | GGGTTCACCGTGACAGTGCCCAAGGCCCTGTACGTG GTGGAGTACGGCAGCAACATGACCAT | SEQ ID NO: 153 |
| | 3-AR | GCTGCCGTACTCCACCACGTACAGGGCCTTGGGCACT GTCACGGTGAACCCGGTTGACCCTG | SEQ ID NO: 154 |
| Y28A | 4-BF | ACCGTGACAGTGCCCAAGGACCTGGCCGTGGTGGAG TACGGCAGCAACATGACCATCGAGTG | SEQ ID NO: 155 |
| | 4-AR | CATGTTGCTGCCGTACTCCACCACGGCCAGGGCCTTG GGCACTGTCACGGTGAACCCGGTTG | SEQ ID NO: 156 |

TABLE 8-continued

| Variants | | mutant primers sequence | |
|---|---|---|---|
| Y32A | 5-BF | CCCAAGGACCTGTACGTGGTGGAGGCCGGCAGCAAC ATGACCATCGAGTGCAAGTTCCCCGT | SEQ ID NO: 157 |
| | 5-AR | GCACTCGATGGTCATGTTGCTGCCGGCCTCCACCACG TACAGGGCCTTGGGCACTGTCACGG | SEQ ID NO: 158 |
| Y56A | 6-BF | CTGGATCTGGCCGCCCTGATCGTGGCCTGGGAGATGG AGGACAAGAACATCATCCAGTTCGT | SEQ ID NO: 159 |
| | 6-AR | GATGTTCTTGTCCTCCATCTCCCAGGCCACGATCAGG GCTTCCAGATCCAGCTGCTTCTCCA | SEQ ID NO: 160 |
| E58A | 7-BF | CTGGCCGCCCTGATCGTGTATTGGGCCATGGAGGACA AGAACATCATCCAGTTCGTGCACGG | SEQ ID NO: 161 |
| | 7-AR | CTGGATGATGTTCTTGTCCTCCATGGCCCAATACACGA TCAGGGCTTCCAGATCCAGCTGCT | SEQ ID NO: 162 |
| E60A | 8-BF | GCCCTGATCGTGTATTGGGAGATGGCCGACAAGAACA TCATCCAGTTCGTGCACGGCGAAGA | SEQ ID NO: 163 |
| | 8-AR | CACGAACTGGATGATGTTCTTGTCGGCCATCTCCCAAT ACACGATCAGGGCTTCCAGATCCA | SEQ ID NO: 164 |
| D61A | 9-BF | CTGATCGTGTATTGGGAGATGGAGGCCAAGAACATCA TCCAGTTCGTGCACGGCGAAGAGGA | SEQ ID NO: 165 |
| | 9-AR | GTGCACGAACTGGATGATGTTCTTGGCCTCCATCTCC CAATACACGATCAGGGCTTCCAGAT | SEQ ID NO: 166 |
| Q66A | 10-BF | GAGATGGAGGACAAGAACATCATCGCCTTCGTGCAC GGCGAAGAGGACCTGAAGGTGCAGCA | SEQ ID NO: 167 |
| | 10-AR | CAGGTCCTCTTCGCCGTGCACGAAGGCGATGATGTTC TTGTCCTCCATCTCCCAATACACGA | SEQ ID NO: 168 |
| K75A | 11-BF | TTCGTGCACGGCGAAGAGGACCTGGCCGTGCAGCAC AGCAGCTACAGGCAGAGGGCCAGACT | SEQ ID NO: 169 |
| | 11-AR | CTGCCTGTAGCTGCTGTGCTGCACGGCCAGGTCCTCT TCGCCGTGCACGAACTGGATGATGT | SEQ ID NO: 170 |
| R82A | 12-BF | CTGAAGGTGCAGCACAGCAGCTACGCCCAGAGGGCC AGACTGCTGAAGGACCAGCTGTCTCT | SEQ ID NO: 171 |
| | 12-AR | GTCCTTCAGCAGTCTGGCCCTCTGGGCGTAGCTGCTG TGCTGCACCTTCAGGTCCTCTTCGC | SEQ ID NO: 172 |
| R113A | 13-BF | AAGCTGCAGGACGCAGGAGTCTACGCCTGCATGATC AGCTACGGCGGAGCCGACTACAAGAG | SEQ ID NO: 173 |
| | 13-AR | GGCTCCGCCGTAGCTGATCATGCAGGCGTAGACTCCT GCGTCCTGCAGCTTCACGTCGGTGA | SEQ ID NO: 174 |
| M115A | 14-BF | CAGGACGCAGGAGTCTACCGCTGCGCCATCAGCTAC GGCGGAGCCGACTACAAGAGGATCAC | SEQ ID NO: 175 |
| | 14-AR | GTAGTCGGCTCCGCCGTAGCTGATGGCGCAGCGGTAG ACTCCTGCGTCCTGCAGCTTCACGT | SEQ ID NO: 176 |
| S117A | 15-BF | GCAGGAGTCTACCGCTGCATGATCGCCTACGGCGGAG CCGACTACAAGAGGATCACCGTGAA | SEQ ID NO: 177 |
| | 15-AR | CCTCTTGTAGTCGGCTCCGCCGTAGGCGATCATGCAG CGGTAGACTCCTGCGTCCTGCAGCT | SEQ ID NO: 178 |
| A121S | 16-BF | CGCTGCATGATCAGCTACGGCGGAAGCGACTACAAG AGGATCACCGTGAAGGTCAACGCCCC | SEQ ID NO: 179 |
| | 16-AR | CTTCACGGTGATCCTCTTGTAGTCGCTTCCGCCGTAG CTGATGGCGCAGCGGTAGACTCCTG | SEQ ID NO: 180 |
| D122A | 17-BF | TGCATGATCAGCTACGGCGGAGCCGCCTACAAGAGG ATCACCGTGAAGGTCAACGCCCCCTA | SEQ ID NO: 181 |
| | 17-AR | GACCTTCACGGTGATCCTCTTGTAGGCGGCTCCGCCG TAGCTGATGCGCAGCGGTAGACTC | SEQ ID NO: 182 |
| Y123A | 18-BF | ATGATCAGCTACGGCGGAGCCGACGCCAAGAGGATC ACCGTGAAGGTCAACGCCCCCTACAA | SEQ ID NO: 183 |
| | 18-AR | GTTGACCTTCACGGTGATCCTCTTGGCGTCGGCTCCG CCGTAGCTGATGGCGCAGCGGTAGA | SEQ ID NO: 184 |
| K124A | 19-BF | ATCAGCTACGGCGGAGCCGACTACGCCAGGATCACC GTGAAGGTCAACGCCCCCTACAACAA | SEQ ID NO: 185 |
| | 19-AR | GGCGTTGACCTTCACGGTGATCCTGGCGTAGTCGGCT CCGCCGTAGCTGATGGCGCAGCGGT | SEQ ID NO: 186 |
| R125A | 20-BF | AGCTACGGCGGAGCCGACTACAAGGCCATCACCGTG AAGGTCAACGCCCCCTACAACAAGAT | SEQ ID NO: 187 |

TABLE 8-continued

| Variants mutant primers sequence | | |
|---|---|---|
| 20-AR | GGGGGCGTTGACCTTCACGGTGATGCCCTTGTAGTCG GCTCCGCCGTAGCTGATGGCGCAGC | SEQ ID NO: 188 |

Note:
AR-reverse primer, BF-forward primer

Subsequently, these plasmids of mutants and wild-type PD-L1 were transfected into 293T (ATCC® CRL3216) cell line. First, Seeding 5×10⁶ 293T cells into 60 mm dish, make sure primary ratio is at 60%80% for transfection. Then dilute 10 g DNA in 4001 µl 1×HBS, incubate for about 5 min. Add 10 µl 25 kDa linear PEI transfection reagent (dissolved in 1×HBS, 1 mg/ml stock solution) to the above mixture, make sure DNA/PEI ratio is 1:2.5. Then the mixture was added into 293T dish drop by drop. Change the medium and replace with complete DMEM about 6-8 hrs later. After 72 hrs, cell culture supernatant was collected with 0.22 m filter respectively, then stored at −80° C. for use.

2. Binding of PD-L1 Antibodies by ELISA

Supernatant was used to detect the binding of PD-L1 antibodies by ELISA as described below.

2.1 for Mouse Abs:

High-binding clear polystyrene 96 well plates (Nunc) were coated with 100 µl/well of coating solution consisting of 0.5 µg/ml anti-human Fc antibody (Abcam) in high pH buffer for one hour at room temperature. Then plates were washed once on an automatic plate washer using washing buffer (PBS+0.1% Tween 20 (Sigma)), followed by adding 200 µl of blocking buffer (PBS+1% BSA+1% normal goat serum+0.05% Tween-20) to each well. The plates were incubated overnight at 4° C. Then the plates were washed with washing buffer once and 160 µl DMEM supernatant containing various mutant human PD-L1-Fc proteins or 500 ng/ml wild type human PD-L1-Fc protein in DMEM were added to each well and incubated for 1 hour at room temperature. The plates were then washed 3 times using the method described above. Mouse anti-PD-L1 antibodies at 0.5 µg/ml were added and incubated for 1 hour at RT. After the plates were washed 3 times using 200 µl/well pH7.4 washing buffer, 100 µl/well of a solution of HRP conjugated mouse IgG antibody (1:20000, Pierce) diluted in dilution buffer was then added to each well of the plate. Afterwards the ELISA plates were incubated for 60 min at room temperature and then were washed three times with 200 µl/well pH7.4 washing buffer. Finally, 100 µl/well of TMB was added to each well and the reaction was terminated using 0.64M H₂SO₄. The plates were read on a Thermo Multiscan FC at 450 nM (see FIG. 24).

2.2 for Abs with Human Fc (Chimeric or Humanized Antibodies):

High-binding clear polystyrene 96 well plates (Nunc) were coated with 100 µl/well of coating solution consisting of 0.5 µg/ml anti-human Fc (for mouse antibodies) or an anti-hPD-L1 antibody which could pair with other PD-L1 antibodies, in high pH buffer for one hour at room temperature. Then plates were washed once on an automatic plate washer using washing buffer (PBS+0.1% Tween 20 (Sigma)), followed by adding 200 µl of blocking buffer (PBS+1% BSA+1% normal goat serum+0.05% Tween-20) to each well. The plates were incubated for overnight at 4° C. Then the plates were washed with washing buffer once and 160 µl DMEM supernatant containing various mutant human PD-L1-Fc proteins or 500 ng/ml wild type human PD-L1-Fc protein in DMEM were added to each well and incubated for 1 hour at room temperature. The plates were then washed 3 times using the method described above. Biotinylated humanized anti-PD-L1 antibodies (23F11-H4L4-bio and 23A11-H3L5-bio) generated above or PD-1 protein at 0.5 µg/ml were added and incubated for 1 hour at RT. After the plates were washed 3 times using 200 µl/well pH7.4 washing buffer, 100 µl/well of a solution of HRP conjugated anti-mouse Fc antibody (Abcam) or HRP conjugated neutravidin (1:5000, Pierce) diluted in dilution buffer was then added to each well of the plate. Afterwards the ELISA plates were incubated for 60 min at room temperature and then were washed three times with 200 µl/well pH7.4 washing buffer. Finally, 100 µl/well of TMB was added to each well and reaction was terminated using 0.64M H₂SO₄. The plates were read on a Thermo Multiscan FC at 450 nM (see FIG. 24).

Table 9 summarizes the key residues on hPD-L1 that are required for each individual antibody tested to human PD-L1 in the ELISA assay. The amino acid residue mutations on the human PD-L1 proteins that lead to significantly reduced binding signal relative to that of the wild type protein is marked.

TABLE 9

Summary of the key residues on hPD-L1 for each antibody

| Mutant number | Mutation | 4B6 | 18G4 | 21F11 | 26F5 | 22C9 | 23A11 | 23A11-H3L5 | 23F11 | 23F11-H4L4 | PD-1-Fc-bio |
|---|---|---|---|---|---|---|---|---|---|---|---|
| 1 | F19A | * | | | | | | | | | *** |
| 2 | T20A | | | | | | | | | | |
| 3 | D26A | | | | | | | | | | |
| 4 | Y28A | | | | | | | | | | |
| 5 | Y32A | | | | | | | | | | |
| 6 | M36-A | | | | | | | | | | |
| 7 | I38A | | | | | | | | | | |
| 8 | K41A | | | | | | | | | | |
| 9 | Q47A | | | | | | | | | | |
| 10 | A51S | | | | | | | | | | |
| 11 | I54A | | | | | | | | | * | ** |
| 12 | Y56A | | | *** | | * | | | | | |
| 13 | E58A | * | | ** | * | *** | ** | *** | *** | *** | |

TABLE 9-continued

Summary of the key residues on hPD-L1 for each antibody

| Mutant number | Mutation | 4B6 | 18G4 | 21F11 | 26F5 | 22C9 | 23A11 | 23A11-H3L5 | 23F11 | 23F11-H4L4 | PD-1-Fc-bio |
|---|---|---|---|---|---|---|---|---|---|---|---|
| 14 | M59A | | | | | | | | | | |
| 15 | E60A | | | | | | | * | | * | |
| 16 | D61A | | | | | | | * | | | |
| 17 | K62A | | | | | | | ** | | | |
| 18 | N63A | | | | | | | ** | ** | ** | |
| 19 | I64A | | | | | | * | | ** | ** | |
| 20 | Q66A | | | * | | | | | | | |
| 21 | H69A | | | | | | | | | | |
| 22 | K75A | | | | | | | | | | |
| 23 | V76A | | | | | | | | | | |
| 24 | S80A | ** | ** | | ** | ** | ** | *** | ** | *** | ** |
| 25 | Y81A | | | | | | | ** | ** | ** | |
| 26 | R82A | | | | | | | | | | |
| 27 | Q83A | | | | | | | | | | |
| 28 | R86A | | | | | | | | | | |
| 29 | L88A | | | | | | | | | | |
| 30 | S93A | | | | | | | | | | |
| 31 | L94A | | | | | | | | | | |
| 32 | R113A | *** | | *** | *** | **** | **** | **** | **** | **** | *** |
| 33 | M115A | * | | * | * | *** | | | | | ** |
| 34 | S117A | | | | | | | | | | |
| 35 | A121S | * | | * | | | | | | | * |
| 36 | D122A | *** | | | ** | | | | | | *** |
| 37 | Y123A | **** | | * | | *** | | * | | * | *** |
| 38 | K124A | * | | | | *** | | * | | ** | ** |
| 39 | R125A | *** | | * | *** | *** | *** | **** | *** | **** | *** |

The data in Table 9 showed that those antibodies with pH-dependent binding properties utilize more of the following amino acids for their binding to human PD-L1.

R125 and S80 are important for PD-1 binding to both types of PD-L1 antibodies (e.g. pH-dependent and non-pH-dependent), wherein the importance of S80 for binding of the present PD-L1 antibodies provided herein were not reported before.

E58 and R113 are more important to 22C9, 23A11, 23F11 and their humanized versions relative to non-pH dependent binding abs (including benchmark antibodies, such as BM-ME), where E58 is a novel site found by our analysis for the antibodies 22C9, 23A11, 23F11 and not revealed by prior art as it is not important for PD-1 binding to PD-L1).

M115 and K124 are unique to 22C9 but these two residues are known to be important for PD-1 binding to PD-L1.

N63 and Y81 are unique to 23F11 and their humanized 23F11 and humanized 23A11 (but not 23A11), while they are not important for PD-1 binding to PD-L1 and also not important for benchmark antibodies to bind to hPD-L1 and thus are novel sites.

I64 is unique to 23F11 and its humanized version, and it is not known to be important for PD-1 binding to PD-L1 in the prior art.

K62 is unique to 23A11 humanized version and it is not known to be important for PD-1 binding to PD-L1 in the prior art.

Y123 is most critical for 4B6 and benchmark antibodies but less critical for other antibodies including pH-dependent antibodies (it is also important for 22C9, another pH dependent binding antibody).

Y56 is unique to 21F11 and it is not known to be important for PD-1 binding to PD-L1 in the prior art.

Although it has been reported that mutation of either R113 and R125 to A in the anti-PD-L1 antibodies will lead to loss of their binding ability to human PD-L1 (see U.S. Pat. No. 8,779,108), they are known to be important for PD-1 binding to PD-L1 as described in Lin D Y et al., *Proc Natl Acad Sci USA*. 2008 Feb. 26; 105(8):3011-6.

Example 19: Large Scale Production of Anti-PD-L1 Antibodies for In Vivo Studies

Antibodies were produced using transient expression in CHO-K1 cells. The produced antibodies were purified using protein-A affinity column and upon desalting, the antibodies were formulated into PBS at 5 mg/ml with endotoxin level at <3 unit/mg. The resulting antibodies were characterized for purity using SDS-PAGE gel and SEC-HPLC.

Transient Expression and Purification of Recombinant Antibody Using CHO-K1 Cells The variable region of the heavy chain and light chain selected antibody genes were synthesized and cloned into an expression vector. The resulting expression contrast was used to transfect CHO-K1 cell adapted to grow in serum free medium. After 10 days' growth in 10 L Applikon bioreactor, the culture medium was harvested and the cells and cell debris were removed using ultra-filters. The clarified supernatant was then concentrated by ultrafiltration and uploaded onto a prepared Protein A (human IgG) or G-sepharose (mouse IgG) column. After being washed with equilibration buffer to baseline under monitoring by a UV monitor, the column was then eluted with 0.1 M citric acid, pH 3.5, and the eluted antibody was immediately neutralized with 1.0 M Tris-HCl buffer, pH 8.0, and dialyzed against PBS, pH 7.2 (Invitrogen), overnight at 2-8° C. with 2 buffer exchanges. The purified antibody was filtered through 0.22 µm sterile syringe filters and stored in aliquots at −80° C. or below.

Example 20: In Vivo Evaluation of Anti-PD-L1 Humanized Antibodies

The in vivo activities of the humanized anti-PD-L1 antibodies were evaluated as described in Example 14.

Figure 25:
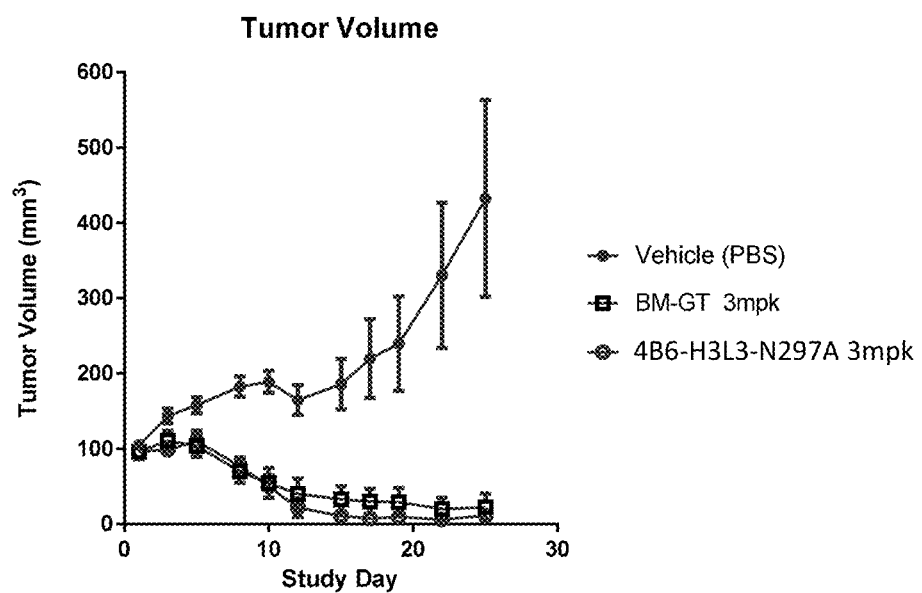
FIG. 25 shows the in vivo anti-tumor activities of the humanized PD-L1 antibodies (vehicle in solid circle, BT-GM in open square and 4B6-H3L3-N297A in open circle) in inhibiting the growth of tumor in MC38/Human-PD-L1 knock-in tumor model as presented by averaged tumor volume over time. Mice (n=8 for each group) were IP injected with 3 mpk antibodies 3 times/week for 3 weeks, the results of which are expressed as mean±S.E.M.

1. Anti-Tumor Activities of the Humanized PD-L1 Antibodies in MC38/Human-PD-L1 Knock-in Tumor Model Tests of anti-tumor activity of the humanized PD-L1 antibodies 4B6-H3L3-N297A in the MC38/Human-PD-L1 knock-in tumor model were conducted as described in Example 14 and the results were shown in Table 10 and FIG. 25 (results of treatment using PBS, BM-GT and 4B6-H3L3-N297A were shown).

TABLE 10

Study design to test the anti-tumor activity of PD-L1 antibodies in the treatment of MC38/hPD-L1 syngeneic murine tumor model

| Group | Treatment | Animal No. | Dosage | Dose Route | Schedule |
|---|---|---|---|---|---|
| 1 | Vehicle (PBS) | 1-8 | — | i.p. | 3 times/week*3 |
| 2 | BM-GT | 1-8 | 3 mpk | i.p. | 3 times/week*3 |
| 3 | 4B6-chimeric | 1-8 | 3 mpk | i.p. | 3 times/week*3 |
| 4 | 4B6-H3L3-N297A | 1-8 | 3 mpk | i.p. | 3 times/week*3 |

Figure 26A:
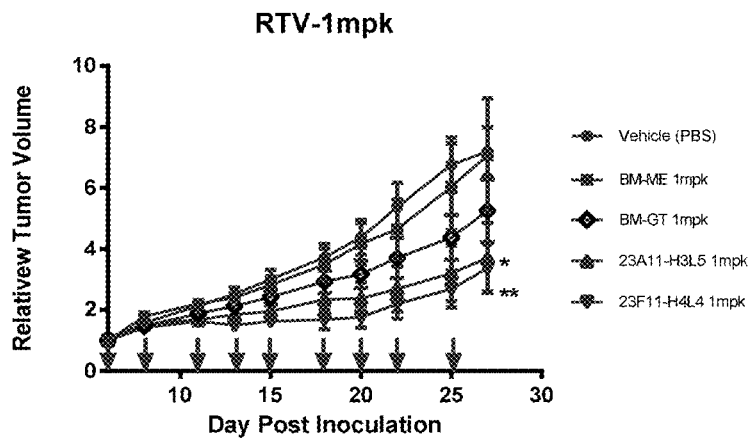
FIG. 26A shows the averaged tumor volume measured over time in MC38/Human-PD-L1 knock-in tumor model dosed with vehicle (solid circle), BM-ME (open square), BM-GT (open diamond), 23A11-H3L5 (open triangle) and 23F11-H4L4 (inverted open triangle), indicating the in vivo anti-tumor activities of the humanized PD-L1 antibodies in inhibiting the growth of tumor.
Figure 26B:
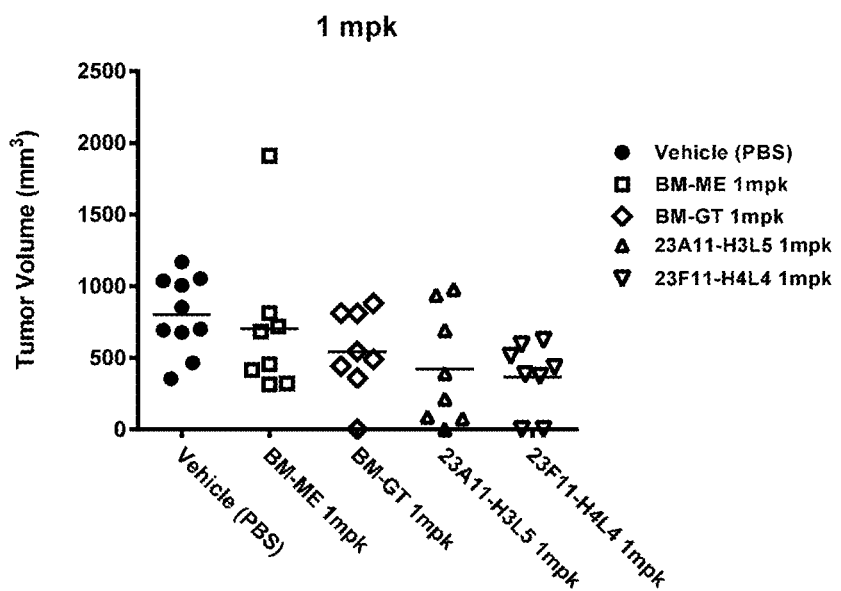
FIG. 26B shows the averaged tumor volume at Day 28 with mice injected with 1 mpk antibodies.
Figure 26C:
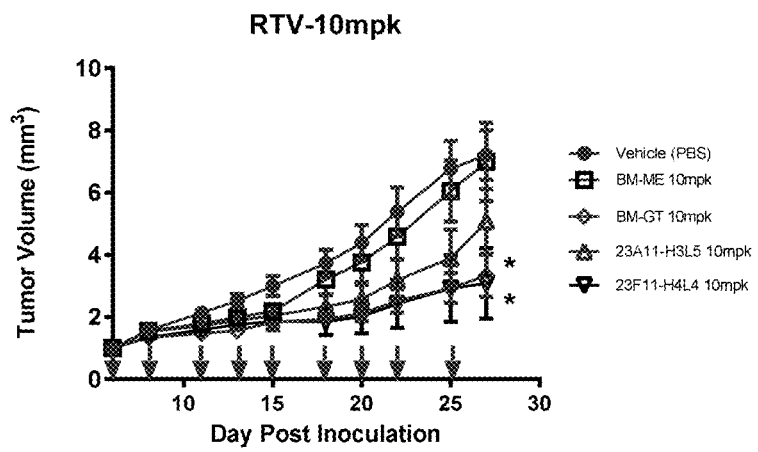
FIG. 26C shows the same tests as FIG. 26A but with 10 mpk antibodies, respectively.
Figure 26D:
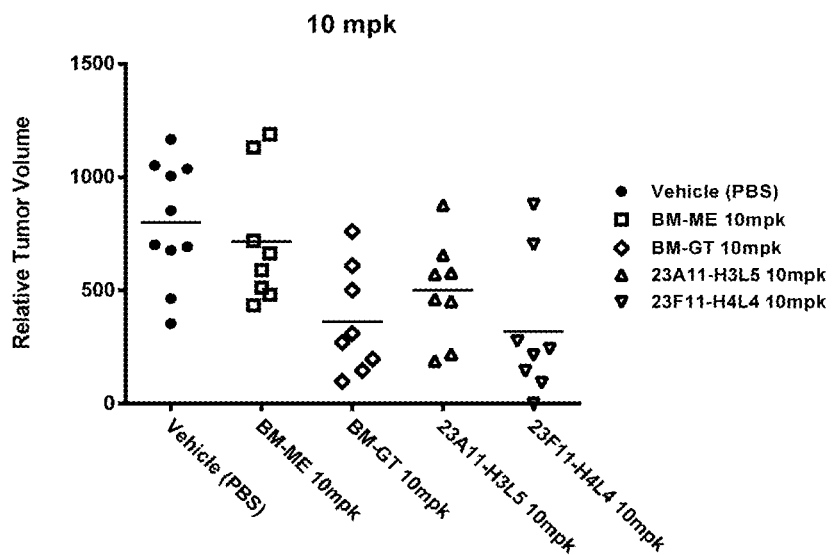
FIG. 26D shows the same tests as FIG. 26B but with 10 mpk antibodies, respectively.
Figure 26E:
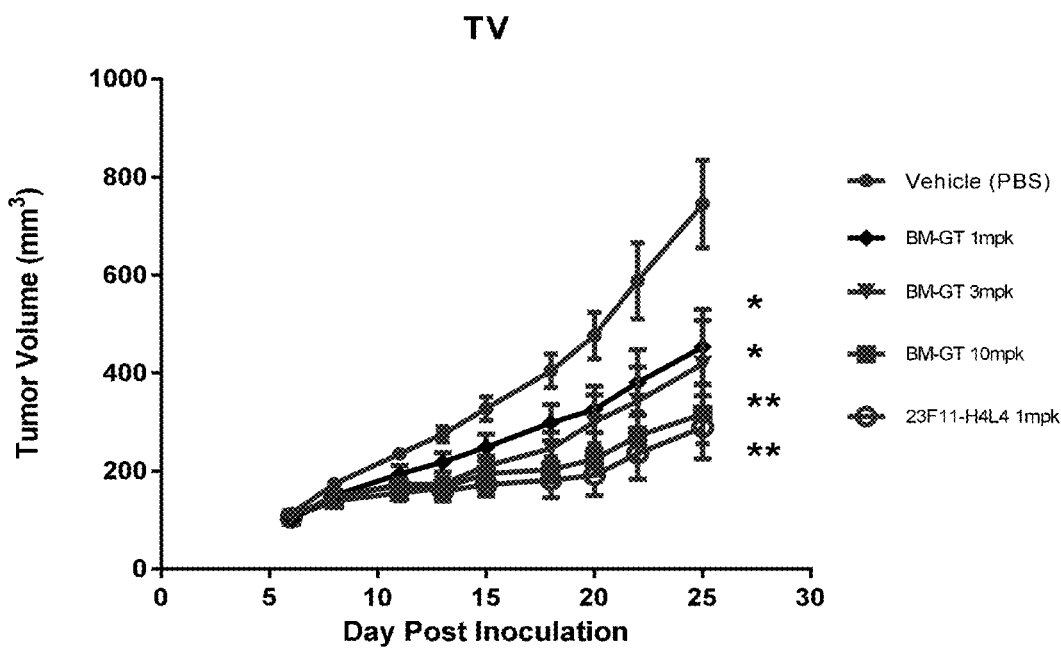
FIG. 26E compares the tumor volume in mice injected with different antibodies and dosages (vehicle in solid circle, BM-GT with 1 mpk in solid diamond, BM-GT with 3 mpk in inverted solid triangle, BM-GT with 10 mpk in solid square and 23F11-H4L4 with 1 mpk in open circle).

2. Inhibition of MC38/hPD-L1 KI Tumor Growth with IP Injection of Humanized Antibodies This study is designed to evaluate the effect of humanized anti-PD-L1 antibodies in inhibiting tumor growth when delivered intra-peritoneally at either 1 mg/kg, 3 mg/kg or 10 mg/kg. Briefly 2×10^6 MC38/hPD-L1 tumor cells were inoculated as did previously in C57/BL6 mice and were allowed to grow for 6 days. At that time, mice with average tumor volume of 80-100 mm^3 were selected and randomized into groups with 8 mice in each group. Each testing antibodies were dosed intra-peritoneally at 1 mg/kg, 3 mg/kg or 10 mg/kg (for BM-GT) or 23F11-H4L4 (1 mg/kg) in equal volume to individual mouse starting on day 6 and three times a week. Animals were sacrificed at the end of the study (day 25) by $CO_2$ inhalation. Tumor size was measured twice weekly in two dimensions using a caliper (INSIZE), and the volume was expressed in $mm^3$ using the formula: $V=0.5 \, a \times b^2$ where a and b are the long and short diameters of the tumor, respectively. Record tumor regressions as partial (PR) if the tumor volume is decreased to <50% of the tumor volume at the start of treatment, without dropping below the measurable size, or as complete (CR) if the tumor burden has become unpalpable (see Table 11). Results were analyzed using Prism GraphPad and expressed as mean±S.E.M. Comparisons between two groups were made by T-test, and the difference is considered significant if P is <0.05. FIG. 26E show the tumor volume measured in individual mouse dosed with various antibodies (BM-GT, BM-ME, 23A11-H3L5 and 23F11-H4L4). RTV represents relative tumor volume compared to the tumor volume measured at day 1 in the same mouse, and TV represents tumor volume measured at the last day (i.e. day 25) of the study).

TABLE 11

Tumor regression measured at DAY 25

| Treatment | Tumor Volume (mm^3) | TGI % | PR | CR |
|---|---|---|---|---|
| Vehicle (PBS) | 745.04 ± 76.86 | | 0/8 | 0/8 |
| BM-GT 1 mg/kg | 453.04 ± 61.70 | 44.46* | 0/8 | 1/8 |
| BM-GT 3 mg/kg | 418.20 ± 88.91 | 50.81* | 1/8 | 0/8 |
| BM-GT 10 mg/kg | 316.66 ± 61.70 | 66.44** | 0/8 | 2/8 |
| 23F11-H4L4 1 mg/kg | 288.86 ± 64.95 | 70.76** | 0/8 | 2/8 |

Note:
vs Vehicle,
*p < 0.05;
**P < 0.01.
PR (Partial Regression): tumor volume decreased to <50% of the tumor volume at the start of treatment, without dropping below measurable size
CR (Complete Regression): tumor burden has become unpalpable 3. Inhibition of MC38/HPD-L1 KI Tumor Growth with Intravenous Injection of Humanized PD-L1 Antibodies This study is designed to evaluate the effect of humanized antibodies in inhibiting tumor growth when delivered intravenously as how one would expect to use them for patients. Briefly, MC38/hPD-L1 tumor cells were inoculated as previously in C57/BL6 mice and allowed to grown for 10 days. At that time, mice with average tumor volume of 180-220 mm^3 were selected and randomized into groups with 12 mice in each group. Each testing antibodies were dosed IV at 1 mg/kg in equal volume to individual mouse at day 0 and at day 15. Animal were sacrificed at the end of the study by $CO_2$ inhalation. Tumor size was measured twice weekly in two dimensions using a caliper (INSIZE), and the volume was expressed in $mm^3$ using the formula: $V=0.5 \, a \times b2$ where a and b are the long and short diameters of the tumor, respectively. Record tumor regressions as partial (PR) if the tumor volume is decreased to <50% of the tumor volume at the start of treatment, without dropping below the measurable size, or as complete (CR) if the tumor burden has become unpalpable (see Table 12). Results were analyzed using Prism GraphPad and expressed as mean±S.E.M. Comparisons between two groups were made by T-test, and the difference is considered significant if P is <0.05.

The data in FIG. 29 showed that at 1 mg/kg dose, 23A11-H3L5 and 23F11-H4L4 were significantly more effective in inhibiting tumor growth under identical conditions than at other doses. FIG. 27A shows that 1 mg/kg of 23F11-H4L4 or 23A11-H3L5 produced tumor growth inhibition of 91% and 82% respectively while benchmark antibody at 1 mg/kg produced 41.6% tumor growth inhibition relative to vehicle control. FIG. 29A shows that 1 mg/kg of 23F11-H4L4 or 23A11-H3L5 inhibited MC38/hPD-L1 knock-in tumor growth to a level similar to BM-GT at 10 mg/kg and they showed no statistically significant difference in tumor inhibition activities under the same conditions. Therefore, those antibodies exemplified by 23F11-H4L4 and 23A11-H3L5 have about ten-fold higher in vivo activities than benchmark antibody BM-GT (also named as MPDL-3280A), which does not bind to antigen in a pH-dependent manner (see FIGS. 29A and 29B).

TABLE 12

Tumor regression measured at Day 26

| Treatment | Tumor Volume (mm^3) | TGI % | PR | CR |
|---|---|---|---|---|
| Vehicle (PBS) | 809.7 ± 563.9 | | 0/12 | 0/12 |
| BM-GT 1 mg/kg | 472.9 ± 221.40 | 41.6 | 0/12 | 1/12 |
| 23A11-H3L5 1 mg/kg | 142.2 ± 235.8 | 82.4** | 2/12 | 7/12 |
| 23F11-H4L4 1 mg/kg | 71.9 ± 116.3 | 91.1*** | 3/12 | 6/12 |

**p value < 0.01 vs. Vehicle;
***p value < 0.005 vs. Vehicle
PR: partial response, >50% reduction from the tumor volume at the starting point
CR: complete response, 100% reduction from the tumor volume at the starting point The change of tumor size in each mouse at the study endpoint were shown in the waterfall graph and was expressed as change from the starting point (see FIG. 28A to 28D). Those mice with tumor size increased by more than 100% were expressed as 100% and those with a tumor size increase less than 100% or decreased from starting point were expressed as the exact change in percentage.

The above result showed that 23F11-H4L4 and 23A11-H3L5 are significantly more potent in inhibiting tumor growth than benchmark antibody BM-GT at 1 mg/kg (see FIG. 27 and FIG. 28). In addition, the ability of 23A11-H3L5 and 23F11-H4L4 in inhibiting tumor growth at 1 mg/kg is comparable to that of BM-GT at 10 mg/kg (see FIGS. 29A and 29B). Furthermore, there is no further increase in tumor growth inhibition activity for 23A11-H3L5 or 23H11-H4L4 when dosed at 10 mg/kg compared to that dosed at 1 mg/kg while there is significant increase of activity for BM-GT. Therefore antibodies with pH-dependent antigen binding could be of a new class of antibodies of capable of inhibiting tumor growth at very low doses.

4. Tumor Re-Challenges Study

To understand whether mice achieved complete tumor clearance with IV treatment with PD-L1 antibody can mount sustained immune response and control new tumor emerged, we re-challenged mice with fresh tumor cells in a subset of mice achieved complete response when dosed with 1 mg/kg of either 23A11-H3L5 or 23F11-H4L4 by day 10-35. Briefly, each of these mice was injected with fresh tumor cells of 2×10^6 at day 35 post inoculation. The newly infused tumor cells were able to grow for the first five to ten days upon infusion but then the tumor started to decrease in size and by day 50 (15 days post re-challenge) none of the mice has any measurable tumor. This demonstrates that these mice have developed memory to the same tumor cells and the tumor inhibitory response is durable although no antibody was present by then (see FIG. 30).

Example 21: Evaluation of Tumor Penetration of Select Dependent Neutralizing Antibodies Antibody needs to penetrate into tumor to exert its effect. To evaluate whether pH dependent antibodies have advantage in penetrating into tumor and whether there is any difference between their residence time in the tumor, we employed in vivo imaging study.

Briefly, test antibodies BM-GT and 23F11-H4L4 were labeled using near-inferred fluorescence labeling dye (CF750, Cat: 99952, Lot: 12M0413, BIOTIUM) with the following method: antibodies were diluted in PBS to 0.1 mg/ml, then 0.8 ml of each antibody solution were pipetted into each pre-warmed 10×Reaction Buffer vial at a ratio of 1:9, so that the antibody solution contained a final concentration of 1× Reaction Buffer. After mixing the solutions by pipetting up and down a few times, transfer the entire solution from each vial to a vial containing the CF dye, vortex the vials for a few second and incubate the vials in the dark for 30 minutes. Afterwards, approximately 0.2 ml antibody-dye solution was intravenously injected to each mouse.

MC38/hPD-L1 Syngeneic Tumor Model

2×10^6 MC38/hPD-L1 cells were implanted to 8 weeks old C57BL/6 mice subcutaneously, 12 mice were selected and randomized into 4 groups. When the tumor grew to around 220 mm^3, animals were intravenously injected with 0.2 ml of antibody-dye solution.

Tumor site was imaged of each mouse with IVIS Lumina II after anesthesia at time point post dose 1 h, 4 h, 24 h, 48 h, 96 h, Day7, Day11, Day15, Day18, and Day21. Briefly each mouse was anesthesia with 50 mg/kg Pentobarbital Sodium before IVIS imaging at each time point. When the animals stopped moving, placed the animal in the observation box (with the tumor side placed up) and closed the door, and then use the Living image software to image each mouse.

An example of the radiant signal was shown BM-GT and humanized 23F11 (i.e. 23F11-H4L4) (see FIG. 31A). The average radiant signal from each mice was quantified for each time point and analyzed with GraphPad prism and shown in FIG. 31B. The result showed that antibody 23F11-H4L4 had significantly higher radiant signal than benchmark antibody and thus much more antibodies are retained in the tumor than benchmark antibodies. Corresponding to the more antibodies in the tumor over time, two out of the three mice treated with 23F11-H4L4 had tumor decreased significantly whereas none of the mice treated with BM-GT had tumor decreased significantly (see FIG. 31C). Thus, 23F11-H4L4, an antibody with pH-dependent property, may have unique advantage and is more efficacious in inhibiting tumor growth. 2-1, 2-2, 2-3, 4-1, 4-2 and 4-3 in the figure legend of FIG. 31B indicates individual mouse 1, 2 or 3 in group 2 # and group 4 #, respectively.

Example 22: Combination Therapy of Select Humanized Anti-PD-L1 Antibody with Other Tumor Modulating Agents To evaluate whether combination of checkpoint inhibitor anti-PD-L1 antibody and anti-VEGFR2 antibody (anti-angiogenesis) can better control tumor growth, hPD-L1/MC38 tumors were treated with DC101, an antibody with neutralizing activity for mouse VEGFR2, at 20 mg/kg; or PD-L1 antibodies 23A11-chimeric at sub-optimal dose 0.3 mg/kg, or both. Briefly, 2×10^6 MC38/hPD-L1 tumor cells were inoculated as did previously in C57/BL6 mice and allowed to grow for 3 days. At that time, mice were randomized into groups with 8 mice in each group. Each testing antibodies were dosed intra-peritoneally at 0.3 mg/kg of 23A11-chimeric, or 20 mg/kg of DC101 or both to individual mouse starting at day 3 and three times a week for three weeks. Animals were sacrificed at the end of the study by $CO_2$ inhalation. Tumor size was measured twice weekly in two dimensions using a caliper (INSIZE), and the volume was expressed in $mm^3$ using the formula: V=0.5 a×$b^2$ where a and b are the long and short diameters of the tumor, respectively. Results were analyzed using Prism GraphPad and expressed as mean S.E.M. Comparisons between two groups were made by T-test, and the difference is considered significant if P is <0.05. The data showed that the combination treatment was much more effective in inhibiting the growth of the tumor cells (see FIG. 32A to FIG. 32C).

To further demonstrate that combination therapy is more effective than monotherapy, we started treatment when the tumor volume is around 180 $mm^3$. We dosed the two antibodies in pairs of either 1 mg/kg or 3 mg/kg in a mouse strain that is not very sensitive to the humanized PD-L1 or VEGFR2 antibody DC101. The treatment was given IV once a week for 2-3 weeks. The data showed that both treatments in combination are significantly more effective than single antibody in inhibiting tumor growth (see FIGS. 32D and 32E).

Thus, we demonstrated that combination of humanized PD-L1 antibodies with angiogenic inhibitory agents such as VEGFR2 antibody could be an effective approach for the treatment for established tumor growth or progression of newly formed tumors.

Example 23: Thermal Stability of the PD-L1 Antibodies

The capillary cell differential scanning calorimetry (DSC) is utilized to evaluate the thermal stability of proteins by detecting the heat differentiation between sample and reference during the temperature increase. Specifically, it is used to measure the thermal transition midpoint (Tm), which is an indicator of the relative stability of protein in liquid. Antibodies 23F11-H4L4 or 23A11-H3L5 (produced in CHO cells) were diluted with buffer (20 mM His-His-HCl, 5% Sucrose, pH=6.0) to 1 mg/ml and added into DSC 96 well tray. The samples were run with MicroCal VP-DSC Capillary Cell Microcalorimeter (GE) with temperature range from 10110° C., and scan rate of 200° C./hr, and the result was analyzed with MicroCal VP Capillary DSC Automated Analysis Software. The Capillary Cell DSC testing results were shown below in Table 13 and in FIGS. 33A and 33B.

As shown in Table 13, the 23F11-H4L4 antibody showed a significant elevated Tm value (i.e. Tm2, which represents the Tm of the Fab fragment, while Tm1 represents the Tm of the CH2 fragment).

TABLE 13

| Sample Name | Scan Temperature | Tm onset (° C.) | Tm1 (° C.) | Tm2 (° C.) |
|---|---|---|---|---|
| 23F11-H4L4 | 10~110° C. | 52.3 | 64.1 | 90.2 |
| 23A11-H3L5 | 10~110° C. | 52.3 | 64.4 | 76.7 |

Example 24: Epitope Mapping of E58 for Anti-PD-L1 Antibodies

The importance of the residue of E58 for the binding of the anti-PD-L1 antibodies provided herein was analyzed for the antibodies using ELISA based binding assay as described in Example 18A. Either wild type anti-PD-L1 protein or a mutant with E58A was produced and the relative binding of the antibodies to the two proteins was performed on the same plate, and the results are shown in Table 14 as below:

TABLE 14

| Name of Ab | Name of the PD-L1 protein | OD450 nM of sample-1 | OD450 nM of sample-2 | Mean | % of binding of Ab to E58A mutant vs. that to WT PD-L1 |
|---|---|---|---|---|---|
| 23F11-H4L4 | Wild type | 1.18 | 1.33 | 1.255 | |
| | E58A | 0.129 | 0.103 | 0.116 | 9.2% |
| 23A11-H3L5 | Wild type | 1.224 | 1.467 | 1.345 | |
| | E58A | 0.128 | 0.094 | 0.111 | 8.3% |
| MEDI4736 (BM-ME) | Wild type | 1.472 | 1.58 | 1.526 | |
| | E58A | 1.059 | 1.072 | 1.0655 | 69.8% |
| MPDL3280A (BM-GT) | Wild type | 1.30 | 1.417 | 1.359 | |
| | E58A | 0.814 | 0.574 | 0.694 | 51% |
| 23F11 | Wild type | 1.65 | 1.765 | 1.71 | |
| | E58A | 0.383 | 0.292 | 0.3375 | 9.9% |
| 22C9 | Wild type | 1.9 | 1.941 | 1.92 | |
| | E58A | 0.35 | 0.309 | 0.3295 | 17.2% |
| 23A11 | Wild type | 1.5 | 1.615 | 1.56 | |
| | E58A | 0.854 | 0.76 | 0.807 | 51.7% |
| 26F5 | Wild type | 1.387 | 1.683 | 1.535 | |
| | E58A | 1.183 | 0.678 | 0.93 | 60.6% |
| 4B6 | Wild type | 1.432 | 1.545 | 1.489 | |
| | E58A | 1.063 | 1.009 | 1.036 | 69.6% |
| 18G4 | Wild type | 1.556 | 1.34 | 1.448 | |
| | E58A | 1.524 | 1.883 | 1.703 | 117% |

The data showed that residue E58 is critical for 23F11 and 23F11-H4L4 whose binding is reduced by more than 90% when this residue is mutated to Alanine in human PD-L1. Similarly, the binding of 23A11-H3L5, 22C9, was also reduced to 8.3%, 17.2% of the binding signal to WT PD-L1 protein. On the other hand, the binding of BM-GT or BM-ME was reduced to 51% or 69.8% of the binding of the antibodies to wild type PD-L1 when the E58 was mutated to Ala. Similarly, the binding of 23A11, 26F5 and 4B6 was also reduced to 51.7%, 60.6% and 69.6% of the wild type PD-L1 protein. Most differently, the binding of 18G4 to PD-L1 was not reduced at all when E58 was mutated to Ala. Thus E58 was differentially required for the binding of different antibodies to PD-L1 protein and it was a critical residue for 23F11, 23F11-H4L4 and 22C9.

Also noted that 18G4 is an antibody which has very different epitope binding profile relative to other anti-PD-L1 antibodies disclosed herein which only requires the binding of S80 among the 39 different amino acid analyzed by alanine scan. This antibody is also very potent in inhibiting tumor growth in vivo.

Example 25: Internalization of Humanized PD-L1 Antibodies

To evaluate whether 23F11-H4L4 (CHO cell derived) can be internalized, we performed the following experiment. The secondary antibody goat anti-human Fc was first labeled with pHAb Amine Reactive Dye (Sigma, G9845), a pH sensitive dye. This dye is not fluorescent at neutral pH but becomes highly fluorescent at acidic pH. When antibody labeled with this dye is internalized into intracellular endosomes (pH6.0-6.5) and lysosomes (4.5-5.5), high fluorescent signal can be detected. Specifically, MC38-hPD-L1 cells (MabSpace) were cultured in RPMI-1640 containing 10% fetal bovine serum (Hyclone). Log phase growing cells were collected by centrifuging and cells were seeded at a density of $2 \times 10^4$/well (50 l/well) into 96-well plate to allow cells to adhere for overnight. Then 2 µg/ml goat anti-human-Fc (Jackson ImmunoResearch, Cat #109-005-098) labeled with pHAb Amine Reactive Dye (25 µl/well) was added into each wells followed by adding serially diluted 23F11-H4L4 or hIgG1 (25 µl/well) into each wells. The antibodies are allowed to incubate with the cells for 6 hrs or 24 hrs at 37° C. After the end of incubation the culture medium was removed and 100 µl PBS was added to each well. The signal of the antibody in each well of the plate was determined using Varioskan Flash (Thermo Scientific) by reading at spectrum of Ex 532 nm/Em 560 nm. The data in graph showed that there is significant increase in fluorescent signal in the cells after 6 or 24 hours in a concentration dependent manner. These results demonstrated that 23F11-H4L4 can be efficiently internalized upon binding to hPD-L1 on the surface of MC38/hPD-L1 cells (see FIG. 35).

Example 26: Binding of Humanized PD-L1 Antibody to Activated T Cells In Vitro

Peripheral blood monocytes were isolated from a leukapheresis pack using Ficoll-Paque density gradient centrifugation and resuspended in PBS plus 2% FBS. The cells were diluted with culture medium to a density at $0.5 \times 10^7$ cells/ml and then added to plates coated with anti-human CD3 antibody (OKT3, ebioscience, Cat #16-0037) (1 µg/ml, 1 ml/well). Anti-human CD28 (BD, Cat #555725) was added to each well and then the cells are then cultured in 6-well plate with RPMI 1640 plus 10% FBS for 3 days at 37° C. After that, the cells are collected and placed into 96-well round bottom plate in FACS buffer (PBS+5% BSA). After centrifuge and the supernatants were discarded, serially diluted 23F11-H4L4 antibody, or hIgG1 with N297A mutation as negative control were added. The plates were incubated for one hour at 4° C., then the cells were washed for three times using PBS. Afterwards, 2.5µ then the cells were washed for three times using PBS. Afterwards, 2.5 Chuman IgG-APC (Biolegend, Cat #409306) were added to each well and the plates were incubated for one hour at 4° C., washed three times before analyzed by flow cytometer (Beckman Cytoflex).

The data in the FIGS. 36A and 36B showed that 23F11-H4L4 can bind to PD-L1 expressed on activated T cells in a dose-dependent manner while it displayed very little binding to non-activated T cells.

Example 27: In Vivo Efficacy Study of PD-L1 Antibody in hPD-1 Knock-in Mouse Model with MC38/hPD-L1 Cells In previous experiments (for instance, Examples 14 and 20), the PD-1 protein in the syngeneic mice is mouse origin and the immune-suppression is mediated by the binding of hPD-L1 to mouse PD-1. To further evaluate whether there would be any difference of the antibody treatment in the MC38/hPD-L1 syngeneic model if the mouse PD-1 is changed to hPD-1, a situation existing in human patients, we implanted the MC38/hPD-L1 tumor cells into a PD-1 knock-in mice. Specifically, the MC38/hPD-L1 tumor cells were maintained in vitro as a monolayer culture in RPMI1640 medium (Thermo Fisher) supplemented with 10% heat inactivated fetal bovine serum (ExCell Biology), 100 U/ml penicillin and 100 g/ml streptomycin (Hyclone) at 37° C. in an atmosphere of 5% $CO_2$ in air. The tumor cells were routinely sub-cultured twice weekly by trypsin-EDTA treatment (Hyclone). The cells growing in an exponential growth phase were harvested and counted for FACS analysis of hPD-L1 expression confirmation and tumor inoculation. Each PD-1 knock-in female mouse of 5-6 week age (C57BL/6-Pdcd/tm1 (hPDCD1), Beijing Biocytogen Co., Ltd) was inoculated subcutaneously at the right flank with MC38/hPD-L1 tumor cells confirmed with PD-L1 expression ($2 \times 10^6$) in 0.1 ml of PBS for tumor development. The treatments were started approximately 7 days after inoculation when the tumor size reached approximately 100 $mm^3$. Each group consisted of 10 tumor-bearing mice (see FIG. 37A). The testing article (i.e. 23F11-H4L4) was prepared by aspirating 200 µl stock solution at 3 mg/ml concentration and diluted into 1.8 ml of formulation buffer (Histidine 20 mM, Sucrose 250 mM, Polysorbate 80 0.02%, pH 6.0±0.2) to obtain working solution of 0.3 mg/ml and was administrated to the mice by intravenous injection. Tumor size was measured twice weekly in two dimensions using a caliper (INSIZE), and the volume was expressed in $mm^3$ using the formula: $V=0.5 \; a \times b^2$ where a and b are the long and short diameters of the tumor, respectively. Record tumor regressions as partial (PR) if the tumor volume decreased to <50% of the tumor volume at the start of treatment, without dropping below measurable size, or as complete (CR) if the tumor burden has become impalpable. The tumor size in each treatment group is shown in Table 15 and FIGS. 37B and 37C. These data demonstrated that treatment with antibody 23F11-H4L4 led to significant tumor growth inhibition with tumor eradication or complete response in 5 out of the 10 mice treated while those treated with saline all grew and had no tumor regression in any of the mice.

TABLE 15

Tumor Growth Inhibition (TGI) Rate on Day 31

| Group | Tumor Volume | TGI % | P value | CR % | PR % | ORR % |
|---|---|---|---|---|---|---|
| PBS | 588.12 ± 364.42 | / | / | 0 | 0 | 0 |
| 23F11-H4L4 (3 mg/kg) | 119.24 ± 163.20 | 79.73 | 0.002 | 50 | 0 | 50 |

To further compare the relative in vivo tumor growth inhibition efficacy, we conducted another experiment. Similarly, each PD-1 knock-in female mouse of 5-6 week age (C57BL/6-Pdcd/tm1 (hPDCD1), Beijing Biocytogen Co., Ltd) was inoculated subcutaneously at the right flank with MC38/hPD-L1 tumor cells confirmed with PD-L1 expression ($2 \times 10^6$) in 0.1 ml of PBS for tumor development. The treatments were started approximately 7 days after inoculation when the tumor size reached approximately 100 mm$^3$. Each group consisted of 8 tumor-bearing mice. The testing article was prepared by aspirating 0.128 ml, 0.384 ml and 1.28 ml stock solution at 3 mg/ml concentration and diluted into 3.712, 3.456 and 2.58 ml sterile PBS (Hyclone, Cat #SH30256.01) to obtaining working solution of 0.1 mg/ml, 0.3 mg/ml and administrated 200 to each mice by intraperitoneal injection twice a week to achieving dosing 1, 3, 10 mg/kg. Similarly, BM-GT (MABSPACE, produced in CHO cells) and Control IgG with N297A mutation (CrownBio, AB160160 from CHO cells) was prepared by aspirating 1.280 mL 3 mg/ml CHO cell derived BM-GT into 2.560 mL PBS or 0.662 ml of 5.8 mg/ml stock into 3.178 ml sterile PBS and administrated 200 μl of the final diluted solution to each mice by intraperitoneal injection twice a week to achieve dosing at 10 mg/kg IP twice a week. Tumor size was measured twice weekly in two dimensions using a caliper (INSIZE), and the volume was expressed in mm$^3$ using the formula: $V=0.5 \text{ a} \times \text{b}^2$ where a and b are the long and short diameters of the tumor, respectively. Record tumor regressions as partial (PR) if the tumor volume decreased to <50% of the tumor volume at the start of treatment, without dropping below measurable size, or as complete (CR) if the tumor burden has become impalpable (see Table 16 and FIG. 38A-38C).

TABLE 16

Tumor growth inhibition rate in MC38/hPD-L1 Syngeneic Tumor Model on hPD-1 Mice (N = 8, Day 27)

| Group | Treatment | Tumor Volume (± SD) | TGI % | PR | CR | ORR % |
|---|---|---|---|---|---|---|
| 1 | Control IgG 10 mpk N = 8 | 691.93 ± 377.72 | | 0/8 | 0/8 | 0 |
| 2 | 23F11-H4L4 1 mpk N = 8 | 138.88 ± 119.50** | 79.93 | 0/8 | 1/8 | 12.5 |
| 3 | 23F11-H4L4 3 mpk N = 8 | 83.14 ± 118.68** | 87.98 | 1/8 | 4/8 | 62.5 |
| 4 | 23F11-H4L4 10 mpk N = 8 | 10.81 ± 20.51**# | 98.44 | 2/8 | 6/8 | 100 |
| 5 | BM-GT 10 mpk N = 8 | 71.27 ± 73.01** | 86.70 | 0/8 | 3/8 | 37.5 |

**: vs Control IgG group p < 0.01; #: vs BM-GT p < 0.05

The data from the above experiment showed in the PD-1 knock-in mice implanted with MC38 expressing human PD-L1 that 1) 23F11-H4L4 displayed potent, dose-dependent tumor growth inhibitory activities with overall response (PR+CR) rate of 12.5%, 62.5% and 100% at 1.3 and 10 mg/kg respectively (see FIG. 38A); 2) 23F11-H4L4 at 3 mg/kg is at least as potent as BM-GT at 10 mg/kg (see FIGS. 38B and 38C); 4) 23F11-H4L4 at 3 mg/kg either dosed via IP or IV displayed similar activity in achieving complete tumor regression (50%) (see FIGS. 37A-37B and 38A-38C). 3) 23F11-H4L4 at 10 mg/kg dose is significantly more potent than BM-GT at 10 mg/kg not only in overall tumor size reduction but also in number of mice achieved complete tumor regression (6/8 vs. 3/8) (see FIG. 38C); Thus the pH-dependent antigen binding and associated recycling property and thus longer drug residence time in tumor could translated into better tumor control and tumor regression, especially at a maximally effective dose for BM-GT.

Example 28: Receptor Occupancy and Mouse Pharmacokinetics/Pharmacodynamics

To measure the duration of the antibody binding to the target protein human PD-L1 in the MC38/hPD-L1 tumor upon single intravenous injection of the antibody, we measured the amount of available target protein binding site in single cells prepared from tumor at different time points post antibody injection using FACS. Specifically, the MC38/hPD-L1 tumor cells were maintained in vitro as a monolayer culture in RPMI1640 medium (Thermo Fisher) supplemented with 10% heat inactivated fetal bovine serum (Ex-Cell Biology), 100 U/ml penicillin and 100 μg/ml streptomycin (Hyclone) at 37° C. in an atmosphere of 5% $CO_2$ in air. The tumor cells were routinely sub-cultured twice weekly by trypsin-EDTA treatment (Hyclone). The cells growing in an exponential growth phase were harvested and counted for FACS analysis of hPD-L1 expression confirmation and tumor inoculation. Each female C57B/L6 mouse of 5-6 week age was inoculated subcutaneously at the right flank with MC38/hPD-L1 tumor cells confirmed with PD-L1 expression ($2 \times 10^6$) in 0.1 ml of PBS for tumor development. The treatments were started approximately 12 days after inoculation when the tumor size reached approximately 200-300 mm$^3$ and dosed with 23F11-H4L4 at 3 mpk (see Table 17). Tumors were collected on Day 2, Day 7, and Day 14 after administration for receptor occupancy evaluation. The tumors were harvested and were minced into small fragments and then ACCUMAX™ cell detachment solution (STEMCELL cat #07921) at a concentration of 10 ml/0.5 g of tissues was added. Then the tumor chunk suspension was shaken gently at room temperature for 1-2 hours and repeatedly pipette up and down during the incubation to further dissociate cells. At the end of the incubation, the cell suspension was passed through a 40 m nylon mesh. The cells were then washed with cold PBS for three times and centrifuged for 5 min at 1500 rpm. The collected cells were then resuspended with 1-2 ml PBS and the total cell number was counted. After this, 50 of cell suspension (about 1000000 cells) was added to each 96 well plate. The cells were washed twice with FACS buffer (1% BSA in PBS). The cells were then incubated with 2 μg/ml 23F11-H4L4 antibody or PBS or isotype control. The mixture was incubated for at least 30 min at 2-8° C. or on ice and protected from light. The cells were washed three times with FACS buffer before centrifuged for 5 minutes at 1500 rpm. An anti-human IgG FC-FITC second antibody was added and incubated for 30 min at 2-8° C. in dark followed by washing the cells with FACS buffer for three times; In the end, the cells were resuspended in 0.5 ml FACS buffer and analyzed using a flow cytometer. Flow cytometer data analysis software (Cytoflex) and GraphPad Prism were used to calculate the percentage of PD-L1 positive cells and the mean fluorescence intensity (MFI) in comparison with the isotype-matched control antibody-stained cells. The ratio of change in relative mean fluorescence intensity (RMFI) among cells preincubated in vitro with saturating amounts of an isotype control hIgG1-N197A (CrownBio, AB160160) to detect in vivo binding of 23F11-H4L4 to PD-L1) or 23F11-H4L4 or BM-GT (to detect available PD-L1 binding site) was used to estimate receptor occupancy (RO). Values were normalized against an appropriate isotype control hIgG1-N297A. The data (see Table 18) showed that a single injection of 23F11-H4L4 at 3 mg/kg can lead to sustained tumor PD-L1 occupancy for at least 7 days. On the other hand, BM-GT at 3 mg/kg showed tumor PD-L1 occupancy more than 2 days but less than 7 days despite initial higher occupancy rate, demonstrating that the pH-dependent PD-L1 binding property of 23F11-H4L4 can allow the antibody to stay in the tumor for longer time and to bind to PD-L1 on tumor cells.

TABLE 17

Study Designs

| Group No. | Treatment | Animal No. | Route | Dosage (mg/kg) | Dosing volume (µl/g) | Schedule* |
|---|---|---|---|---|---|---|
| 1 | PBS | 1-9 | IV | — | 10 | Single |
| 2 | 23F11-H4L4 | 1-9 | IV | 3 | 10 | Single |
| 3 | BM-GT | 1-9 | IV | 3 | 10 | Single |

Note:
Dosing volume: adjusted dosing volume based on body weight. IV: intravenous

TABLE 18

Receptor Occupancy Result

| | RMFI (Day 2) | | | | RMFI (Day 7) | | | | RMFI (Day 14) | | | |
|---|---|---|---|---|---|---|---|---|---|---|---|---|
| Group (n = 3) | Occu-pied | Total | RO (%) | Mean RO (%) | Occu-pied | Total | RO (%) | Mean RO (%) | Occu-pied | Total | Total | Mean RO (%) |
| 23F11-H4L4 3 mpk (n = 3) | 5732.00 | 13018.60 | 44.59 | 52.9 | 7213.67 | 12221.67 | 51.00 | 55.04 | −77.93 | 3013.57 | −2.28 | −3.79 |
| | 8300.40 | 15082.20 | 64.57 | | 7381.97 | 12242.27 | 52.19 | | −109.23 | 3689.27 | −3.20 | |
| | 6368.60 | 10464.90 | 49.54 | | 8760.97 | 17967.97 | 61.94 | | −201.43 | 3551.37 | −5.89 | |
| BM-GT 3 mpk (n = 3) | 6737.60 | 8745.50 | 95.35 | 81.23 | −399.93 | 11237.67 | −3.21 | −2.27 | 16.37 | 5589.47 | 0.23 | −0.19 |
| | 5096.70 | 5661.30 | 72.13 | | −54.73 | 13264.17 | −0.44 | | −168.83 | 7392.47 | −2.35 | |
| | 5386.30 | 6791.90 | 76.23 | | −395.63 | 12872.17 | −3.18 | | 111.27 | 8540.87 | 1.55 | |

Example 29: Tumor Penetration Results

Three mice with MC38/hPD-L1 tumor grown in normal syngeneic C57B/L6 mice were treated with a single intravenous injection of 10 mg/kg 23F11-H4L4 when tumor reached 200-300 mm3. Tumors were collected on Day 7 after antibody administration for tumor penetration and Tumor-infiltrating lymphocytes (TIL) analysis. Specifically tumor blocks were prepared using Optimal Cutting Temperature (O.C.T.) (Tissue Tek) following manufacturer's instruction. Tissue section of 6 m thickness were prepared and tissue slides were fixed with methanol followed by washing with PBS and then permeablized with 0.2% TritonX-100 for 5 minutes. The slides were then washed with PBS and blocked with blocking buffer (3.0% BSA in 1×PBS) for 30-60 minutes at room temperature, followed by washing the slides with PBS-T three times for 5 minutes each. Then Alexa Fluor 488 Goat anti-human IgG (H+L) second antibody (Thermo, Cat #A11013, to detect 23F11-H4L4), Alexa Fluor® 594 anti-mouse CD31 antibody (Biolegend, Cat #102520, to detect vasculature) and Alexa Fluor® 594 anti-mouse CD8a antibody (Biolegend, Cat #100758, to detect CD8 T cells) diluted in PBS was applied to sections, and allowed to incubate in the dark for overnight at 4° C. After draining the secondary antibody and washing the slides with PBS-T for three times (5 minutes each), the slides were counter-stained with DAPI covered with glass cover-slip and stored at 4° C. in the dark. Fluorescent microscope (Nikon Ni-U) was used to analyze the loci and distribution of 23F11-H4L4 and TIL in comparison with the control frozen tissue section.

Representative image of 23F11-H4L4 penetration and TIL on Frozen MC38/hPD-L1 CDx tumor section on Day 7 after dosing at 10 mpk are shown in FIG. 40.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. An isolated PD-L1 antibody, comprising heavy chain HCDR1', HCDR2' and HCDR3' and light chain LCDR1', LCDR2' and LCDR3' sequences, wherein the HCDR1' sequence comprises DYYMN (SEQ ID NO: 23);
the HCDR2' sequence comprises DINPNNGGTSYNX'$_1$KFX'$_2$G (SEQ ID NO: 24);
the HCDR3' sequence comprises VKWGDGPFAY (SEQ ID NO: 25);
the LCDR1' sequence comprises X'$_3$ASQNVGAAVA (SEQ ID NO: 26);
the LCDR2' sequence comprises SASNX'$_4$X'$_5$T (SEQ ID NO: 27);
the LCDR3' sequence comprises QQYSNYPT (SEQ ID NO: 28);
wherein X'$_1$ is H or Q; X'$_2$, is K or Q; X'$_3$ is K or Q; X'$_4$ is R or L; X'$_5$ is Y or E, or
wherein:
a) the heavy chain HCDR1' sequence comprises SEQ ID NO: 29, HCDR2' comprises SEQ ID NO: 30 and HCDR3' sequence comprises SEQ ID NO: 31, the light chain LCDR1' sequence comprises SEQ ID NO: 32, LCDR2' sequence comprises SEQ ID NO: 33 and LCDR3' sequence comprises SEQ ID NO: 34;
b) the heavy chain HCDR1' sequence comprises SEQ ID NO: 35, HCDR2' sequence comprises SEQ ID NO: 36 and HCDR3' sequence comprises SEQ ID NO: 37, the light chain LCDR1' sequence comprises SEQ ID NO: 38, LCDR2' sequence comprises SEQ ID NO: 39 and LCDR3' sequence comprises SEQ ID NO: 40; or
c) the heavy chain HCDR1' sequence comprises SEQ ID NO: 41, HCDR2' sequence comprises SEQ ID NO: 42 and HCDR3' sequence comprises SEQ ID NO: 43, the light chain LCDR1' sequence comprises SEQ ID NO: 44, LCDR2' sequence comprises SEQ ID NO: 45 and LCDR3' sequence comprises SEQ ID NO: 46.

2. The antibody of claim 1, wherein X'$_1$ is Q; X'$_2$, is Q; X'$_3$ is Q; X'$_4$ is R; and X'$_5$ is Y.

3. The antibody of claim 1, comprising heavy chain framework sequences of HFR3' and HFR4' and light chain framework sequences of LFR1', LFR2', LFR3' and LFR4', wherein the sequences of heavy chain variable region is according to the formula: HFR1'-HCDR1'HFR2'-HCDR1'HFR3'-HCDR1'HFR4', and the sequences of light chain variable region is according to the formula LFR1'-LCDR1'-LFR2'-LCDR1'-LFR3'-LCDR1'-LFR4', wherein the HFR1' sequence comprises X'$a_1$VQLX'$a_2$QSGX'$a_3$EX'$a_4$X'$a_5$KPGASVKX'$a_6$SCKASGYVFT (SEQ ID NO: 47);

the HFR2' sequence comprises WVX'$a_7$QX'$a_8$X'$a_9$GX'$a_{10}$X'$a_{11}$LEWIG (SEQ ID NO: 48);

the HFR3' sequence comprises X'$a_{12}$X'$a_{13}$TVTVDX'$a_{14}$SX'$a_{15}$X'$a_{16}$TAYMELX'$a_{17}$X'$a_{18}$LX'$a_{19}$SX'$a_{20}$DX'$a_{21}$AVYYC (SEQ ID NO: 49);

the HFR4' sequence comprises WGQGTLVTVSX'$a_{22}$ (SEQ ID NO: 50);

the LFR1' sequence comprises DIX'$a_{23}$MTQSX'$a_{24}$X'$a_{25}$X'$a_{26}$X'$a_{27}$SX'$a_{28}$SVGDRVX'$a_{29}$ITC (SEQ ID NO: 51);

the LFR2' sequence comprises WYQQKPGX'$a_{30}$X'$a_{31}$PKLLIY (SEQ ID NO: 52);

the LFR3' sequence comprises GVPX'$a_{32}$RFX'$a_{33}$GSGSGTDFTLTISX'$a_{34}$X'$a_{35}$QX'$a_{36}$EDX'$a_{37}$AX'$a_{38}$YFC (SEQ ID NO: 53); and/or the LFR4' sequence comprises FGSGTKLGIK (SEQ ID NO: 54);

wherein X'$a_1$ is Q or E; X'$a_2$ is Q or V; X'$a_3$ is A or P; X'$a_4$ is L or V; X'$a_5$ is V or K; X'$a_6$ is I or V; X'$a_7$ is K or R; X'$a_8$ is S or A; X'$a_9$ is H or P; X'$a_{10}$ is Q or K; X'$a_{11}$ is S or G; X'$a_{12}$ is K or R; X'$a_{13}$ is A or V; X'$a_{14}$ is K or T; X'$a_{15}$ is S, T or I; X'$a_{16}$ is S or R; X'$a_{17}$ is L or S; X'$a_{18}$ is S or R; X'$a_{19}$ is R or T; X'$a_{20}$ is E or D; X'$a_{21}$ is S or T; X'$a_{22}$ is A or S; X'$a_{23}$ is Q or V; X'$a_{24}$ is Q or P; X'$a_{25}$ is K or S; X'$a_{26}$ is F or S; X'$a_{27}$ is M or L; X'$a_{28}$ is T or A; X'$a_{29}$ is S or T; X'$a_{30}$ is Q or K; X'$a_{31}$ is S or A; X'$a_{32}$ is S or D; X'$a_{33}$ is S or T; X'$a_{34}$ is S or N; X'$a_{35}$ is M or L; X'$a_{36}$ is S or P; X'$a_{37}$ is L or I; X'$a_{38}$ is D or T;

wherein X'$a_1$ is Q; X'$a_2$ is V; X'$a_3$ is A; X'$a_4$ is V; X'$a_5$ is V; X'$a_6$ is I; X'$a_7$ is K; X'$a_8$ is A; X'$a_9$ is P; X'$a_{10}$ is Q; X'$a_{11}$ is G; X'$a_{12}$ is R; X'$a_{13}$ is A; X'$a_{14}$ is K; X'$a_{15}$ is T; X'$a_{16}$ is R; X'$a_{17}$ is S; X'$a_{18}$ is R; X'$a_{19}$ is R; X'$a_{20}$ is D; X'$a_{21}$ is T; X'$a_{22}$ is S; X'$a_{23}$ is Q; X'$a_{24}$ is Q; X'$a_{25}$ is S; X'$a_{26}$ is S; X'$a_{27}$ is L; X'$a_{28}$ is A; X'$a_{29}$ is T; X'$a_{30}$ is K; X'$a_{31}$ is A; X'$a_{32}$ is S; X'$a_{33}$ is S; X'$a_{34}$ is S; X'$a_{35}$ is M; X'$a_{36}$ is P; X'$a_{37}$ is I; X'$a_{38}$ is T, wherein X'$a_1$ is Q; X'$a_2$ is V; X'$a_3$ is A; X'$a_4$ is V; X'$a_5$ is K; X'$a_6$ is V; X'$a_7$ is R; X'$a_8$ is A; X'$a_9$ is P; X'$a_{10}$ is Q; X'$a_{11}$ is G; X'$a_{12}$ is R; X'$a_{13}$ is V; X'$a_{14}$ is T; X'$a_{15}$ is I; X'$a_{16}$ is R; X'$a_{17}$ is S; X'$a_{18}$ is R; X'$a_{19}$ is R; X'$a_{20}$ is D; X'$a_{21}$ is T; X'$a_{22}$ is S; X'$a_{23}$ is Q; X'$a_{24}$ is Q; X'$a_{25}$ is S; X'$a_{26}$ is S; X'$a_{27}$ is L; X'$a_{28}$ is A; X'$a_{29}$ is T; X'$a_{30}$ is K; X'$a_{31}$ is A; X'$a_{32}$ is S; X'$a_{33}$ is S; X'$a_{34}$ is S; X'$a_{35}$ is M; X'$a_{36}$ is P; X'$a_{37}$ is I; X'$a_{38}$ is T, X'$a_1$ is Q; X'$a_2$ is V; X'$a_3$ is A; X'$a_4$ is V; X'$a_5$ is V; X'$a_6$ is I; X'$a_7$ is K; X'$a_8$ is A; X'$a_9$ is P; X'$a_{10}$ is Q; X'$a_{11}$ is G; X'$a_{12}$ is R; X'$a_{13}$ is A; X'$a_{14}$ is K; X'$a_{15}$ is T; X'$a_{16}$ is R; X'$a_{17}$ is S; X'$a_{18}$ is R; X'$a_{19}$ is R; X'$a_{20}$ is D; X'$a_{21}$ is T; X'$a_{22}$ is S; X'$a_{23}$ is Q; X'$a_{24}$ is P; X'$a_{25}$ is S; X'$a_{26}$ is S; X'$a_{27}$ is L; X'$a_{28}$ is A; X'$a_{29}$ is T; X'$a_{30}$ is K; X'$a_{31}$ is A; X'$a_{32}$ is S; X'$a_{33}$ is S; X'$a_{34}$ is S; X'$a_{35}$ is L; X'$a_{36}$ is P; X'$a_{37}$ is I; X'$a_{38}$ is T, and/or X'$a_1$ is Q; X'$a_2$ is V; X'$a_3$ is A; X'$a_4$ is V; X'$a_5$ is K; X'$a_6$ is V; X'$a_7$ is R; X'$a_8$ is A; X'$a_9$ is P; X'$a_{10}$ is Q; X'$a_{11}$ is G; X'$a_{12}$ is R; X'$a_{13}$ is V; X'$a_{14}$ is T; X'$a_{15}$ is I; X'$a_{16}$ is D; X'$a_{17}$ is S; X'$a_{18}$ is R; X'$a_{19}$ is R; X'$a_{20}$ is D; X'$a_{21}$ is T; X'$a_{22}$ is S; X'$a_{23}$ is Q; X'$a_{24}$ is P; X'$a_{25}$ is S; X'$a_{26}$ is S; X'$a_{27}$ is L; X'$a_{28}$ is A; X'$a_{29}$ is T; X'$a_{30}$ is K; X'$a_{31}$ is A; X'$a_{32}$ is A; X'$a_{33}$ is S; X'$a_{34}$ is S; X'$a_{35}$ is L; X'$a_{36}$ is P; X'$a_{37}$ is I; X'$a_{38}$ is T.

4. The antibody of claim 1, comprising a heavy chain variable region as set forth in SEQ ID NO: 65 or a sequence having at least 80% sequence identity thereof and a light chain variable region as set forth in SEQ ID NO: 66 or a sequence having at least 80% sequence identity thereof; or comprising a heavy chain variable region as set forth in SEQ ID NO: 67 or a sequence having at least 80% sequence identity thereof and a light chain variable region as set forth in SEQ ID NO: 68 or a sequence having at least 80% sequence identity thereof, or comprising a heavy chain variable region as set forth in SEQ ID NO: 85 or a humanized variant thereof or a sequence having at least 80% sequence identity thereof and a light chain variable region as set forth in SEQ ID NO: 86 or a humanized variant thereof or a sequence having at least 80% sequence identity thereof.

5. The antibody of claim 1, comprising a heavy chain variable region of SEQ ID NO: 55 or a humanized variant thereof or a sequence having at least 80% sequence identity thereof, and a light chain variable region of SEQ ID NO: 56 or a humanized variant thereof or a sequence having at least 80% sequence identity thereof.

6. The antibody of claim 1, comprising a heavy chain variable region of SEQ ID NO: 57 or a humanized variant thereof or a sequence having at least 80% sequence identity thereof, and a light chain variable region of SEQ ID NO: 58 or a humanized variant thereof or a sequence having at least 80% sequence identity thereof.

7. The antibody of claim 1, comprising a heavy chain variable region of SEQ ID NO: 59 or a humanized variant thereof or a sequence having at least 80% sequence identity thereof, and a light chain variable region of SEQ ID NO: 60 or a humanized variant thereof or a sequence having at least 80% sequence identity thereof.

8. The antibody of claim 1, wherein the antibody is a bispecific antibody, humanized antibody, chimeric antibody, monoclonal antibody, recombinant antibody, labeled antibody, bivalent antibody, or anti-idiotypic antibody.

9. The antibody of claim 1, wherein the antibody is a bispecific antibody that further binds to an antigen different from PD-L1.

10. The antibody of claim 1, wherein the antibody is an antigen-binding fragment selected from the group consisting of a diabody, a scFv, an scFv dimer, a BsFv, a dsFv, a (dsFv)2, a dsFv-dsFv', an Fv fragment, a Fab, a Fab', a F(ab')2, and a ds diabody.

11. A pharmaceutical composition comprising the antibody of claim 1.

12. A kit comprising the antibody of claim 1.

13. A polynucleotide encoding the antibody of claim 1.

14. A vector comprising the polynucleotide of claim 13.

15. An isolated host cell comprising the vector of claim 14.

16. A method of producing a PD-L1 antibody, comprising culturing the host cell of claim 15 under the condition at which the polynucleotide is expressed, wherein the host cell comprising a vector comprising the polynucleotide encoding the antibody of claim 1.

17. A method for treating a PD-L1 associated conditions in a subject, comprising administering to the subject the PD-L1 antibody of claim 1, thereby treating the condition.

18. The method of claim 17, further comprising administering a second therapeutic agent.

19. The method of claim 18, wherein the second therapeutic agent is an agent used in a radiation therapy, chemotherapy, targeted therapy, gene therapy, immunotherapy, hormonal therapy, angiogenesis inhibition, palliative care, surgery or any combination thereof.

20. The method of claim 19, wherein the second therapeutic agent is VEGFR2 antibody.

21. The method of claim 17, wherein the PD-L1 associated condition is cancer or tumor.

22. The method of claim 21, wherein the cancer or tumor is a metastatic tumor expressing PD-L1.

23. The method of claim 21, wherein the cancer or tumor is solid tumor.

24. The method of claim 23, wherein the solid tumor is non-small cell lung cancer, small cell lung cancer, renal cell cancer, colorectal cancer, colon cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, melanoma, myelomas, mycoses fungoids, merkel cell cancer, hepatocellular carcinoma, fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, lymphoid malignancy, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, hepatoma, bile duct carcinoma, choriocarcinoma, Wilms' tumor, cervical cancer, testicular tumor, or seminoma.

25. The method of claim 21, wherein the cancer or tumor is non-small cell lung cancer, small cell lung cancer, breast cancer, bladder cancer, hepatoma, colorectal cancer, gastric carcinoma, esophageal cancer, melanoma or colon cancer.

26. The method of claim 17, wherein the PD-L1 associated condition is hematologic disorder, infectious disease, autoimmune disease or fibrotic disease.

27. The method of claim 26, wherein the hematologic disorder is classical Hodgkin lymphoma, primary mediastinal large B-cell lymphoma, T-cell/histiocyte-rich B-cell lymphoma, acute lymphocytic leukemia, acute myelocytic leukemia, acute myelogenous leukemia and myeloblastic, promyelocytic, myelomonocytic, monocytic and erythro-leukemia, chronic myelocytic leukemia, chronic myelogenous leukemia, chronic lymphocytic leukemia, polycythemia vera, mast cell derived tumors, EBV-positive and -negative PTLD, and diffuse large B-cell lymphoma, plasmablastic lymphoma, extranodal NK/T-cell lymphoma, nasopharyngeal carcinoma, and HHV8-associated primary effusion lymphoma, non-Hodgkin's lymphoma, multiple myeloma, Waldenstrom's macroglobulinemia, heavy chain disease, myelodysplastic syndrome, hairy cell leukemia or myelodysplasia.

28. The method of claim 17, wherein the subject is tested as positive for PD-L1 expression, or tested as having elevated level of PD-L1 expression relative to healthy or non-diseased individual.

\* \* \* \* \*

SEQUENCE LISTING

<160> NUMBER OF SEQ ID NOS: 189

<210> SEQ ID NO 1
<211> LENGTH: 5
<212> TYPE: PRT
<213> ORGANISM: Mus musculus
<220> FEATURE:
<221> NAME/KEY: misc_feature
<222> LOCATION: (4)..(4)
<223> OTHER INFORMATION: Xaa can be Ile or Met

<400> SEQUENCE: 1

Thr Tyr Trp Xaa His
1               5

<210> SEQ ID NO 2
<211> LENGTH: 17
<212> TYPE: PRT
<213> ORGANISM: Mus musculus
<220> FEATURE:
<221> NAME/KEY: misc_feature
<222> LOCATION: (13)..(14)
<223> OTHER INFORMATION: Xaa in location 13 can be Asp or Glu, Xaa in
      location 14 can be Gln or Lys
<220> FEATURE:
<221> NAME/KEY: misc_feature
<222> LOCATION: (17)..(17)
<223> OTHER INFORMATION: Xaa can be Asn or Lys

<400> SEQUENCE: 2

Met Ile Gln Pro Asn Ser Gly Gly Thr Lys Tyr Asn Xaa Xaa Phe Lys
1               5                   10                  15

Xaa

<210> SEQ ID NO 3
<211> LENGTH: 10
<212> TYPE: PRT
<213> ORGANISM: Mus musculus

<400> SEQUENCE: 3

Gly Ala Gly Thr Val Asp Tyr Phe Asp Tyr
1               5                   10

<210> SEQ ID NO 4
<211> LENGTH: 15
<212> TYPE: PRT
<213> ORGANISM: Mus musculus

<400> SEQUENCE: 4

Arg Ala Ser Glu Ser Val Asp Ile Tyr Gly Asn Ser Phe Met His
1               5                   10                  15

<210> SEQ ID NO 5
<211> LENGTH: 7
<212> TYPE: PRT
<213> ORGANISM: Mus musculus

<400> SEQUENCE: 5

Arg Ala Ser Asn Leu Glu Ser
1               5

<210> SEQ ID NO 6
<211> LENGTH: 9
<212> TYPE: PRT
<213> ORGANISM: Mus musculus
<220> FEATURE:
<221> NAME/KEY: misc_feature

```
<222> LOCATION: (1)..(1)
<223> OTHER INFORMATION: Xaa can be Gln or His
<220> FEATURE:
<221> NAME/KEY: misc_feature
<222> LOCATION: (4)..(5)
<223> OTHER INFORMATION: Xaa in location 4 can be Asn or Thr, Xaa in
      location 5 can be Asp or Glu

<400> SEQUENCE: 6

Xaa Gln Ser Xaa Xaa Asp Pro Tyr Thr
1               5

<210> SEQ ID NO 7
<211> LENGTH: 5
<212> TYPE: PRT
<213> ORGANISM: Mus musculus

<400> SEQUENCE: 7

Ser Tyr Trp Met His
1               5

<210> SEQ ID NO 8
<211> LENGTH: 17
<212> TYPE: PRT
<213> ORGANISM: Mus musculus

<400> SEQUENCE: 8

Met Ile His Pro Asn Ser Asp Ile Thr Asn Cys Asn Glu Asn Phe Lys
1               5                   10                  15

His

<210> SEQ ID NO 9
<211> LENGTH: 11
<212> TYPE: PRT
<213> ORGANISM: Mus musculus

<400> SEQUENCE: 9

Ser Asp Gly Ser Ser Tyr Trp Tyr Phe Asp Val
1               5                   10

<210> SEQ ID NO 10
<211> LENGTH: 11
<212> TYPE: PRT
<213> ORGANISM: Mus musculus

<400> SEQUENCE: 10

Lys Ala Gly Gln Ser Val Asn Asn Asp Val Ala
1               5                   10

<210> SEQ ID NO 11
<211> LENGTH: 7
<212> TYPE: PRT
<213> ORGANISM: Mus musculus

<400> SEQUENCE: 11

Tyr Ala Ser Asn Arg Tyr Thr
1               5

<210> SEQ ID NO 12
<211> LENGTH: 9
<212> TYPE: PRT
<213> ORGANISM: Mus musculus

<400> SEQUENCE: 12

Gln Gln Asp Phe Ser Ser Pro Leu Thr
```

<210> SEQ ID NO 13
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be Gln or Leu
<220> FEATURE:
<221> NAME/KEY: misc_feature
<222> LOCATION: (5)..(5)
<223> OTHER INFORMATION: Xaa can be Gln or Val
<220> FEATURE:
<221> NAME/KEY: misc_feature
<222> LOCATION: (7)..(7)
<223> OTHER INFORMATION: Xaa can be Ser or Pro
<220> FEATURE:
<221> NAME/KEY: misc_feature
<222> LOCATION: (11)..(12)
<223> OTHER INFORMATION: Xaa in location 11 can be Leu or Val, Xaa in
      location 12 can be Val or Lys
<220> FEATURE:
<221> NAME/KEY: misc_feature
<222> LOCATION: (20)..(20)
<223> OTHER INFORMATION: Xaa can be Leu or Val
<220> FEATURE:
<221> NAME/KEY: misc_feature
<222> LOCATION: (28)..(28)
<223> OTHER INFORMATION: Xaa can be Thr, Ser or Ile

<400> SEQUENCE: 13

Xaa Val Gln Leu Xaa Gln Xaa Gly Ala Glu Xaa Xaa Lys Pro Gly Ala
1               5                   10                  15
Ser Val Lys Xaa Ser Cys Lys Ala Ser Gly Tyr Xaa Phe Thr
            20                  25                  30

<210> SEQ ID NO 14
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be Trp, Lys or Arg
<220> FEATURE:
<221> NAME/KEY: misc_feature
<222> LOCATION: (5)..(5)
<223> OTHER INFORMATION: Xaa can be Arg or Ala

<400> SEQUENCE: 14

Trp Val Xaa Gln Xaa Pro Gly Gln Gly Leu Glu Trp Ile Gly
1               5                   10

<210> SEQ ID NO 15
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa in location 1 can be Arg, Lys or Thr, Xaa
      in location 2 can be Val or Ala
<220> FEATURE:
<221> NAME/KEY: misc_feature
<222> LOCATION: (8)..(8)

```
<223> OTHER INFORMATION: Xaa can be Lys or Thr
<220> FEATURE:
<221> NAME/KEY: misc_feature
<222> LOCATION: (10)..(11)
<223> OTHER INFORMATION: Xaa in location 10 can be Ser or Ile, Xaa in
      location 11 can be Ser or Thr
<220> FEATURE:
<221> NAME/KEY: misc_feature
<222> LOCATION: (14)..(14)
<223> OTHER INFORMATION: Xaa can be Tyr or Ser
<220> FEATURE:
<221> NAME/KEY: misc_feature
<222> LOCATION: (16)..(16)
<223> OTHER INFORMATION: Xaa can be Gln or Glu
<220> FEATURE:
<221> NAME/KEY: misc_feature
<222> LOCATION: (19)..(19)
<223> OTHER INFORMATION: Xaa can be Ser, Gly or Arg
<220> FEATURE:
<221> NAME/KEY: misc_feature
<222> LOCATION: (21)..(21)
<223> OTHER INFORMATION: Xaa can be Thr or Arg
<220> FEATURE:
<221> NAME/KEY: misc_feature
<222> LOCATION: (23)..(23)
<223> OTHER INFORMATION: Xaa can be Glu or Asp
<220> FEATURE:
<221> NAME/KEY: misc_feature
<222> LOCATION: (25)..(25)
<223> OTHER INFORMATION: Xaa can be Ser or Thr
<220> FEATURE:
<221> NAME/KEY: misc_feature
<222> LOCATION: (28)..(28)
<223> OTHER INFORMATION: Xaa can be Phe or Tyr

<400> SEQUENCE: 15

Xaa Xaa Thr Leu Thr Val Asp Xaa Ser Xaa Xaa Thr Ala Xaa Met Xaa
1               5                   10                  15

Leu Ser Xaa Leu Xaa Ser Xaa Asp Xaa Ala Val Xaa Tyr Cys Ala Arg
            20                  25                  30

<210> SEQ ID NO 16
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be Thr or Gln
<220> FEATURE:
<221> NAME/KEY: misc_feature
<222> LOCATION: (5)..(5)
<223> OTHER INFORMATION: Xaa can be Thr or Ser
<220> FEATURE:
<221> NAME/KEY: misc_feature
<222> LOCATION: (7)..(9)
<223> OTHER INFORMATION: Xaa in location 7 can be Val or Leu, Xaa in
      location 8 can be Ser or Thr, Xaa in location 9 can be Val or Ile

<400> SEQUENCE: 16

Trp Gly Xaa Gly Xaa Thr Xaa Xaa Xaa Ser Ser
1               5                   10

<210> SEQ ID NO 17
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
```

```
<223> OTHER INFORMATION: Xaa can be Asp or Ser
<220> FEATURE:
<221> NAME/KEY: misc_feature
<222> LOCATION: (4)..(4)
<223> OTHER INFORMATION: Xaa can be Met or Leu
<220> FEATURE:
<221> NAME/KEY: misc_feature
<222> LOCATION: (6)..(7)
<223> OTHER INFORMATION: Xaa in location 6 can be Gln or His, Xaa in
      location 7 can be Thr or Ser
<220> FEATURE:
<221> NAME/KEY: misc_feature
<222> LOCATION: (9)..(10)
<223> OTHER INFORMATION: Xaa in location 9 can be Ala, Lys or Val, Xaa
      in location 10 can be Phe or Ser
<220> FEATURE:
<221> NAME/KEY: misc_feature
<222> LOCATION: (12)..(12)
<223> OTHER INFORMATION: Xaa can be Ala, Ser or Thr
<220> FEATURE:
<221> NAME/KEY: misc_feature
<222> LOCATION: (15)..(15)
<223> OTHER INFORMATION: Xaa can be Leu, Ala or Val
<220> FEATURE:
<221> NAME/KEY: misc_feature
<222> LOCATION: (17)..(17)
<223> OTHER INFORMATION: Xaa can be Asp or Gln
<220> FEATURE:
<221> NAME/KEY: misc_feature
<222> LOCATION: (19)..(19)
<223> OTHER INFORMATION: Xaa can be Val or Ala
<220> FEATURE:
<221> NAME/KEY: misc_feature
<222> LOCATION: (22)..(22)
<223> OTHER INFORMATION: Xaa can be Ser or Thr

<400> SEQUENCE: 17

Xaa Ile Val Xaa Thr Xaa Xaa Pro Xaa Xaa Leu Xaa Val Ser Xaa Gly
1               5                   10                  15

Xaa Arg Xaa Thr Ile Xaa Cys
            20

<210> SEQ ID NO 18
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa can be Ser, Pro or Ala

<400> SEQUENCE: 18

Trp Tyr Gln Gln Lys Pro Gly Gln Xaa Pro Lys Leu Leu Ile Tyr
1               5                   10                  15

<210> SEQ ID NO 19
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be Val or Ile
<220> FEATURE:
<221> NAME/KEY: misc_feature
<222> LOCATION: (4)..(4)
<223> OTHER INFORMATION: Xaa can be Asn or Ala
<220> FEATURE:
<221> NAME/KEY: misc_feature
<222> LOCATION: (7)..(7)
```

```
<223> OTHER INFORMATION: Xaa can be Thr or Ser
<220> FEATURE:
<221> NAME/KEY: misc_feature
<222> LOCATION: (11)..(12)
<223> OTHER INFORMATION: Xaa in location 11 can be Tyr or Ser, Xaa in
      location 12 can be Gly or Arg
<220> FEATURE:
<221> NAME/KEY: misc_feature
<222> LOCATION: (17)..(17)
<223> OTHER INFORMATION: Xaa can be Phe or Leu
<220> FEATURE:
<221> NAME/KEY: misc_feature
<222> LOCATION: (20)..(21)
<223> OTHER INFORMATION: Xaa in location 20 can be Ser or Asn, Xaa in
      location 21 can be Thr or Pro
<220> FEATURE:
<221> NAME/KEY: misc_feature
<222> LOCATION: (23)..(23)
<223> OTHER INFORMATION: Xaa can be Gln or Glu
<220> FEATURE:
<221> NAME/KEY: misc_feature
<222> LOCATION: (25)..(25)
<223> OTHER INFORMATION: Xaa can be Asp, Glu, Asn or Gln
<220> FEATURE:
<221> NAME/KEY: misc_feature
<222> LOCATION: (27)..(27)
<223> OTHER INFORMATION: Xaa can be Val, Leu or Thr
<220> FEATURE:
<221> NAME/KEY: misc_feature
<222> LOCATION: (29)..(29)
<223> OTHER INFORMATION: Xaa can be Val or Thr
<220> FEATURE:
<221> NAME/KEY: misc_feature
<222> LOCATION: (31)..(31)
<223> OTHER INFORMATION: Xaa can be Phe or Cys

<400> SEQUENCE: 19

Gly Xaa Pro Xaa Arg Phe Xaa Gly Ser Gly Xaa Xaa Thr Asp Phe Thr
1               5                   10                  15

Xaa Thr Ile Xaa Xaa Val Xaa Ala Xaa Asp Xaa Ala Xaa Tyr Xaa Cys
            20                  25                  30

<210> SEQ ID NO 20
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be Ala or Gly
<220> FEATURE:
<221> NAME/KEY: misc_feature
<222> LOCATION: (9)..(9)
<223> OTHER INFORMATION: Xaa can be Leu, Thr or Ile

<400> SEQUENCE: 20

Phe Gly Xaa Gly Thr Lys Leu Glu Xaa Lys
1               5                   10

<210> SEQ ID NO 21
<211> LENGTH: 120
<212> TYPE: PRT
<213> ORGANISM: Mus musculus

<400> SEQUENCE: 21

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30
```

Trp Met His Trp Val Trp Gln Arg Pro Gly Gln Gly Leu Glu Trp Ile
              35                  40                  45

Gly Met Ile His Pro Asn Ser Asp Ile Thr Asn Cys Asn Glu Asn Phe
         50                  55                  60

Lys His Thr Val Thr Leu Thr Val Asp Lys Ser Ser Ser Thr Ala Tyr
65                  70                  75                  80

Met Gln Leu Ser Ser Leu Thr Ser Glu Asp Ser Ala Val Phe Tyr Cys
                 85                  90                  95

Ala Arg Ser Asp Gly Ser Ser Tyr Trp Tyr Phe Asp Val Trp Gly Thr
             100                 105                 110

Gly Thr Thr Val Thr Val Ser Ser
             115                 120

<210> SEQ ID NO 22
<211> LENGTH: 107
<212> TYPE: PRT
<213> ORGANISM: Mus musculus

<400> SEQUENCE: 22

Ser Ile Val Met Thr Gln Thr Pro Lys Phe Leu Ser Val Ser Ala Gly
1               5                   10                  15

Asp Arg Val Thr Ile Thr Cys Lys Ala Gly Gln Ser Val Asn Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Phe Ser Ser Pro Leu
                85                  90                  95

Thr Phe Gly Ala Gly Thr Lys Leu Glu Leu Lys
            100                 105

<210> SEQ ID NO 23
<211> LENGTH: 5
<212> TYPE: PRT
<213> ORGANISM: Mus musculus

<400> SEQUENCE: 23

Asp Tyr Tyr Met Asn
1               5

<210> SEQ ID NO 24
<211> LENGTH: 17
<212> TYPE: PRT
<213> ORGANISM: Mus musculus
<220> FEATURE:
<221> NAME/KEY: misc_feature
<222> LOCATION: (13)..(13)
<223> OTHER INFORMATION: Xaa can be His or Gln
<220> FEATURE:
<221> NAME/KEY: misc_feature
<222> LOCATION: (16)..(16)
<223> OTHER INFORMATION: Xaa can be Lys or Gln

<400> SEQUENCE: 24

Asp Ile Asn Pro Asn Asn Gly Gly Thr Ser Tyr Asn Xaa Lys Phe Xaa
1               5                   10                  15

Gly

```
<210> SEQ ID NO 25
<211> LENGTH: 10
<212> TYPE: PRT
<213> ORGANISM: Mus musculus

<400> SEQUENCE: 25

Val Lys Trp Gly Asp Gly Pro Phe Ala Tyr
1               5                   10

<210> SEQ ID NO 26
<211> LENGTH: 11
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be Lys or Gln

<400> SEQUENCE: 26

Xaa Ala Ser Gln Asn Val Gly Ala Ala Val Ala
1               5                   10

<210> SEQ ID NO 27
<211> LENGTH: 7
<212> TYPE: PRT
<213> ORGANISM: Mus musculus
<220> FEATURE:
<221> NAME/KEY: misc_feature
<222> LOCATION: (5)..(6)
<223> OTHER INFORMATION: Xaa in location 5 can be Arg or Leu, Xaa in
      location 6 can be Tyr or Glu

<400> SEQUENCE: 27

Ser Ala Ser Asn Xaa Xaa Thr
1               5

<210> SEQ ID NO 28
<211> LENGTH: 8
<212> TYPE: PRT
<213> ORGANISM: Mus musculus

<400> SEQUENCE: 28

Gln Gln Tyr Ser Asn Tyr Pro Thr
1               5

<210> SEQ ID NO 29
<211> LENGTH: 6
<212> TYPE: PRT
<213> ORGANISM: Mus musculus

<400> SEQUENCE: 29

Ser Ser Tyr Tyr Ile His
1               5

<210> SEQ ID NO 30
<211> LENGTH: 17
<212> TYPE: PRT
<213> ORGANISM: Mus musculus

<400> SEQUENCE: 30

Asn Ile Asn Pro Phe Asn Gly Gly Ser Ile Tyr Asn Glu Lys Phe Lys
1               5                   10                  15

Asn

<210> SEQ ID NO 31
```

```
<211> LENGTH: 5
<212> TYPE: PRT
<213> ORGANISM: Mus musculus

<400> SEQUENCE: 31

Trp His Phe Asp Tyr
1               5

<210> SEQ ID NO 32
<211> LENGTH: 17
<212> TYPE: PRT
<213> ORGANISM: Mus musculus

<400> SEQUENCE: 32

Lys Ser Ser Gln Ser Leu Leu Trp Ser Gly Asn Gln Asn Asn Tyr Leu
1               5                   10                  15

Ser

<210> SEQ ID NO 33
<211> LENGTH: 7
<212> TYPE: PRT
<213> ORGANISM: Mus musculus

<400> SEQUENCE: 33

Gly Ala Ser Ile Arg Glu Ser
1               5

<210> SEQ ID NO 34
<211> LENGTH: 11
<212> TYPE: PRT
<213> ORGANISM: Mus musculus

<400> SEQUENCE: 34

Gln His Asn His Gly Ser Phe Leu Pro Tyr Thr
1               5                   10

<210> SEQ ID NO 35
<211> LENGTH: 5
<212> TYPE: PRT
<213> ORGANISM: Mus musculus

<400> SEQUENCE: 35

Ser Asn Trp Met His
1               5

<210> SEQ ID NO 36
<211> LENGTH: 17
<212> TYPE: PRT
<213> ORGANISM: Mus musculus

<400> SEQUENCE: 36

Met Met His Pro Asn Ser Gly Ser Ile Asn Tyr Asn Glu Lys Phe Lys
1               5                   10                  15

Asn

<210> SEQ ID NO 37
<211> LENGTH: 12
<212> TYPE: PRT
<213> ORGANISM: Mus musculus

<400> SEQUENCE: 37

Ser Tyr Tyr Gly Ser Ser Pro Tyr Tyr Phe Asp Tyr
1               5                   10
```

```
<210> SEQ ID NO 38
<211> LENGTH: 11
<212> TYPE: PRT
<213> ORGANISM: Mus musculus

<400> SEQUENCE: 38

Arg Ala Ser Gln Asp Ile Ser Asn Tyr Leu Asn
1               5                   10

<210> SEQ ID NO 39
<211> LENGTH: 7
<212> TYPE: PRT
<213> ORGANISM: Mus musculus

<400> SEQUENCE: 39

Tyr Thr Ser Arg Leu His Ser
1               5

<210> SEQ ID NO 40
<211> LENGTH: 9
<212> TYPE: PRT
<213> ORGANISM: Mus musculus

<400> SEQUENCE: 40

Gln Gln Gly Asp Thr Leu Pro Trp Thr
1               5

<210> SEQ ID NO 41
<211> LENGTH: 5
<212> TYPE: PRT
<213> ORGANISM: Mus musculus

<400> SEQUENCE: 41

Ser Tyr Trp Met His
1               5

<210> SEQ ID NO 42
<211> LENGTH: 17
<212> TYPE: PRT
<213> ORGANISM: Mus musculus

<400> SEQUENCE: 42

Met Ile Gln Pro Ser Thr Ser Gly Thr Ile Tyr Asn Glu Arg Phe Lys
1               5                   10                  15

Asn

<210> SEQ ID NO 43
<211> LENGTH: 10
<212> TYPE: PRT
<213> ORGANISM: Mus musculus

<400> SEQUENCE: 43

Gly Thr Gly Thr Val Asp Tyr Phe Asp Tyr
1               5                   10

<210> SEQ ID NO 44
<211> LENGTH: 15
<212> TYPE: PRT
<213> ORGANISM: Mus musculus

<400> SEQUENCE: 44

Arg Ala Ser Glu Ser Val Asp Ser Tyr Gly Asn Ser Phe Ile His
1               5                   10                  15
```

<210> SEQ ID NO 45
<211> LENGTH: 7
<212> TYPE: PRT
<213> ORGANISM: Mus musculus

<400> SEQUENCE: 45

Arg Ala Ser Asn Leu Glu Ser
1               5

<210> SEQ ID NO 46
<211> LENGTH: 10
<212> TYPE: PRT
<213> ORGANISM: Mus musculus

<400> SEQUENCE: 46

Gln Gln Ser Lys Glu Asp Pro Tyr Thr Phe
1               5                   10

<210> SEQ ID NO 47
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be Gln or Glu
<220> FEATURE:
<221> NAME/KEY: misc_feature
<222> LOCATION: (5)..(5)
<223> OTHER INFORMATION: Xaa can be Gln or Val
<220> FEATURE:
<221> NAME/KEY: misc_feature
<222> LOCATION: (9)..(9)
<223> OTHER INFORMATION: Xaa can be Ala or Pro
<220> FEATURE:
<221> NAME/KEY: misc_feature
<222> LOCATION: (11)..(12)
<223> OTHER INFORMATION: Xaa in location 11 can be Leu or Val, Xaa in
      location 12 can be Val or Lys
<220> FEATURE:
<221> NAME/KEY: misc_feature
<222> LOCATION: (20)..(20)
<223> OTHER INFORMATION: Xaa can be Ile or Val

<400> SEQUENCE: 47

Xaa Val Gln Leu Xaa Gln Ser Gly Xaa Glu Xaa Xaa Lys Pro Gly Ala
1               5                   10                  15

Ser Val Lys Xaa Ser Cys Lys Ala Ser Gly Tyr Val Phe Thr
            20                  25                  30

<210> SEQ ID NO 48
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be Lys or Arg
<220> FEATURE:
<221> NAME/KEY: misc_feature
<222> LOCATION: (5)..(6)
<223> OTHER INFORMATION: Xaa in location 5 can be Ser or Ala, Xaa in
      location 6 can be His or Pro
<220> FEATURE:
<221> NAME/KEY: misc_feature
<222> LOCATION: (8)..(9)
<223> OTHER INFORMATION: Xaa in location 8 can be Gln or Lys, Xaa in

```
        location 9 can be Ser or Gly

<400> SEQUENCE: 48

Trp Val Xaa Gln Xaa Xaa Gly Xaa Xaa Leu Glu Trp Ile Gly
1               5                   10

<210> SEQ ID NO 49
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa in location 1 can be Lys or Arg, Xaa in
      location 2 can be Ala or Val
<220> FEATURE:
<221> NAME/KEY: misc_feature
<222> LOCATION: (8)..(8)
<223> OTHER INFORMATION: Xaa can be Lys or Thr
<220> FEATURE:
<221> NAME/KEY: misc_feature
<222> LOCATION: (10)..(11)
<223> OTHER INFORMATION: Xaa in location 10 can be Ser, Thr or Ile, Xaa
      in location 11 can be Ser or Arg
<220> FEATURE:
<221> NAME/KEY: misc_feature
<222> LOCATION: (18)..(19)
<223> OTHER INFORMATION: Xaa in location 18 can be Leu or Ser, Xaa in
      location 19 can be Ser or Arg
<220> FEATURE:
<221> NAME/KEY: misc_feature
<222> LOCATION: (21)..(21)
<223> OTHER INFORMATION: Xaa can be Arg or Thr
<220> FEATURE:
<221> NAME/KEY: misc_feature
<222> LOCATION: (23)..(23)
<223> OTHER INFORMATION: Xaa can be Glu or Asp
<220> FEATURE:
<221> NAME/KEY: misc_feature
<222> LOCATION: (25)..(25)
<223> OTHER INFORMATION: Xaa can be Ser or Thr

<400> SEQUENCE: 49

Xaa Xaa Thr Val Thr Val Asp Xaa Ser Xaa Xaa Thr Ala Tyr Met Glu
1               5                   10                  15

Leu Xaa Xaa Leu Xaa Ser Xaa Asp Xaa Ala Val Tyr Tyr Cys
            20                  25                  30

<210> SEQ ID NO 50
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: Xaa can be Ala or Ser

<400> SEQUENCE: 50

Trp Gly Gln Gly Thr Leu Val Thr Val Ser Xaa
1               5                   10

<210> SEQ ID NO 51
<211> LENGTH: 23
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (3)..(3)
<223> OTHER INFORMATION: Xaa can be Gln or Val
<220> FEATURE:
<221> NAME/KEY: misc_feature
<222> LOCATION: (8)..(11)
<223> OTHER INFORMATION: Xaa in location 8 can be Gln or Pro, Xaa in
      location 9 can be Lys or Ser, Xaa in location 10 can be Phe or
      Ser, Xaa in location 11 can be Met or Leu
<220> FEATURE:
<221> NAME/KEY: misc_feature
<222> LOCATION: (13)..(13)
<223> OTHER INFORMATION: Xaa can be Thr or Ala
<220> FEATURE:
<221> NAME/KEY: misc_feature
<222> LOCATION: (20)..(20)
<223> OTHER INFORMATION: Xaa can be Ser or Thr

<400> SEQUENCE: 51

Asp Ile Xaa Met Thr Gln Ser Xaa Xaa Xaa Xaa Ser Xaa Ser Val Gly
1               5                   10                  15

Asp Arg Val Xaa Ile Thr Cys
            20

<210> SEQ ID NO 52
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(9)
<223> OTHER INFORMATION: Xaa in location 8 can be Gln or Lys, Xaa in
      location 9 can be Ser or Ala

<400> SEQUENCE: 52

Trp Tyr Gln Gln Lys Pro Gly Xaa Xaa Pro Lys Leu Leu Ile Tyr
1               5                   10                  15

<210> SEQ ID NO 53
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be Ser or Asp
<220> FEATURE:
<221> NAME/KEY: misc_feature
<222> LOCATION: (7)..(7)
<223> OTHER INFORMATION: Xaa can be Ser or Thr
<220> FEATURE:
<221> NAME/KEY: misc_feature
<222> LOCATION: (21)..(22)
<223> OTHER INFORMATION: Xaa in location 21 can be Ser or Asn, Xaa in
      location 22 can be Met or Leu
<220> FEATURE:
<221> NAME/KEY: misc_feature
<222> LOCATION: (24)..(24)
<223> OTHER INFORMATION: Xaa can be Ser or Pro
<220> FEATURE:
<221> NAME/KEY: misc_feature
<222> LOCATION: (27)..(27)
<223> OTHER INFORMATION: Xaa can be Leu or Ile
<220> FEATURE:
<221> NAME/KEY: misc_feature
<222> LOCATION: (29)..(29)
<223> OTHER INFORMATION: Xaa can be Asp or Thr

<400> SEQUENCE: 53
```

Gly Val Pro Xaa Arg Phe Xaa Gly Ser Gly Ser Gly Thr Asp Phe Thr
1               5                   10                  15

Leu Thr Ile Ser Xaa Xaa Gln Xaa Glu Asp Xaa Ala Xaa Tyr Phe Cys
            20              25              30

<210> SEQ ID NO 54
<211> LENGTH: 10
<212> TYPE: PRT
<213> ORGANISM: Artificial Sequence
<220> FEATURE:
<223> OTHER INFORMATION: Synthetic

<400> SEQUENCE: 54

Phe Gly Ser Gly Thr Lys Leu Gly Ile Lys
1               5                   10

<210> SEQ ID NO 55
<211> LENGTH: 114
<212> TYPE: PRT
<213> ORGANISM: Mus musculus

<400> SEQUENCE: 55

Gln Val Gln Leu Gln Gln Pro Gly Thr Ala Leu Val Lys Pro Gly Ala
1               5                   10                  15

Ser Val Lys Leu Ser Cys Lys Ala Ser Gly Tyr Thr Phe Ser Ser Tyr
            20              25                  30

Tyr Ile His Trp Val Lys Gln Arg Pro Gly Gln Gly Leu Glu Trp Ile
        35                  40                  45

Gly Asn Ile Asn Pro Phe Asn Gly Gly Ser Ile Tyr Asn Glu Lys Phe
    50                  55                  60

Lys Asn Lys Ala Ser Leu Thr Val Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Trp His Phe Asp Tyr Trp Gly Gln Gly Thr Ser Leu Thr Val
            100                 105                 110

Ser Ser

<210> SEQ ID NO 56
<211> LENGTH: 115
<212> TYPE: PRT
<213> ORGANISM: Mus musculus

<400> SEQUENCE: 56

Asp Ile Val Met Thr Gln Ser Pro Ser Ser Leu Ala Val Thr Ala Gly
1               5                   10                  15

Glu Lys Val Thr Leu Lys Cys Lys Ser Ser Gln Ser Leu Leu Trp Ser
            20              25                  30

Gly Asn Gln Asn Asn Tyr Leu Ser Trp Tyr Gln Gln Lys Gln Gly Gln
        35                  40                  45

Pro Pro Lys Leu Leu Ile Tyr Gly Ala Ser Ile Arg Glu Ser Trp Val
    50                  55                  60

Pro Asp Arg Phe Thr Gly Ser Gly Ser Gly Thr Asp Phe Thr Leu Thr
65                  70                  75                  80

Ile Gly Asn Val Ser Ala Glu Asp Leu Ala Val Tyr Tyr Cys Gln His
                85                  90                  95

Asn His Gly Ser Phe Leu Pro Tyr Thr Phe Gly Gly Gly Thr Arg Leu
            100                 105                 110

Glu Ile Lys
        115

<210> SEQ ID NO 57
<211> LENGTH: 121
<212> TYPE: PRT
<213> ORGANISM: Mus musculus

<400> SEQUENCE: 57

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Asn
            20                  25                  30

Trp Met His Trp Val Lys Gln Arg Pro Gly Gln Gly Leu Glu Trp Ile
        35                  40                  45

Gly Met Met His Pro Asn Ser Gly Ser Ile Asn Tyr Asn Glu Lys Phe
    50                  55                  60

Lys Asn Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Tyr Tyr Gly Ser Ser Pro Tyr Tyr Phe Asp Tyr Trp Gly
            100                 105                 110

Gln Gly Thr Thr Leu Thr Val Ser Ser
        115                 120

<210> SEQ ID NO 58
<211> LENGTH: 107
<212> TYPE: PRT
<213> ORGANISM: Mus musculus

<400> SEQUENCE: 58

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Ser Leu Thr Ile Ser Asn Leu Glu Glu
65                  70                  75                  80

Glu Asp Ile Ala Thr Tyr Phe Cys Gln Gln Gly Asp Thr Leu Pro Trp
                85                  90                  95

Thr Phe Gly Gly Gly Thr Lys Leu Glu Ile Lys
            100                 105

<210> SEQ ID NO 59
<211> LENGTH: 119
<212> TYPE: PRT
<213> ORGANISM: Mus musculus

<400> SEQUENCE: 59

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Pro Ser Tyr
            20                  25                  30

Trp Met His Trp Met Lys Gln Arg Pro Gly Gln Gly Leu Glu Trp Ile

```
                35                  40                  45
Gly Met Ile Gln Pro Ser Thr Ser Gly Thr Ile Tyr Asn Glu Arg Phe
            50                  55                  60
Lys Asn Gln Val Thr Leu Thr Val Asp Lys Ser Ser Ser Thr Ala Tyr
65                  70                  75                  80
Met Gln Leu Ser Ser Gln Thr Ser Glu Asp Ser Ala Val Tyr Tyr Cys
                85                  90                  95
Ala Arg Gly Thr Gly Thr Val Asp Tyr Phe Asp Tyr Trp Gly Gln Gly
            100                 105                 110
Thr Thr Leu Thr Val Ser Ser
            115

<210> SEQ ID NO 60
<211> LENGTH: 111
<212> TYPE: PRT
<213> ORGANISM: Mus musculus

<400> SEQUENCE: 60

Asp Ile Val Leu Thr Gln Ser Pro Ala Ser Leu Ala Val Ser Leu Gly
1               5                   10                  15
Gln Arg Ala Thr Ile Ser Cys Arg Ala Ser Glu Ser Val Asp Ser Tyr
            20                  25                  30
Gly Asn Ser Phe Ile His Trp Tyr Gln Gln Lys Pro Gly Gln Pro Pro
        35                  40                  45
Lys Leu Leu Ile His Arg Ala Ser Asn Leu Glu Ser Gly Ile Pro Ala
    50                  55                  60
Thr Phe Ser Gly Ser Gly Ser Arg Thr Asp Phe Thr Leu Thr Ile Asn
65                  70                  75                  80
Pro Val Glu Ala Asp Asp Val Ala Thr Tyr Tyr Cys Gln Gln Ser Lys
                85                  90                  95
Glu Asp Pro Tyr Thr Phe Gly Gly Gly Thr Lys Leu Glu Ile Lys
            100                 105                 110

<210> SEQ ID NO 61
<211> LENGTH: 119
<212> TYPE: PRT
<213> ORGANISM: Artificial Sequence
<220> FEATURE:
<223> OTHER INFORMATION: synthetic

<400> SEQUENCE: 61

Gln Val Gln Leu Val Gln Ser Gly Ala Glu Val Lys Lys Pro Gly Ala
1               5                   10                  15
Ser Val Lys Leu Ser Cys Lys Ala Ser Gly Tyr Ile Phe Thr Thr Tyr
            20                  25                  30
Trp Ile His Trp Val Lys Gln Arg Pro Gly Gln Gly Leu Glu Trp Ile
        35                  40                  45
Gly Met Ile Gln Pro Asn Ser Gly Gly Thr Lys Tyr Asn Asp Gln Phe
            50                  55                  60
Lys Asn Arg Ala Thr Leu Thr Val Asp Lys Ser Ile Ser Thr Ala Tyr
65                  70                  75                  80
Met Glu Leu Ser Arg Leu Thr Ser Asp Asp Thr Ala Val Tyr Tyr Cys
                85                  90                  95
Ala Arg Gly Ala Gly Thr Val Asp Tyr Phe Asp Tyr Trp Gly Gln Gly
            100                 105                 110
Thr Thr Leu Ser Ile Ser Ser
            115
```

<210> SEQ ID NO 62
<211> LENGTH: 111
<212> TYPE: PRT
<213> ORGANISM: Artificial Sequence
<220> FEATURE:
<223> OTHER INFORMATION: synthetic

<400> SEQUENCE: 62

Asp Ile Val Leu Thr Gln Ser Pro Ala Ser Leu Ala Val Ser Val Gly
1               5                   10                  15

Gln Arg Ala Thr Ile Thr Cys Arg Ala Ser Glu Ser Val Asp Ile Tyr
            20                  25                  30

Gly Asn Ser Phe Met His Trp Tyr Gln Gln Lys Pro Gly Gln Ala Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Gln Asp Thr Ala Thr Tyr Tyr Cys Gln Gln Ser Asn
                85                  90                  95

Asp Asp Pro Tyr Thr Phe Gly Gly Gly Thr Lys Leu Glu Thr Lys
            100                 105                 110

<210> SEQ ID NO 63
<211> LENGTH: 119
<212> TYPE: PRT
<213> ORGANISM: Artificial Sequence
<220> FEATURE:
<223> OTHER INFORMATION: synthetic

<400> SEQUENCE: 63

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Thr Tyr
            20                  25                  30

Trp Met His Trp Val Lys Gln Arg Pro Gly Gln Gly Leu Glu Trp Ile
        35                  40                  45

Gly Met Ile Gln Pro Asn Ser Gly Thr Lys Tyr Asn Glu Lys Phe
    50                  55                  60

Lys Lys Lys Ala Thr Leu Thr Val Asp Lys Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Gly Ala Gly Thr Val Asp Tyr Phe Asp Tyr Trp Gly Gln Gly
            100                 105                 110

Ser Thr Leu Thr Val Ser Ser
        115

<210> SEQ ID NO 64
<211> LENGTH: 111
<212> TYPE: PRT
<213> ORGANISM: Artificial Sequence
<220> FEATURE:
<223> OTHER INFORMATION: synthetic

<400> SEQUENCE: 64

Asp Ile Val Leu Thr Gln Ser Pro Ala Ser Leu Ala Val Ser Val Gly
1               5                   10                  15

```
Gln Arg Ala Thr Ile Thr Cys Arg Ala Ser Glu Ser Val Asp Ile Tyr
                20                  25                  30

Gly Asn Ser Phe Met His Trp Tyr Gln Gln Lys Pro Gly Gln Pro Pro
            35                  40                  45

Lys Leu Leu Ile Tyr Arg Ala Ser Asn Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Gln Asp Thr Ala Thr Tyr Tyr Cys Gln Gln Ser Thr
                85                  90                  95

Glu Asp Pro Tyr Thr Phe Gly Gly Gly Thr Lys Leu Glu Ile Lys
            100                 105                 110
```

<210> SEQ ID NO 65
<211> LENGTH: 117
<212> TYPE: PRT
<213> ORGANISM: Artificial Sequence
<220> FEATURE:
<223> OTHER INFORMATION: synthetic

<400> SEQUENCE: 65

```
Gln Val Gln Leu Val Gln Ser Gly Ala Glu Val Val Lys Pro Gly Ala
 1               5                  10                  15

Ser Val Lys Ile Ser Cys Lys Ala Ser Gly Tyr Val Phe Thr Asp Tyr
                20                  25                  30

Tyr Met Asn Trp Val Lys Gln Ala Pro Gly Gln Gly Leu Glu Trp Ile
            35                  40                  45

Gly Asp Ile Asn Pro Asn Asn Gly Gly Thr Ser Tyr Asn Gln Lys Phe
 50                  55                  60

Gln Gly Arg Ala Thr Val Thr Val Asp Lys Ser Thr Arg Thr Ala Tyr
 65                  70                  75                  80

Met Glu Leu Ser Arg Leu Arg Ser Asp Thr Ala Val Tyr Tyr Cys
                85                  90                  95

Val Lys Trp Gly Asp Gly Pro Phe Ala Tyr Trp Gly Gln Gly Thr Leu
                100                 105                 110

Val Thr Val Ser Ser
        115
```

<210> SEQ ID NO 66
<211> LENGTH: 106
<212> TYPE: PRT
<213> ORGANISM: Artificial Sequence
<220> FEATURE:
<223> OTHER INFORMATION: synthetic

<400> SEQUENCE: 66

```
Asp Ile Gln Met Thr Gln Ser Gln Ser Ser Leu Ser Ala Ser Val Gly
 1               5                  10                  15

Asp Arg Val Thr Ile Thr Cys Gln Ala Ser Gln Asn Val Gly Ala Ala
                20                  25                  30

Val Ala Trp Tyr Gln Gln Lys Pro Gly Lys Ala Pro Lys Leu Leu Ile
            35                  40                  45

Tyr Ser Ala Ser Asn Arg Tyr Thr Gly Val Pro Ser Arg Phe Ser Gly
 50                  55                  60

Ser Gly Ser Gly Thr Asp Phe Thr Leu Thr Ile Ser Ser Met Gln Pro
 65                  70                  75                  80

Glu Asp Ile Ala Thr Tyr Phe Cys Gln Gln Tyr Ser Asn Tyr Pro Thr
                85                  90                  95
```

```
Phe Gly Ser Gly Thr Lys Leu Gly Ile Lys
            100                 105
```

<210> SEQ ID NO 67
<211> LENGTH: 117
<212> TYPE: PRT
<213> ORGANISM: Artificial Sequence
<220> FEATURE:
<223> OTHER INFORMATION: synthetic

<400> SEQUENCE: 67

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Asn Pro Asn Asn Gly Gly Thr Ser Tyr Asn Gln Lys Phe
    50                  55                  60

Gln Gly Arg Val Thr Val Thr Val Asp Thr Ser Ile Arg Thr Ala Tyr
65                  70                  75                  80

Met Glu Leu Ser Arg Leu Arg Ser Asp Asp Thr Ala Val Tyr Tyr Cys
                85                  90                  95

Val Lys Trp Gly Asp Gly Pro Phe Ala Tyr Trp Gly Gln Gly Thr Leu
            100                 105                 110

Val Thr Val Ser Ser
        115
```

<210> SEQ ID NO 68
<211> LENGTH: 106
<212> TYPE: PRT
<213> ORGANISM: Artificial Sequence
<220> FEATURE:
<223> OTHER INFORMATION: synthetic

<400> SEQUENCE: 68

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Val Gly Ala Ala
            20                  25                  30

Val Ala Trp Tyr Gln Gln Lys Pro Gly Lys Ala Pro Lys Leu Leu Ile
        35                  40                  45

Tyr Ser Ala Ser Asn Leu Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Phe Cys Gln Gln Tyr Ser Asn Tyr Pro Thr
                85                  90                  95

Phe Gly Ser Gly Thr Lys Leu Gly Ile Lys
            100                 105
```

<210> SEQ ID NO 69
<211> LENGTH: 119
<212> TYPE: PRT
<213> ORGANISM: Artificial Sequence
<220> FEATURE:
<223> OTHER INFORMATION: synthetic

<400> SEQUENCE: 69

```
Leu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Thr Tyr
            20                  25                  30

Trp Ile His Trp Val Arg Gln Ala Pro Gly Gln Gly Leu Glu Trp Ile
            35                  40                  45

Gly Met Ile Gln Pro Asn Ser Gly Gly Thr Lys Tyr Asn Asp Gln Phe
50                      55                  60

Lys Asn Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Gly Thr Val Asp Tyr Phe Asp Tyr Trp Gly Gln Gly
            100                 105                 110

Thr Thr Leu Ser Ile Ser Ser
            115
```

<210> SEQ ID NO 70
<211> LENGTH: 111
<212> TYPE: PRT
<213> ORGANISM: Artificial Sequence
<220> FEATURE:
<223> OTHER INFORMATION: synthetic

<400> SEQUENCE: 70

```
Asp Ile Val Leu Thr Gln Ser Pro Ala Ser Leu Ala Val Ser Val Gly
1               5                   10                  15

Gln Arg Ala Thr Ile Thr Cys Arg Ala Ser Glu Ser Val Asp Ile Tyr
            20                  25                  30

Gly Asn Ser Phe Met His Trp Tyr Gln Gln Lys Pro Gly Gln Ala Pro
            35                  40                  45

Lys Leu Leu Ile Tyr Arg Ala Ser Asn Leu Glu Ser Gly Ile Pro Ala
50                  55                      60

Arg Phe Ser Gly Ser Gly Ser Arg Thr Asp Phe Thr Leu Thr Ile Asn
65                  70                  75                  80

Pro Val Glu Ala Asn Asp Thr Ala Thr Tyr Tyr Cys Gln Gln Ser Asn
                85                  90                  95

Asp Asp Pro Tyr Thr Phe Gly Gly Gly Thr Lys Leu Glu Thr Lys
            100                 105                 110
```

<210> SEQ ID NO 71
<211> LENGTH: 119
<212> TYPE: PRT
<213> ORGANISM: Artificial Sequence
<220> FEATURE:
<223> OTHER INFORMATION: synthetic

<400> SEQUENCE: 71

```
Leu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Thr Tyr
            20                  25                  30

Trp Ile His Trp Val Lys Gln Arg Pro Gly Gln Gly Leu Glu Trp Ile
            35                  40                  45

Gly Met Ile Gln Pro Asn Ser Gly Gly Thr Lys Tyr Asn Asp Gln Phe
50                      55                  60

Lys Asn Arg Ala Thr Leu Thr Val Asp Lys Ser Ile Ser Thr Ala Tyr
65                  70                  75                  80
```

Met Glu Leu Ser Arg Leu Thr Ser Asp Asp Thr Ala Val Tyr Tyr Cys
                85                  90                  95

Ala Arg Gly Ala Gly Thr Val Asp Tyr Phe Asp Tyr Trp Gly Gln Gly
            100                 105                 110

Thr Thr Leu Ser Ile Ser Ser
        115

<210> SEQ ID NO 72
<211> LENGTH: 111
<212> TYPE: PRT
<213> ORGANISM: Artificial Sequence
<220> FEATURE:
<223> OTHER INFORMATION: synthetic

<400> SEQUENCE: 72

Asp Ile Val Leu Thr Gln Ser Pro Ala Ser Leu Ala Val Ser Val Gly
1               5                   10                  15

Gln Arg Ala Thr Ile Thr Cys Arg Ala Ser Glu Ser Val Asp Ile Tyr
            20                  25                  30

Gly Asn Ser Phe Met His Trp Tyr Gln Gln Lys Pro Gly Gln Ser Pro
        35                  40                  45

Lys Leu Leu Ile Tyr Arg Ala Ser Asn Leu Glu Ser Gly Ile Pro Ala
50                  55                  60

Arg Phe Ser Gly Ser Gly Ser Arg Thr Asp Phe Thr Leu Thr Ile Asn
65                  70                  75                  80

Pro Val Glu Ala Asn Asp Thr Ala Thr Tyr Tyr Cys His Gln Ser Asn
                85                  90                  95

Asp Asp Pro Tyr Thr Phe Gly Gly Gly Thr Lys Leu Glu Thr Lys
            100                 105                 110

<210> SEQ ID NO 73
<211> LENGTH: 119
<212> TYPE: PRT
<213> ORGANISM: Mus musculus

<400> SEQUENCE: 73

Leu Val Gln Leu Gln Gln Pro Gly Ala Glu Leu Val Lys Pro Gly Ala
1               5                   10                  15

Ser Val Lys Leu Ser Cys Lys Ala Ser Gly Tyr Ile Phe Thr Thr Tyr
            20                  25                  30

Trp Ile His Trp Val Lys Gln Arg Pro Gly Gln Gly Leu Glu Trp Ile
        35                  40                  45

Gly Met Ile Gln Pro Asn Ser Gly Gly Thr Lys Tyr Asn Asp Gln Phe
50                  55                  60

Lys Asn Arg Ala Thr Leu Thr Val Asp Lys Ser Ser Thr Thr Ala Ser
65                  70                  75                  80

Met Gln Leu Ser Gly Leu Thr Ser Glu Asp Ser Ala Val Tyr Tyr Cys
                85                  90                  95

Ala Arg Gly Ala Gly Thr Val Asp Tyr Phe Asp Tyr Trp Gly Gln Gly
            100                 105                 110

Thr Thr Leu Ser Ile Ser Ser
        115

<210> SEQ ID NO 74
<211> LENGTH: 111
<212> TYPE: PRT
<213> ORGANISM: Mus musculus

<400> SEQUENCE: 74

Asp Ile Val Leu Thr Gln Ser Pro Ala Ser Leu Thr Val Ser Leu Gly
1               5                   10                  15

Gln Arg Ala Thr Ile Ser Cys Arg Ala Ser Glu Ser Val Asp Ile Tyr
            20                  25                  30

Gly Asn Ser Phe Met His Trp Tyr Gln Gln Lys Pro Gly Gln Ser Pro
        35                  40                  45

Lys Leu Leu Ile Tyr Arg Ala Ser Asn Leu Glu Ser Gly Ile Pro Ala
50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys His Gln Ser Asn
                85                  90                  95

Asp Asp Pro Tyr Thr Phe Gly Gly Gly Thr Lys Leu Glu Thr Lys
            100                 105                 110

<210> SEQ ID NO 75
<211> LENGTH: 119
<212> TYPE: PRT
<213> ORGANISM: Artificial Sequence
<220> FEATURE:
<223> OTHER INFORMATION: synthetic

<400> SEQUENCE: 75

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Thr Tyr
            20                  25                  30

Trp Met His Trp Val Lys Gln Arg Pro Gly Gln Gly Leu Glu Trp Ile
        35                  40                  45

Gly Met Ile Gln Pro Asn Ser Gly Gly Thr Lys Tyr Asn Glu Lys Phe
50                  55                  60

Lys Lys Lys Ala Thr Leu Thr Val Asp Lys Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Gly Ala Gly Thr Val Asp Tyr Phe Asp Tyr Trp Gly Gln Gly
            100                 105                 110

Ser Thr Leu Thr Val Ser Ser
        115

<210> SEQ ID NO 76
<211> LENGTH: 111
<212> TYPE: PRT
<213> ORGANISM: Artificial Sequence
<220> FEATURE:
<223> OTHER INFORMATION: synthetic

<400> SEQUENCE: 76

Asp Ile Val Leu Thr Gln Ser Pro Ala Ser Leu Ala Val Ser Val Gly
1               5                   10                  15

Gln Arg Ala Thr Ile Thr Cys Arg Ala Ser Glu Ser Val Asp Ile Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
50                  55                  60

```
Arg Phe Ser Gly Ser Gly Ser Arg Thr Asp Phe Thr Leu Thr Ile Asn
 65                  70                  75                  80

Pro Val Glu Ala Asn Asp Thr Ala Thr Tyr Tyr Cys Gln Gln Ser Thr
                 85                  90                  95

Glu Asp Pro Tyr Thr Phe Gly Gly Gly Thr Lys Leu Glu Ile Lys
            100                 105                 110
```

<210> SEQ ID NO 77
<211> LENGTH: 119
<212> TYPE: PRT
<213> ORGANISM: Artificial Sequence
<220> FEATURE:
<223> OTHER INFORMATION: synthetic

<400> SEQUENCE: 77

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ile Phe Thr Thr Tyr
                 20                  25                  30

Trp Met His Trp Val Arg Gln Ala Pro Gly Gln Gly Leu Glu Trp Ile
             35                  40                  45

Gly Met Ile Gln Pro Asn Ser Gly Gly Thr Lys Tyr Asn Glu Lys Phe
 50                  55                  60

Lys Lys Lys Ala Thr Leu Thr Val Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Gly Ala Gly Thr Val Asp Tyr Phe Asp Tyr Trp Gly Gln Gly
            100                 105                 110

Ser Thr Leu Thr Val Ser Ser
            115
```

<210> SEQ ID NO 78
<211> LENGTH: 111
<212> TYPE: PRT
<213> ORGANISM: Artificial Sequence
<220> FEATURE:
<223> OTHER INFORMATION: synthetic

<400> SEQUENCE: 78

```
Asp Ile Val Leu Thr Gln Ser Pro Ala Ser Leu Ala Val Ser Val Gly
 1               5                  10                  15

Gln Arg Ala Thr Ile Thr Cys Arg Ala Ser Glu Ser Val Asp Ile Tyr
                 20                  25                  30

Gly Asn Ser Phe Met His Trp Tyr Gln Gln Lys Pro Gly Gln Pro Pro
             35                  40                  45

Lys Leu Leu Ile Tyr Arg Ala Ser Asn Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asn Asp Thr Ala Thr Tyr Tyr Cys His Gln Ser Thr
                 85                  90                  95

Glu Asp Pro Tyr Thr Phe Gly Gly Gly Thr Lys Leu Glu Ile Lys
            100                 105                 110
```

<210> SEQ ID NO 79
<211> LENGTH: 119
<212> TYPE: PRT
<213> ORGANISM: Mus musculus

<400> SEQUENCE: 79

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Ser Phe Thr Thr Tyr
            20                  25                  30

Trp Met His Trp Val Lys Gln Arg Pro Gly Gln Gly Leu Glu Trp Ile
        35                  40                  45

Gly Met Ile Gln Pro Asn Ser Gly Gly Thr Lys Tyr Asn Glu Lys Phe
    50                  55                  60

Lys Lys Lys Ala Thr Leu Thr Val Asp Lys Ser Ser Thr Thr Ala Ser
65                  70                  75                  80

Met Glu Leu Ser Ser Leu Thr Ser Glu Asp Ser Ala Val Tyr Tyr Cys
                85                  90                  95

Ala Arg Gly Ala Gly Thr Val Asp Tyr Phe Asp Tyr Trp Gly Gln Gly
            100                 105                 110

Ser Thr Leu Thr Val Ser Ser
        115
```

<210> SEQ ID NO 80
<211> LENGTH: 111
<212> TYPE: PRT
<213> ORGANISM: Mus musculus

<400> SEQUENCE: 80

```
Asp Ile Val Leu Thr His Ser Pro Val Ser Leu Ala Val Ser Leu Gly
1               5                   10                  15

Gln Arg Ala Thr Ile Ser Cys Arg Ala Ser Glu Ser Val Asp Ile Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Thr
                85                  90                  95

Glu Asp Pro Tyr Thr Phe Gly Gly Gly Thr Lys Leu Glu Ile Lys
            100                 105                 110
```

<210> SEQ ID NO 81
<211> LENGTH: 117
<212> TYPE: PRT
<213> ORGANISM: Artificial Sequence
<220> FEATURE:
<223> OTHER INFORMATION: synthetic

<400> SEQUENCE: 81

```
Gln Val Gln Leu Val Gln Ser Gly Ala Glu Val Val Lys Pro Gly Ala
1               5                   10                  15

Ser Val Lys Ile Ser Cys Lys Ala Ser Gly Tyr Val Phe Thr Asp Tyr
            20                  25                  30

Tyr Met Asn Trp Val Lys Gln Ala Pro Gly Gln Gly Leu Glu Trp Ile
        35                  40                  45

Gly Asp Ile Asn Pro Asn Asn Gly Gly Thr Ser Tyr Asn Gln Lys Phe
    50                  55                  60

Gln Gly Arg Ala Thr Val Thr Val Asp Lys Ser Thr Arg Thr Ala Tyr
```

```
                65                  70                  75                  80
Met Glu Leu Ser Arg Leu Arg Ser Asp Asp Thr Ala Val Tyr Tyr Cys
                    85                  90                  95

Val Lys Trp Gly Asp Gly Pro Phe Ala Tyr Trp Gly Gln Gly Thr Leu
                100                 105                 110

Val Thr Val Ser Ser
        115

<210> SEQ ID NO 82
<211> LENGTH: 106
<212> TYPE: PRT
<213> ORGANISM: Artificial Sequence
<220> FEATURE:
<223> OTHER INFORMATION: synthetic

<400> SEQUENCE: 82

Asp Ile Gln Met Thr Gln Ser Gln Ser Leu Ser Ala Ser Val Gly
1               5                   10                  15

Asp Arg Val Thr Ile Thr Cys Gln Ala Ser Gln Asn Val Gly Ala Ala
                20                  25                  30

Val Ala Trp Tyr Gln Gln Lys Pro Gly Lys Ala Pro Lys Leu Leu Ile
            35                  40                  45

Tyr Ser Ala Ser Asn Arg Tyr Thr Gly Val Pro Ser Arg Phe Ser Gly
        50                  55                  60

Ser Gly Ser Gly Thr Asp Phe Thr Leu Thr Ile Ser Ser Met Gln Pro
65                  70                  75                  80

Glu Asp Ile Ala Thr Tyr Phe Cys Gln Gln Tyr Ser Asn Tyr Pro Thr
                85                  90                  95

Phe Gly Ser Gly Thr Lys Leu Gly Ile Lys
                100                 105

<210> SEQ ID NO 83
<211> LENGTH: 117
<212> TYPE: PRT
<213> ORGANISM: Artificial Sequence
<220> FEATURE:
<223> OTHER INFORMATION: synthetic

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Thr Asp Tyr
                20                  25                  30

Tyr Met Asn Trp Val Arg Gln Ala Pro Gly Gln Gly Leu Glu Trp Ile
            35                  40                  45

Gly Asp Ile Asn Pro Asn Asn Gly Gly Thr Ser Tyr Asn Gln Lys Phe
        50                  55                  60

Gln Gly Arg Val Thr Val Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Lys Trp Gly Asp Gly Pro Phe Ala Tyr Trp Gly Gln Gly Thr Leu
                100                 105                 110

Val Thr Val Ser Ser
        115

<210> SEQ ID NO 84
<211> LENGTH: 106
```

```
<212> TYPE: PRT
<213> ORGANISM: Artificial Sequence
<220> FEATURE:
<223> OTHER INFORMATION: synthetic

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Val Gly Ala Ala
            20                  25                  30

Val Ala Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Phe Cys Gln Gln Tyr Ser Asn Tyr Pro Thr
                85                  90                  95

Phe Gly Ser Gly Thr Lys Leu Gly Ile Lys
            100                 105

<210> SEQ ID NO 85
<211> LENGTH: 117
<212> TYPE: PRT
<213> ORGANISM: Mus musculus

<400> SEQUENCE: 85

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Val Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Ser Tyr Asn His Lys Phe
50                  55                  60

Lys Gly Lys Ala Thr Val Thr Val Asp Lys Ser Ser Arg Thr Ala Tyr
65                  70                  75                  80

Met Glu Leu Leu Ser Leu Thr Ser Glu Asp Ser Ala Val Tyr Tyr Cys
                85                  90                  95

Val Lys Trp Gly Asp Gly Pro Phe Ala Tyr Trp Gly Gln Gly Thr Leu
            100                 105                 110

Val Thr Val Ser Ala
        115

<210> SEQ ID NO 86
<211> LENGTH: 106
<212> TYPE: PRT
<213> ORGANISM: Mus musculus

<400> SEQUENCE: 86

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Ala Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
50                  55                  60
```

```
Ser Gly Ser Gly Thr Asp Phe Thr Leu Thr Ile Ser Asn Met Gln Ser
 65                  70                  75                  80

Glu Asp Leu Ala Asp Tyr Phe Cys Gln Gln Tyr Ser Asn Tyr Pro Thr
                 85                  90                  95

Phe Gly Ser Gly Thr Lys Leu Gly Ile Lys
            100                 105

<210> SEQ ID NO 87
<211> LENGTH: 98
<212> TYPE: PRT
<213> ORGANISM: Artificial Sequence
<220> FEATURE:
<223> OTHER INFORMATION: synthetic

<400> SEQUENCE: 87

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg

<210> SEQ ID NO 88
<211> LENGTH: 95
<212> TYPE: PRT
<213> ORGANISM: Artificial Sequence
<220> FEATURE:
<223> OTHER INFORMATION: synthetic

<400> SEQUENCE: 88

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Asn Tyr Pro
                 85                  90                  95

<210> SEQ ID NO 89
<211> LENGTH: 98
<212> TYPE: PRT
<213> ORGANISM: Artificial Sequence
<220> FEATURE:
<223> OTHER INFORMATION: synthetic

<400> SEQUENCE: 89

Gln Val Gln Leu Val Gln Ser Gly Ala Glu Val Lys Lys Pro Gly Ala
```

```
1               5                   10                  15
Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg
```

<210> SEQ ID NO 90
<211> LENGTH: 99
<212> TYPE: PRT
<213> ORGANISM: Artificial Sequence
<220> FEATURE:
<223> OTHER INFORMATION: synthetic

<400> SEQUENCE: 90

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Glu Leu
                20                  25                  30

Gly Ile Asn Leu Ile His Trp Tyr Gln Gln Lys Pro Gly Gln Pro Pro
            35                  40                  45

Lys Leu Leu Ile Tyr Gln Ala Ser Asn Lys Asp Thr Gly Val Pro Ala
        50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Leu Gln Ser Lys
                85                  90                  95

Asn Phe Pro
```

<210> SEQ ID NO 91
<211> LENGTH: 97
<212> TYPE: PRT
<213> ORGANISM: Artificial Sequence
<220> FEATURE:
<223> OTHER INFORMATION: synthetic

<400> SEQUENCE: 91

```
Val Gln Leu Val Gln Ser Gly Ala Glu Val Lys Lys Pro Gly Ala Ser
1               5                   10                  15

Val Lys Val Ser Cys Lys Ala Ser Gly Tyr Thr Phe Thr Gly Tyr Tyr
                20                  25                  30

Met His Trp Val Arg Gln Ala Pro Gly Gln Gly Leu Glu Trp Met Gly
            35                  40                  45

Trp Ile Asn Pro Asn Ser Gly Gly Thr Asn Tyr Ala Gln Lys Phe Gln
        50                  55                  60

Gly Arg Val Thr Met Thr Arg Asp Thr Ser Ile Ser Thr Ala Tyr Met
65                  70                  75                  80

Glu Leu Ser Arg Leu Arg Ser Asp Asp Thr Ala Val Tyr Tyr Cys Ala
                85                  90                  95

Arg
```

<210> SEQ ID NO 92
<211> LENGTH: 99
<212> TYPE: PRT
<213> ORGANISM: Artificial Sequence
<220> FEATURE:
<223> OTHER INFORMATION: synthetic

<400> SEQUENCE: 92

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Glu Leu
            20                  25                  30

Gly Ile Asn Leu Ile His Trp Tyr Gln Gln Lys Pro Gly Gln Pro Pro
        35                  40                  45

Lys Leu Leu Ile Tyr Gln Ala Ser Asn Lys Asp Thr Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Leu Gln Ser Lys
                85                  90                  95

Asn Phe Pro
```

<210> SEQ ID NO 93
<211> LENGTH: 342
<212> TYPE: DNA
<213> ORGANISM: Mus musculus

<400> SEQUENCE: 93

```
caggtccagc tgcagcagcc tgggactgca ctggtgaagc ctggggcttc agtgaagctg    60
tcctgcaagg cttctggcta caccttctcc agctactaca cacactgggt gaaacagagg   120
cctggacaag gccttgagtg gattggaaat attaatcctt caatggtggt tctatctac   180
aatgagaagt tcaagaacaa ggcctcgctg actgtagaca catcctccaa cacagcctac   240
atgcagctca gcagcctgac atctgaggac tctgcggtct attattgtgc aaggtggcac   300
tttgactact ggggccaagg cacctctctc acagtctcct ca                     342
```

<210> SEQ ID NO 94
<211> LENGTH: 345
<212> TYPE: DNA
<213> ORGANISM: Mus musculus

<400> SEQUENCE: 94

```
gacattgtga tgacccagtc tccatcctcc ctggctgtga cagcaggaga gaaggtcact    60
ttgaaatgca gtccagtca gagtcttttg tggagtggaa accaaaataa ctacttatcc    120
tggtaccagc agaaacaagg gcagcctcct aaactgctta tctatggggc atccattaga   180
gaatctgggg tccctgatcg attcacagga agtggatctg gacagactt cactcttacc   240
attggcaatg tgtctgctga agacctagca gtttattact gtcagcacaa tcatggcagc   300
tttctcccct acacgttcgg aggggggacc aggctggaaa taaaa                  345
```

<210> SEQ ID NO 95
<211> LENGTH: 363
<212> TYPE: DNA
<213> ORGANISM: Mus musculus

<400> SEQUENCE: 95

```
caggtccaac tgcagcagcc tggggctgag ctggtaaagc ctggggcttc agtgaagttg    60
```
tcctgcaagg cttctggcta cactttcacc agcaactgga tgcactgggt gaagcagagg    120
cctggacaag gccttgagtg gattggaatg atgcatccta atagtggtag tatcaattac    180
aatgagaagt tcaagaacaa ggccacactg actgcagaca atcctccag cacagcctac     240 atgcaactca gtagcctgac atctgaggac tctgcggtct actactgtgc aagatcctac    300
tacggtagta gcccgtacta ctttgactac tggggccaag gcaccactct cacagtctcc    360
tca                                                                  363

<210> SEQ ID NO 96
<211> LENGTH: 321
<212> TYPE: DNA
<213> ORGANISM: Mus musculus

<400> SEQUENCE: 96
gatatccaga tgacacagac tacatcctcc ctgtctgcct ctctgggaga cagagtcacc    60
atcagttgca gggcaagtca ggacattagc aattatttaa actggtatca gcagaaacca    120
gatggaactg ttaaactcct gatctactac acatcaagat tacactcagg agtcccatca    180
aggttcagtg gcagtgggtc tggaacagat ttttctctca ccattagcaa cctggaggaa    240
gaagatattg ccacttactt ttgccagcag ggtgatacgc ttccgtggac gttcggtgga    300
ggcaccaagc tggaaatcaa a                                              321

<210> SEQ ID NO 97
<211> LENGTH: 357
<212> TYPE: DNA
<213> ORGANISM: Mus musculus

<400> SEQUENCE: 97
caggtccaac ttcagcagcc tggggctgag ctggtaaagc ctggggcttc agtgaagttg    60
tcctgcaagg cttctggcta cactttcccc agctactgga tgcactggat gaagcagagg    120
cctggacaag gccttgagtg gattggaatg attcagccta gtacttctgg tactatctac    180
aatgagagat tcaagaacca ggtcacactg actgtagaca atcttccag cacagcctac    240 atgcaactca gcagccagac atctgaggac tctgcggtct attactgtgc aagaggaact    300
gggacggtgg actactttga ttactggggc caaggcacca ctctcacagt ctcctca      357

<210> SEQ ID NO 98
<211> LENGTH: 333
<212> TYPE: DNA
<213> ORGANISM: Mus musculus

<400> SEQUENCE: 98
gacattgtgc tgacccaatc tccagcttct ttggctgtgt ctctagggca gagggccacc    60
atatcctgca gagccagcga agtgttgat agttatggca atagttttat acactggtac    120
caacagaagc caggacagcc acccaaactc ctcatccatc gtgcatccaa cctagaatct    180
gggatccctg ccacattcag cggcagtggg tctaggacag acttcaccct caccataaat    240
cctgtggagg ctgatgatgt tgcaacctat tactgtcaac aaagtaagga ggacccgtac    300
acgttcggag gggggaccaa gctggaaata aaa                                 333

<210> SEQ ID NO 99
<211> LENGTH: 351
<212> TYPE: DNA
<213> ORGANISM: Artificial Sequence
<220> FEATURE:

<223> OTHER INFORMATION: synthetic

<400> SEQUENCE: 99

| | |
|---|---:|
| caggtgcagc tggtgcagag cggcgcagaa gtggtcaagc caggagcctc agtgaagatc | 60 |
| agctgcaagg ccagcggcta cgtgttcacc gactactata tgaactgggt gaaacaggca | 120 |
| ccaggacagg gactggagtg gatcggggat attaacccta caatggcgg aacaagctac | 180 |
| aatcagaagt ttcagggcag ggcaaccgtg acagtggaca aatctactag taccgcctat | 240 |
| atggaactgt ctcggctgag aagcgacgat accgctgtgt actattgtgt caagtggggc | 300 |
| gacggaccct tcgcatattg gggccagggg acactggtga ctgtcagctc c | 351 |

<210> SEQ ID NO 100
<211> LENGTH: 318
<212> TYPE: DNA
<213> ORGANISM: Artificial Sequence
<220> FEATURE:
<223> OTHER INFORMATION: synthetic

<400> SEQUENCE: 100

| | |
|---|---:|
| gacattcaga tgacacagtc tcagagtagc ctgtcagcca gcgtgggcga ccgagtcacc | 60 |
| atcacatgcc aggccagtca gaacgtggga gccgctgtcg cttggtacca gcagaagcca | 120 |
| ggcaaagctc ccaagctgct gatctactcc gcatctaatc ggtacacagg ggtgcccagc | 180 |
| agattcagtg gctcagggag cggaactgac tttactctga ccatcagctc catgcagcct | 240 |
| gaagatattg ccacctactt ctgccagcag tactcaaaact atccaacctt tggcagcggg | 300 |
| acaaaactgg ggatcaag | 318 |

<210> SEQ ID NO 101
<211> LENGTH: 360
<212> TYPE: DNA
<213> ORGANISM: Mus musculus

<400> SEQUENCE: 101

| | |
|---|---:|
| caggtccaac tgcagcagtc tggggctgag ttggtaaagc cgggggcttc agtgaagttg | 60 |
| tcctgcaagg cttctggcta cactttcacc agctactgga tgcactgggt gtggcagagg | 120 |
| cctggacaag gccttgagtg gattggaatg attcatccta atagtgatat tactaactgc | 180 |
| aatgagaatt tcaagcacac ggtcacactg actgttgaca atcctccag tacagcctac | 240 |
| atgcaactca gcagcctgac atctgaggac tctgcggtct tttactgtgc aagatcggac | 300 |
| ggtagtagct actggtactt cgatgtctgg ggcacaggga ccacggtcac cgtctcctca | 360 |

<210> SEQ ID NO 102
<211> LENGTH: 322
<212> TYPE: DNA
<213> ORGANISM: Mus musculus

<400> SEQUENCE: 102

| | |
|---|---:|
| agtattgtga tgacccagac tcccaaattc ctgtctgtat cagcaggaga cagggttacc | 60 |
| ataacctgca aggccggtca gagtgtgaat aatgatgtag cttggtacca acagaagcca | 120 |
| gggcagtctc ctaaactgct gatatattat gcatccaatc gttatactgg agtccctgat | 180 |
| cgcttcactg gcagtggata tgggacggat ttcactttca ccatcagcac tgtgcaggct | 240 |
| gaagacctgg cagtttattt ctgtcagcag gatttagct ctccgctcac gttcggtgct | 300 |
| gggaccaagc tggaactgaa ac | 322 |

<210> SEQ ID NO 103
<211> LENGTH: 322
<212> TYPE: DNA
<213> ORGANISM: Artificial Sequence
<220> FEATURE:
<223> OTHER INFORMATION: synthetic

<400> SEQUENCE: 103

```
agtattgtga tgacccagac tcccaaattc ctgtctgtat cagcaggaga cagggttacc     60
ataacctgca aggccggtca gagtgtgaat aatgatgtag cttggtacca acagaagcca    120
gggcagtctc ctaaactgct gatatattat gcatccaatc gttatactgg agtccctgat    180
cgcttcactg gcagtggata tgggacggat ttcactttca ccatcagcac tgtgcaggct    240
gaagacctgg cagtttattt ctgtcagcag gattttagct ctccgctcac gttcggtgct    300
gggaccaagc tggaactgaa ac                                             322
```

<210> SEQ ID NO 104
<211> LENGTH: 333
<212> TYPE: DNA
<213> ORGANISM: Artificial Sequence
<220> FEATURE:
<223> OTHER INFORMATION: synthetic

<400> SEQUENCE: 104

```
gacatcgtgc tgacccagag ccccgccagc ctggccgtga gcgtgggcca gagagccacc     60
atcacctgca gagccagcga gagcgtggac atctacggca acagcttcat gcattggtat    120
caacagaagc ccggccaggc ccccaagctg ctgatctatc gggccagcaa cctggagagc    180
ggcatccccg ccagattcag cggcagcggc agcagaaccg acttcaccct gaccatcaac    240
cccgtggagg ccaacgacac cgccacctac tactgccaac agagcaacga cgacccctac    300
accttcggcg gcggcaccaa gctggagacc aag                                 333
```

<210> SEQ ID NO 105
<211> LENGTH: 357
<212> TYPE: DNA
<213> ORGANISM: Artificial Sequence
<220> FEATURE:
<223> OTHER INFORMATION: synthetic

<400> SEQUENCE: 105

```
caggtgcagc tggtgcagag cggcgccgag gtgaagaagc ccggcgccag cgtgaagctg     60
agctgcaagg ccagcggcta catcttcacc acctactgga tgcactgggt gaagcagaga    120
cccggccagg gcctggagtg gatcggcatg atccagccca acagcggcgg caccaagtac    180
aacgagaagt tcaagaagaa ggccaccctg accgtggaca gagcatcag caccgcctac    240
atggagctga gcagactgac cagcgacgac accgccgtgt actactgcgc cagaggcgcc    300
ggcaccgtgg actacttcga ctactggggc cagggcagca ccctgaccgt ctcgagc       357
```

<210> SEQ ID NO 106
<211> LENGTH: 333
<212> TYPE: DNA
<213> ORGANISM: Artificial Sequence
<220> FEATURE:
<223> OTHER INFORMATION: synthetic

<400> SEQUENCE: 106

```
gacatcgtgc tgacccagag ccccgccagc ctggccgtga gcgtgggcca gagagccacc     60
atcacctgca gagccagcga gagcgtggac atctacggca acagcttcat gcattggtat    120
```

```
caacagaagc cggccagcc ccccaagctg ctgatctatc gggccagcaa cctggagagc    180
ggcatccccg ccagattcag cggcagcggc agcagaaccg acttcaccct gaccatcaac    240
cccgtggagg ccaacgacac cgccacctac tactgccagc agagcaccga agacccctac    300
accttcggcg cggcaccaa gctggagatc aag                                  333
```

<210> SEQ ID NO 107
<211> LENGTH: 464
<212> TYPE: PRT
<213> ORGANISM: Artificial Sequence
<220> FEATURE:
<223> OTHER INFORMATION: synthetic

<400> SEQUENCE: 107

```
Met Glu Thr Asp Thr Leu Leu Leu Trp Val Leu Leu Leu Trp Val Pro
1               5                   10                  15

Gly Ser Thr Gly Phe Thr Val Thr Val Pro Lys Asp Leu Tyr Val Val
            20                  25                  30

Glu Tyr Gly Ser Asn Met Thr Ile Glu Cys Lys Phe Pro Val Glu Lys
        35                  40                  45

Gln Leu Asp Leu Ala Ala Leu Ile Val Tyr Trp Glu Met Glu Asp Lys
    50                  55                  60

Asn Ile Ile Gln Phe Val His Gly Glu Glu Asp Leu Lys Val Gln His
65                  70                  75                  80

Ser Ser Tyr Arg Gln Arg Ala Arg Leu Leu Lys Asp Gln Leu Ser Leu
                85                  90                  95

Gly Asn Ala Ala Leu Gln Ile Thr Asp Val Lys Leu Gln Asp Ala Gly
            100                 105                 110

Val Tyr Arg Cys Met Ile Ser Tyr Gly Gly Ala Asp Tyr Lys Arg Ile
        115                 120                 125

Thr Val Lys Val Asn Ala Pro Tyr Asn Lys Ile Asn Gln Arg Ile Leu
    130                 135                 140

Val Val Asp Pro Val Thr Ser Glu His Glu Leu Thr Cys Gln Ala Glu
145                 150                 155                 160

Gly Tyr Pro Lys Ala Glu Val Ile Trp Thr Ser Ser Asp His Gln Val
                165                 170                 175

Leu Ser Gly Lys Thr Thr Thr Thr Asn Ser Lys Arg Glu Glu Lys Leu
            180                 185                 190

Phe Asn Val Thr Ser Thr Leu Arg Ile Asn Thr Thr Thr Asn Glu Ile
        195                 200                 205

Phe Tyr Cys Thr Phe Arg Arg Leu Asp Pro Glu Glu Asn His Thr Ala
    210                 215                 220

Glu Leu Val Ile Pro Glu Leu Pro Leu Ala His Pro Pro Asn Glu Arg
225                 230                 235                 240

Glu Asn Leu Tyr Phe Gln Gly Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
```

```
                 325                 330                 335
Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
            355                 360                 365

Pro Pro Ser Arg Asp Glu Leu Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
                420                 425                 430

Arg Trp Gln Gln Gly Asn Val Phe Ser Cys Ser Val Met His Glu Ala
                435                 440                 445

Leu His Asn His Tyr Thr Gln Lys Ser Leu Ser Leu Ser Pro Gly Lys
            450                 455                 460
```

<210> SEQ ID NO 108
<211> LENGTH: 1416
<212> TYPE: DNA
<213> ORGANISM: Artificial Sequence
<220> FEATURE:
<223> OTHER INFORMATION: synthetic

<400> SEQUENCE: 108

```
aagcttgccg ccaccatgga aaccgacact ctgctgctgt gggtgctgct gctgtgggtg      60
ccagggtcaa ccgggttcac cgtgacagtg cccaaggacc tgtacgtggt ggagtacggc     120
agcaacatga ccatcgagtg caagttcccc gtggagaagc agctggatct ggccgccctg     180
atcgtgtatt gggagatgga ggacaagaac atcatccagt tcgtgcacgg cgaagaggac     240
ctgaaggtgc agcacagcag ctacaggcag agggccagac tgctgaagga ccagctgtct     300
ctgggaaacg cagctctgca gatcaccgac gtgaagctgc aggacgcagg agtctaccgc     360
tgcatgatca gctacggcgg agccgactac aagaggatca ccgtgaaggt caacgccccc     420
tacaacaaga tcaaccagag aatcctggtg gtggaccccg tgaccagcga gcacgagctg     480
acttgtcagg cagagggcta ccccaaggcc gaagtgattt ggaccagcag cgaccatcag     540
gtgctgagcg gaaagaccac caccaccaac agcaagcggg aggagaagct gttcaacgtg     600
accagcaccc tgcggatcaa caccaccacc aacgagatct ctactgcac cttccggaga     660 ctggacccag aggagaacca cacagccgag ctggtcatcc agaactgcc tctggctcac     720 cctcctaacg agagagagaa tctgtatttt cagggagcac cagaactgct gggaggacca     780
tccgtgttcc tgtttccacc caaacctaag gacaccctga tgattagcag aacaccagaa     840
gtcacttgcg tggtcgtgga cgtgtcccac gaggaccccg aagtcaaatt caactggtac     900
gtggatggcg tcgaggtgca taatgctaag accaaaccaa gagaggaaca gtacaacagc     960
acctataggg tcgtgtccgt cctgacagtg ctgcaccagg actggctgaa cggaaaggag    1020
tataaatgca aggtgtctaa caaggccctg ccagctccca tcgagaagac tattagtaaa    1080
gctaagggcc agccccgcga acctcaggtg tacaccctgc ctccatcccg agacgagctg    1140
accaagaacc aggtctctct gacttgtctg gtgaagggat tctatccatc agatatcgca    1200
gtggagtggg aaagcaatgg ccagcccgag acaattaca agactacccc ccctgtgctg    1260
gactccgatg gctcttttct ttctgtattct aaactgaccg tggataagag tcggtggcag    1320
```

```
cagggggaatg tctttttcatg cagcgtgatg cacgaggcac tgcacaatca ttacactcag    1380
aagtccctgt cactgtcacc tggaaagtag ggatcc                                1416
```

<210> SEQ ID NO 109
<211> LENGTH: 65
<212> TYPE: DNA
<213> ORGANISM: Artificial Sequence
<220> FEATURE:
<223> OTHER INFORMATION: synthetic

<400> SEQUENCE: 109

```
tatagggaga cccaagctgg ctagcgttta aacttaagct tgccgccacc atggaaaccg    60
acact                                                                 65
```

<210> SEQ ID NO 110
<211> LENGTH: 70
<212> TYPE: DNA
<213> ORGANISM: Artificial Sequence
<220> FEATURE:
<223> OTHER INFORMATION: synthetic

<400> SEQUENCE: 110

```
tggatatctg cagaattcca ccacactgga ctagtggatc cctactttcc aggtgacagt    60
gacagggact                                                            70
```

<210> SEQ ID NO 111
<211> LENGTH: 62
<212> TYPE: DNA
<213> ORGANISM: Artificial Sequence
<220> FEATURE:
<223> OTHER INFORMATION: synthetic

<400> SEQUENCE: 111

```
cacggggaac ttgcactcga tggtggcgtt gctgccgtac tccaccacgt acaggtcctt    60
gg                                                                    62
```

<210> SEQ ID NO 112
<211> LENGTH: 62
<212> TYPE: DNA
<213> ORGANISM: Artificial Sequence
<220> FEATURE:
<223> OTHER INFORMATION: synthetic

<400> SEQUENCE: 112

```
tacgtggtgg agtacggcag caacgccacc atcgagtgca agttccccgt ggagaagcag    60
ct                                                                    62
```

<210> SEQ ID NO 113
<211> LENGTH: 62
<212> TYPE: DNA
<213> ORGANISM: Artificial Sequence
<220> FEATURE:
<223> OTHER INFORMATION: synthetic

<400> SEQUENCE: 113

```
cttctccacg gggaacttgc actcggcggt catgttgctg ccgtactcca ccacgtacag    60
gt                                                                    62
```

<210> SEQ ID NO 114
<211> LENGTH: 62
<212> TYPE: DNA

<213> ORGANISM: Artificial Sequence
<220> FEATURE:
<223> OTHER INFORMATION: synthetic

<400> SEQUENCE: 114
gtggagtacg gcagcaacat gaccgccgag tgcaagttcc ccgtggagaa gcagctggat    60
ct                                                                   62

<210> SEQ ID NO 115
<211> LENGTH: 62
<212> TYPE: DNA
<213> ORGANISM: Artificial Sequence
<220> FEATURE:
<223> OTHER INFORMATION: synthetic

<400> SEQUENCE: 115
atccagctgc ttctccacgg ggaaggcgca ctcgatggtc atgttgctgc cgtactccac    60
ca                                                                   62

<210> SEQ ID NO 116
<211> LENGTH: 62
<212> TYPE: DNA
<213> ORGANISM: Artificial Sequence
<220> FEATURE:
<223> OTHER INFORMATION: synthetic

<400> SEQUENCE: 116
ggcagcaaca tgaccatcga gtgcgccttc cccgtggaga agcagctgga tctggccgcc    60
ct                                                                   62

<210> SEQ ID NO 117
<211> LENGTH: 62
<212> TYPE: DNA
<213> ORGANISM: Artificial Sequence
<220> FEATURE:
<223> OTHER INFORMATION: synthetic

<400> SEQUENCE: 117
cacgatcagg gcggccagat ccagggcctt ctccacgggg aacttgcact cgatggtcat    60
gt                                                                   62

<210> SEQ ID NO 118
<211> LENGTH: 62
<212> TYPE: DNA
<213> ORGANISM: Artificial Sequence
<220> FEATURE:
<223> OTHER INFORMATION: synthetic

<400> SEQUENCE: 118
gagtgcaagt tccccgtgga gaaggccctg gatctggccg ccctgatcgt gtattgggag    60
at                                                                   62

<210> SEQ ID NO 119
<211> LENGTH: 62
<212> TYPE: DNA
<213> ORGANISM: Artificial Sequence
<220> FEATURE:
<223> OTHER INFORMATION: synthetic

<400> SEQUENCE: 119
catctcccaa tacacgatca gggcgctcag atccagctgc ttctccacgg ggaacttgca    60
ct                                                                   62

<210> SEQ ID NO 120
<211> LENGTH: 62
<212> TYPE: DNA
<213> ORGANISM: Artificial Sequence
<220> FEATURE:
<223> OTHER INFORMATION: synthetic

<400> SEQUENCE: 120
cccgtggaga agcagctgga tctgagcgcc ctgatcgtgt attgggagat ggaggacaag    60
aa                                                                  62

<210> SEQ ID NO 121
<211> LENGTH: 62
<212> TYPE: DNA
<213> ORGANISM: Artificial Sequence
<220> FEATURE:
<223> OTHER INFORMATION: synthetic

<400> SEQUENCE: 121
tcttgtcctc catctcccaa tacacggcca gggcggccag atccagctgc ttctccacgg    60
gg                                                                  62

<210> SEQ ID NO 122
<211> LENGTH: 62
<212> TYPE: DNA
<213> ORGANISM: Artificial Sequence
<220> FEATURE:
<223> OTHER INFORMATION: synthetic

<400> SEQUENCE: 122
aagcagctgg atctggccgc cctggccgtg tattgggaga tggaggacaa gaacatcatc    60
ca                                                                  62

<210> SEQ ID NO 123
<211> LENGTH: 62
<212> TYPE: DNA
<213> ORGANISM: Artificial Sequence
<220> FEATURE:
<223> OTHER INFORMATION: synthetic

<400> SEQUENCE: 123
gaactggatg atgttcttgt cctcggcctc ccaatacacg atcagggcgg ccagatccag    60
ct                                                                  62

<210> SEQ ID NO 124
<211> LENGTH: 62
<212> TYPE: DNA
<213> ORGANISM: Artificial Sequence
<220> FEATURE:
<223> OTHER INFORMATION: synthetic

<400> SEQUENCE: 124
gccgccctga tcgtgtattg ggaggccgag gacaagaaca tcatccagtt cgtgcacggc    60
ga                                                                  62

<210> SEQ ID NO 125
<211> LENGTH: 62
<212> TYPE: DNA
<213> ORGANISM: Artificial Sequence
<220> FEATURE:
<223> OTHER INFORMATION: synthetic

<400> SEQUENCE: 125
gccgtgcacg aactggatga tgttggcgtc ctccatctcc caatacacga tcagggcggc    60
ca    62

<210> SEQ ID NO 126
<211> LENGTH: 62
<212> TYPE: DNA
<213> ORGANISM: Artificial Sequence
<220> FEATURE:
<223> OTHER INFORMATION: synthetic

<400> SEQUENCE: 126
atcgtgtatt gggagatgga ggacgccaac atcatccagt tcgtgcacgg cgaagaggac    60
ct    62

<210> SEQ ID NO 127
<211> LENGTH: 62
<212> TYPE: DNA
<213> ORGANISM: Artificial Sequence
<220> FEATURE:
<223> OTHER INFORMATION: synthetic

<400> SEQUENCE: 127
ttcgccgtgc acgaactgga tgatggcctt gtcctccatc tcccaataca cgatcagggc    60
gg    62

<210> SEQ ID NO 128
<211> LENGTH: 62
<212> TYPE: DNA
<213> ORGANISM: Artificial Sequence
<220> FEATURE:
<223> OTHER INFORMATION: synthetic

<400> SEQUENCE: 128
gtgtattggg agatggagga caaggccatc atccagttcg tgcacggcga agaggacctg    60
aa    62

<210> SEQ ID NO 129
<211> LENGTH: 62
<212> TYPE: DNA
<213> ORGANISM: Artificial Sequence
<220> FEATURE:
<223> OTHER INFORMATION: synthetic

<400> SEQUENCE: 129
ctcttcgccg tgcacgaact ggatggcgtt cttgtcctcc atctcccaat acacgatcag    60
gg    62

<210> SEQ ID NO 130
<211> LENGTH: 62
<212> TYPE: DNA
<213> ORGANISM: Artificial Sequence
<220> FEATURE:
<223> OTHER INFORMATION: synthetic

<400> SEQUENCE: 130
tattgggaga tggaggacaa gaacgccatc cagttcgtgc acggcgaaga ggacctgaag    60
gt    62

<210> SEQ ID NO 131
<211> LENGTH: 62

```
<212> TYPE: DNA
<213> ORGANISM: Artificial Sequence
<220> FEATURE:
<223> OTHER INFORMATION: synthetic

<400> SEQUENCE: 131
ctgcaccttc aggtcctctt cgccggccac gaactggatg atgttcttgt cctccatctc    60
cc                                                                  62

<210> SEQ ID NO 132
<211> LENGTH: 62
<212> TYPE: DNA
<213> ORGANISM: Artificial Sequence
<220> FEATURE:
<223> OTHER INFORMATION: synthetic

<400> SEQUENCE: 132
gacaagaaca tcatccagtt cgtggccggc gaagaggacc tgaaggtgca gcacagcagc    60
ta                                                                  62

<210> SEQ ID NO 133
<211> LENGTH: 62
<212> TYPE: DNA
<213> ORGANISM: Artificial Sequence
<220> FEATURE:
<223> OTHER INFORMATION: synthetic

<400> SEQUENCE: 133
cctctgcctg tagctgctgt gctgggcctt caggtcctct tcgccgtgca cgaactggat    60
ga                                                                  62

<210> SEQ ID NO 134
<211> LENGTH: 62
<212> TYPE: DNA
<213> ORGANISM: Artificial Sequence
<220> FEATURE:
<223> OTHER INFORMATION: synthetic

<400> SEQUENCE: 134
gtgcacggcg aagaggacct gaaggcccag cacagcagct acaggcagag ggccagactg    60
ct                                                                  62

<210> SEQ ID NO 135
<211> LENGTH: 62
<212> TYPE: DNA
<213> ORGANISM: Artificial Sequence
<220> FEATURE:
<223> OTHER INFORMATION: synthetic

<400> SEQUENCE: 135
cagcagtctg gccctctgcc tgtaggcgct gtgctgcacc ttcaggtcct cttcgccgtg    60
ca                                                                  62

<210> SEQ ID NO 136
<211> LENGTH: 62
<212> TYPE: DNA
<213> ORGANISM: Artificial Sequence
<220> FEATURE:
<223> OTHER INFORMATION: synthetic

<400> SEQUENCE: 136
gaggacctga aggtgcagca cagcgcctac aggcagaggg ccagactgct gaaggaccag    60
```

<210> SEQ ID NO 137
<211> LENGTH: 62
<212> TYPE: DNA
<213> ORGANISM: Artificial Sequence
<220> FEATURE:
<223> OTHER INFORMATION: synthetic

<400> SEQUENCE: 137
cttcagcagt ctggccctct gcctggcgct gctgtgctgc accttcaggt cctcttcgcc    60
gt    62

<210> SEQ ID NO 138
<211> LENGTH: 62
<212> TYPE: DNA
<213> ORGANISM: Artificial Sequence
<220> FEATURE:
<223> OTHER INFORMATION: synthetic

<400> SEQUENCE: 138
gacctgaagg tgcagcacag cagcgccagg cagagggcca gactgctgaa ggaccagctg    60
tc    62

<210> SEQ ID NO 139
<211> LENGTH: 62
<212> TYPE: DNA
<213> ORGANISM: Artificial Sequence
<220> FEATURE:
<223> OTHER INFORMATION: synthetic

<400> SEQUENCE: 139
ctggtccttc agcagtctgg ccctggccct gtagctgctg tgctgcacct tcaggtcctc    60
tt    62

<210> SEQ ID NO 140
<211> LENGTH: 62
<212> TYPE: DNA
<213> ORGANISM: Artificial Sequence
<220> FEATURE:
<223> OTHER INFORMATION: synthetic

<400> SEQUENCE: 140
aaggtgcagc acagcagcta cagggccagg gccagactgc tgaaggacca gctgtctctg    60
gg    62

<210> SEQ ID NO 141
<211> LENGTH: 62
<212> TYPE: DNA
<213> ORGANISM: Artificial Sequence
<220> FEATURE:
<223> OTHER INFORMATION: synthetic

<400> SEQUENCE: 141
cagagacagc tggtccttca gcagggcggc cctctgcctg tagctgctgt gctgcacctt    60
ca    62

<210> SEQ ID NO 142
<211> LENGTH: 62
<212> TYPE: DNA
<213> ORGANISM: Artificial Sequence
<220> FEATURE:
<223> OTHER INFORMATION: synthetic

<400> SEQUENCE: 142
cacagcagct acaggcagag ggccgccctg ctgaaggacc agctgtctct gggaaacgca    60
gc                                                                   62

<210> SEQ ID NO 143
<211> LENGTH: 62
<212> TYPE: DNA
<213> ORGANISM: Artificial Sequence
<220> FEATURE:
<223> OTHER INFORMATION: synthetic

<400> SEQUENCE: 143
gtttcccaga gacagctggt ccttggccag tctggccctc tgcctgtagc tgctgtgctg    60
ca                                                                   62

<210> SEQ ID NO 144
<211> LENGTH: 62
<212> TYPE: DNA
<213> ORGANISM: Artificial Sequence
<220> FEATURE:
<223> OTHER INFORMATION: synthetic

<400> SEQUENCE: 144
agctacaggc agagggccag actggccaag gaccagctgt ctctgggaaa cgcagctctg    60
ca                                                                   62

<210> SEQ ID NO 145
<211> LENGTH: 62
<212> TYPE: DNA
<213> ORGANISM: Artificial Sequence
<220> FEATURE:
<223> OTHER INFORMATION: synthetic

<400> SEQUENCE: 145
gatctgcaga gctgcgtttc ccagggccag ctggtccttc agcagtctgg ccctctgcct    60
gt                                                                   62

<210> SEQ ID NO 146
<211> LENGTH: 62
<212> TYPE: DNA
<213> ORGANISM: Artificial Sequence
<220> FEATURE:
<223> OTHER INFORMATION: synthetic

<400> SEQUENCE: 146
gccagactgc tgaaggacca gctggccctg ggaaacgcag ctctgcagat caccgacgtg    60
aa                                                                   62

<210> SEQ ID NO 147
<211> LENGTH: 62
<212> TYPE: DNA
<213> ORGANISM: Artificial Sequence
<220> FEATURE:
<223> OTHER INFORMATION: synthetic

<400> SEQUENCE: 147
ggtgatctgc agagctgcgt tccggcaga cagctggtcc ttcagcagtc tggccctctg    60
cc                                                                   62

<210> SEQ ID NO 148

```
<211> LENGTH: 62
<212> TYPE: DNA
<213> ORGANISM: Artificial Sequence
<220> FEATURE:
<223> OTHER INFORMATION: synthetic

<400> SEQUENCE: 148
agactgctga aggaccagct gtctgccgga aacgcagctc tgcagatcac cgacgtgaag    60
ct                                                                  62

<210> SEQ ID NO 149
<211> LENGTH: 62
<212> TYPE: DNA
<213> ORGANISM: Artificial Sequence
<220> FEATURE:
<223> OTHER INFORMATION: synthetic

<400> SEQUENCE: 149
ctgtgggtgc cagggtcaac cggggccacc gtgacagtgc ccaaggacct gtacgtggtg    60
ga                                                                  62

<210> SEQ ID NO 150
<211> LENGTH: 62
<212> TYPE: DNA
<213> ORGANISM: Artificial Sequence
<220> FEATURE:
<223> OTHER INFORMATION: synthetic

<400> SEQUENCE: 150
caggtccttg ggcactgtca cggtggcccc ggttgaccct ggcacccaca gcagcagcac    60
cc                                                                  62

<210> SEQ ID NO 151
<211> LENGTH: 62
<212> TYPE: DNA
<213> ORGANISM: Artificial Sequence
<220> FEATURE:
<223> OTHER INFORMATION: synthetic

<400> SEQUENCE: 151
tgggtgccag ggtcaaccgg gttcgccgtg acagtgccca aggacctgta cgtggtggag    60
ta                                                                  62

<210> SEQ ID NO 152
<211> LENGTH: 62
<212> TYPE: DNA
<213> ORGANISM: Artificial Sequence
<220> FEATURE:
<223> OTHER INFORMATION: synthetic

<400> SEQUENCE: 152
gtacaggtcc ttgggcactg tcacggcgaa cccggttgac cctggcaccc acagcagcag    60
ca                                                                  62

<210> SEQ ID NO 153
<211> LENGTH: 62
<212> TYPE: DNA
<213> ORGANISM: Artificial Sequence
<220> FEATURE:
<223> OTHER INFORMATION: synthetic

<400> SEQUENCE: 153
gggttcaccg tgacagtgcc caaggccctg tacgtggtgg agtacggcag caacatgacc    60
``` at 62

<210> SEQ ID NO 154
<211> LENGTH: 62
<212> TYPE: DNA
<213> ORGANISM: Artificial Sequence
<220> FEATURE:
<223> OTHER INFORMATION: synthetic

<400> SEQUENCE: 154
gctgccgtac tccaccacgt acagggcctt gggcactgtc acggtgaacc cggttgaccc    60
tg    62

<210> SEQ ID NO 155
<211> LENGTH: 62
<212> TYPE: DNA
<213> ORGANISM: Artificial Sequence
<220> FEATURE:
<223> OTHER INFORMATION: synthetic

<400> SEQUENCE: 155
accgtgacag tgcccaagga cctggccgtg gtggagtacg gcagcaacat gaccatcgag    60
tg    62

<210> SEQ ID NO 156
<211> LENGTH: 62
<212> TYPE: DNA
<213> ORGANISM: Artificial Sequence
<220> FEATURE:
<223> OTHER INFORMATION: synthetic

<400> SEQUENCE: 156
catgttgctg ccgtactcca ccacggccag ggccttgggc actgtcacgg tgaacccggt    60
tg    62

<210> SEQ ID NO 157
<211> LENGTH: 62
<212> TYPE: DNA
<213> ORGANISM: Artificial Sequence
<220> FEATURE:
<223> OTHER INFORMATION: synthetic

<400> SEQUENCE: 157
cccaaggacc tgtacgtggt ggaggccggc agcaacatga ccatcgagtg caagttcccc    60
gt    62

<210> SEQ ID NO 158
<211> LENGTH: 62
<212> TYPE: DNA
<213> ORGANISM: Artificial Sequence
<220> FEATURE:
<223> OTHER INFORMATION: synthetic

<400> SEQUENCE: 158
gcactcgatg gtcatgttgc tgccggcctc caccacgtac agggccttgg gcactgtcac    60
gg    62

<210> SEQ ID NO 159
<211> LENGTH: 62
<212> TYPE: DNA
<213> ORGANISM: Artificial Sequence
<220> FEATURE:

<223> OTHER INFORMATION: synthetic

<400> SEQUENCE: 159
ctggatctgg ccgccctgat cgtggcctgg gagatggagg acaagaacat catccagttc    60
gt    62

<210> SEQ ID NO 160
<211> LENGTH: 62
<212> TYPE: DNA
<213> ORGANISM: Artificial Sequence
<220> FEATURE:
<223> OTHER INFORMATION: synthetic

<400> SEQUENCE: 160
gatgttcttg tcctccatct cccaggccac gatcagggct tccagatcca gctgcttctc    60
ca    62

<210> SEQ ID NO 161
<211> LENGTH: 62
<212> TYPE: DNA
<213> ORGANISM: Artificial Sequence
<220> FEATURE:
<223> OTHER INFORMATION: synthetic

<400> SEQUENCE: 161
ctggccgccc tgatcgtgta ttgggccatg gaggacaaga acatcatcca gttcgtgcac    60
gg    62

<210> SEQ ID NO 162
<211> LENGTH: 62
<212> TYPE: DNA
<213> ORGANISM: Artificial Sequence
<220> FEATURE:
<223> OTHER INFORMATION: synthetic

<400> SEQUENCE: 162
ctggatgatg ttcttgtcct ccatggccca atacacgatc agggcttcca gatccagctg    60
ct    62

<210> SEQ ID NO 163
<211> LENGTH: 62
<212> TYPE: DNA
<213> ORGANISM: Artificial Sequence
<220> FEATURE:
<223> OTHER INFORMATION: synthetic

<400> SEQUENCE: 163
gccctgatcg tgtattggga gatggccgac aagaacatca tccagttcgt gcacggcgaa    60
ga    62

<210> SEQ ID NO 164
<211> LENGTH: 62
<212> TYPE: DNA
<213> ORGANISM: Artificial Sequence
<220> FEATURE:
<223> OTHER INFORMATION: synthetic

<400> SEQUENCE: 164
cacgaactgg atgatgttct tgtcggccat ctcccaatac acgatcaggg cttccagatc    60
ca    62

<210> SEQ ID NO 165
<211> LENGTH: 62
<212> TYPE: DNA
<213> ORGANISM: Artificial Sequence
<220> FEATURE:
<223> OTHER INFORMATION: synthetic

<400> SEQUENCE: 165
ctgatcgtgt attgggagat ggaggccaag aacatcatcc agttcgtgca cggcgaagag    60
ga    62

<210> SEQ ID NO 166
<211> LENGTH: 62
<212> TYPE: DNA
<213> ORGANISM: Artificial Sequence
<220> FEATURE:
<223> OTHER INFORMATION: synthetic

<400> SEQUENCE: 166
gtgcacgaac tggatgatgt tcttggcctc catctcccaa tacacgatca gggcttccag    60
at    62

<210> SEQ ID NO 167
<211> LENGTH: 62
<212> TYPE: DNA
<213> ORGANISM: Artificial Sequence
<220> FEATURE:
<223> OTHER INFORMATION: synthetic

<400> SEQUENCE: 167
gagatggagg acaagaacat catcgccttc gtgcacggcg aagaggacct gaaggtgcag    60
ca    62

<210> SEQ ID NO 168
<211> LENGTH: 62
<212> TYPE: DNA
<213> ORGANISM: Artificial Sequence
<220> FEATURE:
<223> OTHER INFORMATION: synthetic

<400> SEQUENCE: 168
caggtcctct tcgccgtgca cgaaggcgat gatgttcttg tcctccatct cccaatacac    60
ga    62

<210> SEQ ID NO 169
<211> LENGTH: 62
<212> TYPE: DNA
<213> ORGANISM: Artificial Sequence
<220> FEATURE:
<223> OTHER INFORMATION: synthetic

<400> SEQUENCE: 169
ttcgtgcacg gcgaagagga cctggccgtg cagcacagca gctacaggca gagggccaga    60
ct    62

<210> SEQ ID NO 170
<211> LENGTH: 62
<212> TYPE: DNA
<213> ORGANISM: Artificial Sequence
<220> FEATURE:
<223> OTHER INFORMATION: synthetic

<400> SEQUENCE: 170

```
ctgcctgtag ctgctgtgct gcacggccag gtcctcttcg ccgtgcacga actggatgat    60
gt                                                                   62

<210> SEQ ID NO 171
<211> LENGTH: 62
<212> TYPE: DNA
<213> ORGANISM: Artificial Sequence
<220> FEATURE:
<223> OTHER INFORMATION: synthetic

<400> SEQUENCE: 171
ctgaaggtgc agcacagcag ctacgcccag agggccagac tgctgaagga ccagctgtct    60
ct                                                                   62

<210> SEQ ID NO 172
<211> LENGTH: 62
<212> TYPE: DNA
<213> ORGANISM: Artificial Sequence
<220> FEATURE:
<223> OTHER INFORMATION: synthetic

<400> SEQUENCE: 172
gtccttcagc agtctggccc tctgggcgta gctgctgtgc tgcaccttca ggtcctcttc    60
gc                                                                   62

<210> SEQ ID NO 173
<211> LENGTH: 62
<212> TYPE: DNA
<213> ORGANISM: Artificial Sequence
<220> FEATURE:
<223> OTHER INFORMATION: synthetic

<400> SEQUENCE: 173
aagctgcagg acgcaggagt ctacgcctgc atgatcagct acggcggagc cgactacaag    60
ag                                                                   62

<210> SEQ ID NO 174
<211> LENGTH: 62
<212> TYPE: DNA
<213> ORGANISM: Artificial Sequence
<220> FEATURE:
<223> OTHER INFORMATION: synthetic

<400> SEQUENCE: 174
ggctccgccg tagctgatca tgcaggcgta gactcctgcg tcctgcagct tcacgtcggt    60
ga                                                                   62

<210> SEQ ID NO 175
<211> LENGTH: 62
<212> TYPE: DNA
<213> ORGANISM: Artificial Sequence
<220> FEATURE:
<223> OTHER INFORMATION: synthetic

<400> SEQUENCE: 175
caggacgcag gagtctaccg ctgcgccatc agctacggcg agccgactac aagaggatc     60 ac                                                                   62

<210> SEQ ID NO 176
<211> LENGTH: 62
<212> TYPE: DNA
<213> ORGANISM: Artificial Sequence
```

<220> FEATURE:
<223> OTHER INFORMATION: synthetic

<400> SEQUENCE: 176
gtagtcggct ccgccgtagc tgatggcgca gcggtagact cctgcgtcct gcagcttcac    60
gt                                                                  62

<210> SEQ ID NO 177
<211> LENGTH: 62
<212> TYPE: DNA
<213> ORGANISM: Artificial Sequence
<220> FEATURE:
<223> OTHER INFORMATION: synthetic

<400> SEQUENCE: 177
gcaggagtct accgctgcat gatcgcctac ggcggagccg actacaagag gatcaccgtg    60
aa                                                                  62

<210> SEQ ID NO 178
<211> LENGTH: 62
<212> TYPE: DNA
<213> ORGANISM: Artificial Sequence
<220> FEATURE:
<223> OTHER INFORMATION: synthetic

<400> SEQUENCE: 178
cctcttgtag tcggctccgc cgtaggcgat ggcgcagcgg tagactcctg cgtcctgcag    60
ct                                                                  62

<210> SEQ ID NO 179
<211> LENGTH: 62
<212> TYPE: DNA
<213> ORGANISM: Artificial Sequence
<220> FEATURE:
<223> OTHER INFORMATION: synthetic

<400> SEQUENCE: 179
cgctgcatga tcagctacgg cggaagcgac tacaagagga tcaccgtgaa ggtcaacgcc    60
cc                                                                  62

<210> SEQ ID NO 180
<211> LENGTH: 62
<212> TYPE: DNA
<213> ORGANISM: Artificial Sequence
<220> FEATURE:
<223> OTHER INFORMATION: synthetic

<400> SEQUENCE: 180
cttcacggtg atcctcttgt agtcgcttcc gccgtagctg atggcgcagc ggtagactcc    60
tg                                                                  62

<210> SEQ ID NO 181
<211> LENGTH: 62
<212> TYPE: DNA
<213> ORGANISM: Artificial Sequence
<220> FEATURE:
<223> OTHER INFORMATION: synthetic

<400> SEQUENCE: 181
tgcatgatca gctacggcgg agccgcctac aagaggatca ccgtgaaggt caacgcccc    60 ta                                                                  62

<210> SEQ ID NO 182
<211> LENGTH: 62
<212> TYPE: DNA
<213> ORGANISM: Artificial Sequence
<220> FEATURE:
<223> OTHER INFORMATION: synthetic

<400> SEQUENCE: 182
gaccttcacg gtgatcctct tgtaggcggc tccgccgtag ctgatggcgc agcggtagac    60
tc                                                                  62

<210> SEQ ID NO 183
<211> LENGTH: 62
<212> TYPE: DNA
<213> ORGANISM: Artificial Sequence
<220> FEATURE:
<223> OTHER INFORMATION: synthetic

<400> SEQUENCE: 183
atgatcagct acggcggagc cgacgccaag aggatcaccg tgaaggtcaa cgccccctac    60
aa                                                                  62

<210> SEQ ID NO 184
<211> LENGTH: 62
<212> TYPE: DNA
<213> ORGANISM: Artificial Sequence
<220> FEATURE:
<223> OTHER INFORMATION: synthetic

<400> SEQUENCE: 184
gttgaccttc acggtgatcc tcttggcgtc ggctccgccg tagctgatgg cgcagcggta    60
ga                                                                  62

<210> SEQ ID NO 185
<211> LENGTH: 62
<212> TYPE: DNA
<213> ORGANISM: Artificial Sequence
<220> FEATURE:
<223> OTHER INFORMATION: synthetic

<400> SEQUENCE: 185
atcagctacg gcggagccga ctacgccagg atcaccgtga aggtcaacgc ccctacaac    60 aa                                                                  62

<210> SEQ ID NO 186
<211> LENGTH: 62
<212> TYPE: DNA
<213> ORGANISM: Artificial Sequence
<220> FEATURE:
<223> OTHER INFORMATION: synthetic

<400> SEQUENCE: 186
ggcgttgacc ttcacggtga tcctggcgta gtcggctccg ccgtagctga tggcgcagcg    60
gt                                                                  62

<210> SEQ ID NO 187
<211> LENGTH: 62
<212> TYPE: DNA
<213> ORGANISM: Artificial Sequence
<220> FEATURE:
<223> OTHER INFORMATION: synthetic

<400> SEQUENCE: 187

-continued

```
agctacggcg gagccgacta caaggccatc accgtgaagg tcaacgcccc ctacaacaag    60
at                                                                   62
```

<210> SEQ ID NO 188
<211> LENGTH: 62
<212> TYPE: DNA
<213> ORGANISM: Artificial Sequence
<220> FEATURE:
<223> OTHER INFORMATION: synthetic

<400> SEQUENCE: 188

```
gggggcgttg accttcacgg tgatgccctt gtagtcggct ccgccgtagc tgatggcgca    60
gc                                                                   62
```

<210> SEQ ID NO 189
<211> LENGTH: 119
<212> TYPE: PRT
<213> ORGANISM: Artificial Sequence
<220> FEATURE:
<223> OTHER INFORMATION: Synthetic

<400> SEQUENCE: 189

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Thr Tyr
            20                  25                  30

Trp Ile His Trp Val Arg Gln Ala Pro Gly Gln Gly Leu Glu Trp Ile
        35                  40                  45

Gly Met Ile Gln Pro Asn Ser Gly Gly Thr Lys Tyr Asn Asp Gln Phe
    50                  55                  60

Lys Asn Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Gly Thr Val Asp Tyr Phe Asp Tyr Trp Gly Gln Gly
            100                 105                 110

Thr Thr Leu Ser Ile Ser Ser
            115
```